US007501485B2

(12) United States Patent  
Cowsar

(10) Patent No.: US 7,501,485 B2
(45) Date of Patent: Mar. 10, 2009

(54) BIOACTIVE KERATIN PEPTIDES

(75) Inventor: Donald R. Cowsar, Savannah, GA (US)

(73) Assignee: Keraplast Technologies, Ltd., San Antonio, TX (US)

( * ) Notice: Subject to any disclaimer, the term of this patent is extended or adjusted under 35 U.S.C. 154(b) by 250 days.

(21) Appl. No.: 10/352,786

(22) Filed: Jan. 28, 2003

(65) Prior Publication Data

US 2003/0228353 A1 Dec. 11, 2003

Related U.S. Application Data

(60) Provisional application No. 60/352,396, filed on Jan. 28, 2002.

(51) Int. Cl.
*C07K 14/435* (2006.01)
(52) U.S. Cl. .......................... 530/324; 514/12
(58) Field of Classification Search ................ 530/324, 530/325–330; 514/12–18, 2
See application file for complete search history.

(56) References Cited

U.S. PATENT DOCUMENTS

| 922,692 | A | 5/1909 | Goldsmith |
| 926,999 | A | 7/1909 | Neuberg |
| 960,914 | A | 6/1910 | Heinemann |
| 1,214,299 | A | 1/1917 | Grosvenor et al. |
| 2,434,688 | A | 1/1948 | Evans .......................... 18/47.5 |
| 2,445,028 | A | 7/1948 | Jones et al. ................. 106/155 |
| 2,517,572 | A | 8/1950 | Jones et al. ................. 106/155 |
| 2,814,851 | A | 12/1957 | Hervey ........................... 28/82 |
| 3,033,755 | A | 5/1962 | Jacobi et al. ................... 167/90 |
| 3,642,498 | A | 2/1972 | Anker .......................... 99/166 |
| 3,655,416 | A | 4/1972 | Vinson et al. ............... 106/155 |
| 4,178,361 | A | 12/1979 | Cohen et al. .................. 424/22 |
| 4,357,274 | A | 11/1982 | Werner ..................... 260/123.7 |
| 4,423,032 | A | 12/1983 | Abe et al. ...................... 424/70 |
| 4,495,173 | A | 1/1985 | Matsunaga et al. ............ 424/70 |
| 4,570,629 | A | 2/1986 | Widra ......................... 128/156 |
| 4,751,074 | A | 6/1988 | Matsunaga et al. ............ 424/70 |
| 4,816,441 | A * | 3/1989 | Zeuthen et al. ............... 514/12 |
| 4,895,722 | A | 1/1990 | Abe et al. ...................... 424/71 |
| 4,959,213 | A | 9/1990 | Brod et al. .................... 514/21 |
| 5,047,249 | A | 9/1991 | Rothman et al. ............. 424/543 |
| 5,320,796 | A | 6/1994 | Harashima et al. .......... 264/349 |
| 5,634,945 | A | 6/1997 | Pernia et al. .................. 623/11 |
| 5,679,819 | A | 10/1997 | Jones et al. .................. 556/418 |
| 5,712,252 | A | 1/1998 | Smith ............................ 514/21 |
| 5,763,583 | A | 6/1998 | Arai et al. ................... 530/353 |
| 6,037,135 | A * | 3/2000 | Kubo et al. ................. 435/7.24 |
| 6,110,889 | A * | 8/2000 | Miller et al. .................. 514/17 |
| 6,586,570 | B1 * | 7/2003 | Frudakis et al. ............. 530/350 |

FOREIGN PATENT DOCUMENTS

| EP | 0468797 B1 | 12/1995 |
| GB | 531446 | 1/1941 |
| JP | S55-187190 | 12/1980 |
| JP | SHO 54-124043 | 2/1982 |
| JP | SHO 60-220068 | 11/1985 |
| JP | 1988-202582 | 8/1988 |
| JP | 3-223207 | 10/1991 |
| JP | 1992-174659 | 5/1992 |
| JP | HEI 4-189833 | 7/1992 |
| JP | 1993285374 A | 11/1993 |
| JP | 1993285375 A | 11/1993 |
| JP | 1994100600 A | 4/1994 |
| JP | 1994116300 A | 4/1994 |
| JP | 8-157342 | 6/1996 |
| JP | 1998291999 A | 11/1998 |
| JP | 1998337466 A | 12/1998 |
| JP | 2001-114647 | 4/2001 |
| WO | WO 91/02538 | 3/1991 |
| WO | WO 98/08550 | 3/1998 |
| WO | 99/54345 | * 10/1999 |
| WO | WO 03/011894 A1 | 2/2003 |
| WO | WO 03/018673 A1 | 3/2003 |

OTHER PUBLICATIONS

Bayer (EMBO Journal 3(8), 1925-30, 1984).*
Buchta (International Journal of Peptide & Protein Research 28(3), 289-97, 1986).*
Aoki, "Isolation and characterization of mouse high-glycine/tyrosine proteins," The Journal of Biological Chemistry, Nov. 28, 1997, 30512-30518, 272:48, The American Society for Biochemistry and Molecular Biology, Inc., USA.
Thomas et al., "Isolation of microfibrillar proteins of wool in disulfide form," Melliand Textiberichte, 65(3):20809, 1984.
van de Löcht, "Reconstitution of microfibrils from wool and filaments from epidermis proteins," Melliand Textiberichte, 10:780-6, 1987.
Yoshioka et al., "Cosmetic base," unexamined Japanese Patent Application No. 3-223207, Oct. 2, 1991.
Yoshioka et al., "Water-soluble hair dressing agent," unexamined Japanese Patent Application No. 8-157342, Jun. 18, 1996.
Hyuku et al., "Novel amino acid silicone polymer, production thereof, cosmetic particles surface treated with the polymer, and cosmetic containing said particles," unexamined Japanese Patent Application No. 2001-114647, Apr. 24, 2001.
Yamauchi, "The development of keratin: characteristics of polymer films," *Fragrance J*, 21(5), 62-7, 1993.
Sauk et al, "Reconstitution of cytokeratin filaments in vitro: further evidence for the role of nonhelical peptides in filament assembly," *The Journal of Cell Biology*, 99, 1590-1597, Nov. 1984.
Weber et al., "The structural relation between intermediate filament proteins in living cells and the α-keratins of sheep wool," *The EMBO Journal*, 1:10, 1155-1160, 1982.
Hanukoglu et al., "The cDNA sequence of a human epidermal keratin: divergence of sequence but conservation of structure among intermediate filament proteins," *Cell*, 31, 243-252, Nov. 1982.
Fraser et al., "Intermediate filaments in α-keratins," *Proc. Natl. Acad. Sci. USA*, 83, 1179-1183, Mar. 1986.

(Continued)

*Primary Examiner*—David Lukton
(74) *Attorney, Agent, or Firm*—Vinson & Elkins LLP

(57) ABSTRACT

Compositions containing biologically active peptides are disclosed. Active peptides are isolated fragments derived from human hair or sheep wool keratin proteins. Compositions may be prepared for pharmaceutical or topical administration or for use in cosmetic preparations.

38 Claims, No Drawings

OTHER PUBLICATIONS

Jones, "Studies on microfibrils from α-keratin," *Biochimica et Biophysica Acta*, 446, 515-524, Received Apr. 5, 1976.

Zackroff, et al., "In vitro assembly of intermediate filaments from baby hamster kidney (BHK-21) cells," *Proc. Natl. Acad. Sci. USA*, 76:12, 6226-6230, Dec. 1979.

Mack, et al., "Solid-state NMR studies of the dynamics and structure of mouse keratin intermediate filaments," *Biochemistry*, 27, 5418-5426, 1988.

Skerrow, et al., "Epidermal α-keratin is neutral-buffer-soluble and forms intermediate philam . . . physiological conditions in vitro," *Biochimica et Biophysica Acta*, 915, 125-131, 1987.

Kvedar, et al., "Cytokeratins of the bovine hoof: classification and studies on expression," *Biochimica et Biophysica Acta*, 884, 462-473, 1986.

Moll, et al., "The catalog of human cytokeratins: patterns of expression in normal epithelia, tumors and cultured cells," *Cell*, 31, Nov. 11-24, 1982.

Iwatsuki, et al., "Comparative studies on naturally occurring antikeratin antibodies in human sera," *The Journal of Investigative Dermatology*, 87:2, 179-184, Aug. 1986.

Lambré, et al., "An enzyme immunoassay for auto-antibodies to keratin in normal human serum and in pleural fluids from patients with various malignant or non-malignant lung diseases," *J. Clin. Lab. Immunol.*, 20, 171-176, 1986.

Stokes, et al., "Passage of water and electrolytes through natural and artificial keratin membranes," *Desalination*, 42, 321-328, 1982.

Dedeurwaerder, et al., "Selective extraction of a protein fraction from wool keratin," *Nature*, 265, 48-49 and 274-276, Jan. 20, 1977.

Brunner, et al., "Fractionation of tyrosine-rich proteins from oxidized wool by ion-exchange chromatography and preparative electrophoresis," *Eur. J. Biochem.*, 32, 350-355, 1973.

Mies, et al., "Chromatographic and electrophoretic investigations of the properties of unprotected low-sulphur wool kerateins," *Journal of Chromatography*, 405, 365-370, 1987.

Katsuumi, et al., "Two-dimensional electrophoretic analysis of human hair keratins, especially hair matrix proteins," *Arch. Dermatol Res.*, 281, 495-501, 1989.

Horn, et al., "Relative molecular masses of reduced wool keratin polypeptides," *Biochem Soc Trans*, 14, 333-334, 1986.

Harrap, et al., "Species differences in the proteins of feathers," *Comp. Biochem. Physiol.*, 20, 449-460, 1967.

Harrap, et al., "Soluble derivatives of feather keratin," *Biochem. J.*, 92, 8-18, 1964.

Yoshimizu, et al., "$^{13}$C CP/MAS NMR study of the conformation of stretched or heated low-sulfur keratin protein films," *Macromolecules*, 24, 862-866, 1991.

Schaller, et al., "Membranes prepared from keratin-polyacrylonitrile graft copolymers," *Journal of Applied Polymer Science*, 25, 783-794, 1980.

Weiss, et al., "The use of monoclonal antibody to keratin in human epidermal disease: alterations in immunohistochemical staining pattern," *The Journal of Investigative Dermatology*, 81, 224-230, 1983.

Starger, et al., "Biochemical and immunological analysis of rapidly purified 10-nm filaments from baby hamster kidney (BHK-21) cells," *J. Cell Biology*, 78, 93-109, 1978.

Valherie, "Chemical modifications of keratins. Application to the preparation of biomaterials and study of their physical, physiocochemical and biological properties," Ph.D. Thesis presented to the National Institute of Applied Sciences of Lyon, 1992.

Dale, "Keratin and other coatings for pills," *Pharm. J.*, 129, 494-495, 1932, Abstract.

Schrooyen, et al., "Biodegradable films from selectively modified feather keratin dispersions," *Polymer Preprints (American Chemical Society, Division of Polmer Chemistry)*, 39(2), 160, 1998, Abstract.

Schrooyen, et al., "Polymer films from chicken feather keratin," Book of Abstracts, 216th ACS National Meeting, Boston, Aug. 23-27, 1998, Abstract.

Gillespie, et al., "Amino acid composition of a sulphur-rich protein from wool," *Biochimica et Biophysica Acta*, 39, 538-539, 1960.

Gough, et al., "Amino acid sequences of α-helical segments from S-carboxymethylkerateine-A. Complete sequence of a type-I segment," *Biochem. J.*, 173, 373-385, 1978.

Elleman, et al., "Amino acid sequences of α-helical segments from S-carboxymethylkerateine-A. Statistical analysis," *Biochem. J.*, 173, 387-391, 1978.

Hogg, et al., "Amino acid sequences of α-helical segments from S-carboxymethylkerateine-A. Tryptic and chymotryptic peptides from a type-II segment," *Biochem. J.*, 173, 353-363, 1978.

Earland, et al., "Studies on the structure of keratin. II. The amino acid content of fractions isolated from oxidized wool," *Biochimica et Biophysica Acta*, 22, 405-411, 1956.

Crewther, et al., "Amino acid sequences of α-helical segments from S-carboxymethylkerateine-A. Complete sequence of a type-II segment," *Biochem. J.*, 173, 365-371, 1978.

Fraser, et al., "Microscopic observations of the alkaline-thioglycollate extraction of wool," *Biochimica et Biophysica Acta*, 22, 484-485, 1953.

Gillespie, et al., "Preparation of an electrophoretically homogeneous keratin derivative from wool," *Biochimica et Biophysica Acta*, 12, 481-483, 1953.

Blagrove, et al., "The electrophoresis of the high-tyrosine proteins of keratins on cellulose acetate strips," *Comp. Biochem. Physiol.*, 50B, 571-572, 1975.

Frenkel, et al., "The isolation and properties of a tyrosine-rich protein from wool: component 0.62." *Eur. J. Biochem.*, 34, 112-119, 1973.

Marshall, et al., "Successful isolelectric focusing of wool low-sulphur proteins," *Journal of Chromatography*, 172, 351-356, 1979.

Marshall, "Characterization of the proteins of human hair and nail by electrophoresis," *The Journal of Investigative Dermatology*, 80:6, 519-524, 1983.

Lindley, et al., "Occurrence of the cys-cys sequence in keratins," *J. Mol. Biol.*, 30, 63-67, 1967.

Marshall, "Genetic variation in the proteins of human nail," *The Journal of Investigative Dermatology*, 75:3, 264-269, 1980.

Goddard, et al., "A study on keratin," *J. Bio. Chem.*, 106, 605-614, 1934.

Dowling, et al., "Isolation of components from the low-sulphur proteins of wool by fractional precipitation," *Preparative Biochemistry*, 4(3), 203-226, 1974.

Crewther, et al., "Reduction of S-carboxymethylcysteine and methionine with sodium in liquid ammonia," *Biochimica et Biophysica Acta*, 194, 606-609, 1969.

Gillespie, "The isolation from wool of a readily extractable protein of low sulphur content," *Biochimica et Biophysica Acta*, 27, 225-226, 1958.

Lindley, et al., "The reactivity of the disulphide bonds of wool," *Biochem. J.*, 139, 515-523, 1974.

Mitsui, et al., "Genes for a range of growth factors and cyclin-dependent kinase inhibitors are expressed by isolated human hair follicles," *British Journal of Dermatology*, 137(5), 693-698, 1997, Abstract.

Schörnig, et al., "Synthesis of nerve growth factor mRNA in cultures of developing mouse whisker pad, a peripheral target tissue of sensory trigeminal neurons." *The Journal of Cell Biology*, 120:6, 1471-1479, 1993.

Filshie, et al., "The fine structure of α-keratin," *J. Mol. Biol.*, 3, 784-786, 1961.

Filshie, et al., "An electron microscope study of the fine structure of feather keratin," *The Journal of Cell Biology*, 13, 1-12, 1962.

Crewther, et al., "Low-sulfur proteins from α-keratins. Interrelationships between their amino acid compositions, α-helix contents, and the supercontraction of the parent keratin," *Biopolymers*, 4, 905-916. 1966.

Bhatnagar, et al., "The conformation of the high-sulphur proteins of wool. I. The preparation and properties of a water-soluble metakeratin," *Int. J. Protein Research I*, 199-212, 1969.

Crewther, et al., "The preparation and properties of a helix-rich fraction obtained by partial proteolysis of low sulfur S-carboxymethylkerateine from wool," *The Journal of Biological Chemistry*, 242:19, 4310-4319, 1967.

Parry, et al., "Structure of α-keratin: structural implication of the amino acid sequences of the type I and type II chain segments," *J. Mol. Biol.*, 113, 449-454, 1977.

Suzuki, et al, "X-ray diffraction and infrared studies of an α-helical fragment from α-keratin," *J. Mol. Biol.*, 73, 275-278, 1973.

Bhatnagar, et al., "The conformation of the high-sulphur proteins of wool. II. Difference spectra of kerateine-B," *Int. J. Protein Research I*, 213-219, 1969.

Steinert, et al., "In vitro studies on the synthesis of guinea pig hair keratin proteins," *Biochimica et Biophysica Acta*, 312, 403-412, 1973.

Rogers, "Some observations on the proteins of the inner root sheath cells of hair follicles," *Biochimica et Biophysica Acta*, 29, 33-42, 1958.

Tachibana, et al., "Fabrication of wool keratin sponge scaffolds for long-term cell cultivation," *Journal of Biotechnology*, 93, 165-170, 2002.

Gillespie, "Proteins rich in glycine and tyrosine from keratins," *Comp. Biochem. Physiol.*, 41B, 723-734, 1972.

Fraser, et al., "Tyrosine-rich proteins in keratins," *Comp. Biochem. Physiol.*, 44B, 943-947, 1973.

Bendit, et al., "Communications to the Editor. The probable role and location of high glycine-tyrosine proteins in the structure of keratins," *Biopolymers*, 17, 2743-2745, 1978.

Lindley, et al., "The preparation and properties of a group of proteins from the high-sulphur fraction of wool," *Biochem. J.*, 128, 859-867, 1972.

Gillespie, et al., "Evidence of homology in a high-sulphur protein fraction (SCMK-B2) of wool and hair α-keratins," *Biochem. J.*,110, 193-198, 1968.

Gillespie, et al., "A comparative study of high-sulphur proteins from α-keratins," *Comp. Biochem. Physiol.*, 15, 175-185, 1965.

Wormell, "Regenerated protein fibres from wool and casein," *The Journal of the Textile Institute*, 18, T219-T224, 1948.

Harding, et al., "Formation of the $_e$-(γ-glutamyl) lysine cross-link in hair proteins. Investigation of transamidases in hair follicles," *Biochemistry*, 11:15, 2858-2863, 1972.

Powell, et al., "Control of feather keratin synthesis by the availability of keratin mRNA," *Biochemical and Biophysical Research Communications*, 68:4, 1263-1271, 1976.

Strüssmann, et al., "Specific radiolabelling of keratin proteins by amidination,"*Journal of Chromatography*, 268, 306-310, 1983.

Lindley, et al., "Disulphide interchange reactions involving cyclocystine and their relevance to problems of α-keratin structure," *Biochem. J.*, 108, 701-703, 1968.

Damoglou, et al., "The hydrolysis by thermolysin of dipeptide derivatives that contain substituted cysteine," *Biochem. J.*, 123, 379-384, 1971.

Lennox, et al., "Photochemical degradation of keratins," *Photochemistry and Photobiology*, 9, 359-367, 1969.

Crewther, et al., "Preliminary Notes. The relation between the disulphide content of wool and the two-stage supercontraction of wool fibres in solutions of LiBr," *Biochimica et Biophysica Acta*, 46, 605-606. 1961.

Gillespie, et al., "A comparison of the proteins of normal and trichothiodystrophic human hair" *The Journal of Investigative Dermatology*, 80, 195-202, 1983.

Gillespie, et al., "Changes in the proteins of wool following treatment of sheep with epidermal growth factor," *The Journal of Investigative Dermatology*, 79:3, 197-200, 1982.

Gillespie, et al., "Changes in the matrix proteins of wool and mouse hair following the administration of depilatory compounds," *Aust. J. Biol. Sci.*, 33, 125-136, 1980.

Darskus, et al., "Breed and species differences in the hair proteins of four genera of caprini," *Aust. J. Biol. Sci.*, 24, 515-524, 1971.

Kemp, et al., "Differentiation of avian keratinocytes. Characterization and relationships of the keratin proteins of adult and embryonic feathers and scales," *Biochemistry*, 11:6, 969-975, 1972.

Gillespie, et al., "The diversity of keratins," *Comp. Biochem. Physiol.*, 47B, 339-346, 1974.

Fraser, et al., "Wool structure and biosynthesis," *Nature*, 261, 650-654, 1976.

Stenn, et al., editors, "The molecular and structural biology of hair," *Annals of the New York Academy of Sciences*, vol. 642, Title Page - 31, 1991.

Reis, et al., "The utilization of abomasal supplements of proteins and amino acids by sheep with special reference to wool growth," *Aust. J. Biol. Sci.*, 25, 1057-1071, 1972.

Broad, et al., "The influence of sulphur-containing amino acids on the biosynthesis of high-sulphur wool proteins," *Aust. J. Biol. Sci.*, 23, 149-164, 1970.

Reis, "The influence of dietary protein and methionine on the sulphur content and growth rate of wool in milk-fed lambs," *Aust. J. Biol. Sci.*, 23, 193-200, 1970.

Downes, et al., "Metabolic fate of parenterally administered sulphur-containing amino acids in sheep and effects on growth and composition of wool," *Aust. J. Biol. Sci.*, 23, 1077-1088, 1970.

Reis, "The growth and composition of wool. IV. The differential response of growth and content of wool to the level of sulphur-containing amino acids given per abomasum," *Aust. J. Biol. Sci.*, 20, 809-825, 1967.

Reis, et al., "Effects of phenylalanine and analogues of methionine and phenylalanine on the composition of wool and mouse hair," *Aust. J. Biol. Sci.*, 38:2, 151-163.

Frenkel, et al., "Studies on the inhibition of synthesis of the tyrosine-rich proteins of wool," *Aust. J. Biol. Sci.*, 28, 331-338, 1975.

Frenkel, et al., "Factors influencing the biosynthesis of the tyrosine-rich proteins of wool," *Aust. J. Biol. Sci.*, 27, 31-38, 1974.

Reis, "The growth and composition of wool. III. Variations in the sulphur content of wool," *Aust. J. Biol. Sci.*, 18, 671-687, 1965.

Reis, et al., "The influence of abomasal and intravenous supplements of sulphur-containing amino acids on wool growth rate," *Aust. J. Biol. Sci.*, 26, 249-258, 1973.

Gillespie, et al., "A further study on the dietary-regulated biosynthesis of high-sulphur wool proteins," *Biochem. J.*, 112, 41-49, 1969.

Gillespie, et al., "The dietary-regulated biosynthesis of high-sulphur wool proteins," *Biochem. J.*, 98, 669-677, 1966.

Powell, et al., "Characterization of a gene encoding a cysteine-rich keratin associated protein synthesized late in rabbit hair follicle differentiation," *Differentiation*, 58, 227-232, 1995.

Powell, et al., "Cyclic hair-loss and regrowth in transgenic mice overexpressing an intermediate filament gene," *The EMBO Journal*, 9:5, 1485-1493, 1990.

Raphael, et al., "Protein and amino acid composition of hair from mice carrying the naked (N) gene," *Genet. Res. Camb.*, 44:1, 29-38, 1984.

Frenkel, et al., "The keratin BIIIB gene family: isolation of cDNA clones and structure of a gene and a related pseudogene," *Genomics*, 4, 182-191, 1989.

Dowling, et al., "The primary structure of component 8c-1, a subunit protein of intermediate filaments in wool keratin," *Biochem. J.*, 236, 695-703, 1986.

Dowling, et al., "Secondary structure of component 8c-1 of α-keratin," *Biochem. J.*, 236, 705-712, 1986.

Kuczek, et al., "Sheep wool (glycine + tyrosine)-rich keratin genes," *Eur. J. Biochem.*, 166, 79-85, 1987.

Sakabe, et al., "Differential thermal analysis of component proteins from wool," Sen-I Gakkaishi 39(12): T-517-T-522 (1982).

Edwards, "Chemical studies on powdered keratins," *The Journal of Biological Chemistry*, 154, 593-596, 1944.

* cited by examiner

BIOACTIVE KERATIN PEPTIDES

CROSS-REFERENCE TO RELATED APPLICATIONS

This application relies for priority on co-pending U.S. Provisional Application No. 60/352,396, filed Jan. 28, 2002, the disclosure of which is incorporated herein in its entirety by reference.

STATEMENT REGARDING FEDERALLY SPONSORED RESEARCH OR DEVELOPMENT

N/A

BACKGROUND OF THE INVENTION

Chronic wounds can be caused by a variety of events, including surgery, prolonged bedrest and traumatic injuries. Partial thickness wounds can include second degree burns, abrasions, and skin graft donor sites. Healing of these wounds can be problematic, especially in cases of diabetes mellitus or chronic immune disorders. Full thickness wounds have no skin remaining, and can be the result of trauma, diabetes (e.g., leg ulcers) and venous stasis disease, which can cause full thickness ulcers of the lower extremities. Full thickness wounds tend to heal very slowly or not at all. Proper wound care technique including the use of wound dressings is extremely important to successful chronic wound management. Chronic wounds affect an estimated four million people a year, resulting in health care costs in the billions of dollars. T. Phillips, O. Kehinde, and H. Green, "Treatment of Skin Ulcers with Cultivated Epidermal Allografts," J. Am. Acad. Dermatol, V. 21, pp. 191-199 (1989).

The wound-healing process involves a complex series of biological interactions at the cellular level which can be grouped into three phases: homeostasis and inflammation; granulation tissue formation and reepithelization; and remodeling. R. A. F. Clark, "Cutaneous Tissue Repair: Basic Biological Considerations," J. Am. Acad. Dermatol, Vol. 13, pp. 701-725 (1985). Keratinocytes (epidermal cells that manufacture and contain keratin) migrate from wound edges to cover the wound. Growth factors such as transforming growth factor-$\beta$ (TGF-$\beta$) play a critical role in stimulating the migration process. The migration occurs optimally under the cover of a moist layer. Keratins have also been found to be necessary for reepithelization. Specifically, keratin types K5 and K14 have been found in the lower, generating, epidermal cells, and types K1 and K10 have been found in the upper, differentiated cells. I. K. Cohen, R. F. Diegleman, and W. J. Lindblad, eds., Wound Healing: Biochemical and Clinical Aspects, W. W. Saunders Company, 1992. Keratin types K6 and K10 are believed to be present in healing wounds, but not in normal skin. Keratins are major structural proteins of all epithelial cell types and appear to play a major role in wound healing.

Although not ideal for chronic wounds, several wound dressings are currently on the market, including occlusive dressings, non-adherent dressings, absorbent dressings, and dressings in the form of sheets, foams, powders and gels. S. Thomas, Wound Management and Dressing, The Pharmaceutical Press, London, 1990.

Attempts have been made to provide improved dressings that would assist in the wound☐healing process using biological materials such as growth factors. These biologicals have proven very costly and, due to the lack of an appropriate delivery vehicle, have shown minimal clinical relevance in accelerating the chronic wound-healing process relative to their cost. In cases of severe full thickness wounds, autografts (skin grafts from the patient's body) are often used. Although the graft is non-antigenic, it must be harvested from a donor site on the patient's body, creating an additional wound. In addition, availability of autologous tissue may not be adequate. Allografts (skin grafts from donors other than the patient) are also used when donor sites are not an option. Allografts essentially provide a "wound dressing" that provides a moist, water-permeable layer, but are rejected by the patient, usually within two weeks, and do not become part of the new epidermis.

SUMMARY

The present disclosure arises from the surprising discovery that certain peptides derived from keratin proteins exhibit biological activity. The activity of these peptides has been demonstrated by their ability to stimulate growth of dermal fibroblasts comparable with known fibroblast growth factors. Compositions containing the peptides are thus useful in the treatment of conditions involving damaged, aged, or diseased epithelial tissue and skin. Because of the cytokine-like activity of the peptides, compositions containing these peptides are also contemplated to be useful in stimulation of tissue or cell growth in applications including, but not limited to tissue growth and repair including skin and bone tissue. The amino acid sequences of the active peptides indicate that the peptides are derived from a region of 39 amino acids that appears in various human hair and sheep wool keratin proteins. This conserved segment contains single amino acid changes in several locations in the consensus. The claimed compositions include peptides of from 4 to 39 amino acids in length that incorporate each of the sequence variations.

The present disclosure may be described therefore, in a preferred embodiment, as a composition that includes one or more biologically active peptides and in which the peptides are from about 4 to about 39 amino acids in length and occur as contiguous sequences in the peptides disclosed herein as SEQ ID NOs:1-32. The peptides may be made by any means known in the art, including isolation from natural sources, recombinant production or chemical synthesis. Natural sources would include keratin proteins that naturally occur in inter alia, human hair, animal hair, wool, fur, nails, hooves, horns, beaks, skin and feathers. Recombinantly produced peptides may also be expressed in a bacterial host cell or a eukaryotic host cell.

An alternative embodiment of the present disclosure is an isolated nucleic acid molecule that encodes any of the peptides disclosed herein and described in the previous paragraph, and more specifically, an isolated nucleic acid molecule that encodes any peptide of from about 4 to about 39 amino acids that occurs as a contiguous amino acid sequence in the peptides designated herein as SEQ ID NOs:1-32. Such peptides include all the peptides disclosed herein as SEQ ID NOS:1-6270, inclusively. The isolated nucleic acid sequences or molecules may be fragments of naturally occurring nucleic acid sequences that encode keratin proteins, for example, or they may be variations of such sequences that encode the disclosed peptides due to redundancies in the genetic code. Alternatively, the nucleic acid molecules may be chemically synthesized based on the desired amino acid sequences to be expressed. The isolated nucleic acid sequences or molecules are preferably contained in vectors, including expression vectors capable of directing expression of the peptides in an appropriate host cell. The host cell may preferably be a bacterial cell or a eukaryotic cell. Certain embodiments of the present disclosure are vectors containing the described nucleic acid segments and host cells that contain those vectors.

In certain embodiments of the disclosure, the peptides are contained in, or combined with pharmaceutically acceptable carriers. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the peptide ingredients, its use in the therapeutic or cosmetic compositions is contemplated.

The pharmaceutical compositions are preferably formulated for administration to veterinary or human subjects, and may be optionally formulated for oral, topical or optical administration. Similarly, the claimed compositions may be formulated for implantation, coated on a surface to be implanted or contained within an implant. Additionally, in certain preferred embodiments, the compositions are formulated for application to wounds. In certain embodiments, the claimed compositions are formulated for application to burned, aged, wrinkled, scarred, or damaged skin, and are also useful in the relief of pain, burning, or itching. In certain embodiments, the peptide containing compositions of the present disclosure are formulated for the treatment of gastrointestinal, anal, vaginal, ear, eye, lung, nasal, oral or urogential epithelial tissue, including, but not limited to, for example, the treatment of Crohn's disease, skin grafts or ulcers, including diabetic ulcers.

The biological activity of the disclosed peptides may be any activity that is beneficial as a research tool for or for the benefit of a human or animal recipient of the formulations, including cell growth activation or inhibition, or cytokine-like activity. The cytokine-like activity is preferably cell differentiation, cell proliferation, cell adhesion, effect on cell morphology, cell migration, inflammatory response, angiogenesis, cell death or the like. The disclosed peptides may also be combined with other growth factors in order to enhance the healing activity of damaged skin, for example. In certain embodiments, then, a composition may contain any of the peptides derived from the peptides designated as SEQ ID NO:1-32 in combination with a growth factor such as epidermal growth factor (EGF), transforming growth factor-alpha (TGF-a), fibroblast growth factor (FGF), keratinocyte growth factor (KGF), platelet derived growth factor (PDGF) or a mixture of these in any combination.

An additional preferred embodiment of the present disclosure is compositions containing the described peptides in which the peptide or peptides are present in an amount effective to inhibit microbial growth. It has been observed by the present inventor that solutions containing the disclosed peptides may be kept "on the shelf" for extended periods of time without becoming contaminated with microbial growth. The compositions are contemplated, therefore, to be effective in inhibition of microbial contamination or growth.

In certain embodiments, the compositions of the present disclosure may be formulated as cosmetics. The cosmetic preparations may be in the form of a powder, lotion, hydrogel, oil, emulsion, paste, polish or cream. The cosmetics may optionally contain a coloring agent and/or a fragrance.

The compositions of the present disclosure may be used with benefit in virtually all categories of skin cosmetics for both women and men. These would include, but are not limited to preparations formulated as moisturizers, deodorants, anti-aging/skin repair preparations, cleansers and toners, eye care, lip care, fingernail or toenail care, scalp care, sun care, and hand and body preparations. Moreover, after-care products for such skin insults as chemical peels, sunburn, depilatory irritation, razor-shaving nicks and abrasions, scalp irritation from hair perming and straightening, and the like that include the disclosed peptides would fill a much needed void in the cosmetics arena. Many water-based make-up products may be fortified with the disclosed compositions to provide continuing skin therapy during their daily use. The disclosed peptide compositions will also find use in hair care products, such as shampoo, for example. Because of the benefits to skin, shampoos and conditioners are contemplated to be an effective way to deliver the peptides to the scalp.

Compositions including the peptides disclosed herein may also include a cell or tissue growth scaffold. The tissue growth scaffold may preferably be defined as a spinal implant, bone growth scaffold, scaffold for growth of epithelial tissue, a bandage, a non-woven sheet or a woven sheet. It may also be preferable for the non-woven or woven sheets to be keratin derived or to contain natural keratins, including, but not limited to wool pads, woven keratin, keratin bonded to polymer sheets, or cross-linked keratin. Additionally, the tissue growth scaffold may include an envelope containing the peptides or peptides coated or bonded to the surface of a metal, silicone or polymer implant.

DETAILED DESCRIPTION

The present disclosure provides a new family of biologically active peptides derived from plentiful and renewable resources. In a significant number of in vitro cell-culture studies, the present inventor has shown that the cell proliferation activity of the keratin-derived peptides mimic most all of the known growth factors, including FGF, KGF, EGF, and PDGF. In vivo studies in animals have shown that these peptides are potent anti-irritants and that they promote and/or accelerate wound healing. Moreover, these peptides, when applied topically to human volunteers, significantly restore skin barrier properties and rejuvenate aged skin. Based on these early findings, it is concluded that these keratin-derived peptides are "potent" cellular activators effecting both cell proliferation and cell differentiation in mammals, and that they have multiple uses in the medical and cosmetics arenas.

When isolated from natural sources such as human hair or wool, the biologically active peptides can yield one or several soluble peptide fractions from each raw material. These fractions appear to differ from each other mostly in their average molecular weight and their acid solubility. All fractions are readily soluble in the near-neutral pH range used for most cosmetics formulary. In cell culture studies with human fibroblasts, peptide preparations exhibited significant activation of cell proliferation at a concentration of from 100 to 0.001 µg/mL. Based on the data and the activities of known bioactive peptides, it is contemplated that the peptide compositions are active in the range of from 0.0001 to 0.00001 µg/mL. Although the specific cosmetic formulations may affect the delivery of these peptides to and/or through the skin, this in vitro cell-culture result suggests that a useful concentration of the peptides for cell activation could be less than 1%, or less than 0.4%, less than 0.1%, less than 0.01% or even less than 0.001%.

In addition to the in vitro and in vivo studies mentioned above, addition anecdotal information has been gathered regarding the disclosed peptides when opportunities for human experimentation were available. From these studies, it is contemplated that the peptide compositions are both anti-inflammatory and anti-microbial and that they mediate pain at wound-healing sites. Moreover, application of the peptide compositions to skin burns, including chemical burns and sunburn, expedites healing and minimizes discomfort.

The present disclosure arises from the surprising discovery that certain peptide fragments disclosed herein have beneficial biological activities, primarily demonstrated in in vitro studies by their effect on the growth of certain types of biological cells, and particularly dermal fibroblast cells. Because of the ability of certain of the disclosed peptide containing compositions to stimulate or to inhibit growth of fibroblast cells, the compositions find particular utility in applications that involve healing of aging, damage or pathologies of epithelial or connective tissues.

The cytokine-like properties of the peptide compositions can be used to promote healing, repair, and cell growth in keratinous tissue generally. The peptides can be used to treat damaged skin and skin wounds including, for example, rashes, including diaper rash, burns including sunburn, cuts, abrasions, punctures, sores including bed sores, ulcers including diabetic ulcers and other skin injuries or irritations. The peptide compositions can also be used to treat aging, weakened or damaged skin, including, for example, wrinkled skin. Particular applications include the treatment of damaged tissue in the external skin, or epidermal layers, in oral, pulmonary, gastro-intestinal, or spinal tissues.

The peptide containing compositions may be formulated as a powder, lotion, hydrogel, oil, emulsion, paste, cream, or gel for application to the skin or gums, or it may be formulated as an aerosol, an implant, an implant coating or a scaffolding material for tissue growth. For example, the peptide compositions may be contained in a woven or non-woven sheet material, or adsorbed in a hydrogel, or in a hydrogel contained in a biocompatible envelope material.

Preparation of Peptides

In certain embodiments the disclosed peptides may be isolated from naturally occurring sources such as human hair or sheep wool, for example. Preferred methods of preparing a small sample composition containing the claimed peptides follows. It is understood, of course, that this preparation may be made at a much larger scale in order to obtain larger, commercial quantities of the composition.

General methods of producing the peptide containing compositions from a keratin substrate include oxidizing the keratin substrate with an oxidizing agent, to substantially break the disulfide bonds that make keratins insoluble and inert. Examples of oxidizing agents that can be used include, but are not limited to, hydrogen peroxide, peracetic acid, percarbonates, persulfates, chlorine dioxide, sodium and calcium peroxides, perborates, and hypochlorite. The oxidized hair is filtered, the filtrate collected, and neutralized with base. Water soluble peptides from the neutralized filtrate may be precipitated from solution by mixing the filtrate with a water-miscible organic solvent such as methanol. Alternatively the oxidized keratin may be partially or totally dissolved in dilute aqueous alkali, filtered to remove solids, and the filtrate may be precipitated by acidification or by adding a miscible non-solvent such as ethanol or methanol, to obtain a greater fraction of the keratin material. The precipitate is collected with filtration and the collected filtrate is dried.

A more specific protocol follows:

Hot Method

Weigh 100 g of washed cut-up keratin substrate (hair, scoured unbleached, or un-dyed wool, ~0.25-0.5 inches in length) into a 3 L RB flask containing a stirring assembly and gas adaptor Add 1565 mL of distilled, de-ionized (DI) $H_2O$
Add 110 mL of 30% $H_2O_2$
Heat to reflux with stirring
Stir at reflux for ~2 hours
Remove heating mantle
Continue to stir and cool to <50° C. allow to settle and filter using Buchner funnel and fast filter paper
Rinse filtrate twice with 250 mL hot (~50° C.) DI $H_2O$
Save oxidized keratin filtrant (Intermediate A) for further processing later
Allow filtrate to cool to ~room temperature
Neutralize filtrate to pH=7.0±0.2 with ~3N $NH_4OH$
Concentrate with aspirator vacuum to ~165 mL.
Cool to about freezing
Precipitate into 1 L of freezer-cold MeOH
Filter immediately in Buchner funnel with medium-fast filter paper, washing filtrant with 2-250 mL portions of freezer cold MeOH
Alternatively:
Store entire mixture overnight in freezer allowing precipitate to settle
Decant excess MeOH
Filter remaining mixture in Buchner funnel with medium-fast filter paper, washing filtrant with 2-250 mL portions of freezer cold MeOH
Dry filtrant on filter paper overnight in a vacuum oven
Carefully scrape dried material from filter paper into mortar and grind if necessary with a pestle
Weigh product into a labeled glass jar with a Teflon-lined cap, record % SKP (soluble keratin peptide) yield based on keratin substrate, and store product at room temperature.

Enhanced Peptide Yields

Put oxidized keratin filtrant (Intermediate A from Hot Process above) in a 5-L beaker, add 4 L of 0.1 N ammonium hydroxide and stir for 24 hr at room temperature.
Filter solution and discard filtrant.
To filtrate, add glacial acetic acid dropwise with constant stirring to pH 4 causing acid-insoluble peptides to precipitate. Filter with Buchner funnel and save filtrate (acid soluble gamma fraction).
Wash filtrant (acid-insoluble alpha fraction) with 1 L of water and reject washings. Redissolve filtrant in 2 L of 0.01 N ammonium hydroxide and add this solution with constant stirring to 4 L of ethanol containing 10 mL of acetic acid. Filter with Buchner funnel and discard filtrate.
Wash filtrant with 1 L of ethanol and dry filtrant (alpha peptides) in a warm vacuum oven.
Carefully scrape dried material from filter paper and store in a glass jar labeled "alpha peptide".
Take acid-soluble gamma filtrate from the first step, and concentrate it in vacuo to about 200 mL. Pour concentrate into 2 L of ethanol with constant stirring to precipitate gamma peptides.
Recover gamma peptides by filtration with a Buchner funnel and discard filtrate.
Suspend filtrant in 1 L of ethanol and stir for 2 hr to dissolve residual ammonium acetate. Filter with Buchner funnel, discard filtrant, and dry filtrant in a warm vacuum oven.
Carefully scrape dried material from filter paper and store in a glass jar labeled "gamma peptide".

In certain embodiments, the peptides in the disclosed compositions may be chemically synthesized by methods well known in the art. Solid phase peptide synthesis involves a stepwise assembly of a peptide chain while anchored to a support or solid phase peptide resin. There are two generally well-known methods of the solid phase synthesis of peptides.

The first, known as the Merrifield method, utilizes a solid support or resin which holds the C-terminal amino acid by the carboxyl group as the peptide is being synthesized through the attachment of amino acid or peptide residues as building blocks. The N-terminus of the resin-bound peptide is deblocked and N-protected amino acids are added, usually with a coupling agent. Activating agents may be used to improve rate and selectivity. After the peptide bond is formed, the protected group is removed and the cycle is repeated, if desired, until all the amino acids have been added to the peptide in the desired order.

The second method of chemical synthesis is the "polymeric reagent synthesis", also known as the "inverse Merrifield" method. This technique involves reagents bound to solid supports in a series of columns and passing the amino acid or peptide residues through the columns to form the peptide or amino acid sequence.

In certain embodiments, the peptides may be produced recombinantly from isolated nucleic acid molecules that encode the disclosed peptides. For example, the present disclosure provides recombinant cloning and expression vectors containing DNA, as well as host cells containing the recombinant vectors. Expression vectors comprising DNA may be used to prepare the disclosed peptides encoded by the DNA. A method for producing peptides comprises culturing host cells transformed with a recombinant expression vector encoding the peptide, under conditions that promote expression of the peptide, then recovering the expressed peptides from the culture. The skilled artisan will recognize that the procedure for purifying the expressed peptides will vary according to such factors as the type of host cells employed, and the level of purity required for the particular preparation. It is understood that the peptide compositions of the present invention can be of any useful purity, including crude extracts of cell or tissue culture.

Any suitable expression system may be employed. The vectors include a DNA encoding a peptide of the invention, operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence. An origin of replication that confers the ability to replicate in the desired host cells, and a selection gene by which transformants are identified, are generally incorporated into the expression vector.

In addition, a sequence encoding an appropriate signal peptide (native or heterologous) can be incorporated into expression vectors. A DNA sequence for a signal peptide (secretory leader) may be fused in frame to the nucleic acid sequence of the invention so that the DNA is initially transcribed, and the mRNA translated, into a fusion protein comprising the signal peptide. A signal peptide that is functional in the intended host cells promotes extracellular secretion of the peptide. The signal peptide is cleaved from the peptide upon secretion of peptide from the cell.

Suitable host cells for expression of peptides include prokaryotes, yeast or higher eukaryotic cells. Prokaryotic host cells, such as bacterial cells are generally preferred for use as host cells. Appropriate cloning and expression vectors for use with bacterial, fungal, yeast, and mammalian cellular hosts are described, for example, in Pouwels et al. *Cloning Vectors: A Laboratory Manual*, Elsevier, N.Y., (1985). Cell-free translation systems could also be employed to produce peptides using RNAs derived from DNA constructs disclosed herein.

Prokaryotes include gram-negative or gram-positive organisms. Suitable prokaryotic host cells for transformation include, for example, *E. coli, Bacillus subtilis, Salmonella typhimurium*, and various other species within the genera *Pseudomonas, Streptomyces*, and *Staphylococcus*. In a prokaryotic host cell, such as *E. coli*, a peptide may include an N-terminal methionine residue to facilitate expression of the recombinant peptide in the prokaryotic host cell. The N-terminal Met may be cleaved from the expressed recombinant peptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. An appropriate promoter and a DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (Maniatis, *Molecular Cloning: A Laboratory Manual*, Cold Spring Harbor Laboratory, p. 412, 1982). A particularly useful prokaryotic host cell expression system employs a phage $\lambda P_L$ promoter and a cI857ts thermolabile repressor sequence. Plasmid vectors available from the American Type Culture Collection which incorporate derivatives of the $\lambda P_L$ promoter include plasmid pHUB2 (resident in *E. coli* strain JMB9, ATCC 37092) and pPLc28 (resident in *E. coli* RR1, ATCC 53082).

Alternatively, the peptides may be expressed in yeast host cells, preferably from the *Saccharomyces* genus (e.g., *S. cerevisiae*). Other genera of yeast, such as *Pichia* or *Kluyveromyces*, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phospho-glucose isomerase, and glucokinase. Other suitable vectors and promoters for use in yeast expression are further described in Hitzeman, EPA-73,657. Another alternative is the glucose-repressible ADH2 promoter described by Russell et al. (*J. Biol. Chem.* 258:2674, 1982) and Beier et al. (*Nature* 300: 724, 1982). Shuttle vectors replicable in both yeast and *E. coli* may be constructed by inserting DNA sequences from pBR322 for selection and replication in *E. coli* (Amp$^r$ gene and origin of replication) into the above-described yeast vectors.

The yeast α-factor leader sequence may be employed to direct secretion of the peptide. The α-factor leader sequence is often inserted between the promoter sequence and the structural gene sequence. See, e.g., Kurjan et al., *Cell* 30:933, 1982 and Bitter et al., *Proc. Natl. Acad. Sci. USA* 81:5330, 1984. Other leader sequences suitable for facilitating secretion of recombinant peptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 mg/ml adenine and 20 mg/ml uracil.

Yeast host cells transformed by vectors containing an ADH2 promoter sequence may be grown for inducing expression in a "rich" medium. An example of a rich medium is one consisting of 1% yeast extract, 2% peptone, and 1% glucose supplemented with 80 mg/ml adenine and 80 mg/ml uracil. Derepression of the ADH2 promoter occurs when glucose is exhausted from the medium.

Mammalian or insect host cell culture systems also may be employed to express recombinant peptides. Bacculovirus systems for production of heterologous proteins in insect cells are reviewed by Luckow and Summers, *Bio/Technology* 6:47 (1988). Established cell lines of mammalian origin also may be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV1/EBNA cell line derived from the African green monkey kidney cell line CV1 (ATCC CCL 70) as described by McMahan et al. (*EMBO J.* 10: 2821, 1991).

Established methods for introducing DNA into mammalian cells have been described (Kaufman, R. J., *Large Scale Mammalian Cell Culture*, 1990, pp. 15-69). Additional protocols using commercially available reagents, such as Lipofectamine lipid reagent (Gibco/BRL) or Lipofectamine-Plus lipid reagent, can be used to transfect cells (Felgner et al., *Proc. Natl. Acad. Sci. USA* 84:7413-7417, 1987). In addition, electroporation can be used to transfect mammalian cells using conventional procedures, such as those in Sambrook et al. (*Molecular Cloning: A Laboratory Manual*, 2 ed. Vol. 1-3, Cold Spring Harbor Laboratory Press, 1989). Selection of stable transformants can be performed using methods known in the art, such as, for example, resistance to cytotoxic drugs. Kaufman et al., *Meth. in Enzymology* 185:487-511, 1990, describes several selection schemes, such as dihydrofolate reductase (DHFR) resistance. A suitable host strain for DHFR selection can be CHO strain DX-B 11, which is deficient in DHFR (Urlaub and Chasin, *Proc. Natl. Acad. Sci. USA* 77:4216-4220, 1980). A plasmid expressing the DHFR cDNA can be introduced into strain DX-B 11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector can be selected on the basis of resistance to these compounds.

Transcriptional and translational control sequences for mammalian host cell expression vectors can be excised from viral genomes. Commonly used promoter sequences and enhancer sequences are derived from polyoma virus, adenovirus 2, simian virus 40 (SV40), and human cytomegalovirus. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., *Nature* 273:113, 1978; Kaufman, *Meth. in Enzymology*, 1990). Smaller or larger SV40 fragments can also be used, provided the approximately 250 bp sequence extending from the Hind III site toward the Bgl I site located in the SV40 viral origin of replication site is included.

Additional control sequences shown to improve expression of heterologous genes from mammalian expression vectors include such elements as the expression augmenting sequence element (EASE) derived from CHO cells (Morris et al., *Animal Cell Technology*, 1997, pp. 529-534 and PCT Application WO 97/25420) and the tripartite leader (TPL) and VA gene RNAs from Adenovirus 2 (Gingeras et al., *J. Biol. Chem.* 257:13475-13491, 1982). The internal ribosome entry site (IRES) sequences of viral origin allows dicistronic mRNAs to be translated efficiently (Oh and Sarnow, *Current Opinion in Genetics and Development* 3:295-300, 1993; Ramesh et al., *Nucleic Acids Research* 24:2697-2700, 1996). Expression of a heterologous cDNA as part of a dicistronic mRNA followed by the gene for a selectable marker (e.g. DHFR) has been shown to improve transfectability of the host and expression of the heterologous cDNA (Kaufman, *Meth. in Enzymology*, 1990). Exemplary expression vectors that employ dicistronic mRNAs are pTR-DC/GFP described by Mosser et al., *Biotechniques* 22:150-161, 1997, and p2A5I described by Morris et al., *Animal Cell Technology*, 1997, pp. 529-534.

A useful high expression vector, pCAVNOT, has been described by Mosley et al., *Cell* 59:335-348, 1989. Other expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells can be constructed substantially as described by Cosman et al. (*Mol. Immunol.* 23:935, 1986). A useful high expression vector, PMLSV N1/N4, described by Cosman et al., *Nature* 312:768, 1984, has been deposited as ATCC 39890. Additional useful mammalian expression vectors are described in EP-A-0367566, and in WO 91/18982, incorporated by reference herein. In yet another alternative, the vectors can be derived from retroviruses.

The disclosure also includes methods of isolating and purifying the peptides. The "isolated" peptides encompassed by this invention are peptides that are not in an environment identical to an environment in which they can be found in nature. The "purified" peptides or fragments thereof encompassed by this invention are essentially free of association with other proteins or polypeptides, for example, as a purification product of recombinant expression systems such as those described above or as a purified product from a nonrecombinant source such as naturally occurring cells and/or tissues, or as peptides isolated from the native keratin proteins in which they occur.

In one preferred embodiment, the purification of recombinant peptides or fragments can be accomplished using fusions of peptides or fragments of the invention to another polypeptide to aid in the purification of peptides or fragments of the invention. Such fusion partners can include the poly-His or other antigenic identification peptides described above as well as the Fc moieties.

Pharmaceutical Compositions

Compositions comprising an effective amount of a peptide or combination of peptides of the present invention, in combination with other components such as a physiologically acceptable diluent, carrier, or excipient, are provided herein. The peptides can be formulated according to known methods used to prepare pharmaceutically useful compositions. They can be combined in admixture, either as the sole active material or with other known active materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants and/or carriers. A peptide may be formulated into a composition in a neutral or salt form. Pharmaceutically acceptable salts, include the acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The compositions disclosed herein may be formulated in any appropriate delivery vehicle, including, but not limited to hydrogels, lotions, aqueous solutions, non-aqueous solutions, non-woven mediums, woven mediums, tissue or cell growth scaffolds and powders. Suitable formulations for pharmaceutical compositions include those described in *Remington's Pharmaceutical Sciences*, 16th ed. 1980, Mack Publishing Company, Easton, Pa.

In addition, such compositions can be complexed with polyethylene glycol (PEG), metal ions, or incorporated into polymeric compounds such as polylactic acid, polyglycolic acid, hydrogels, dextran, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance, and are thus chosen according to the intended application.

The compositions of the invention can be administered in any suitable manner, e.g., topically, parenterally, or by inhalation. The term "parenteral" includes injection, e.g., by subcutaneous, intravenous, or intramuscular routes, also including localized administration, e.g., at a site of disease or injury. Sustained release from implants is also contemplated. One skilled in the pertinent art will recognize that suitable dosages will vary, depending upon such factors as the nature of the disorder to be treated, the patient's body weight, age, and general condition, and the route of administration. Preliminary doses can be determined according to animal tests, and the scaling of dosages for human administration is performed according to art-accepted practices.

In certain preferred embodiments of use, the peptide containing compositions may be formulated as a powder to be placed over a wound, for example. The peptide powder can also be formulated into any water-based solution, cream, gel, or other vehicle for convenient application to a wound. In addition, a peptide solution could be incorporated into or cast onto a polymer wound dressing or a keratin wound dressing sheet for application to a wound. In in vitro trials, compositions containing the disclosed peptides were shown to enhance proliferation of human skin keratinocytes, human dermal fibroblasts, and microvascular endothelial cells, thus demonstrating the efficacy of the peptides in wound-healing applications.

The peptides can also be added as a cell growth stimulant to a tissue engineering scaffold such as the sheet described in U.S. Pat. No. 6,110,487, incorporated herein by reference. The peptides are contemplated to speed repair of sun or weather damaged skin. The peptides may be mixed with a carrier lotion such as lanolin and applied to the skin. The peptides may also be added to cosmetics to impart a skin healing property to the cosmetic. Cosmetic bases are believed suitable for inclusion of peptides made according to the present invention.

In certain embodiments, the peptides compositions disclosed herein may be included in, attached to, or adhered to other products, including wound dressings, woven or non-woven sheets or films, hydrogel preparations, tissue engineering scaffolds, implants, or metal or polymer materials. Such materials are described in commonly owned U.S. Pat. Nos. 5,358,935, 5,932,552, 6,274,163, 6,124,265, 6,432,435, 6,316,598, 6,371,984, 6274,155, 6,270,793, 6,461,628, and U.S. patent application Ser. No. 09/815,387, all of which are incorporated herein by reference.

Peptide Containing Compositions

In previous studies, crude compositions containing the disclosed peptides have been used to investigate the mitogenic effects on keratinocytes after 3 days of exposure. Peptide concentrations of 0.5 to 10 ug/ml produced increases in optical densities (OD) at 530 nanometer (nm) of greater than 20% compared to negative controls. One exception was the 5 ug/ml concentration that produced over a 15% greater response. The positive control in these studies, epidermal growth factor (EGF25), produced greater than 20% increase in cell proliferation. In a similar study, after 5 days of exposure the keratinocyte proliferation was 25% or greater for peptide concentrations of 0.5 to 10 ug/ml. The positive control, EGF25, also produced a greater than 25% increase.

A second set of studies was performed that tested the biological effect of the peptide compositions on human dermal fibroblasts after three and five days of exposure. After three days of exposure, the peptide composition produced a greater than 25% increase in cell proliferation at concentrations between 0.5 and 10 ug/ml. The positive control, bovine-derived fibroblast growth factor (bFGF25), produced a greater than 30% increase in cell proliferation. After five days of exposure, peptide compositions at a concentration of 0.5 to 10 ug/ml produced increases in cell proliferation of between 9% and 12%. The positive control produced a greater than 13% increase.

Related in vitro tests confirmed that the mitogenic effect of the peptide compositions on dermal fibroblasts increased with concentration up to nearly 150% of the negative control at 1000 ug/ml concentration. Compositions with greater purity increased the mitogenic effect to over 1000% of the negative control. The positive control in these studies, platelet derived growth factor (PDGF), increased the mitogenic effect to nearly 700% of the negative control.

The present disclosure includes further refined preparations that can be separated into two distinct components, the first, alpha-keratose comprises about 60% of the total peptides and is water soluble and acid insoluble. The gamma keratose is both acid and water soluble. Compositions containing mixtures of the disclosed peptides at various concentrations from the alpha and gamma fractions from hair and wool were added to dermal fibroblast cell cultures for three and five days. The cellular response was measured using optical density techniques (OD490) to quantify the cell proliferation. In all cases the highest concentrations produced a greater cell proliferation response than the lower concentrations after three days of exposure. The 100 ug/ml concentration of the peptides from hair and wool produced approximately a 35% and 30% increase in cell proliferation respectively compared to the negative control.

Human dermal fibroblasts were also exposed to alpha and gamma fractions of the peptide compositions products from hair and wool for five days. The negative control was saline, and FGF was used as a positive control. The compositions containing the alpha and gamma fractions of the peptides from hair and wool at 1 and 10 ug/ml concentrations produced an increase in cell proliferation of between 30% and 60% compared to the control.

The peptide compositions reported above were fractionated and amino acid sequences obtained using tandem mass spectrometry (MS/MS). Based on the amino acid sequence data and comparison to known hair and wool keratin proteins, the peptides were localized to a conserved region of human hair and sheep wool keratin proteins. By these sequence comparisons the bioactive peptides are shown to be derived from the following conserved consensus sequence:

```
EVNTLR(C/S)(Q/P)LGDRLNVEVD(A/T)APTVDLN(Q/R)VLNETR(S/N)
QYEAL
The peptide compositions of the present disclosure may contain, therefore,
any of the following peptides in any combination.
EVNTLRCQLGDRLNVEVDAAPTVDLNQVLNETRSQYEAL,               SEQ ID NO:1
EVNTLRSQLGDRLNVEVDAAPTVDLNQVLNETRSQYEAL,               SEQ ID NO:2
EVNTLRCPLGDRLNVEVDAAPTVDLNQVLNETRSQYEAL,               SEQ ID NO:3
EVNTLRSPLGDRLNVEVDAAPTVDLNQVLNETRSQYEAL,               SEQ ID NO:4
EVNTLRCQLGDRLNVEVDTAPTVDLNQVLNETRSQYEAL,               SEQ ID NO:5
EVNTLRSQLGDRLNVEVDTAPTVDLNQVLNETRSQYEAL,               SEQ ID NO:6
EVNTLRCPLGDRLNVEVDTAPTVDLNQVLNETRSQYEAL,               SEQ ID NO:7
EVNTLRSPLGDRLNVEVDTAPTVDLNQVLNETRSQYEAL,               SEQ ID NO:8
EVNTLRCQLGDRLNVEVDAAPTVDLNRVLNETRSQYEAL,               SEQ ID NO:9
EVNTLRSQLGDRLNVEVDAAPTVDLNRVLNETRSQYEAL,               SEQ ID NO:10
EVNTLRCPLGDRLNVEVDAAPTVDLNRVLNETRSQYEAL,               SEQ ID NO:11
EVNTLRSPLGDRLNVEVDAAPTVDLNRVLNETRSQYEAL,               SEQ ID NO:12
EVNTLRCQLGDRLNVEVDTAPTVDLNRVLNETRSQYEAL,               SEQ ID NO:13
EVNTLRSQLGDRLNVEVDTAPTVDLNRVLNETRSQYEAL,               SEQ ID NO:14
EVNTLRCPLGDRLNVEVDTAPTVDLNRVLNETRSQYEAL,               SEQ ID NO:15
EVNTLRSPLGDRLNVEVDTAPTVDLNRVLNETRSQYEAL,               SEQ ID NO:16
EVNTLRCQLGDRLNVEVDAAPTVDLNQVLNETRNQYEAL,               SEQ ID NO:17
EVNTLRSQLGDRLNVEVDAAPTVDLNQVLNETRNQYEAL,               SEQ ID NO:18
EVNTLRCPLGDRLNVEVDAAPTVDLNQVLNETRNQYEAL,               SEQ ID NO:19
EVNTLRSPLGDRLNVEVDAAPTVDLNQVLNETRNQYEAL,               SEQ ID NO:20
EVNTLRCQLGDRLNVEVDTAPTVDLNQVLNETRNQYEAL,               SEQ ID NO:21
EVNTLRSQLGDRLNVEVDTAPTVDLNQVLNETRNQYEAL,               SEQ ID NO:22
EVNTLRCPLGDRLNVEVDTAPTVDLNQVLNETRNQYEAL,               SEQ ID NO:23
EVNTLRSPLGDRLNVEVDTAPTVDLNQVLNETRNQYEAL,               SEQ ID NO:24
EVNTLRCQLGDRLNVEVDAAPTVDLNRVLNETRNQYEAL,               SEQ ID NO:25
EVNTLRSQLGDRLNVEVDAAPTVDLNRVLNETRNQYEAL,               SEQ ID NO:26
EVNTLRCPLGDRLNVEVDAAPTVDLNRVLNETRNQYEAL,               SEQ ID NO:27
EVNTLRSPLGDRLNVEVDAAPTVDLNRVLNETRNQYEAL,               SEQ ID NO:28
EVNTLRCQLGDRLNVEVDTAPTVDLNRVLNETRNQYEAL,               SEQ ID NO:29
EVNTLRSQLGDRLNVEVDTAPTVDLNRVLNETRNQYEAL,               SEQ ID NO:30
EVNTLRCPLGDRLNVEVDTAPTVDLNRVLNETRNQYEAL,               SEQ ID NO:31
EVNTLRSPLGDRLNVEVDTAPTVDLNRVLNETRNQYEAL,               SEQ ID NO:32
EVNT, SEQ ID NO:33;         VNTL, SEQ ID NO:34;     NTLR, SEQ ID NO:35;
TLRC, SEQ ID NO:36;         TLRS, SEQ ID NO:37;     LRCQ, SEQ ID NO:38;
LRCP, SEQ ID NO:39;         LRSQ, SEQ ID NO:40;     LRSP, SEQ ID NO:41;
RCQL, SEQ ID NO:42,         RSQL, SEQ ID NO:43;     RCPL, SEQ ID NO:44;
RSPL, SEQ ID NO:45;         CQLG, SEQ ID NO:46;     CPLG, SEQ ID NO:47;
SQLG, SEQ ID NO:48;         SPLG, SEQ ID NO:49;     QLGD, SEQ ID NO:50;
PLGD, SEQ ID NO:51;         LGDR, SEQ ID NO:52;     GDRL, SEQ ID NO:53;
DRLN, SEQ ID NO:54;         RLNV, SEQ ID NO:55;     LNVE, SEQ ID NO:56;
NVEV, SEQ ID NO:57;         VEVD, SEQ ID NO:58;     EVDA, SEQ ID NO:59;
EVDT, SEQ ID NO:60;         VDAA, SEQ ID NO:61;     VDTA, SEQ ID NO:62;
DAAP, SEQ ID NO:63;         DTAP, SEQ ID NO:64;     AAPT, SEQ ID NO:65;
TATP, SEQ ID NO:66;         APTV, SEQ ID NO:67;     PTVD, SEQ ID NO:68;
TVDL, SEQ ID NO:69;         VDLN, SEQ ID NO:70;     DLNQ, SEQ ID NO:71;
DLNR, SEQ ID NO:72;         LNQV, SEQ ID NO:73;     LNRV, SEQ ID NO:74;
NQVL, SEQ ID NO:75;         NRVL, SEQ ID NO:76;     QVLN, SEQ ID NO:77;
RVLN, SEQ ID NO:78;         VLNE, SEQ ID NO:79;     LNET, SEQ ID NO:80;
NETR, SEQ ID NO:81;         ETRS, SEQ ID NO:82;     ETRN, SEQ ID NO:83;
TRSQ, SEQ ID NO:84;         TRNQ, SEQ ID NO:85;     RSQY, SEQ ID NO:86;
RNQY, SEQ ID NO:87;         SQYB, SEQ ID NO:88;     NQYE, SEQ ID NO:89;
QYEA, SEQ ID NO:90;         YEAL, SEQ ID NO:91;     EVNTL, SEQ ID NO:92;
VNTLR, SEQ ID NO:93;        NTLRC, SEQ ID NO:94;    NTLRS, SEQ ID NO:95;
TLRCQ, SEQ ID NO:96;        TLRSQ, SEQ ID NO:97;    TLRCP98; TLRSP; SEQ ID
                                                    NO:99;
```

-continued

| | | |
|---|---|---|
| LRCPL, SEQ ID NO:100; | LRCPL, SEQ ID NO:101; | LRSQL, SEQ ID NO:102; |
| LRSPL, SEQ ID NO:103; | RCQLG, SEQ ID NO:104; | RCPLG, SEQ ID NO:105; |
| RSQLG, SEQ ID NO:106; | RSPLG, SEQ ID NO:107; | CQLGD, SEQ ID NO:108; |
| CPLGD, SEQ ID NO:109; | SQLGD, SEQ ID NO:110; | SPLUD, SEQ ID NO:111; |
| QLGDR, SEQ ID NO:112; | PLGDR, SEQ ID NO:112; | LGDRL, SEQ ID NO:113; |
| GDRLN, SEQ ID NO:114; | DRLNV, SEQ ID NO:115; | RLNVE, SEQ ID NO:116; |
| LNVEV, SEQ ID NO:117; | NVEVD, SEQ ID NO:118; | VEVDA, SEQ ID NO:119; |
| VEVDT, SEQ ID NO:120; | EVDAA, SEQ ID NO:121; | EVDTA, SEQ ID NO:122; |
| VDAAP, SEQ ID NO:123; | VDTAP, SEQ ID NO:124; | DAAPT, SEQ ID NO:125; |
| DTAPT, SEQ ID NO:126; | AAPTV, SEQ ID NO:127; | TAPTV, SEQ ID NO:128; |
| APTVD, SEQ ID NO:129; | PTVDL, SEQ ID NO:130; | TVDLN, SEQ ID NO:131; |
| VDLNQ, SEQ ID NO:132; | VDLNR, SEQ ID NO:133; | DLNQV, SEQ ID NO:134; |
| DLNRV, SEQ ID NO:135; | LNQVL, SEQ ID NO:136; | LNRVL, SEQ ID NO:137; |
| NQVLN, SEQ ID NO:138; | NRVLN, SEQ ID NO:139; | QVLNE, SEQ ID NO:140; |
| RVLNE, SEQ ID NO:141; | VLNET, SEQ ID NO:142; | LNETR, SEQ ID NO:143; |
| NETRS, SEQ ID NO:144; | NETRN, SEQ ID NO:145; | ETRSQ, SEQ ID NO:146; |
| ETRNQ, SEQ ID NO:147; | TRSQY, SEQ ID NO:148; | TRNQY, SEQ ID NO:149; |
| RSQYE, SEQ ID NO:150; | RNQYE, SEQ ID NO:151; | SQYEA, SEQ ID NO:152; |
| NQYEA, SEQ ID NO:153; | QYEAL, SEQ ID NO:154; | EVNTLR, SEQ ID NO:155; |
| VNTLRC, SEQ ID NO:156; | VNTLRS, SEQ ID NO:157; | NTLRCQ, SEQ ID NO:158; |
| NTLRCP, SEQ ID NO:159; | NTLRSQ, SEQ ID NO:160; | NTLRSP, SEQ ID NO:161; |
| TLRCQL, SEQ ID NO:162; | TLRCPL, SEQ ID NO:163; | TLRSQL, SEQ ID NO:164; |
| TLRSPL, SEQ ID NO:165; | LRCQLG, SEQ ID NO:166; | LRCPLG, SEQ ID NO:167; |
| LRSQLG, SEQ ID NO:168; | LRSPLG, SEQ ID NO:169; | RCQLGD, SEQ ID NO:170; |
| RCPLGD, SEQ ID NO:171; | RSQLGD, SEQ ID NO:172; | RSPLGD, SEQ ID NO:173; |
| CQLGDR, SEQ ID NO:174; | CPLGDR, SEQ ID NO:175; | SQLGDR, SEQ ID NO:176; |
| SPLGDR, SEQ ID NO:177; | QLGDRL, SEQ ID NO:178; | PLGDRL, SEQ ID NO:179; |
| LGDRLN, SEQ ID NO:180; | GDRLNV, SEQ ID NO:181; | DRLNVE, SEQ ID NO:182; |
| RLNVEV, SEQ ID NO:183; | LNVEVD, SEQ ID NO:184; | NVEVDA, SEQ ID NO:185; |
| NVEVDT, SEQ ID NO:186; | VEVDAA, SEQ ID NO:187; | VEVDTA, SEQ ID NO:188; |
| EVDAAP, SEQ ID NO:189; | EVDTAP, SEQ ID NO:190; | VDAAPT, SEQ ID NO:191; |
| VDTAPT, SEQ ID NO:192; | DAAPTV, SEQ ID NO:193; | DTAPTV, SEQ ID NO:194; |
| AAPTVD, SEQ ID NO:195; | TAPTVD, SEQ ID NO:196; | APTVDL, SEQ ID NO:197; |
| PTVDLN, SEQ ID NO:198; | TVDLNQ, SEQ ID NO:199; | TVDLNR, SEQ ID NO:200; |
| VDLNQV, SEQ ID NO:201; | VDLNRV, SEQ ID NO:202; | DLNQVL, SEQ ID NO:203; |
| DLNRVL, SEQ ID NO:204; | LNQVLN, SEQ ID NO:205; | LNRVLN, SEQ ID NO:206; |
| NQVLNE, SEQ ID NO:207; | NRVLNE, SEQ ID NO:208; | QVLNET, SEQ ID NO:209; |
| RVLNET, SEQ ID NO:210; | VLNETR, SEQ ID NO:211; | LNETRS, SEQ ID NO:212; |
| LNETRN, SEQ ID NO:213; | NETRSQ, SEQ ID NO:214; | NETRNQ, SEQ ID NO:215; |
| ETRSQY, SEQ ID NO:216; | ETRNQY, SEQ ID NO:217; | TRSQYE, SEQ ID NO:218; |
| TRNQYE, SEQ ID NO:219; | RSQYEA, SEQ ID NO:220; | RNQYEA, SEQ ID NO:221; |
| SQYEAL, SEQ ID NO:222; | NQYEAL, SEQ ID NO:223; | EVNTLRC, SEQ ID NO:224; |
| EVNTLRS, SEQ ID NO:225; | VNTLRCQ, SEQ ID NO:226; | VNTLRCP, SEQ ID NO:227; |
| VNTLRSQ, SEQ ID NO:228; | VNTLRSP, SEQ ID NO:229; | NTLRCQL, SEQ ID NO:230; |
| NTLRCPL SEQ ID NO 231; | NTLRSQL, SEQ ID NO:232; | NTLRSPL, SEQ ID NO:233; |
| TLRCQLG, SEQ ID NO:234; | TLRCPLG, SEQ ID NO:235; | |
| TLRSQLG, SEQ ID NO:236; | TLRSPLG, SEQ ID NO:237; | |
| LRCQLGD, SEQ ID NO:238; | LRCPLGD, SEQ ID NO:239; | |
| LRSQLGD, SEQ ID NO:240; | LRSPLGD, SEQ ID NO:241; | |
| RCQLGDR, SEQ ID NO:242; | RCPLGDR, SEQ ID NO:243; | |
| RSQLGDR, SEQ ID NO:244; | RSPLGDR, SEQ ID NO:245; | |
| CQLGDRL, SEQ ID NO:246; | CPLGDRL, SEQ ID NO:247; | |
| SQLGDRL, SEQ ID NO:248; | SPLGDRL, SEQ ID NO:249; | |
| QLGDRLN, SEQ ID NO:250; | PLGDRLN, SEQ ID NO:251; | |
| LGDRLNV, SEQ ID NO:252; | GDRLNVE, SEQ ID NO:253; | |
| DRLNVEV, SEQ ID NO:254; | RLNVEVD, SEQ ID NO:255; | |
| LNVEVDA, SEQ ID NO:256; | LNVEVDT, SEQ ID NO:257; | |
| NVEVDAA, SEQ ID NO:258; | NVEVDTA, SEQ ID NO:259; | |
| VEVDAAP, SEQ ID NO:260; | VEVDTAP, SEQ ID NO:261; | |
| EVDAAPT, SEQ ID NO:262; | EVDTAPT, SEQ ID NO:263; | |
| VDAAPTV, SEQ ID NO:264; | VDTAPTV, SEQ ID NO:265; | |
| DAAPTVD, SEQ ID NO:266; | DTAPTVD, SEQ ID NO:267; | |
| AAPTVDL, SEQ ID NO:268; | TAPTVDL, SEQ ID NO:269; | |
| APTVDLN, SEQ ID NO:270; | PTVDLNQ, SEQ ID NO:271; | |
| PTVDLNR, SEQ ID NO:272; | TVDLNQV, SEQ ID NO:273; | |
| TVDLNRV, SEQ ID NO:274; | VDLNQVL, SEQ ID NO:275; | |
| VDLNRVL, SEQ ID NO:276; | DLNQVLN, SEQ ID NO:277; | |
| DLNRVLN, SEQ ID NO:278; | LNQVLNE, SEQ ID NO:279; | |
| LNRVLNE, SEQ ID NO:280; | NQVLNET, SEQ ID NO:281; | |
| NRVLNET, SEQ ID NO:282; | QVLNETR, SEQ ID NO:283; | |
| RVLNETR, SEQ ID NO:284; | VLNETRS, SEQ ID NO:285; | |
| VLNETRN, SEQ ID NO:286; | LNETRSQ, SEQ ID NO:287; | |
| LNETRNQ, SEQ ID NO:288; | NETRSQY, SEQ ID NO:289; | |
| NETRNQY, SEQ ID NO:290; | ETRSQYE, SEQ ID NO:291; | |
| ETRNQYE, SEQ ID NO:292; | TRSQYEA, SEQ ID NO:293; | |
| TRNQYEA, SEQ ID NO:294; | RSQYEAL, SEQ ID NO:295; | |
| RNQYEAL, SEQ ID NO:296; | EVNTLRCQ, SEQ ID NO:297; | |
| EVNTLRCP, SEQ ID NO:298; | EVNTLRSQ, SEQ ID NO:299; | |
| EVNTLRSP, SEQ ID NO:300; | VNTLRCQL, SEQ ID NO:301; | |
| VNTLRCPL, SEQ ID NO:302; | VNTLRSQL, SEQ ID NO:303; | |

-continued

| | |
|---|---|
| VNTLRSPL, SEQ ID NO:304; | NTLRCQLG, SEQ ID NO:305; |
| NTLRCPLG, SEQ ID NO:306; | NTLRSQLG, SEQ ID NO:307; |
| NTLRSPLG, SEQ ID NO:308; | TLRCQLGD, SEQ ID NO:309; |
| TLRCPLGD, SEQ ID NO:310; | TLRSQLGD, SEQ ID NO:311; |
| TLRSPLGD, SEQ ID NO:312; | LRCQLGDR, SEQ ID NO:313; |
| LRCPLGDR, SEQ ID NO:314; | LRSQLGDR, SEQ ID NO:315; |
| LRSPLGDR, SEQ ID NO:316; | RCQLGDRL, SEQ ID NO:317; |
| RCPLGDRL, SEQ ID NO:318; | RSQLGDRL, SEQ ID NO:319; |
| RSPLGDRL, SEQ ID NO:320; | CQLGDRLN, SEQ ID NO:321; |
| CPLGDRLN, SEQ ID NO:322; | SQLGDRLN, SEQ ID NO:323; |
| SPLGDRLN, SEQ ID NO:324; | QLGDRLNV, SEQ ID NO:325; |
| PLGDRLNV, SEQ ID NO:326; | LGDRLNVE, SEQ ID NO:327; |
| GDRLNVEV, SEQ ID NO:328; | DRLNVEVD, SEQ ID NO:329; |
| RLNVEVDA, SEQ ID NO:330; | RLNVEVDT, SEQ ID NO:331; |
| LNVEVDAA, SEQ ID NO:332; | LNVEVDTA, SEQ ID NO:333; |
| NVEVDAAP, SEQ ID NO:334; | NVEVDTAP, SEQ ID NO:335; |
| VEVDAAPT, SEQ ID NO:336; | VEVDTAPT, SEQ ID NO:337; |
| EVDAAPTV, SEQ ID NO:338; | EVDTAPTV, SEQ ID NO:339; |
| VDAAPTVD, SEQ ID NO:340; | VDTAPTVD, SEQ ID NO:341; |
| DAAPTVDL, SEQ ID NO:342; | DTAPTVDL, SEQ ID NO:343; |
| AAPTVDLN, SEQ ID NO:344; | TAPTVDLN, SEQ ID NO:345; |
| APTVDLNQ, SEQ ID NO:346; | APTVDLNR, SEQ ID NO:347; |
| PTVDLNQV, SEQ ID NO:348; | PTVDLNRV, SEQ ID NO:349; |
| TVDLNQVL, SEQ ID NO:350; | TVDLNRVL, SEQ ID NO:351; |
| VDLNQVLN, SEQ ID NO:352; | VDLNRVLN, SEQ ID NO:353; |
| DLNQVLNE, SEQ ID NO:354; | DLNRVLNE, SEQ ID NO:355; |
| LNQVLNET, SEQ ID NO:356; | LNRVLNET, SEQ ID NO:357; |
| NQVLNETR, SEQ ID NO:358; | NRVLNETR, SEQ ID NO:359; |
| QVLNETRS, SEQ ID NO:360; | QVLNETRN, SEQ ID NO:361; |
| RVLNETRS, SEQ ID NO:362; | RVLNETRN, SEQ ID NO:363; |
| VLNETRSQ, SEQ ID NO:364; | VLNETRNQ, SEQ ID NO:365; |
| LNETRSQY, SEQ ID NO:366; | LNETRNQY, SEQ ID NO:367; |
| NETRSQYE, SEQ ID NO:368; | NETRNQYE, SEQ ID NO:369; |
| ETRSQYEA, SEQ ID NO:370; | ETRNQYEA, SEQ ID NO:371; |
| TRSQYEAL, SEQ ID NO:372; | TRNQYEAL, SEQ ID NO:373; |
| EVNTLRCQL, SEQ ID NO:374; | EVNTLRCPL, SEQ ID NO:375; |
| EVNTLRSQL, SEQ ID NO:376; | EVNTLRSPL, SEQ ID NO:377; |
| VNTLRCQLG, SEQ ID NO:378; | VNTLRCPLG, SEQ ID NO:379; |
| VNTLRSQLG, SEQ ID NO:380; | VNTLRSPLG, SEQ ID NO:381; |
| NTLRCQLGD, SEQ ID NO:382; | NTLRCPLGD, SEQ ID NO:383; |
| NTLRSQLGD, SEQ ID NO:384; | NTLRSPLGD, SEQ ID NO:385; |
| TLRCQLGDR, SEQ ID NO:386; | TLRCPLGDR, SEQ ID NO:387; |
| TLRSQLGDR, SEQ ID NO:388; | TLRSPLGDR, SEQ ID NO:389; |
| LRCQLGDRL, SEQ ID NO:390; | LRCPLGDRL, SEQ ID NO:391; |
| LRSQLGDRL, SEQ ID NO:392; | LRSPLGDRL, SEQ ID NO:393; |
| RCQLGDRLN, SEQ ID NO:394; | RCPLGDRLN, SEQ ID NO:395; |
| RSQLGDRLN, SEQ ID NO:396; | RSPLGDRLN, SEQ ID NO:397; |
| CQLGDRLNV, SEQ ID NO:398; | CPLGDRLNV, SEQ ID NO:399; |
| SQLGDRLNV, SEQ ID NO:400; | SPLGDRLNV, SEQ ID NO:401; |
| QLGDRLNVE, SEQ ID NO:402; | PLGDRLNVE, SEQ ID NO:403; |
| LGDRLNVEV, SEQ ID NO:404; | GDRLNVEVD, SEQ ID NO:405; |
| DRLNVEVDA, SEQ ID NO:406; | DRLNVEVDT, SEQ ID NO:407; |
| RLNVEVDAA, SEQ ID NO:408; | RLNVEVDTA, SEQ ID NO:409; |
| LNVEVDAAP, SEQ ID NO:410; | LNVEVDTAP, SEQ ID NO:411; |
| NVEVDTAPT, SEQ ID NO:412; | NVEVDAAPT, SEQ ID NO:413; |
| VEVDAAPTV, SEQ ID NO:414; | VEVDTAPTV, SEQ ID NO:415; |
| EVDAAPTVD, SEQ ID NO:416; | EVDTAPTVD, SEQ ID NO:417; |
| VDAAPTVDL, SEQ ID NO:418; | VDTAPTVDL, SEQ ID NO:419; |
| DAAPTVDLN, SEQ ID NO:420; | DTAPTVDLN, SEQ ID NO:421; |
| AAPTVDLNQ, SEQ ID NO:422; | AAPTVDLNR, SEQ ID NO:423; |
| TAPTVDLNQ, SEQ ID NO:424; | TAPTVDLNR, SEQ ID NO:425; |
| APTVDLNQV, SEQ ID NO:426; | APTVDLNRV, SEQ ID NO:427; |
| PTVDLNQVL, SEQ ID NO:428; | PTVDLNRVL, SEQ ID NO:429; |
| TVDLNQVLN, SEQ ID NO:430; | TVDLNRVLN, SEQ ID NO:431; |
| VDLNQVLNE, SEQ ID NO:432; | VDLNRVLNE, SEQ ID NO:433; |
| DLNQVLNET, SEQ ID NO:434; | DLNRVLNET, SEQ ID NO:435; |
| LNQVLNETR, SEQ ID NO:436; | LNRVLNETR, SEQ ID NO:437; |
| NQVLNETRS, SEQ ID NO:438; | NQVLNETRN, SEQ ID NO:439; |
| NRVLNETRS, SEQ ID NO:440; | NRVLNETRN, SEQ ID NO:441; |
| QVLNETRSQ, SEQ ID NO:442; | QVLNETRNQ, SEQ ID NO:443; |
| RVLNETRSQ, SEQ ID NO:444; | RVLNETRNQ, SEQ ID NO:445; |
| VLNETRSQY, SEQ ID NO:446; | VLNETRNQY, SEQ ID NO:447; |
| LNETRSQYE, SEQ ID NO:448; | LNETRNQYE, SEQ ID NO:449; |
| NETRSQYEA, SEQ ID NO:450; | NETRNQYEA, SEQ ID NO:451; |
| ETRSQYEAL, SEQ ID NO:452; | ETRNQYEAL, SEQ ID NO:453; |
| EVNTLRCQLG, SEQ ID NO:454; | EVNTLRCPLG, SEQ ID NO:455; |
| EVNTLRSQLG, SEQ ID NO:456; | EVNTLRSPLG, SEQ ID NO:457; |
| VNTLRCQLGD, SEQ ID NO:458; | VNTLRCPLGD, SEQ ID NO:459; |
| VNTLRSQLGD, SEQ ID NO:460; | VNTLRSPLGD, SEQ ID NO:461; |
| NTLRCQLGDR, SEQ ID NO:462; | NTLRCPLGDR, SEQ ID NO:463; |

-continued

```
NTLRSQLGDR, SEQ ID NO:464;      NTLRSPLGDR, SEQ ID NO:465;
TLRCQLGDRL, SEQ ID NO:466;      TLRCPLGDRL, SEQ ID NO:467;
TLRSQLGDRL, SEQ ID NO:468;      TLRSPLGDRL, SEQ ID NO:469;
LRCQLGDRLN, SEQ ID NO:470;      LRCPLGDRLN, SEQ ID NO:471;
LRSQLGDRLN, SEQ ID NO:472;      LRSPLGDRLN, SEQ ID NO:473;
RCQLGDRLNV, SEQ ID NO:474;      RCPLGDRLNV, SEQ ID NO:475;
RSQLGDRLNV, SEQ ID NO:476;      RSPLGDRLNV, SEQ ID NO:477;
CQLGDRLNVE, SEQ ID NO:478;      CPLGDRLNVE, SEQ ID NO:479;
SQLGDRLNVE, SEQ ID NO:480;      SPLGDRLNVE, SEQ ID NO:481;
QLGDRLNVEV, SEQ ID NO:482;      PLGDRLNVEV, SEQ ID NO:483;
LGDRLNVEVD, SEQ ID NO:484;      GDRLNVEVDA, SEQ ID NO:485;
GDRLNVEVDT, SEQ ID NO:486;      DRLNVEVDAA, SEQ ID NO:487;
DRLNVEVDTA, SEQ ID NO:488;      RLNVEVDAAP, SEQ ID NO:489;
RLNVEVDTAP, SEQ ID NO:490;      LNVEVDAAPT, SEQ ID NO:491;
LNVEVDTAPT, SEQ ID NO:492;      NVEVDAAPTV, SEQ ID NO:493;
NVEVDTAPTV, SEQ ID NO:494;      VEVDAAPTVD, SEQ ID NO:495;
VEVDTAPTVD, SEQ ID NO:496;      EVDAAPTVDL, SEQ ID NO:497;
EVDTAPTVDL, SEQ ID NO:498;      VDAAPTVDLN, SEQ ID NO:499;
VDTAPTVDLN, SEQ ID NO:500;      DAAPTVDLNR, SEQ ID NO:501;
DAAPTVDLNQ, SEQ ID NO:502;      DTAPTVDLNR, SEQ ID NO:503;
DTAPTVDLNQ, SEQ ID NO:504;      AAPTVDLNQV, SEQ ID NO:505;
AAPTVDLNRV, SEQ ID NO:506;      TAPTVDLNQV, SEQ ID NO:507;
TAPTVDLNRV, SEQ ID NO:508;      APTVDLNQVL, SEQ ID NO:509;
APTVDLNRVL, SEQ ID NO:510;      PTVDLNQVLN, SEQ ID NO:511;
PTVDLNRVLN, SEQ ID NO:512;      TVDLNQVLNE, SEQ ID NO:513;
TVDLNRVLNE, SEQ ID NO:514;      VDLNQVLNET, SEQ ID NO:515;
VDLNRVLNET, SEQ ID NO:516;      DLNQVLNETR, SEQ ID NO:517;
DLNRVLNETR, SEQ ID NO:518;      LNQVLNETRS, SEQ ID NO:519;
LNQVLNETRN, SEQ ID NO:520;      LNRVLNETRS, SEQ ID NO:521;
LNRVLNETRN, SEQ ID NO:522;      NQVLNETRSQ, SEQ ID NO:523;
NQVLNETRNQ, SEQ ID NO:524;      NRVLNETRSQ, SEQ ID NO:525;
NRVLNETRNQ, SEQ ID NO:526;      QVLNETRSQY, SEQ ID NO:527;
QVLNETRNQY, SEQ ID NO:528;      RVLNETRSQY, SEQ ID NO:529;
RVLNETRNQY, SEQ ID NO:530;      QVLNETRSQY, SEQ ID NO:531;
QVLNETRNQY, SEQ ID NO:532;      RVLNETRSQY, SEQ ID NO:533;
RVLNETRNQY, SEQ ID NO:534;      VLNETRSQYE, SEQ ID NO:535;
VLNETRNQYE, SEQ ID NO:536;      LNETRSQYEA, SEQ ID NO:537;
LNETRNQYEA, SEQ ID NO:538;      NETRSQYEAL, SEQ ID NO:539;
NETRNQYEAL, SEQ ID NO:540;      EVNTLRCQLGD, SEQ ID NO:541;
EVNTLRCPLGD, SEQ ID NO:542;     EVNTLRSQLGD, SEQ ID NO:543;
EVNTLRSPLGD, SEQ ID NO:544;     VNTLRCQLGDR, SEQ ID NO:545;
VNTLRCPLGDR, SEQ ID NO:546;     VNTLRSQLGDR, SEQ ID NO:547;
VNTLRSPLGDR, SEQ ID NO:548;     NTLRCQLGDRL, SEQ ID NO:549;
NTLRCPLGDRL, SEQ ID NO:550;     NTLRSQLGDRL, SEQ ID NO:551;
NTLRSPLGDRL, SEQ ID NO:552;     TLRCQLGDRLN, SEQ ID NO:553;
TLRCPLGDRLN, SEQ ID NO:554;     TLRSQLGDRLN, SEQ ID NO:555;
TLRSPLGDRLN, SEQ ID NO:556;     LRCQLGDRLNV, SEQ ID NO:557;
LRCPLGDRLNV, SEQ ID NO:558;     LRSQLGDRLNV, SEQ ID NO:559;
LRSPLGDRLNV, SEQ ID NO:560;     RCQLGDRLNVE, SEQ ID NO:561;
RCPLGDRLNVE, SEQ ID NO:562;     RSQLGDRLNVE, SEQ ID NO:563;
RSPLGDRLNVE, SEQ ID NO:564;     CQLGDRLNVEV, SEQ ID NO:565;
CPLGDRLNVEV, SEQ ID NO:566;     SQLGDRLNVEV, SEQ ID NO:567;
SPLGDRLNVEV, SEQ ID NO:568;     QLGDRLNVEVD, SEQ ID NO:569;
PLGDRLNVEVD, SEQ ID NO:570;     LGDRLNVEVDA, SEQ ID NO:571;
LGDRLNVEVDT, SEQ ID NO:572;     GDRLNVEVDAA, SEQ ID NO:573;
GDRLNVEVDTA, SEQ ID NO:574;     DRLNVEVDAAP, SEQ ID NO:575;
DRLNVEVDTAP, SEQ ID NO:576;     RLNVEVDAAPT, SEQ ID NO:577;
RLNVEVDTAPT, SEQ ID NO:578;     LNVEVDAAPTV, SEQ ID NO:579;
LNVEVDTAPTV, SEQ ID NO:580;     NVEVDAAPTVD, SEQ ID NO:581;
NVEVDTAPTVD, SEQ ID NO:582;     VEVDAAPTVDL, SEQ ID NO:583;
VEVDTAPTVDL, SEQ ID NO:584;     EVDAAPTVDLN, SEQ ID NO:585;
EVDTAPTVDLN, SEQ ID NO:586;     VDAAPTVDLNQ, SEQ ID NO:587;
VDAAPTVDLNR, SEQ ID NO:588;     VDTAPTVDLNQ, SEQ ID NO:589;
VDTAPTVDLNR, SEQ ID NO:590;     DAAPTVDLNQV, SEQ ID NO:591;
DAAPTVDLNRV, SEQ ID NO:592;     DTAPTVDLNQV, SEQ ID NO:593;
DTAPTVDLNRV, SEQ ID NO:594;     AAPTVDLNQVL, SEQ ID NO:595;
AAPTVDLNRVL, SEQ ID NO:596;     TAPTVDLNQVL, SEQ ID NO:597;
TAPTVDLNRVL, SEQ ID NO:598;     APTVDLNQVLN, SEQ ID NO:599;
APTVDLNRVLN, SEQ ID NO:600;     PTVDLNQVLNE, SEQ ID NO:601;
PTVDLNRVLNE, SEQ ID NO:602;     TVDLNQVLNET, SEQ ID NO:603;
TVDLNRVLNET, SEQ ID NO:604;     VDLNQVLNETR, SEQ ID NO:605;
VDLNRVLNETR, SEQ ID NO:606;     DLNQVLNETRS, SEQ ID NO:607;
DLNQVLNETRN, SEQ ID NO:608;     DLNRVLNETRS, SEQ ID NO:609;
DLNRVLNETRN, SEQ ID NO:610;     LNQVLNETRSQ, SEQ ID NO:611;
LNQVLNETRNQ, SEQ ID NO:612;     LNRVLNETRSQ, SEQ ID NO:613;
LNRVLNETRNQ, SEQ ID NO:614;     NQVLNETRSQY, SEQ ID NO:615;
NQVLNETRNQY, SEQ ID NO:616;     NRVLNETRSQY, SEQ ID NO:617;
NRVLNETRNQY, SEQ ID NO:618;     QVLNETRSQYE, SEQ ID NO:619;
QVLNETRNQYE, SEQ ID NO:620;     RVLNETRSQYE, SEQ ID NO:621;
RVLNETRNQYE, SEQ ID NO:622;     VLNETRSQYEA, SEQ ID NO:623;
```

-continued

```
VLNETRNQYEA, SEQ ID NO:624;        LNETRSQYEAL, SEQ ID NO:625;
LNETRNQYEAL, SEQ ID NO:626;        EVNTLRCQLGDR, SEQ ID NO:627;
EVNTLRCPLGDR, SEQ ID NO:628;       EVNTLRSQLGDR, SEQ ID NO:629;
EVNTLRSPLGDR, SEQ ID NO:630;       VNTLRCQLGDRL, SEQ ID NO:631;
VNTLRCPLGDRL, SEQ ID NO:632;       VNTLRSQLGDRL, SEQ ID NO:633;
VNTLRSPLGDRL, SEQ ID NO:634;       NTLRCQLGDRLN, SEQ ID NO:635;
NTLRCPLGDRLN, SEQ ID NO:636;       NTLRSQLGDRLN, SEQ ID NO:637;
NTLRSPLGDRLN, SEQ ID NO:638;       TLRCQLGDRLNV, SEQ ID NO:639;
TLRCPLGDRLNV, SEQ ID NO:640;       TLRSQLGDRLNV, SEQ ID NO:641;
TLRSPLGDRLNV, SEQ ID NO:642;       LRCQLGDRLNVE, SEQ ID NO:643;
LRCPLGDRLNVE, SEQ ID NO:644;       LRSQLGDRLNVE, SEQ ID NO:645;
LRSPLGDRLNVE, SEQ ID NO:646;       RCQLGDRLNVEV, SEQ ID NO:647;
RCPLGDRLNVEV, SEQ ID NO:648;       RSQLGDRLNVEV, SEQ ID NO:649;
RSPLGDRLNVEV, SEQ ID NO:650;       CQLGDRLNVEVD, SEQ ID NO:651;
CPLGDRLNVEVD, SEQ ID NO:652;       SQLGDRLNVEVD, SEQ ID NO:653;
SPLGDRLNVEVD, SEQ ID NO:654;       QLGDRLNVEVDA, SEQ ID NO:655;
QLGDRLNVEVDT, SEQ ID NO:656;       PLGDRLNVEVDA, SEQ ID NO:657;
PLGDRLNVEVDT, SEQ ID NO:658;       LGDRLNVEVDAA, SEQ ID NO:659;
LGDRLNVEVDTA, SEQ ID NO:660;       GDRLNVEVDAAP, SEQ ID NO:661;
GDRLNVEVDTAP, SEQ ID NO:662;       DRLNVEVDAAPT, SEQ ID NO:663;
DRLNVEVDTAPT, SEQ ID NO:664;       RLNVEVDAAPTV, SEQ ID NO:665;
RLNVEVDTAPTV, SEQ ID NO:666;       LNVEVDAAPTVD, SEQ ID NO:667;
LNVEVDTAPTVD, SEQ ID NO:668;       NVEVDAAPTVDL, SEQ ID NO:669;
NVEVDTAPTVDL, SEQ ID NO:670;       VEVDAAPTVDLN, SEQ ID NO:671;
VEVDTAPTVDLN, SEQ ID NO:672;       EVDAAPTVDLNQ, SEQ ID NO:673;
EVDAAPTVDLNR, SEQ ID NO:674;       EVDTAPTVDLNQ, SEQ ID NO:675;
EVDTAPTVDLNR, SEQ ID NO:676;       VDAAPTVDLNQV, SEQ ID NO:677;
VDAAPTVDLNRV, SEQ ID NO:678;       VDTAPTVDLNQV, SEQ ID NO:679;
VDTAPTVDLNRV, SEQ ID NO:680;       DAAPTVDLNQVL, SEQ ID NO:681;
DAAPTVDLNRVL, SEQ ID NO:682;       DTAPTVDLNQVL, SEQ ID NO:683;
DTAPTVDLNRVL, SEQ ID NO:684;       AAPTVDLNQVLN, SEQ ID NO:685;
AAPTVDLNRVLN, SEQ ID NO:686;       TAPTVDLNQVLN, SEQ ID NO:687;
TAPTVDLNRVLN, SEQ ID NO:688;       APTVDLNQVLNE, SEQ ID NO:689;
APTVDLNRVLNE, SEQ ID NO:690;       PTVDLNQVLNET, SEQ ID NO:691;
PTVDLNRVLNET, SEQ ID NO:692;       TVDLNQVLNETR, SEQ ID NO:693;
TVDLNRVLNETR, SEQ ID NO:694;       VDLNQVLNETRS, SEQ ID NO:695;
VDLNQVLNETRN, SEQ ID NO:696;       VDLNRVLNETRS, SEQ ID NO:697;
VDLNRVLNETRN, SEQ ID NO:698;       DLNQVLNETRSQ, SEQ ID NO:699;
DLNQVLNETRNQ, SEQ ID NO:700;       DLNRVLNETRSQ, SEQ ID NO:701;
DLNRVLNETRNQ, SEQ ID NO:702;       LNQVLNETRSQY, SEQ ID NO:703;
LNQVLNETRNQY, SEQ ID NO:704;       LNRVLNETRSQY, SEQ ID NO:705;
LNRVLNETRNQY, SEQ ID NO:706;       NQVLNETRSQYE, SEQ ID NO:707;
LNQVLNETRNQY, SEQ ID NO:708;       LNRVLNETRSQY, SEQ ID NO:709;
LNRVLNETRNQY, SEQ ID NO:710;       QVLNETRSQYEA, SEQ ID NO:711;
QVLNETRNQYEA, SEQ ID NO:712;       RVLNETRSQYEA, SEQ ID NO:713;
RVLNETRNQYEA, SEQ ID NO:714;       VLNETRSQYEAL, SEQ ID NO:715;
VLNETRNQYEAL, SEQ ID NO:716;       EVNTLRCQLGDRL, SEQ ID NO:717;
EVNTLRCPLGDRL, SEQ ID NO:718;      EVNTLRSQLGDRL, SEQ ID NO:719;
EVNTLRSPLGDRL, SEQ ID NO:720;      VNTLRCQLGDRLN, SEQ ID NO:721;
VNTLRCPLGDRLN, SEQ ID NO:722;      VNTLRSQLGDRLN, SEQ ID NO:723;
VNTLRSPLGDRLN, SEQ ID NO:724;      NTLRCQLGDRLNV, SEQ ID NO:725;
NTLRCPLGDRLNV, SEQ ID NO:726;      NTLRSQLGDRLNV, SEQ ID NO:727;
NTLRSPLGDRLNV, SEQ ID NO:728;      TLRCQLGDRLNVE, SEQ ID NO:729;
TLRCPLGDRLNVE, SEQ ID NO:730;      TLRSQLGDRLNVE, SEQ ID NO:731;
TLRSPLGDRLNVE, SEQ ID NO:732;      LRCQLGDRLNVEV, SEQ ID NO:733;
LRCPLGDRLNVEV, SEQ ID NO:734;      LRSQLGDRLNVEV, SEQ ID NO:735;
LRSPLGDRLNVEV, SEQ ID NO:736;      RCQLGDRLNVEVD, SEQ ID NO:737;
RCPLGDRLNVEVD, SEQ ID NO:738;      RSQLGDRLNVEVD, SEQ ID NO:739;
RSPLGDRLNVEVD, SEQ ID NO:740;      CQLGDRLNVEVDA, SEQ ID NO:741;
CQLGDRLNVEVDT, SEQ ID NO:742;      CPLGDRLNVEVDA, SEQ ID NO:743;
CPLGDRLNVEVDT, SEQ ID NO:744;      SQLGDRLNVEVDA, SEQ ID NO:745;
SQLGDRLNVEVDT, SEQ ID NO:746;      SPLGDRLNVEVDA, SEQ ID NO:747;
SPLGDRLNVEVDT, SEQ ID NO:748;      QLGDRLNVEVDAA, SEQ ID NO:749;
QLGDRLNVEVDTA, SEQ ID NO:750;      PLGDRLNVEVDAA, SEQ ID NO:751;
PLGDRLNVEVDTA, SEQ ID NO:752;      LGDRLNVEVDAAP, SEQ ID NO:753;
LGDRLNVEVDTAP, SEQ ID NO:754;      GDRLNVEVDAAPT, SEQ ID NO:755;
GDRLNVEVDTAPT, SEQ ID NO:756;      DRLNVEVDAAPTV, SEQ ID NO:757;
DRLNVEVDTAPTV, SEQ ID NO:758;      RLNVEVDAAPTVD, SEQ ID NO:759;
RLNVEVDTAPTVD, SEQ ID NO:760;      LNVEVDAAPTVDL, SEQ ID NO:761;
LNVEVDTAPTVDL, SEQ ID NO:762;      NVEVDAAPTVDLN, SEQ ID NO:763;
NVEVDTAPTVDLN, SEQ ID NO:764;      VEVDAAPTVDLNQ, SEQ ID NO:765;
VEVDAAPTVDLNR, SEQ ID NO:766;      VEVDTAPTVDLNQ, SEQ ID NO:767;
VEVDTAPTVDLNR, SEQ ID NO:768;      EVDAAPTVDLNQV, SEQ ID NO:769;
EVDAAPTVDLNRV, SEQ ID NO:770;      EVDTAPTVDLNQV, SEQ ID NO:771;
EVDTAPTVDLNRV, SEQ ID NO:772;      VDAAPTVDLNQVL, SEQ ID NO:773;
VDAAPTVDLNRVL, SEQ ID NO:774;      VDTAPTVDLNQVL, SEQ ID NO:775;
VDTAPTVDLNRVL, SEQ ID NO:776;      DAAPTVDLNQVLN, SEQ ID NO:777;
DAAPTVDLNRVLN, SEQ ID NO:778;      DTAPTVDLNQVLN, SEQ ID NO:779;
DTAPTVDLNRVLN, SEQ ID NO:780;      AAPTVDLNQVLNE, SEQ ID NO:781;
AAPTVDLNRVLNE, SEQ ID NO:782;      TAPTVDLNQVLNE, SEQ ID NO:783;
```

-continued

```
TAPTVDLNRVLNE,   SEQ ID NO:784;    APTVDLNQVLNET,   SEQ ID NO:785;
APTVDLNRVLNET,   SEQ ID NO:786;    PTVDLNQVLNETR,   SEQ ID NO:787;
PTVDLNRVLNETR,   SEQ ID NO:788;    TVDLNQVLNETRS,   SEQ ID NO:789;
TVDLNQVLNETRN,   SEQ ID NO:790;    TVDLNRVLNETRS,   SEQ ID NO:791;
TVDLNRVLNETRN,   SEQ ID NO:792;    VDLNQVLNETRSQ,   SEQ ID NO:793;
VDLNQVLNETRNQ,   SEQ ID NO:794;    VDLNRVLNETRSQ,   SEQ ID NO:795;
VDLNRVLNETRNQ,   SEQ ID NO:796;    DLNQVLNETRSQY,   SEQ ID NO:797;
DLNQVLNETRNQY,   SEQ ID NO:798;    DLNRVLNETRSQY,   SEQ ID NO:799;
DLNRVLNETRNQY,   SEQ ID NO:800;    LNQVLNETRSQYE,   SEQ ID NO:801;
LNQVLNETRNQYE,   SEQ ID NO:802;    LNRVLNETRSQYE,   SEQ ID NO:803;
LNRVLNETRNQYE,   SEQ ID NO:804;    NQVLNETRSQYEA,   SEQ ID NO:805;
NQVLNETRNQYEA,   SEQ ID NO:806;    NRVLNETRSQYEA,   SEQ ID NO:807;
NRVLNETRNQYEA,   SEQ ID NO:808;    QVLNETRSQYEAL,   SEQ ID NO:809;
QVLNETRNQYEAL,   SEQ ID NO:810;    RVLNETRSQYEAL,   SEQ ID NO:811;
RVLNETRNQYEAL,   SEQ ID NO:812;    EVNTLRCQLGDRLN,  SEQ ID NO:813;
EVNTLRCPLGDRLN,  SEQ ID NO:814;    EVNTLRSQLGDRLN,  SEQ ID NO:815;
EVNTLRSPLGDRLN,  SEQ ID NO:816;    VNTLRCQLGDRLNV,  SEQ ID NO:817;
VNTLRCPLGDRLNV,  SEQ ID NO:818;    VNTLRSQLGDRLNV,  SEQ ID NO:819;
VNTLRSPLGDRLNV,  SEQ ID NO:820;    NTLRCQLGDRLNVE,  SEQ ID NO:821;
NTLRCPLGDRLNVE,  SEQ ID NO:822;    NTLRSQLGDRLNVE,  SEQ ID NO:823;
NTLRSPLGDRLNVE,  SEQ ID NO:824;    TLRCQLGDRLNVEV,  SEQ ID NO:825;
TLRCPLGDRLNVEV,  SEQ ID NO:826;    TLRSQLGDRLNVEV,  SEQ ID NO:827;
TLRSPLGDRLNVEV,  SEQ ID NO:828;    LRCQLGDRLNVEVD,  SEQ ID NO:829;
LRCPLGDRLNVEVD,  SEQ ID NO:830;    LRSQLGDRLNVEVD,  SEQ ID NO:831;
LRSPLGDRLNVEVD,  SEQ ID NO:832;    RCQLGDRLNVEVDA,  SEQ ID NO:833;
RCQLGDRLNVEVDT,  SEQ ID NO:834;    RCPLGDRLNVEVDA,  SEQ ID NO:835;
RCPLGDRLNVEVDT,  SEQ ID NO:836;    RSQLGDRLNVEVDA,  SEQ ID NO:837;
RSQLGDRLNVEVDT,  SEQ ID NO:838;    RSPLGDRLNVEVDA,  SEQ ID NO:839;
RSPLGDRLNVEVDT,  SEQ ID NO:840;    CQLGDRLNVEVDAA,  SEQ ID NO:841;
CQLGDRLNVEVDTA,  SEQ ID NO:842;    CPLGDRLNVEVDAA,  SEQ ID NO:843;
CPLGDRLNVEVDTA,  SEQ ID NO:844;    SQLGDRLNVEVDAA,  SEQ ID NO:845;
SQLGDRLNVEVDTA,  SEQ ID NO:846;    SPLGDRLNVEVDAA,  SEQ ID NO:847;
SPLGDRLNVEVDTA,  SEQ ID NO:848;    QLGDRLNVEVDAAP,  SEQ ID NO:849;
QLGDRLNVEVDTAP,  SEQ ID NO:850;    PLGDRLNVEVDAAP,  SEQ ID NO:851;
PLGDRLNVEVDTAP,  SEQ ID NO:852;    LGDRLNVEVDAAPT,  SEQ ID NO:853;
LGDRLNVEVDTAPT,  SEQ ID NO:854;    GDRLNVEVDAAPTV,  SEQ ID NO:855;
GDRLNVEVDTAPTV,  SEQ ID NO:856;    DRLNVEVDAAPTVD,  SEQ ID NO:857;
DRLNVEVDTAPTVD,  SEQ ID NO:858;    RLNVEVDAAPTVDL,  SEQ ID NO:859;
RLNVEVDTAPTVDL,  SEQ ID NO:860;    LNVEVDAAPTVDLN,  SEQ ID NO:861;
LNVEVDTAPTVDLN,  SEQ ID NO:862;    NVEVDAAPTVDLNQ,  SEQ ID NO:863;
NVEVDAAPTVDLNR,  SEQ ID NO:864;    NVEVDTAPTVDLNQ,  SEQ ID NO:865;
NVEVDTAPTVDLNR,  SEQ ID NO:866;    VEVDAAPTVDLNQV,  SEQ ID NO:867;
VEVDAAPTVDLNRV,  SEQ ID NO:868;    VEVDTAPTVDLNQV,  SEQ ID NO:869;
VEVDTAPTVDLNRV,  SEQ ID NO:870;    EVDAAPTVDLNQVL,  SEQ ID NO:871;
EVDAAPTVDLNRVL,  SEQ ID NO:872;    EVDTAPTVDLNQVL,  SEQ ID NO:873;
EVDTAPTVDLNRVL,  SEQ ID NO:874;    VDAAPTVDLNQVLN,  SEQ ID NO:875;
VDAAPTVDLNRVLN,  SEQ ID NO:876;    VDTAPTVDLNQVLN,  SEQ ID NO:877;
VDTAPTVDLNRVLN,  SEQ ID NO:878;    DAAPTVDLNQVLNE,  SEQ ID NO:879;
DAAPTVDLNRVLNE,  SEQ ID NO:880;    DTAPTVDLNQVLNE,  SEQ ID NO:881;
DTAPTVDLNRVLNE,  SEQ ID NO:882;    AAPTVDLNQVLNET,  SEQ ID NO:883;
AAPTVDLNRVLNET,  SEQ ID NO:884;    TAPTVDLNQVLNET,  SEQ ID NO:885;
TAPTVDLNRVLNET,  SEQ ID NO:886;    APTVDLNQVLNETR,  SEQ ID NO:887;
APTVDLNRVLNETR,  SEQ ID NO:888;    PTVDLNQVLNETRS,  SEQ ID NO:889;
PTVDLNQVLNETRN,  SEQ ID NO:890;    PTVDLNRVLNETRS,  SEQ ID NO:891;
PTVDLNRVLNETRN,  SEQ ID NO:892;    TVDLNQVLNETRSQ,  SEQ ID NO:893;
TVDLNQVLNETRNQ,  SEQ ID NO:894;    TVDLNRVLNETRSQ,  SEQ ID NO:895;
TVDLNRVLNETRNQ,  SEQ ID NO:896;    VDLNQVLNETRSQY,  SEQ ID NO:897;
VDLNQVLNETRNQY,  SEQ ID NO:898;    VDLNRVLNETRSQY,  SEQ ID NO:899;
VDLNRVLNETRNQY,  SEQ ID NO:900;    DLNQVLNETRSQYE,  SEQ ID NO:901;
DLNQVLNETRNQYE,  SEQ ID NO:902;    DLNRVLNETRSQYE,  SEQ ID NO:903;
DLNRVLNETRNQYE,  SEQ ID NO:904;    LNQVLNETRSQYEA,  SEQ ID NO:905;
LNQVLNETRNQYEA,  SEQ ID NO:906;    LNRVLNETRSQYEA,  SEQ ID NO:907;
LNRVLNETRNQYEA,  SEQ ID NO:908;    NQVLNETRSQYEAL,  SEQ ID NO:909;
NQVLNETRNQYEAL,  SEQ ID NO:910;    NRVLNETRSQYEAL,  SEQ ID NO:911;
NRVLNETRNQYEAL,  SEQ ID NO:912;    EVNTLRCQLGDRLNV, SEQ ID NO:913;
EVNTLRCPLGDRLNV, SEQ ID NO:914;    EVNTLRSQLGDRLNV, SEQ ID NO:915;
EVNTLRSPLGDRLNV, SEQ ID NO:916;    VNTLRCQLGDRLNVE, SEQ ID NO:917;
VNTLRCPLGDRLNVE, SEQ ID NO:918;    VNTLRSQLGDRLNVE, SEQ ID NO:919;
VNTLRSPLGDRLNVE, SEQ ID NO:920;    NTLRCQLGDRLNVEV, SEQ ID NO:921;
NTLRCPLGDRLNVEV, SEQ ID NO:922;    NTLRSQLGDRLNVEV, SEQ ID NO:923;
NTLRSPLGDRLNVEV, SEQ ID NO:924;    TLRCQLGDRLNVEVD, SEQ ID NO:925;
TLRCPLGDRLNVEVD, SEQ ID NO:926;    TLRSQLGDRLNVEVD, SEQ ID NO:927;
TLRSPLGDRLNVEVD, SEQ ID NO:928;    LRCQLGDRLNVEVDA, SEQ ID NO:929;
LRCQLGDRLNVEVDT, SEQ ID NO:930;    LRCPLGDRLNVEVDA, SEQ ID NO:931;
LRCPLGDRLNVEVDT, SEQ ID NO:932;    LRSQLGDRLNVEVDA, SEQ ID NO:933;
LRSQLGDRLNVEVDT, SEQ ID NO:934;    LRSPLGDRLNVEVDA, SEQ ID NO:935;
LRSPLGDRLNVEVDT, SEQ ID NO:936;    RCQLGDRLNVEVDAA, SEQ ID NO:937;
RCQLGDRLNVEVDTA, SEQ ID NO:938;    RCPLGDRLNVEVDAA, SEQ ID NO:939;
RCPLGDRLNVEVDTA, SEQ ID NO:940;    RSQLGDRLNVEVDAA, SEQ ID NO:941;
RSQLGDRLNVEVDTA, SEQ ID NO:942;    RSPLGDRLNVEVDAA, SEQ ID NO:943;
```

-continued

```
RSPLGDRLNVEVDTA,   SEQ ID NO:944;      CQLGDRLNVEVDAAP,   SEQ ID NO:945;
CQLGDRLNVEVDTAP,   SEQ ID NO:946;      CPLGDRLNVEVDANP,   SEQ ID NO:947;
CPLGDRLNVEVDTAP,   SEQ ID NO:948;      SQLGDRLNVEVDAAP,   SEQ ID NO:949;
SQLGDRLNVEVDTAP,   SEQ ID NO:950;      SPLGDRLNVEVDAAP,   SEQ ID NO:951;
SPLGDRLNVEVDTAP,   SEQ ID NO:952;      QLGDRLNVEVDANPT,   SEQ ID NO:953;
QLGDRLNVEVDTAPT,   SEQ ID NO:954;      PLGDRLNVEVDAAPT,   SEQ ID NO:955;
PLGDRLNVEVDTAPT,   SEQ ID NO:956;      LGDRLNVEVDAAPTV,   SEQ ID NO:957;
LGDRLNVEVDTAPTV,   SEQ ID NO:958;      GDRLNVEVDAAPTVD,   SEQ ID NO:959;
GDRLNVEVDTAPTVD,   SEQ ID NO:960;      DRLNVEVDAAPTVDL,   SEQ ID NO:961;
DRLNVEVDTAPTVDL,   SEQ ID NO:962;      RLNVEVDAAPTVDLN,   SEQ ID NO:963;
RLNVEVDTAPTVDLN,   SEQ ID NO:964;      LNVEVDAAPTVDLNQ,   SEQ ID NO:965;
LNVEVDANPTVDLNR,   SEQ ID NO:966;      LNVEVDTAPTVDLNQ,   SEQ ID NO:967;
LNVEVDTAPTVDLNR,   SEQ ID NO:968;      NVEVDAAPTVDLNQV,   SEQ ID NO:969;
NVEVDAAPTVDLNRV,   SEQ ID NO:970;      NVEVDTAPTVDLNQV,   SEQ ID NO:971;
NVEVDTAPTVDLNRV,   SEQ ID NO:972;      VEVDAAPTVDLNQVL,   SEQ ID NO:973;
VEVDAAPTVDLNRVL,   SEQ ID NO:974;      VEVDTAPTVDLNQVL,   SEQ ID NO:975;
VEVDTAPTVDLNRVL,   SEQ ID NO:976;      EVDAAPTVDLNQVLN,   SEQ ID NO:977;
EVDAAPTVDLNRVLN,   SEQ ID NO:978;      EVDTAPTVDLNQVLN,   SEQ ID NO:979;
EVDTAPTVDLNRVLN,   SEQ ID NO:980;      VDAAPTVDLNQVLNE,   SEQ ID NO:981;
VDAAPTVDLNRVLNE,   SEQ ID NO:982;      VDTAPTVDLNQVLNE,   SEQ ID NO:983;
VDTAPTVDLNRVLNE,   SEQ ID NO:984;      DAAPTVDLNQVLNET,   SEQ ID NO:985;
DAAPTVDLNRVLNET,   SEQ ID NO:986;      DTAPTVDLNQVLNET,   SEQ ID NO:987;
DTAPTVDLNRVLNET,   SEQ ID NO:988;      AAPTVDLNQVLNETR,   SEQ ID NO:989;
AAPTVDLNRVLNETR,   SEQ ID NO:990;      TAPTVDLNQVLNETR,   SEQ ID 140:991;
TAPTVDLNRVLNETR,   SEQ ID NO:992;      APTVDLNQVLNETRS,   SEQ ID 140:993;
APTVDLNQVLNETRN,   SEQ ID NO:994;      APTVDLNRVLNETRS,   SEQ ID NO:995;
APTVDLNRVLNETRN,   SEQ ID NO:996;      PTVDLNQVLNETRSQ,   SEQ ID NO:997;
PTVDLNQVLNETRNQ,   SEQ ID NO:998;      PTVDLNRVLNETRSQ,   SEQ ID NO:999;
PTVDLNRVLNETRNQ,   SEQ ID NO:1000;
                                       TVDLNQVLNETRNQY,   SEQ ID NO:1002;
TVDLNQVLNETRSQY,   SEQ ID NO:1001;
TVDLNRVLNETRSQY,   SEQ ID NO:1003;     TVDLNRVLNETRNQY,   SEQ ID NO:1004;
VDLNQVLNETRSQYE,   SEQ ID NO:1005;     VDLNQVLNETRNQYE,   SEQ ID NO:1006;
VDLNRVLNETRSQYE,   SEQ ID NO:1007;     VDLNRVLNETRNQYE,   SEQ ID NO:1008;
DLNQVLNETRSQYEA,   SEQ ID NO:1009;     DLNQVLNETRNQYEA,   SEQ ID NO:1110;
DLNRVLNETRSQYEA,   SEQ ID NO:1111;     DLNRVLNETRNQYEA,   SEQ ID NO:1112;
LNQVLNETRSQYEAL,   SEQ ID NO:1113;     LNQVLNETRNQYEAL,   SEQ ID NO:1114;
LNRVLNETRSQYEAL,   SEQ ID NO:1115;     LNRVLNETRNQYEAL,   SEQ ID NO:1116;
EVNTLRCQLGDRLNVE,  SEQ ID NO:1117;     EVNTLRCPLGDRLNVE,  SEQ ID NO:1118;
EVNTLRSQLGDRLNVE,  SEQ ID NO:1119;     EVNTLRSPLGDRLNVE,  SEQ ID NO:1120;
VNTLRCQLGDRLNVEV,  SEQ ID NO:1121;     VNTLRCPLGDRLNVEV,  SEQ ID NO:1122;
VNTLRSQLGDRLNVEV,  SEQ ID NO:1123;     VNTLRSPLGDRLNVEV,  SEQ ID NO:1124;
NTLRCQLGDRLNVEVD,  SEQ ID NO:1125;     NTLRCPLGDRLNVEVD,  SEQ ID NO:1126;
NTLRSQLGDRLNVEVD,  SEQ ID NO:1127;     NTLRSPLGDRLNVEVD,  SEQ ID NO:1128;
TLRCQLGDRLNVEVDA,  SEQ ID NO:1129;     TLRCQLGDRLNVEVDT,  SEQ ID NO:1130;
TLRCPLGDRLNVEVDA,  SEQ ID NO:1131;     TLRCPLGDRLNVEVDT,  SEQ ID NO:1132;
TLRSQLGDRLNVEVDA,  SEQ ID NO:1133;     TLRSQLGDRLNVEVDT,  SEQ ID NO:1134;
TLRSPLGDRLNVEVDA,  SEQ ID NO:1135;     TLRSPLGDRLNVEVDT,  SEQ ID NO:1136;
LRCQLGDRLNVEVDAA,  SEQ ID NO:1137;     LRCQLGDRLNVEVDTA,  SEQ ID NO:1138;
LRCPLGDRLNVEVDAA,  SEQ ID NO:1139;     LRCPLGDRLNVEVDTA,  SEQ ID NO:1140;
LRSQLGDRLNVEVDAA,  SEQ ID NO:1141;     LRSQLGDRLNVEVDTA,  SEQ ID NO:1142;
LRSPLGDRLNVEVDAA,  SEQ ID NO:1143;     LRSPLGDRLNVEVDTA,  SEQ ID NO:1144;
RCQLGDRLNVEVDAAP,  SEQ ID NO:1145;     RCQLGDRLNVEVDTAP,  SEQ ID NO:1146;
RCPLGDRLNVEVDAAP,  SEQ ID NO:1147;     RCPLGDRLNVEVDTAP,  SEQ ID NO:1148;
RSQLGDRLNVEVDAAP,  SEQ ID NO:1149;     RSQLGDRLNVEVDTAP,  SEQ ID NO:1150;
RSPLGDRLNVEVDAAP,  SEQ ID NO:1151;     RSPLGDRLNVEVDTAP,  SEQ ID NO:1152;
CQLGDRLNVEVDAAPT,  SEQ ID NO:1153;     CQLGDRLNVEVDTAPT,  SEQ ID NO:1154;
CPLGDRLNVEVDAAPT,  SEQ ID NO:1155;     CPLGDRLNVEVDTAPT,  SEQ ID NO:1156;
SQLGDRLNVEVDAAPT,  SEQ ID NO:1157;     SQLGDRLNVEVDTAPT,  SEQ ID NO:1158;
SPLGDRLNVEVDAAPT,  SEQ ID NO:1159;     SPLGDRLNVEVDTAPT,  SEQ ID NO:1160;
QLGDRLNVEVDAAPTV,  SEQ ID NO:1161;     QLGDRLNVEVDTAPTV,  SEQ ID NO:1162;
PLGDRLNVEVDAAPTV,  SEQ ID NO:1163;     PLGDRLNVEVDTAPTV,  SEQ ID NO:1164;
LGDRLNVEVDAAPTVD,  SEQ ID NO:1165;     LGDRLNVEVDTAPTVD,  SEQ ID NO:1166;
GDRLNVEVDAAPTVDL,  SEQ ID NO:1167;     GDRLNVEVDTAPTVDL,  SEQ ID NO:1168;
DRLNVEVDAAPTVDLN,  SEQ ID NO:1169;     DRLNVEVDTAPTVDLN,  SEQ ID NO:1170;
RLNVEVDAAPTVDLNQ,  SEQ ID NO:1171;     RLNVEVDAAPTVDLNR,  SEQ ID NO:1172;
RLNVEVDTAPTVDLNQ,  SEQ ID NO:1173;     RLNVEVDTAPTVDLNR,  SEQ ID NO:1174;
LNVEVDAAPTVDLNQV,  SEQ ID NO:1175;     LNVEVDAAPTVDLNRV,  SEQ ID NO:1176;
LNVEVDTAPTVDLNQV,  SEQ ID NO:1177;     LNVEVDTAPTVDLNRV,  SEQ ID NO:1178;
NVEVDAAPTVDLNQVL,  SEQ ID NO:1179;     NVEVDAAPTVDLNRVL,  SEQ ID NO:1180;
NVEVDTAPTVDLNQVL,  SEQ ID NO:1181;     NVEVDTAPTVDLNRVL,  SEQ ID NO:1182;
VEVDAAPTVDLNQVLN,  SEQ ID NO:1183;     VEVDAAPTVDLNRVLN,  SEQ ID NO:1184;
VEVDTAPTVDLNQVLN,  SEQ ID NO:1185;     VEVDTAPTVDLNRVLN,  SEQ ID NO:1186;
EVDAAPTVDLNQVLNE,  SEQ ID NO:1187;     EVDAAPTVDLNRVLNE,  SEQ ID NO:1188;
EVDTAPTVDLNQVLNE,  SEQ ID NO:1189;     EVDTAPTVDLNRVLNE,  SEQ ID NO:1190;
VDAAPTVDLNQVLNET,  SEQ ID NO:1191;     VDAAPTVDLNRVLNET,  SEQ ID NO:1192;
VDTAPTVDLNQVLNET,  SEQ ID NO:1193;     VDTAPTVDLNRVLNET,  SEQ ID NO:1194;
DAAPTVDLNQVLNETR,  SEQ ID NO:1195;     DAAPTVDLNRVLNETR,  SEQ ID NO:1196;
DTAPTVDLNQVLNETR,  SEQ ID NO:1197;     DTAPTVDLNRVLNETR,  SEQ ID NO:1198;
AAPTVDLNQVLNETRS,  SEQ ID NO:1199;     AAPTVDLNQVLNETRN,  SEQ ID NO:1200;
AAPTVDLNRVLNETRS,  SEQ ID NO:1201;     AAPTVDLNRVLNETRN,  SEQ ID NO:1202;
```

-continued

| | |
|---|---|
| TAPTVDLNQVLNETRS, SEQ ID NO:1203; | TAPTVDLNQVLNETRN, SEQ ID NO:1204; |
| TAPTVDLNRVLNETRS, SEQ ID NO:1205; | TAPTVDLNRVLNETRN, SEQ ID NO:1206; |
| APTVDLNQVLNETRSQ, SEQ ID NO:1207; | APTVDLNQVLNETRNQ, SEQ ID NO:1208; |
| APTVDLNRVLNETRSQ, SEQ ID NO:1209; | APTVDLNRVLNETRNQ, SEQ ID NO:1210; |
| PTVDLNQVLNETRSQY, SEQ ID NO:1211; | PTVDLNQVLNETRNQY, SEQ ID NO:1212; |
| PTVDLNRVLNETRSQY, SEQ ID NO:1213; | PTVDLNRVLNETRNQY, SEQ ID NO:1214; |
| TVDLNQVLNETRSQYE, SEQ ID NO:1215; | TVDLNQVLNETRNQYE, SEQ ID NO:1216; |
| TVDLNRVLNETRSQYE, SEQ ID NO:1217; | TVDLNRVLNETRNQYE, SEQ ID NO:1218; |
| VDLNQVLNETRSQYEA, SEQ ID NO:1219; | VDLNQVLNETRNQYEA, SEQ ID NO:1220; |
| VDLNRVLNETRSQYEA, SEQ ID NO:1221; | VDLNRVLNETRNQYEA, SEQ ID NO:1222; |
| DLNQVLNETRSQYEAL, SEQ ID NO:1223; | DLNQVLNETRNQYEAL, SEQ ID NO:1224; |
| DLNRVLNETRSQYEAL, SEQ ID NO:1225; | DLNRVLNETRNQYEAL, SEQ ID NO:1226; |
| EVNTLRCQLGDRLNVEV, SEQ ID NO:1227; | EVNTLRCPLGDRLNVEV, SEQ ID NO:1228; |
| EVNTLRSQLGDRLNVEV, SEQ ID NO:1229; | EVNTLRSPLGDRLNVEV, SEQ ID NO:1230; |
| VNTLRCQLGDRLNVEVD, SEQ ID NO:1231; | VNTLRCPLGDRLNVEVD, SEQ ID NO:1232; |
| VNTLRSQLGDRLNVEVD, SEQ ID NO:1233; | VNTLRSPLGDRLNVEVD, SEQ ID NO:1234; |
| NTLRCQLGDRLNVEVDA, SEQ ID NO:1235; | NTLRCQLGDRLNVEVDT, SEQ ID NO:1236; |
| NTLRCPLGDRLNVEVDA, SEQ ID NO:1237; | NTLRCPLGDRLNVEVDT, SEQ ID NO:1238; |
| NTLRSQLGDRLNVEVDA, SEQ ID NO:1239; | NTLRSQLGDRLNVEVDT, SEQ ID NO:1240; |
| NTLRSPLGDRLNVEVDA, SEQ ID NO:1241; | NTLRSPLGDRLNVEVDT, SEQ ID NO:1242; |
| TLRCQLGDRLNVEVDAA, SEQ ID NO:1243; | TLRCQLGDRLNVEVDTA, SEQ ID NO:1244; |
| TLRCPLGDRLNVEVDAA, SEQ ID NO:1245; | TLRCPLGDRLNVEVDTA, SEQ ID NO:1246; |
| TLRSQLGDRLNVEVDAA, SEQ ID NO:1247; | TLRSQLGDRLNVEVDTA, SEQ ID NO:1248; |
| TLRSPLGDRLNVEVDAA, SEQ ID NO:1249; | TLRSPLGDRLNVEVDTA, SEQ ID NO:1250; |
| LRCQLGDRLNVEVDAAP, SEQ ID NO:1251; | LRCQLGDRLNVEVDTAP, SEQ ID NO:1252; |
| LRCPLGDRLNVEVDAAP, SEQ ID NO:1253; | LRCPLGDRLNVEVDTAP, SEQ ID NO:1254; |
| LRSQLGDRLNVEVDAAP, SEQ ID NO:1255; | LRSQLGDRLNVEVDTAP, SEQ ID NO:1256; |
| LRSPLGDRLNVEVDAAP, SEQ ID NO:1257; | LRSPLGDRLNVEVDTAP, SEQ ID NO:1258; |
| RCQLGDRLNVEVDAAPT, SEQ ID NO:1259; | RCQLGDRLNVEVDTAPT, SEQ ID NO:1260; |
| RCPLGDRLNVEVDAAPT, SEQ ID NO:1261; | RCPLGDRLNVEVDTAPT, SEQ ID NO:1262; |
| RSQLGDRLNVEVDAAPT, SEQ ID NO:1263; | RSQLGDRLNVEVDTAPT, SEQ ID NO:1264; |
| RSPLGDRLNVEVDAAPT, SEQ ID NO:1265; | RSPLGDRLNVEVDTAPT, SEQ ID NO:1266; |
| CQLGDRLNVEVDAAPTV, SEQ ID NO:1267; | CQLGDRLNVEVDTAPTV, SEQ ID NO:1268; |
| CPLGDRLNVEVDAAPTV, SEQ ID NO:1269; | CPLGDRLNVEVDTAPTV, SEQ ID NO:1270; |
| SQLGDRLNVEVDAAPTV, SEQ ID NO:1271; | SQLGDRLNVEVDTAPTV, SEQ ID NO:1272; |
| SPLGDRLNVEVDAAPTV, SEQ ID NO:1273; | SPLGDRLNVEVDTAPTV, SEQ ID NO:1274; |
| QLGDRLNVEVDAAPTVD, SEQ ID NO:1275; | QLGDRLNVEVDTAPTVD, SEQ ID NO:1276; |
| PLGDRLNVEVDAAPTVD, SEQ ID NO:1277; | PLGDRLNVEVDTAPTVD, SEQ ID NO:1278; |
| LGDRLNVEVDAAPTVDL, SEQ ID NO:1279; | LGDRLNVEVDTAPTVDL, SEQ ID NO:1280; |
| GDRLNVEVDAAPTVDLN, SEQ ID NO:1281; | GDRLNVEVDTAPTVDLN, SEQ ID NO:1282; |
| DRLNVEVDAAPTVDLNQ, SEQ ID NO:1283; | DRLNVEVDAAPTVDLNR, SEQ ID NO:1284; |
| DRLNVEVDTAPTVDLNQ, SEQ ID NO:1285; | DRLNVEVDTAPTVDLNR, SEQ ID NO:1286; |
| RLNVEVDAAPTVDLNQV, SEQ ID NO:1287; | RLNVEVDAAPTVDLNRV, SEQ ID NO:1288; |
| RLNVEVDTAPTVDLNQV, SEQ ID NO:1289; | RLNVEVDTAPTVDLNRV, SEQ ID NO:1290; |
| LNVEVDAAPTVDLNQVL, SEQ ID NO:1291; | LNVEVDAAPTVDLNRVL, SEQ ID NO:1292; |
| LNVEVDTAPTVDLNQVL, SEQ ID NO:1293; | LNVEVDTAPTVDLNRVL, SEQ ID NO:1294; |
| NVEVDAAPTVDLNQVLN, SEQ ID NO:1295; | NVEVDAAPTVDLNRVLN, SEQ ID NO:1296; |
| NVEVDTAPTVDLNQVLN, SEQ ID NO:1297; | NVEVDTAPTVDLNRVLN, SEQ ID NO:1298; |
| VEVDAAPTVDLNQVLNE, SEQ ID NO:1299; | VEVDAAPTVDLNRVLNE, SEQ ID NO:1300; |
| VEVDTAPTVDLNQVLNE, SEQ ID NO:1301; | VEVDTAPTVDLNRVLNE, SEQ ID NO:1302; |
| EVDAAPTVDLNQVLNET, SEQ ID NO:1303; | EVDAAPTVDLNRVLNET, SEQ ID NO:1304; |
| EVDTAPTVDLNQVLNET, SEQ ID NO:1305; | EVDTAPTVDLNRVLNET, SEQ ID NO:1306; |
| VDAAPTVDLNQVLNETR, SEQ ID NO:1307; | VDAAPTVDLNRVLNETR, SEQ ID NO:1308; |
| VDTAPTVDLNQVLNETR, SEQ ID NO:1309; | VDTAPTVDLNRVLNETR, SEQ ID NO:1310; |
| DAAPTVDLNQVLNETRS, SEQ ID NO:1311; | DAAPTVDLNQVLNETRN, SEQ ID NO:1312; |
| DAAPTVDLNRVLNETRS, SEQ ID NO:1313; | DAAPTVDLNRVLNETRN, SEQ ID NO:1314; |
| DTAPTVDLNQVLNETRS, SEQ ID NO:1315; | DTAPTVDLNQVLNETRN, SEQ ID NO:1316; |
| DTAPTVDLNRVLNETRS, SEQ ID NO:1317; | DTAPTVDLNRVLNETRN, SEQ ID NO:1318; |
| AAPTVDLNQVLNETRSQ, SEQ ID NO:1319; | AAPTVDLNQVLNETRNQ, SEQ ID NO:1320; |
| AAPTVDLNRVLNETRSQ, SEQ ID NO:1321; | AAPTVDLNRVLNETRNQ, SEQ ID NO:1322; |
| TAPTVDLNQVLNETRSQ, SEQ ID NO:1323; | TAPTVDLNQVLNETRNQ, SEQ ID NO:1324; |
| TAPTVDLNRVLNETRSQ, SEQ ID NO:1325; | TAPTVDLNRVLNETRNQ, SEQ ID NO:1326; |
| APTVDLNQVLNETRSQY, SEQ ID NO:1327; | APTVDLNQVLNETRNQY, SEQ ID NO:1328; |
| APTVDLNRVLNETRSQY, SEQ ID NO:1329; | APTVDLNRVLNETRNQY, SEQ ID NO:1330; |
| PTVDLNQVLNETRSQYE, SEQ ID NO:1331; | PTVDLNQVLNETRNQYE, SEQ ID NO:1332; |
| PTVDLNRVLNETRSQYE, SEQ ID NO:1333; | PTVDLNRVLNETRNQYE, SEQ ID NO:1334; |
| TVDLNQVLNETRSQYEA, SEQ ID NO:1335; | TVDLNQVLNETRNQYEA, SEQ ID NO:1336; |
| TVDLNRVLNETRSQYEA, SEQ ID NO:1337; | TVDLNRVLNETRNQYEA, SEQ ID NO:1338; |
| VDLNQVLNETRSQYEAL, SEQ ID NO:1339; | VDLNQVLNETRNQYEAL, SEQ ID NO:1340; |
| VDLNRVLNETRSQYEAL, SEQ ID NO:1341; | VDLNRVLNETRNQYEAL, SEQ ID NO:1342; |
| EVNTLRCQLGDRLNVEVD, SEQ ID NO:1343; | EVNTLRCPLGDRLNVEVD, SEQ ID NO:1344; |
| EVNTLRSQLGDRLNVEVD, SEQ ID NO:1345; | EVNTLRSPLGDRLNVEVD, SEQ ID NO:1346; |
| VNTLRCQLGDRLNVEVDA, SEQ ID NO:1347; | VNTLRCQLGDRLNVEVDT, SEQ ID NO:1348; |
| VNTLRCPLGDRLNVEVDA, SEQ ID NO:1349; | VNTLRCPLGDRLNVEVDT, SEQ ID NO:1350; |
| VNTLRSQLGDRLNVEVDA, SEQ ID NO:1351; | VNTLRSQLGDRLNVEVDT, SEQ ID NO:1352; |
| VNTLRSPLGDRLNVEVDA, SEQ ID NO:1353; | VNTLRSPLGDRLNVEVDT, SEQ ID NO:1354; |
| NTLRCQLGDRLNVEVDAA, SEQ ID NO:1355; | NTLRCQLGDRLNVEVDTA, SEQ ID NO:1356; |
| NTLRCPLGDRLNVEVDAA, SEQ ID NO:1357; | NTLRCPLGDRLNVEVDTA, SEQ ID NO:1358; |
| NTLRSQLGDRLNVEVDAA, SEQ ID NO:1359; | NTLRSQLGDRLNVEVDTA, SEQ ID NO:1360; |
| NTLRSPLGDRLNVEVDAA, SEQ ID NO:1361; | NTLRSPLGDRLNVEVDTA, SEQ ID NO:1362; |

-continued

```
TLRCQLGDRLNVEVDAAP, SEQ ID NO:1363;      TLRCQLGDRLNVEVDTAP, SEQ ID NO:1364;
TLRCPLGDRLNVEVDAAP, SEQ ID NO:1365;      TLRCPLGDRLNVEVDTAP, SEQ ID NO:1366;
TLRSQLGDRLNVEVDAAP, SEQ ID NO:1367;      TLRSQLGDRLNVEVDTAP, SEQ ID NO:1368;
TLRSPLGDRLNVEVDAAP, SEQ ID NO:1369;      TLRSPLGDRLNVEVDTAP, SEQ ID NO:1370;
LRCQLGDRLNVEVDAAPT, SEQ ID NO:1371;      LRCQLGDRLNVEVDTAPT, SEQ ID NO:1372;
LRCPLGDRLNVEVDAAPT, SEQ ID NO:1373;      LRCPLGDRLNVEVDTAPT, SEQ ID NO:1374;
LRSQLGDRLNVEVDAAPT, SEQ ID NO:1375;      LRSQLGDRLNVEVDTAPT, SEQ ID NO:1376;
LRSPLGDRLNVEVDAAPT, SEQ ID NO:1377;      LRSPLGDRLNVEVDTAPT, SEQ ID NO:1378;
RCQLGDRLNVEVDAAPTV, SEQ ID NO:1379;      RCQLGDRLNVEVDTAPTV, SEQ ID NO:1380;
RCPLGDRLNVEVDAAPTV, SEQ ID NO:1381;      RCPLGDRLNVEVDTAPTV, SEQ ID NO:1382;
RSQLGDRLNVEVDAAPTV, SEQ ID NO:1383;      RSQLGDRLNVEVDTAPTV, SEQ ID NO:1384;
RSPLGDRLNVEVDAAPTV, SEQ ID NO:1385;      RSPLGDRLNVEVDTAPTV, SEQ ID NO:1386;
CQLGDRLNVEVDAAPTVD, SEQ ID NO:1387;      CQLGDRLNVEVDTAPTVD, SEQ ID NO:1388;
CPLGDRLNVEVDAAPTVD, SEQ ID NO:1389;      CPLGDRLNVEVDTAPTVD, SEQ ID NO:1390;
SQLGDRLNVEVDAAPTVD, SEQ ID NO:1391;      SQLGDRLNVEVDTAPTVD, SEQ ID NO:1392;
SPLGDRLNVEVDAAPTVD, SEQ ID NO:1393;      SPLGDRLNVEVDTAPTVD, SEQ ID NO:1394;
QLGDRLNVEVDAAPTVDL, SEQ ID NO:1395;      QLGDRLNVEVDTAPTVDL, SEQ ID NO:1396;
PLGDRLNVEVDAAPTVDL, SEQ ID NO:1397;      PLGDRLNVEVDTAPTVDL, SEQ ID NO:1398;
LGDRLNVEVDAAPTVDLN, SEQ ID NO:1399;      LGDRLNVEVDTAPTVDLN, SEQ ID NO:1400;
GDRLNVEVDAAPTVDLNQ, SEQ ID NO:1401;      GDRLNVEVDAAPTVDLNR, SEQ ID NO:1402;
GDRLNVEVDTAPTVDLNQ, SEQ ID NO:1403;      GDRLNVEVDTAPTVDLNR, SEQ ID NO:1404;
DRLNVEVDAAPTVDLNQV, SEQ ID NO:1405;      DRLNVEVDAAPTVDLNRV, SEQ ID NO:1406;
DRLNVEVDTAPTVDLNQV, SEQ ID NO:1407;      DRLNVEVDTAPTVDLNRV, SEQ ID NO:1408;
RLNVEVDAAPTVDLNQVL, SEQ ID NO:1409;      RLNVEVDAAPTVDLNRVL, SEQ ID NO:1410;
RLNVEVDTAPTVDLNQVL, SEQ ID NO:1411;      RLNVEVDTAPTVDLNRVL, SEQ ID NO:1412;
LNVEVDAAPTVDLNQVLN, SEQ ID NO:1413;      LNVEVDAAPTVDLNRVLN, SEQ ID NO:1414;
LNVEVDTAPTVDLNQVLN, SEQ ID NO:1415;      LNVEVDTAPTVDLNRVLN, SEQ ID NO:1416;
NVEVDAAPTVDLNQVLNE, SEQ ID NO:1417;      NVEVDAAPTVDLNRVLNE, SEQ ID NO:1418;
NVEVDTAPTVDLNQVLNE, SEQ ID NO:1419;      NVEVDTAPTVDLNRVLNE, SEQ ID NO:1420;
VEVDAAPTVDLNQVLNET, SEQ ID NO:1421;      VEVDAAPTVDLNRVLNET, SEQ ID NO:1422;
VEVDTAPTVDLNQVLNET, SEQ ID NO:1423;      VEVDTAPTVDLNRVLNET, SEQ ID NO:1424;
EVDAAPTVDLNQVLNETR, SEQ ID NO:1425;      EVDAAPTVDLNRVLNETR, SEQ ID NO:1426;
EVDTAPTVDLNQVLNETR, SEQ ID NO:1427;      EVDTAPTVDLNRVLNETR, SEQ ID NO:1428;
VDAAPTVDLNQVLNETRS, SEQ ID NO:1429;      VDAAPTVDLNQVLNETRN, SEQ ID NO:1430;
VDAAPTVDLNRVLNETRS, SEQ ID NO:1431;      VDAAPTVDLNRVLNETRN, SEQ ID NO:1432;
VDTAPTVDLNQVLNETRS, SEQ ID NO:1433;      VDTAPTVDLNQVLNETRN, SEQ ID NO:1434;
VDTAPTVDLNRVLNETRS, SEQ ID NO:1435;      VDTAPTVDLNRVLNETRN, SEQ ID NO:1436;
DAAPTVDLNQVLNETRSQ, SEQ ID NO:1437;      DAAPTVDLNQVLNETRNQ, SEQ ID NO:1438;
DAAPTVDLNRVLNETRSQ, SEQ ID NO:1439;      DAAPTVDLNRVLNETRNQ, SEQ ID NO:1440;
DTAPTVDLNQVLNETRSQ, SEQ ID NO:1441;      DTAPTVDLNQVLNETRNQ, SEQ ID NO:1442;
DTAPTVDLNRVLNETRSQ, SEQ ID NO:1443;      DTAPTVDLNRVLNETRNQ, SEQ ID NO:1444;
AAPTVDLNQVLNETRSQY, SEQ ID NO:1445;      AAPTVDLNQVLNETRNQY, SEQ ID NO:1446;
AAPTVDLNRVLNETRSQY, SEQ ID NO:1447;      AAPTVDLNRVLNETRNQY, SEQ ID NO:1448;
TAPTVDLNQVLNETRSQY, SEQ ID NO:1449;      TAPTVDLNQVLNETRNQY, SEQ ID NO:1450;
TAPTVDLNRVLNETRSQY, SEQ ID NO:1451;      TAPTVDLNRVLNETRNQY, SEQ ID NO:1452;
APTVDLNQVLNETRSQYE, SEQ ID NO:1453;      APTVDLNQVLNETRNQYE, SEQ ID NO:1454;
APTVDLNRVLNETRSQYE, SEQ ID NO:1455;      APTVDLNRVLNETRNQYE, SEQ ID NO:1456;
PTVDLNQVLNETRSQYEA, SEQ ID NO:1457;      PTVDLNQVLNETRSQYEA, SEQ ID NO:1458;
PTVDLNRVLNETRSQYEA, SEQ ID NO:1459;      PTVDLNRVLNETRNQYEA, SEQ ID NO:1460;
TVDLNQVLNETRSQYEAL, SEQ ID NO:1461;      TVDLNQVLNETRNQYEAL, SEQ ID NO:1462;
TVDLNRVLNETRSQYEAL, SEQ ID NO:1463;      TVDLNRVLNETRNQYEAL, SEQ ID NO:1464;
EVNTLRCQLGDRLNVEVDA, SEQ ID NO:1465;     EVNTLRCQLGDRLNVEVDT, SEQ ID NO:1466;
EVNTLRCPLGDRLNVEVDA, SEQ ID NO:1467;     EVNTLRCPLGDRLNVEVDT, SEQ ID NO:1468;
EVNTLRSQLGDRLNVEVDA, SEQ ID NO:1469;     EVNTLRSQLGDRLNVEVDT, SEQ ID NO:1470;
EVNTLRSPLGDRLNVEVDA, SEQ ID NO:1471;     EVNTLRSPLGDRLNVEVDT, SEQ ID NO:1472;
VNTLRCQLGDRLNVEVDAA, SEQ ID NO:1473;     VNTLRCQLGDRLNVEVDTA, SEQ ID NO:1474;
VNTLRCPLGDRLNVEVDAA, SEQ ID NO:1475;     VNTLRCPLGDRLNVEVDTA, SEQ ID NO:1476;
VNTLRSQLGDRLNVEVDAA, SEQ ID NO:1477;     VNTLRSQLGDRLNVEVDTA, SEQ ID NO:1478;
VNTLRSPLGDRLNVEVDAA, SEQ ID NO:1479;     VNTLRSPLGDRLNVEVDTA, SEQ ID NO:1480;
VNTLRCQLGDRLNVEVDAA, SEQ ID NO:1481;     VNTLRCQLGDRLNVEVDTA, SEQ ID NO:1482;
VNTLRCPLGDRLNVEVDAA, SEQ ID NO:1483;     VNTLRCPLGDRLNVEVDTA, SEQ ID NO:1484;
VNTLRSQLGDRLNVEVDAA, SEQ ID NO:1485;     VNTLRSQLGDRLNVEVDTA, SEQ ID NO:1486;
VNTLRSPLGDRLNVEVDAA, SEQ ID NO:1487;     VNTLRSPLGDRLNVEVDTA, SEQ ID NO:1488;
TLRCQLGDRLNVEVDAAPT, SEQ ID NO:1489;     TLRCQLGDRLNVEVDTAPT, SEQ ID NO:1490;
TLRCPLGDRLNVEVDAAPT, SEQ ID NO:1491;     TLRCPLGDRLNVEVDTAPT, SEQ ID NO:1492;
TLRSQLGDRLNVEVDAAPT, SEQ ID NO:1493;     TLRSQLGDRLNVEVDTAPT, SEQ ID NO:1494;
TLRSPLGDRLNVEVDAAPT, SEQ ID NO:1495;     TLRSPLGDRLNVEVDTAPT, SEQ ID NO:1496;
LRCQLGDRLNVEVDAAPTV, SEQ ID NO:1497;     LRCQLGDRLNVEVDTAPTV, SEQ ID NO:1498;
LRCPLGDRLNVEVDAAPTV, SEQ ID NO:1499;     LRCPLGDRLNVEVDTAPTV, SEQ ID NO:1500;
LRSQLGDRLNVEVDAAPTV, SEQ ID NO:1501;     LRSQLGDRLNVEVDTAPTV, SEQ ID NO:1502;
LRSPLGDRLNVEVDAAPTV, SEQ ID NO:1503;     LRSPLGDRLNVEVDTAPTV, SEQ ID NO:1504;
LRCQLGDRLNVEVDAAPTV, SEQ ID NO:1505;     LRCQLGDRLNVEVDTAPTV, SEQ ID NO:1506;
LRCPLGDRLNVEVDAAPTV, SEQ ID NO:1507;     LRCPLGDRLNVEVDTAPTV, SEQ ID NO:1508;
LRSQLGDRLNVEVDAAPTV, SEQ ID NO:1509;     LRSQLGDRLNVEVDTAPTV, SEQ ID NO:1510;
LRSPLGDRLNVEVDAAPTV, SEQ ID NO:1511;     LRSPLGDRLNVEVDTAPTV, SEQ ID NO:1512;
LRCQLGDRLNVEVDAAPTV, SEQ ID NO:1513;     LRCQLGDRLNVEVDTAPTV, SEQ ID NO:1514;
LRCPLGDRLNVEVDAAPTV, SEQ ID NO:1515;     LRCPLGDRLNVEVDTAPTV, SEQ ID NO:1516;
LRSQLGDRLNVEVDAAPTV, SEQ ID NO:1517;     LRSQLGDRLNVEVDTAPTV, SEQ ID NO:1518;
LRSPLGDRLNVEVDAAPTV, SEQ ID NO:1519;     LRSPLGDRLNVEVDTAPTV, SEQ ID NO:1520;
QLGDRLNVEVDAAPTVDLN, SEQ ID NO:1521;     QLGDRLNVEVDTAPTVDLN, SEQ ID NO:1522;
```

-continued

| | |
|---|---|
| PLGDRLNVEVDAAPTVDLN, SEQ ID NO:1523; | PLGDRLNVEVDTAPTVDLN, SEQ ID NO:1524; |
| LGDRLNVEVDAAPTVDLNQ, SEQ ID NO:1525; | LGDRLNVEVDAAPTVDLNR, SEQ ID NO:1526; |
| LGDRLNVEVDTAPTVDLNQ, SEQ ID NO:1527; | LGDRLNVEVDTAPTVDLNR, SEQ ID NO:1528; |
| GDRLNVEVDAAPTVDLNQV, SEQ ID NO:1529; | GDRLNVEVDAAPTVDLNRV, SEQ ID NO:1530; |
| GDRLNVEVDTAPTVDLNQV, SEQ ID NO:1531; | GDRLNVEVDTAPTVDLNRV, SEQ ID NO:1532; |
| DRLNVEVDAAPTVDLNQVL, SEQ ID NO:1533; | DRLNVEVDAAPTVDLNRVL, SEQ ID NO:1534; |
| DRLNVEVDTAPTVDLNQVL, SEQ ID NO:1535; | DRLNVEVDTAPTVDLNRVL, SEQ ID NO:1536; |
| RLNVEVDAAPTVDLNQVLN, SEQ ID NO:1537; | RLNVEVDAAPTVDLNRVLN, SEQ ID NO:1538; |
| RLNVEVDTAPTVDLNQVLN, SEQ ID NO:1539; | RLNVEVDTAPTVDLNRVLN, SEQ ID NO:1540; |
| LNVEVDAAPTVDLNQVLNE, SEQ ID NO:1541; | LNVEVDAAPTVDLNRVLNE, SEQ ID NO:1542; |
| LNVEVDTAPTVDLNQVLNE, SEQ ID NO:1543; | LNVEVDTAPTVDLNRVLNE, SEQ ID NO:1544; |
| NVEVDAAPTVDLNQVLNET, SEQ ID NO:1545; | NVEVDAAPTVDLNRVLNET, SEQ ID NO:1546; |
| NVEVDTAPTVDLNQVLNET, SEQ ID NO:1547; | NVEVDTAPTVDLNRVLNET, SEQ ID NO:1548; |
| VEVDAAPTVDLNQVLNETR, SEQ ID NO:1549; | VEVDAAPTVDLNRVLNETR, SEQ ID NO:1550; |
| VEVDTAPTVDLNQVLNETR, SEQ ID NO:1551; | VEVDTAPTVDLNRVLNETR, SEQ ID NO:1552; |
| EVDAAPTVDLNQVLNETRS, SEQ ID NO:1553; | EVDAAPTVDLNQVLNETRN, SEQ ID NO:1554; |
| EVDAAPTVDLNRVLNETRS, SEQ ID NO:1555; | EVDAAPTVDLNRVLNETRN, SEQ ID NO:1556; |
| EVDTAPTVDLNQVLNETRS, SEQ ID NO:1557; | EVDTAPTVDLNQVLNETRN, SEQ ID NO:1558; |
| EVDTAPTVDLNRVLNETRS, SEQ ID NO:1559; | EVDTAPTVDLNRVLNETRN, SEQ ID NO:1560; |
| VDAAPTVDLNQVLNETRSQ, SEQ ID NO:1561; | VDAAPTVDLNQVLNETRNQ, SEQ ID NO:1562; |
| VDAAPTVDLNRVLNETRSQ, SEQ ID NO:1563; | VDAAPTVDLNRVLNETRNQ, SEQ ID NO:1564; |
| VDTAPTVDLNQVLNETRSQ, SEQ ID NO:1565; | VDTAPTVDLNQVLNETRNQ, SEQ ID NO:1566; |
| VDTAPTVDLNRVLNETRSQ, SEQ ID NO:1567; | VDTAPTVDLNRVLNETRNQ, SEQ ID NO:1568; |
| DAAPTVDLNQVLNETRSQY, SEQ ID NO:1569; | DAAPTVDLNQVLNETRNQY, SEQ ID NO:1570; |
| DAAPTVDLNRVLNETRSQY, SEQ ID NO:1571; | DAAPTVDLNRVLNETRNQY, SEQ ID NO:1572; |
| DTAPTVDLNQVLNETRSQY, SEQ ID NO:1573; | DTAPTVDLNQVLNETRNQY, SEQ ID NO:1574; |
| DTAPTVDLNRVLNETRSQY, SEQ ID NO:1575; | DTAPTVDLNRVLNETRNQY, SEQ ID NO:1576; |
| AAPTVDLNQVLNETRSQYE, SEQ ID NO:1577; | AAPTVDLNQVLNETRNQYE, SEQ ID NO:1578; |
| AAPTVDLNRVLNETRSQYE, SEQ ID NO:1579; | AAPTVDLNRVLNETRNQYE, SEQ ID NO:1580; |
| TAPTVDLNQVLNETRSQYE, SEQ ID NO:1581; | TAPTVDLNQVLNETRNQYE, SEQ ID NO:1582; |
| TAPTVDLNRVLNETRSQYE, SEQ ID NO:1583; | TAPTVDLNRVLNETRNQYE, SEQ ID NO:1584; |
| APTVDLNQVLNETRSQYEA, SEQ ID NO:1585; | APTVDLNQVLNETRNQYEA, SEQ ID NO:1586; |
| APTVDLNRVLNETRSQYEA, SEQ ID NO:1587; | APTVDLNRVLNETRNQYEA, SEQ ID NO:1588; |
| PTVDLNQVLNETRSQYEAL, SEQ ID NO:1589; | PTVDLNQVLNETRNQYEAL, SEQ ID NO:1590; |
| PTVDLNRVLNETRSQYEAL, SEQ ID NO:1591; | PTVDLNRVLNETRNQYEAL, SEQ ID NO:1592; |
| EVNTLRCQLGDRLNVEVDAA, SEQ ID NO:1593; | EVNTLRCQLGDRLNVEVDTA, SEQ ID NO:1594; |
| EVNTLRCPLGDRLNVEVDAA, SEQ ID NO:1595; | EVNTLRCPLGDRLNVEVDTA, SEQ ID NO:1596; |
| EVNTLRSQLGDRLNVEVDAA, SEQ ID NO:1597; | EVNTLRSQLGDRLNVEVDTA, SEQ ID NO:1598; |
| EVNTLRSPLGDRLNVEVDAA, SEQ ID NO:1599; | EVNTLRSPLGDRLNVEVDTA, SEQ ID NO:1600; |
| VNTLRCQLGDRLNVEVDAAP, SEQ ID NO:1601; | VNTLRCQLGDRLNVEVDTAP, SEQ ID NO:1602; |
| VNTLRCPLGDRLNVEVDAAP, SEQ ID NO:1603; | VNTLRCPLGDRLNVEVDTAP, SEQ ID NO:1604; |
| VNTLRSQLGDRLNVEVDAAP, SEQ ID NO:1605; | VNTLRSQLGDRLNVEVDTAP, SEQ ID NO:1606; |
| VNTLRSPLGDRLNVEVDAAP, SEQ ID NO:1607; | VNTLRSPLGDRLNVEVDTAP, SEQ ID NO:1608; |
| NTLRCQLGDRLNVEVDAAPT, SEQ ID NO:1609; | NTLRCQLGDRLNVEVDTAPT, SEQ ID NO:1610; |
| NTLRCPLGDRLNVEVDAAPT, SEQ ID NO:1611; | NTLRCPLGDRLNVEVDTAPT, SEQ ID NO:1612; |
| NTLRSQLGDRLNVEVDAAPT, SEQ ID NO:1613; | NTLRSQLGDRLNVEVDTAPT, SEQ ID NO:1614; |
| NTLRSPLGDRLNVEVDAAPT, SEQ ID NO:1615; | NTLRSPLGDRLNVEVDTAPT, SEQ ID NO:1616; |
| TLRCQLGDRLNVEVDAAPTV, SEQ ID NO:1617; | TLRCQLGDRLNVEVDTAPTV, SEQ ID NO:1618; |
| TLRCPLGDRLNVEVDAAPTV, SEQ ID NO:1619; | TLRCPLGDRLNVEVDTAPTV, SEQ ID NO:1620; |
| TLRSQLGDRLNVEVDAAPTV, SEQ ID NO:1621; | TLRSQLGDRLNVEVDTAPTV, SEQ ID NO:1622; |
| TLRSPLGDRLNVEVDAAPTV, SEQ ID NO:1623; | TLRSPLGDRLNVEVDTAPTV, SEQ ID NO:1624; |
| LRCQLGDRLNVEVDAAPTVD, SEQ ID NO:1625; | LRCQLGDRLNVEVDTAPTVD, SEQ ID NO:1626; |
| LRCPLGDRLNVEVDAAPTVD, SEQ ID NO:1627; | LRCPLGDRLNVEVDTAPTVD, SEQ ID NO:1628; |
| LRSQLGDRLNVEVDAAPTVD, SEQ ID NO:1629; | LRSQLGDRLNVEVDTAPTVD, SEQ ID NO:1630; |
| LRSPLGDRLNVEVDAAPTVD, SEQ ID NO:1631; | LRSPLGDRLNVEVDTAPTVD, SEQ ID NO:1632; |
| RCQLGDRLNVEVDAAPTVDL, SEQ ID NO:1633; | RCQLGDRLNVEVDTAPTVDL, SEQ ID NO:1634; |
| RCPLGDRLNVEVDAAPTVDL, SEQ ID NO:1635; | RCPLGDRLNVEVDTAPTVDL, SEQ ID NO:1636; |
| RSQLGDRLNVEVDAAPTVDL, SEQ ID NO:1637; | RSQLGDRLNVEVDTAPTVDL, SEQ ID NO:1638; |
| RSPLGDRLNVEVDAAPTVDL, SEQ ID NO:1639; | RSPLGDRLNVEVDTAPTVDL, SEQ ID NO:1640; |
| CQLGDRLNVEVDAAPTVDLN, SEQ ID NO:1641; | CQLGDRLNVEVDTAPTVDLN, SEQ ID NO:1642; |
| CPLGDRLNVEVDAAPTVDLN, SEQ ID NO:1643; | CPLGDRLNVEVDTAPTVDLN, SEQ ID NO:1644; |
| SQLGDRLNVEVDAAPTVDLN, SEQ ID NO:1645; | SQLGDRLNVEVDTAPTVDLN, SEQ ID NO:1646; |
| SPLGDRLNVEVDAAPTVDLN, SEQ ID NO:1647; | SPLGDRLNVEVDTAPTVDLN, SEQ ID NO:1648; |
| QLGDRLNVEVDAAPTVDLNQ, SEQ ID NO:1649; | QLGDRLNVEVDAAPTVDLNR, SEQ ID NO:1650; |
| QLGDRLNVEVDTAPTVDLNQ, SEQ ID NO:1651; | QLGDRLNVEVDTAPTVDLNR, SEQ ID NO:1652; |
| PLGDRLNVEVDAAPTVDLNQ, SEQ ID NO:1653; | PLGDRLNVEVDAAPTVDLNR, SEQ ID NO:1654; |
| PLGDRLNVEVDTAPTVDLNQ, SEQ ID NO:1655; | PLGDRLNVEVDTAPTVDLNR, SEQ ID NO:1656; |
| LGDRLNVEVDAAPTVDLNQV, SEQ ID NO:1657; | LGDRLNVEVDAAPTVDLNRV, SEQ ID NO:1658; |
| LGDRLNVEVDTAPTVDLNQV, SEQ ID NO:1659; | LGDRLNVEVDTAPTVDLNRV, SEQ ID NO:1660; |
| GDRLNVEVDAAPTVDLNQVL, SEQ ID NO:1661; | GDRLNVEVDAAPTVDLNRVL, SEQ ID NO:1662; |
| GDRLNVEVDTAPTVDLNQVL, SEQ ID NO:1663; | GDRLNVEVDTAPTVDLNRVL, SEQ ID NO:1664; |
| DRLNVEVDAAPTVDLNQVLN, SEQ ID NO:1665; | DRLNVEVDAAPTVDLNRVLN, SEQ ID NO:1666; |
| DRLNVEVDTAPTVDLNQVLN, SEQ ID NO:1667; | DRLNVEVDTAPTVDLNRVLN, SEQ ID NO:1668; |
| RLNVEVDAAPTVDLNQVLNE, SEQ ID NO:1669; | RLNVEVDAAPTVDLNRVLNE, SEQ ID NO:1670; |
| RLNVEVDTAPTVDLNQVLNE, SEQ ID NO:1671; | RLNVEVDTAPTVDLNRVLNE, SEQ ID NO:1672; |
| LNVEVDAAPTVDLNQVLNET, SEQ ID NO:1673; | LNVEVDAAPTVDLNRVLNET, SEQ ID NO:1674; |
| LNVEVDTAPTVDLNQVLNET, SEQ ID NO:1675; | LNVEVDTAPTVDLNRVLNET, SEQ ID NO:1676; |
| NVEVDAAPTVDLNQVLNETR, SEQ ID NO:1677; | NVEVDAAPTVDLNRVLNETR, SEQ ID NO:1678; |
| NVEVDTAPTVDLNQVLNETR, SEQ ID NO:1679; | NVEVDTAPTVDLNRVLNETR, SEQ ID NO:1680; |
| VEVDAAPTVDLNQVLNETRS, SEQ ID NO:1681; | VEVDAAPTVDLNQVLNETRN, SEQ ID NO:1682; |

-continued

| | |
|---|---|
| VEVDAAPTVDLNRVLNETRS, SEQ ID NO:1683; | VEVDAAPTVDLNRVLNETRN, SEQ ID NO:1684; |
| VEVDTAPTVDLNQVLNETRS, SEQ ID NO:1685; | VEVDTAPTVDLNQVLNETRN, SEQ ID NO:1686; |
| VEVDTAPTVDLNRVLNETRS, SEQ ID NO:1687; | VEVDTAPTVDLNRVLNETRN, SEQ ID NO:1688; |
| EVDAAPTVDLNQVLNETRSQ, SEQ ID NO:1689; | EVDAAPTVDLNQVLNETRNQ, SEQ ID NO:1690; |
| EVDAAPTVDLNRVLNETRSQ, SEQ ID NO:1691; | EVDAAPTVDLNRVLNETRNQ, SEQ ID NO:1692; |
| EVDTAPTVDLNQVLNETRSQ, SEQ ID NO:1693; | EVDTAPTVDLNQVLNETRNQ, SEQ ID NO:1694; |
| EVDTAPTVDLNRVLNETRSQ, SEQ ID NO:1695; | EVDTAPTVDLNRVLNETRNQ, SEQ ID NO:1696; |
| VDAAPTVDLNQVLNETRSQY, SEQ ID NO:1697; | VDAAIPTVDLNQVLNETRNQY, SEQ ID NO:1698; |
| VDAAPTVDLNRVLNETRSQY, SEQ ID NO:1699; | VDAAPTVDLNRVLNETRNQY, SEQ ID NO:1700; |
| VDTAPTVDLNQVLNETRSQY, SEQ ID NO:1701; | VDTAPTVDLNQVLNETRNQY, SEQ ID NO:1702; |
| VDTAPTVDLNRVLNETRSQY, SEQ ID NO:1703; | VDTAPTVDLNRVLNETRSQY, SEQ ID NO:1704; |
| DAAPTVDLNQVLNETRSQYE, SEQ ID NO:1705; | DAAPTVDLNQVLNETRNQYE, SEQ ID NO:1706; |
| DAAPTVDLNRVLNETRSQYE, SEQ ID NO:1707; | DAAPTVDLNRVLNETRNQYE, SEQ ID NO:1708; |
| DTAPTVDLNQVLNETRSQYE, SEQ ID NO:1709; | DTAPTVDLNQVLNETRNQYE, SEQ ID NO:1710; |
| DTAPTVDLNRVLNETRSQYE, SEQ ID NO:1711; | DTAPTVDLNRVLNETRNQYE, SEQ ID NO:1712; |
| AAPTVDLNQVLNETRSQYEA, SEQ ID NO:1713; | AAPTVDLNQVLNETRNQYEA, SEQ ID NO:1714; |
| AAPTVDLNRVLNETRSQYEA, SEQ ID NO:1715; | AAPTVDLNRVLNETRNQYEA, SEQ ID NO:1716; |
| TAPTVDLNQVLNETRSQYEA, SEQ ID NO:1717; | TAPTVDLNQVLNETRNQYEA, SEQ ID NO:1718; |
| TAPTVDLNRVLNETRSQYEA, SEQ ID NO:1719; | TAPTVDLNRVLNETRNQYEA, SEQ ID NO:1720; |
| APTVDLNQVLNETRSQYEAL, SEQ ID NO:1721; | APTVDLNQVLNETRNQYEAL, SEQ ID NO:1722; |
| APTVDLNRVLNETRSQYEAL, SEQ ID NO:1723; | APTVDLNRVLNETRNQYEAL, SEQ ID NO:1724; |

EVNTLRCQLGDRLNVEVDAAP, SEQ ID NO:1725;
EVNTLRCQLGDRLNVEVDTAP, SEQ ID NO:1726;
EVNTLRCPLGDRLNVEVDAAP, SEQ ID NO:1727;
EVNTLRCPLGDRLNVEVDTAP, SEQ ID NO:1728;
EVNTLRSQLGDRLNVEVDAAP, SEQ ID NO:1729;
EVNTLRSQLGDRLNVEVDTAP, SEQ ID NO:1730;
EVNTLRSPLGDRLNVEVDAAP, SEQ ID NO:1731;
EVNTLRSPLGDRLNVEVDTAP, SEQ ID NO:1732;
VNTLRCQLGDRLNVEVDAAPT, SEQ ID NO:1733;
VNTLRCQLGDRLNVEVDTAPT, SEQ ID NO:1734;
VNTLRCPLGDRLNVEVDAAPT, SEQ ID NO:1735;
VNTLRCPLGDRLNVEVDTAPT, SEQ ID NO:1736;
VNTLRSQLGDRLNVEVDAAPT, SEQ ID NO:1737;
VNTLRSQLGDRLNVEVDTAPT, SEQ ID NO:1738;
VNTLRSPLGDRLNVEVDAAPT, SEQ ID NO:1739;
VNTLRSPLGDRLNVEVDTAPT, SEQ ID NO:1740;
NTLRCQLGDRLNVEVDAAPTV, SEQ ID NO:1741;
NTLRCQLGDRLNVEVDTAPTV, SEQ ID NO:1742;
NTLRCPLGDRLNVEVDAAPTV, SEQ ID NO:1743;
NTLRCPLGDRLNVEVDTAPTV, SEQ ID NO:1744;
NTLRSQLGDRLNVEVDAAPTV, SEQ ID NO:1745;
NTLRSQLGDRLNVEVDTAPTV, SEQ ID NO:1746;
NTLRSPLGDRLNVEVDAAPTV, SEQ ID NO:1747;
NTLRSPLGDRLNVEVDTAPTV, SEQ ID NO:1748;
TLRCQLGDRLNVEVDAAPTVD, SEQ ID NO:1749;
TLRCQLGDRLNVEVDTAPTVD, SEQ ID NO:1750;
TLRCPLGDRLNVEVDAAPTVD, SEQ ID NO:1751;
TLRCPLGDRLNVEVDTAPTVD, SEQ ID NO:1752;
TLRSQLGDRLNVEVDAAPTVD, SEQ ID NO:1753;
TLRSQLGDRLNVEVDTAPTVD, SEQ ID NO:1754;
TLRSPLGDRLNVEVDAAPTVD, SEQ ID NO:1755;
TLRSPLGDRLNVEVDTAPTVD, SEQ ID NO:1756;
LRCQLGDRLNVEVDAAPTVDL, SEQ ID NO:1757;
LRCQLGDRLNVEVDTAPTVDL, SEQ ID NO:1758;
LRCPLGDRLNVEVDAAPTVDL, SEQ ID NO:1759;
LRCPLGDRLNVEVDTAPTVDL, SEQ ID NO:1760;
LRSQLGDRLNVEVDAAPTVDL, SEQ ID NO:1761;
LRSQLGDRLNVEVDTAPTVDL, SEQ ID NO:1762;
LRCPLGDRLNVEVDAAPTVDL, SEQ ID NO:1763;
LRSPLGDRLNVEVDTAPTVDL, SEQ ID NO:1764;
RCQLGDRLNVEVDAAPTVDLN, SEQ ID NO:1765;
RCQLGDRLNVEVDTAPTVDLN, SEQ ID NO:1766;
RCPLGDRLNVEVDAAPTVDLN, SEQ ID NO:1767;
RCPLGDRLNVEVDTAPTVDLN, SEQ ID NO:1768;
RSQLGDRLNVEVDAAPTVDLN, SEQ ID NO:1769;
RSQLGDRLNVEVDTAPTVDLN, SEQ ID NO:1770;
RSPLGDRLNVEVDAAPTVDLN, SEQ ID NO:1771;
RSPLGDRLNVEVDTAPTVDLN, SEQ ID NO:1772;
CQLGDRLNVEVDAAPTVDLNQ, SEQ ID NO:1773;
SQLGDRLNVEVDAAPTVDLNQ, SEQ ID NO:1774;
CPLGDRLNVEVDAAPTVDLNQ, SEQ ID NO:1775;
SPLGDRLNVEVDAAPTVDLNQ, SEQ ID NO:1776;
CQLGDRLNVEVDTAPTVDLNQ, SEQ ID NO:1777;
SQLGDRLNVEVDTAPTVDLNQ, SEQ ID NO:1778;
CPLGDRLNVEVDTAPTVDLNQ, SEQ ID NO:1779;
SPLGDRLNVEVDTAPTVDLNQ, SEQ ID NO:1780;
CQLGDRLNVEVDAAPTVDLNR, SEQ ID NO:1781;
SQLGDRLNVEVDAAPTVDLNR, SEQ ID NO:1782;
CPLGDRLNVEVDAAPTVDLNR, SEQ ID NO:1783;

```
                       -continued
SPLGDRLNVEVDAAPTVDLNR,  SEQ ID NO:1784;
CQLGDRLNVEVDTAPTVDLNR,  SEQ ID NO:1785;
SQLGDRLNVEVDTAPTVDLNR,  SEQ ID NO:1786;
CPLGDRLNVEVDTAPTVDLNR,  SEQ ID NO:1787;
SPLGDRLNVEVDTAPTVDLNR,  SEQ ID NO:1788;
QLGDRLNVEVDAAPTVDLNQV,  SEQ ID NO:1789;
QLGDRLNVEVDAAPTVDLNRV,  SEQ ID NO:1790;
QLGDRLNVEVDTAPTVDLNQV,  SEQ ID NO:1791;
QLGDRLNVEVDTAPTVDLNRV,  SEQ ID NO:1792;
PLGDRLNVEVDAAPTVDLNQV,  SEQ ID NO:1793;
PLGDRLNVEVDAAPTVDLNRV,  SEQ ID NO:1794;
PLGDRLNVEVDTAPTVDLNQV,  SEQ ID NO:1795;
PLGDRLNVEVDTAPTVDLNRV,  SEQ ID NO:1796;
LGDRLNVEVDAAPTVDLNQVL,  SEQ ID NO:1797;
LGDRLNVEVDAAPTVDLNRVL,  SEQ ID NO:1798;
LGDRLNVEVDTAPTVDLNQVL,  SEQ ID NO:1799;
LGDRLNVEVDTAPTVDLNRVL,  SEQ ID NO:1800;
GDRLNVEVDAAPTVDLNQVLN,  SEQ ID NO:1801;
GDRLNVEVDAAPTVDLNRVLN,  SEQ ID NO:1802;
GDRLNVEVDTAPTVDLNQVLN,  SEQ ID NO:1803;
GDRLNVEVDTAPTVDLNRVLN,  SEQ ID NO:1804;
DRLNVEVDAAPTVDLNQVLNE,  SEQ ID NO:1805;
DRLNVEVDAAPTVDLNRVLNE,  SEQ ID NO:1806;
DRLNVEVDTAPTVDLNQVLNE,  SEQ ID NO:1807;
DRLNVEVDTAPTVDLNRVLNE,  SEQ ID NO:1808;
RLNVEVDAAPTVDLNQVLNET,  SEQ ID NO:1809;
RLNVEVDAAPTVDLNRVLNET,  SEQ ID NO:1810;
RLNVEVDTAPTVDLNQVLNET,  SEQ ID NO:1811;
RLNVEVDTAPTVDLNRVLNET,  SEQ ID NO:1812;
LNVEVDAAPTVDLNQVLNETR,  SEQ ID NO:1813;
LNVEVDAAPTVDLNRVLNETR,  SEQ ID NO:1814;
LNVEVDTAPTVDLNQVLNETR,  SEQ ID NO:1815;
LNVEVDTAPTVDLNRVLNETR,  SEQ ID NO:1816;
NVEVDAAPTVDLNQVLNETRS,  SEQ ID NO:1817;
NVEVDAAPTVDLNQVLNETRN,  SEQ ID NO:1818;
NVEVDAAPTVDLNRVLNETRS,  SEQ ID NO:1819;
NVEVDAAPTVDLNRVLNETRN,  SEQ ID NO:1820;
NVEVDTAPTVDLNQVLNETRS,  SEQ ID NO:1821;
NVEVDTAPTVDLNQVLNETRN,  SEQ ID NO:1822;
NVEVDTAPTVDLNRVLNETRS,  SEQ ID NO:1823;
NVEVDTAPTVDLNRVLNETRN,  SEQ ID NO:1824;
VEVDAAPTVDLNQVLNETRSQ,  SEQ ID NO:1825;
VEVDAAPTVDLNQVLNETRNQ,  SEQ ID NO:1826;
VEVDAAPTVDLNRVLNETRSQ,  SEQ ID NO:1827;
VEVDAAPTVDLNRVLNETRNQ,  SEQ ID NO:1828;
VEVDTAPTVDLNQVLNETRSQ,  SEQ ID NO:1829;
VEVDTAPTVDLNQVLNETRNQ,  SEQ ID NO:1830;
VEVDTAPTVDLNRVLNETRSQ,  SEQ ID NO:1831;
VEVDTAPTVDLNRVLNETRNQ,  SEQ ID NO:1832;
EVDAAPTVDLNQVLNETRSQY,  SEQ ID NO:1833;
EVDAAPTVDLNQVLNETRNQY,  SEQ ID NO:1834;
EVDAAPTVDLNRVLNETRSQY,  SEQ ID NO:1835;
EVDAAPTVDLNRVLNETRNQY,  SEQ ID NO:1836;
EVDTAPTVDLNQVLNETRSQY,  SEQ ID NO:1837;
EVDTAPTVDLNQVLNETRNQY,  SEQ ID NO:1838;
EVDTAPTVDLNRVLNETRSQY,  SEQ ID NO:1839;
EVDTAPTVDLNRVLNETRNQY,  SEQ ID NO:1840;
VDAAPTVDLNQVLNETRSQYE,  SEQ ID NO:1841;
VDAAPTVDLNQVLNETRNQYE,  SEQ ID NO:1842;
VDAAPTVDLNRVLNETRSQYE,  SEQ ID NO:1843;
VDAAPTVDLNRVLNETRNQYE,  SEQ ID NO:1844;
VDTAPTVDLNQVLNETRSQYE,  SEQ ID NO:1845;
VDTAPTVDLNQVLNETRNQYE,  SEQ ID NO:1846;
VDTAPTVDLNRVLNETRSQYE,  SEQ ID NO:1847;
VDTAPTVDLNRVLNETRNQYE,  SEQ ID NO:1848;
DAAPTVDLNQVLNETRSQYEA,  SEQ ID NO:1849;
DAAPTVDLNQVLNETRNQYEA,  SEQ ID NO:1850;
DAAPTVDLNRVLNETRSQYEA,  SEQ ID NO:1851;
DAAPTVDLNRVLNETRNQYEA,  SEQ ID NO:1852;
DTAPTVDLNQVLNETRSQYEA,  SEQ ID NO:1853;
DTAPTVDLNQVLNETRNQYEA,  SEQ ID NO:1854;
DTAPTVDLNRVLNETRSQYEA,  SEQ ID NO:1855;
DTAPTVDLNRVLNETRNQYEA,  SEQ ID NO:1856;
AAPTVDLNQVLNETRSQYEAL,  SEQ ID NO:1857;
AAPTVDLNQVLNETRNQYEAL,  SEQ ID NO:1858;
AAPTVDLNRVLNETRSQYEAL,  SEQ ID NO:1859;
AAPTVDLNRVLNETRNQYEAL,  SEQ ID NO:1860;
TAPTVDLNQVLNETRSQYEAL,  SEQ ID NO:1861;
TAPTVDLNQVLNETRNQYEAL,  SEQ ID NO:1862;
TAPTVDLNRVLNETRSQYEAL,  SEQ ID NO:1863;
```

-continued

```
TAPTVDLNRVLNETRNQYEAL,    SEQ ID NO:1864;
EVNTLRCQLGDRLNVEVDAAPT,   SEQ ID NO;1865:
EVNTLRCQLGDRLNVEVDTAPT,   SEQ ID NO;1866:
EVNTLRCPLGDRLNVEVDAAPT,   SEQ ID NO;1867:
EVNTLRCPLGDRLNVEVDTAPT,   SEQ ID NO;1868:
EVNTLRSQLGDRLNVEVDAAPT,   SEQ ID NO;1869:
EVNTLRSQLGDRLNVEVDTAPT,   SEQ ID NO:1870;
EVNTLRSPLGDRLNVEVDAAPT,   SEQ ID NO;1871:
EVNTLRSPLGDRLNVEVDTAPT,   SEQ ID NO:1872;
VNTLRCQLGDRLNVEVDAAPTV,   SEQ ID NO:1873;
VNTLRCQLGDRLNVEVDTAPTV,   SEQ ID NO:1874;
VNTLRCPLGDRLNVEVDAAPTV,   SEQ ID NO:1875;
VNTLRCPLGDRLNVEVDTAPTV,   SEQ ID NO:1876;
VNTLRSQLGDRLNVEVDAAPTV,   SEQ ID NO:1877;
VNTLRSQLGDRLNVEVDTAPTV,   SEQ ID NO:1878;
VNTLRSPLGDRLNVEVDAAPTV,   SEQ ID NO:1879;
VNTLRSPLGDRLNVEVDTAPTV,   SEQ ID NO:1880;
NTLRCQLGDRLNVEVDAAPTVD,   SEQ ID NO:1881;
NTLRCQLGDRLNVEVDTAPTVD,   SEQ ID NO:1882;
NTLRCPLGDRLNVEVDAAPTVD,   SEQ ID NO:1883;
NTLRCPLGDRLNVEVDTAPTVD,   SEQ ID NO:1884;
NTLRSQLGDRLNVEVDAAPTVD,   SEQ ID NO:1885;
NTLRSQLGDRLNVEVDTAPTVD,   SEQ ID NO:1886;
NTLRSPLGDRLNVEVDAAPTVD,   SEQ ID NO:1887;
NTLRSPLGDRLNVEVDTAPTVD,   SEQ ID NO:1888;
TLRCQLGDRLNVEVDAAPTVDL,   SEQ ID NO:1889;
TLRCQLGDRLNVEVDTAPTVDL,   SEQ ID NO:1890;
TLRCPLGDRLNVEVDAAPTVDL,   SEQ ID NO:1891;
TLRCPLGDRLNVEVDTAPTVDL,   SEQ ID NO:1892;
TLRSQLGDRLNVEVDAAPTVDL,   SEQ ID NO:1893;
TLRSQLGDRLNVEVDTAPTVDL,   SEQ ID NO:1894;
TLRSPLGDRLNVEVDAAPTVDL,   SEQ ID NO:1895;
TLRSPLGDRLNVEVDTAPTVDL,   SEQ ID NO:1896;
LRCQLGDRLNVEVDAAPTVDLN,   SEQ ID NO:1897;
LRCQLGDRLNVEVDTAPTVDLN,   SEQ ID NO:1898;
LRCPLGDRLNVEVDAAPTVDLN,   SEQ ID NO:1899;
LRCPLGDRLNVEVDTAPTVDLN,   SEQ ID NO:1900;
LRSQLGDRLNVEVDAAPTVDLN,   SEQ ID NO:1901;
LRSQLGDRLNVEVDTAPTVDLN,   SEQ ID NO:1902;
LRSPLGDRLNVEVDAAPTVDLN,   SEQ ID NO:1903;
LRSPLGDRLNVEVDTAPTVDLN,   SEQ ID NO:1904;
RCQLGDRLNVEVDAAPTVDLNQ,   SEQ ID NO:1905;
RSQLGDRLNVEVDAAPTVDLNQ,   SEQ ID NO:1906
RCPLGDRLNVEVDAAPTVDLNQ,   SEQ ID NO:1907
RSPLGDRLNVEVDAAPTVDLNQ,   SEQ ID NO:1908
RCQLGDRLNVEVDTAPTVDLNQ,   SEQ ID NO:1909
RSQLGDRLNVEVDTAPTVDLNQ,   SEQ ID NO:1910
RCPLGDRLNVEVDTAPTVDLNQ,   SEQ ID NO:1911
RSPLGDRLNVEVDTAPTVDLNQ,   SEQ ID NO:1912
RCQLGDRLNVEVDAAPTVDLNR,   SEQ ID NO:1913
RSQLGDRLNVEVDAAPTVDLNR,   SEQ ID NO:1914
RCPLGDRLNVEVDAAPTVDLNR,   SEQ ID NO:1915
RSPLGDRLNVEVDAAPTVDLNR,   SEQ ID NO:1916
RCQLGDRLNVEVDTAPTVDLNR,   SEQ ID NO:1917
RSQLGDRLNVEVDTAPTVDLNR,   SEQ ID NO:1918
RCPLGDRLNVEVDTAPTVDLNR,   SEQ ID NO:1919
RSPLGDRLNVEVDTAPTVDLNR,   SEQ ID NO:1920
CQLGDRLNVEVDAAPTVDLNQV,   SEQ ID NO:1921
SQLGDRLNVEVDAAPTVDLNQV,   SEQ ID NO:1922
CPLGDRLNVEVDAAPTVDLNQV,   SEQ ID NO:1923
SPLGDRLNVEVDAAPTVDLNQV,   SEQ ID NO:1924
CQLGDRLNVEVDTAPTVDLNQV,   SEQ ID NO:1925
SQLGDRLNVEVDTAPTVDLNQV,   SEQ ID NO:1926
CPLGDRLNVEVDTAPTVDLNQV,   SEQ ID NO:1927
SPLGDRLNVEVDTAPTVDLNQV,   SEQ ID NO:1928
CQLGDRLNVEVDAAPTVDLNRV,   SEQ ID NO:1929
SQLGDRLNVEVDAAPTVDLNRV,   SEQ ID NO:1930
CPLGDRLNVEVDAAPTVDLNRVL,  SEQ ID NO:1931
SPLGDRLNVEVDAAPTVDLNRV,   SEQ ID NO:1932
CQLGDRLNVEVDTAPTVDLNRV,   SEQ ID NO:1933
SQLGDRLNVEVDTAPTVDLNRV,   SEQ ID NO:1934
CPLGDRLNVEVDTAPTVDLNRV,   SEQ ID NO:1935
SPLGDRLNVEVDTAPTVDLNRV,   SEQ ID NO:1936
QLGDRLNVEVDAAPTVDLNQVL,   SEQ ID NO:1937;
QLGDRLNVEVDAAPTVDLNRVL,   SEQ ID NO:1938;
QLGDRLNVEVDTAPTVDLNQVL,   SEQ ID NO:1939;
QLGDRLNVEVDTAPTVDLNRVL,   SEQ ID NO:1940;
PLGDRLNVEVDAAPTVDLNQVL,   SEQ ID NO:1941;
PLGDRLNVEVDAAPTVDLNRVL,   SEQ ID NO:1942;
PLGDRLNVEVDTAPTVDLNQVL,   SEQ ID NO:1943;
```

-continued

```
PLGDRLNVEVDTAPTVDLNRVL,   SEQ ID NO:1944;
LGDRLNVEVDAAPTVDLNQVLN,   SEQ ID NO:1945;
LGDRLNVEVDAAPTVDLNRVLN,   SEQ ID NO:1946;
LGDRLNVEVDTAPTVDLNQVLN,   SEQ ID NO:1947;
LGDRLNVEVDTAPTVDLNRVLN,   SEQ ID NO:1948;
GDRLNVEVDAAPTVDLNQVLNE,   SEQ ID NO:1949;
GDRLNVEVDAAPTVDLNRVLNE,   SEQ ID NO:1950;
GDRLNVEVDTAPTVDLNQVLNE,   SEQ ID NO:1951;
GDRLNVEVDTAPTVDLNRVLNE,   SEQ ID NO:1952;
DRLNVEVDAAPTVDLNQVLNET,   SEQ ID NO:1953;
DRLNVEVDAAPTVDLNRVLNET,   SEQ ID NO:1954;
DRLNVEVDTAPTVDLNQVLNET,   SEQ ID NO:1955;
DRLNVEVDTAPTVDLNRVLNET,   SEQ ID NO:1956;
RLNVEVDAAPTVDLNQVLNETR,   SEQ ID NO:1957;
RLNVEVDAAPTVDLNRVLNETR,   SEQ ID NO:1958;
RLNVEVDTAPTVDLNQVLNETR,   SEQ ID NO:1959;
RLNVEVDTAPTVDLNRVLNETR,   SEQ ID NO:1960;
LNVEVDAAPTVDLNQVLNETRS,   SEQ ID NO:1961;
LNVEVDAAPTVDLNQVLNETRN,   SEQ ID NO:1962;
LNVEVDAAPTVDLNRVLNETRS,   SEQ ID NO:1963;
LNVEVDAAPTVDLNRVLNETRN,   SEQ ID NO:1964;
LNVEVDTAPTVDLNQVLNETRS,   SEQ ID NO:1965;
LNVEVDTAPTVDLNQVLNETRN,   SEQ ID NO:1966;
LNVEVDTAPTVDLNRVLNETRS,   SEQ ID NO:1967;
LNVEVDTAPTVDLNRVLNETRN,   SEQ ID NO:1968;
NVEVDAAPTVDLNQVLNETRSQ,   SEQ ID NO:1969;
NVEVDAAPTVDLNQVLNETRNQ,   SEQ ID NO:1970;
NVEVDAAPTVDLNRVLNETRSQ,   SEQ ID NO:1971;
NVEVDAAPTVDLNRVLNETRNQ,   SEQ ID NO:1972;
NVEVDTAPTVDLNQVLNETRSQ,   SEQ ID NO:1973;
NVEVDTAPTVDLNQVLNETRNQ,   SEQ ID NO:1974;
NVEVDTAPTVDLNRVLNETRSQ,   SEQ ID NO:1975;
NVEVDTAPTVDLNRVLNETRNQ,   SEQ ID NO:1976;
EVNTLRCQLGDRLNVEVDAAPTV,  SEQ ID NO:1977;
EVNTLRCQLGDRLNVEVDTAPTV,  SEQ ID NO:1978;
EVNTLRCPLGDRLNVEVDAAPTV,  SEQ ID NO:1979;
EVNTLRCPLGDRLNVEVDTAPTV,  SEQ ID NO:1980;
EVNTLRSQLGDRLNVEVDAAPTV,  SEQ ID NO:1981;
EVNTLRSQLGDRLNVEVDTAPTV,  SEQ ID NO:1982;
EVNTLRSPLGDRLNVEVDAAPTV,  SEQ ID NO:1983;
EVNTLRSPLGDRLNVEVDTAPTV,  SEQ ID NO:1984;
VNTLRCQLGDRLNVEVDAAPTVD,  SEQ ID NO:1985
VNTLRSQLGDRLNVEVDAAPTVD,  SEQ ID NO:1986
VNTLRCPLGDRLNVEVDAAPTVD,  SEQ ID NO:1987
VNTLRSPLGDRLNVEVDAAPTVD,  SEQ ID NO:1988
VNTLRCQLGDRLNVEVDTAPTVD,  SEQ ID NO:1989
VNTLRSQLGDRLNVEVDTAPTVD,  SEQ ID NO:1990
VNTLRCPLGDRLNVEVDTAPTVD,  SEQ ID NO:1991
VNTLRSPLGDRLNVEVDTAPTVD,  SEQ ID NO:1992
NTLRCQLGDRLNVEVDAAPTVDL,  SEQ ID NO:1993      NTLRSQLGDRLNVEVDAAPTVDL,  SEQ ID NO:1994
NTLRCPLGDRLNVEVDAAPTVDL,  SEQ ID NO:1995      NTLRSPLGDRLNVEVDAAPTVDL,  SEQ ID NO:1996
NTLRCQLGDRLNVEVDTAPTVDL,  SEQ ID NO:1997      NTLRSQLGDRLNVEVDTAPTVDL,  SEQ ID NO:1998
NTLRCPLGDRLNVEVDTAPTVDL,  SEQ ID NO:1999      NTLRSPLGDRLNVEVDTAPTVDL,  SEQ ID NO:2000
TLRCQLGDRLNVEVDAAPTVDLN,  SEQ ID NO:2001      TLRSQLGDRLNVEVDAAPTVDLN,  SEQ ID NO:2002
TLRCPLGDRLNVEVDAAPTVDLN,  SEQ ID NO:2003      TLRSPLGDRLNVEVDAAPTVDLN,  SEQ ID NO:2004
TLRCQLGDRLNVEVDTAPTVDLN,  SEQ ID NO:2005      TLRSQLGDRLNVEVDTAPTVDLN,  SEQ ID NO:2006
TLRCPLGDRLNVEVDTAPTVDLN,  SEQ ID NO:2007      TLRSPLGDRLNVEVDTAPTVDLN,  SEQ ID NO:2008
LRCQLGDRLNVEVDAAPTVDLNQ,  SEQ ID NO:2009      LRSQLGDRLNVEVDAAPTVDLNQ,  SEQ ID NO:2010
LRCPLGDRLNVEVDAAPTVDLNQ,  SEQ ID NO:2011      LRSPLGDRLNVEVDAAPTVDLNQ,  SEQ ID NO:2012
LRCQLGDRLNVEVDTAPTVDLNQ,  SEQ ID NO:2013      LRSQLGDRLNVEVDTAPTVDLNQ,  SEQ ID NO:2014
LRCPLGDRLNVEVDTAPTVDLNQ,  SEQ ID NO:2015      LRSPLGDRLNVEVDTAPTVDLNQ,  SEQ ID NO:2016
LRCQLGDRLNVEVDAAPTVDLNR,  SEQ ID NO:2017      LRSQLGDRLNVEVDAAPTVDLNR,  SEQ ID NO:2018
LRCPLGDRLNVEVDAAPTVDLNR,  SEQ ID NO:2019      LRSPLGDRLNVEVDAAPTVDLNR,  SEQ ID NO:2020
LRCQLGDRLNVEVDTAPTVDLNR,  SEQ ID NO:2021      LRSQLGDRLNVEVDTAPTVDLNR,  SEQ ID NO:2022
LRCPLGDRLNVEVDTAPTVDLNR,  SEQ ID NO:2023      LRSPLGDRLNVEVDTAPTVDLNR,  SEQ ID ID:2024
RCQLGDRLNVEVDAAPTVDLNQV,  SEQ ID NO:2025      RSQLGDRLNVEVDAAPTVDLNQV,  SEQ ID NO:2026
RCPLGDRLNVEVDAAPTVDLNQV,  SEQ ID NO:2027      RSPLGDRLNVEVDAAPTVDLNQV,  SEQ ID NO:2028
RCQLGDRLNVEVDTAPTVDLNQV,  SEQ ID NO:2029      RSQLGDRLNVEVDTAPTVDLNQV,  SEQ ID NO:2030
RCPLGDRLNVEVDTAPTVDLNQV,  SEQ ID NO:2031      RSPLGDRLNVEVDTAPTVDLNQV,  SEQ ID NO:2032
RCQLGDRLNVEVDAAPTVDLNRV,  SEQ ID NO:2033      RSQLGDRLNVEVDAAPTVDLNRV,  SEQ ID NO:2034
RCPLGDRLNVEVDAAPTVDLNRV,  SEQ ID NO:2035      RSPLGDRLNVEVDAAPTVDLNRV,  SEQ ID NO:2036
RCQLGDRLNVEVDTAPTVDLNRV,  SEQ ID NO:2037      RSQLGDRLNVEVDTAPTVDLNRV,  SEQ ID NO:2038
RCPLGDRLNVEVDTAPTVDLNRV,  SEQ ID NO:2039      RSPLGDRLNVEVDTAPTVDLNRV,  SEQ ID NO:2040
CQLGDRLNVEVDAAPTVDLNQVL,  SEQ ID NO:2041      SQLGDRLNVEVDAAPTVDLNQVL,  SEQ ID NO:2042
CPLGDRLNVEVDAAPTVDLNQVL,  SEQ ID NO:2043      SPLGDRLNVEVDAAPTVDLNQVL,  SEQ ID NO:2044
CQLGDRLNVEVDTAPTVDLNQVL,  SEQ ID NO:2045      SQLGDRLNVEVDTAPTVDLNQVL,  SEQ ID NO:2046
CPLGDRLNVEVDTAPTVDLNQVL,  SEQ ID NO:2047      SPLGDRLNVEVDTAPTVDLNQVL,  SEQ ID NO:2048
CQLGDRLNVEVDAAPTVDLNRVL,  SEQ ID NO:2049      SQLGDRLNVEVDAAPTVDLNRVL,  SEQ ID NO:2050
CPLGDRLNVEVDAAPTVDLNRVL,  SEQ ID NO:2051      SPLGDRLNVEVDAAPTVDLNRVL,  SEQ ID NO:2052
CQLGDRLNVEVDTAPTVDLNRVL,  SEQ ID NO:2053      SQLGDRLNVEVDTAPTVDLNRVL,  SEQ ID NO:2054
```

-continued

```
CPLGDRLNVEVDTAPTVDLNRVL,   SEQ ID NO:2055   SPLGDRLNVEVDTAPTVDLNRVL,   SEQ ID NO:2056
QLGDRLNVEVDAAPTVDLNQVLN,   SEQ ID NO:2057   PLGDRLNVEVDAAPTVDLNQVLN,   SEQ ID NO:2058
QLGDRLNVEVDTAPTVDLNQVLN,   SEQ ID NO:2059   PLGDRLNVEVDTAPTVDLNQVLN,   SEQ ID NO:2060
QLGDRLNVEVDAAPTVDLNRVLN,   SEQ ID NO:2061   PLGDRLNVEVDAAPTVDLNRVLN,   SEQ ID NO:2062
QLGDRLNVEVDTAPTVDLNRVLN,   SEQ ID NO:2063   PLGDRLNVEVDTAPTVDLNRVLN,   SEQ ID NO:2064
LGDRLNVEVDAAPTVDLNQVLNE,   SEQ ID NO:2065;  LGDRLNVEVDAAPTVDLNRVLNE,   SEQ ID NO:2066;
LGDRLNVEVDTAPTVDLNQVLNE,   SEQ ID NO:2067;  LGDRLNVEVDTAPTVDLNRVLNE,   SEQ ID NO:2068;
GDRLNVEVDAAPTVDLNQVLNET,   SEQ ID NO:2069;  GDRLNVEVDAAPTVDLNRVLNET,   SEQ ID NO:2070;
GDRLNVEVDTAPTVDLNQVLNET,   SEQ ID NO:2071;  GDRLNVEVDTAPTVDLNRVLNET,   SEQ ID NO:2072;
DRLNVEVDAAPTVDLNQVLNETR,   SEQ ID NO:2073;  DRLNVEVDAAPTVDLNRVLNETR,   SEQ ID NO:2074;
DRLNVEVDTAPTVDLNQVLNETR,   SEQ ID NO:2075;  DRLNVEVDTAPTVDLNRVLNETR,   SEQ ID NO:2076;
RLNVEVDAAPTVDLNQVLNETRS,   SEQ ID NO:2077   RLNVEVDTAPTVDLNQVLNETRS,   SEQ ID NO:2078
RLNVEVDAAPTVDLNRVLNETRS,   SEQ ID NO:2079   RLNVEVDTAPTVDLNRVLNETRS,   SEQ ID NO:2080
RLNVEVDAAPTVDLNQVLNETRN,   SEQ ID NO:2081   RLNVEVDTAPTVDLNQVLNETRN,   SEQ ID NO:2082
RLNVEVDAAPTVDLNRVLNETRN,   SEQ ID NO:2083   RLNVEVDTAPTVDLNRVLNETRN,   SEQ ID NO:2084
LNVEVDAAPTVDLNQVLNETRSQ,   SEQ ID NO:2085   LNVEVDTAPTVDLNQVLNETRSQ,   SEQ ID NO:2086
LNVEVDAAPTVDLNRVLNETRSQ,   SEQ ID NO:2087   LNVEVDTAPTVDLNRVLNETRSQ,   SEQ ID NO:2088
LNVEVDAAPTVDLNQVLNETRNQ,   SEQ ID NO:2089   LNVEVDTAPTVDLNQVLNETRNQ,   SEQ ID NO:2090
LNVEVDAAPTVDLNRVLNETRNQ,   SEQ ID NO:2091   LNVEVDTAPTVDLNRVLNETRNQ,   SEQ ID NO:2092
NVEVDAAPTVDLNQVLNETRSQY,   SEQ ID NO:2093   NVEVDTAPTVDLNQVLNETRSQY,   SEQ ID NO:2094
NVEVDAAPTVDLNRVLNETRSQY,   SEQ ID NO:2095   NVEVDTAPTVDLNRVLNETRSQY,   SEQ ID NO:2096
NVEVDAAPTVDLNQVLNETRNQY,   SEQ ID NO:2097   NVEVDTAPTVDLNQVLNETRNQY,   SEQ ID NO:2098
NVEVDAAPTVDLNRVLNETRNQY,   SEQ ID NO:2099   NVEVDTAPTVDLNRVLNETRNQY,   SEQ ID NO:3000
VEVDAAPTVDLNQVLNETRSQYE,   SEQ ID NO:3001   VEVDTAPTVDLNQVLNETRSQYE,   SEQ ID NO:3002
VEVDANPTVDLNRVLNETRSQYE,   SEQ ID NO:3003   VEVDTAPTVDLNRVLNETRSQYE,   SEQ ID NO:3004
VEVDAAPTVDLNQVLNETRNQYE,   SEQ ID NO:3005   VEVDTAPTVDLNQVLNETRNQYE,   SEQ ID NO:3006
VEVDAAPTVDLNRVLNETRNQYE,   SEQ ID NO:3007   VEVDTAPTVDLNRVLNETRNQYE,   SEQ ID NO:3008
EVDAAPTVDLNQVLNETRSQYEA,   SEQ ID NO:3009   EVDTAPTVDLNQVLNETRSQYEA,   SEQ ID NO:3010
EVDAAPTVDLNRVLNETRSQYEA,   SEQ ID NO:3011   EVDTAPTVDLNRVLNETRSQYEA,   SEQ ID NO:3012
EVDAAPTVDLNQVLNETRNQYEA,   SEQ ID NO:3013   EVDTAPTVDLNQVLNETRNQYEA,   SEQ ID NO:3014
EVDAAPTVDLNRVLNETRNQYEA,   SEQ ID NO:3015   EVDTAPTVDLNRVLNETRNQYEA,   SEQ ID NO:3016
VDAAPTVDLNQVLNETRSQYEAL,   SEQ ID NO:3017   VDTAPTVDLNQVLNETRSQYEAL,   SEQ ID NO:3018
VDAAPTVDLNRVLNETRSQYEAL,   SEQ ID NO:3019   VDTAPTVDLNRVLNETRSQYEAL,   SEQ ID NO:3020
VDAAPTVDLNQVLNETRNQYEAL,   SEQ ID NO:3021   VDTAPTVDLNQVLNETRNQYEAL,   SEQ ID NO:3022
VDAAPTVDLNRVLNETRNQYEAL,   SEQ ID NO:3023   VDTAPTVDLNRVLNETRNQYEAL,   SEQ ID NO:3024
EVNTLRCQLGDRLNVEVDAAPTVD, SEQ ID NO:3025   EVNTLRSQLGDRLNVEVDAAPTVD, SEQ ID NO:3026
EVNTLRCPLGDRLNVEVDAAPTVD, SEQ ID NO:3027   EVNTLRSPLGDRLNVEVDAAPTVD, SEQ ID NO:3028
EVNTLRCQLGDRLNVEVDTAPTVD, SEQ ID NO:3029   EVNTLRSQLGDRLNVEVDTAPTVD, SEQ ID NO:3030
EVNTLRCPLGDRLNVEVDTAPTVD, SEQ ID NO:3031   EVNTLRSPLGDRLNVEVDTAPTVD, SEQ ID NO:3032
VNTLRCQLGDRLNVEVDAAPTVDL, SEQ ID NO:3033   VNTLRSQLGDRLNVEVDAAPTVDL, SEQ ID NO:3034
VNTLRCPLGDRLNVEVDAAPTVDL, SEQ ID NO:3035   VNTLRSPLGDRLNVEVDAAPTVDL, SEQ ID NO:3036
VNTLRCQLGDRLNVEVDTAPTVDL, SEQ ID NO:3037   VNTLRSQLGDRLNVEVDTAPTVDL, SEQ ID NO:3038
VNTLRCPLGDRLNVEVDTAPTVDL, SEQ ID NO:3039   VNTLRSPLGDRLNVEVDTAPTVDL, SEQ ID NO:3040
NTLRCQLGDRLNVEVDAAPTVDLN, SEQ ID NO:3041   NTLRSQLGDRLNVEVDAAPTVDLN, SEQ ID NO:3042
NTLRCPLGDRLNVEVDAAPTVDLN, SEQ ID NO:3043   NTLRSPLGDRLNVEVDAAPTVDLN, SEQ ID NO:3044
NTLRCQLGDRLNVEVDTAPTVDLN, SEQ ID NO:3045   NTLRSQLGDRLNVEVDTAPTVDLN, SEQ ID NO:3046
NTLRCPLGDRLNVEVDTAPTVDLN, SEQ ID NO:3047   NTLRSPLGDRLNVEVDTAPTVDLN, SEQ ID NO:3048
TLRCQLGDRLNVEVDAAPTVDLNQ, SEQ ID NO:3049   TLRSQLGDRLNVEVDAAPTVDLNQ, SEQ ID NO:3050
TLRCPLGDRLNVEVDAAPTVDLNQ, SEQ ID NO:3051   TLRSPLGDRLNVEVDAAPTVDLNQ, SEQ ID NO:3052
TLRCQLGDRLNVEVDTAPTVDLNQ, SEQ ID NO:3053   TLRSQLGDRLNVEVDTAPTVDLNQ, SEQ ID NO:3054
TLRCPLGDRLNVEVDTAPTVDLNQ, SEQ ID NO:3055   TLRSPLGDRLNVEVDTAPTVDLNQ, SEQ ID NO:3056
TLRCQLGDRLNVEVDAAPTVDLNR, SEQ ID NO:3057   TLRSQLGDRLNVEVDAAPTVDLNR, SEQ ID NO:3058
TLRCPLGDRLNVEVDAAPTVDLNR, SEQ ID NO:3059   TLRSPLGDRLNVEVDAAPTVDLNR, SEQ ID NO:3060
TLRCQLGDRLNVEVDTAPTVDLNR, SEQ ID NO:3061   TLRSQLGDRLNVEVDTAPTVDLNR, SEQ ID NO:3062
TLRCPLGDRLNVEVDTAPTVDLNR, SEQ ID NO:3063   TLRSPLGDRLNVEVDTAPTVDLNR, SEQ ID NO:3064
LRCQLGDRLNVEVDAAPTVDLNQV, SEQ ID NO:3065   LRSQLGDRLNVEVDAAPTVDLNQV, SEQ ID NO:3066
LRCPLGDRLNVEVDAAPTVDLNQV, SEQ ID NO:3067   LRSPLGDRLNVEVDAAPTVDLNQV, SEQ ID NO:3068
LRCQLGDRLNVEVDTAPTVDLNQV, SEQ ID NO:3069   LRSQLGDRLNVEVDTAPTVDLNQV, SEQ ID NO:3070
LRCPLGDRLNVEVDTAPTVDLNQV, SEQ ID NO:3071   LRSPLGDRLNVEVDTAPTVDLNQV, SEQ ID NO:3072
LRCQLGDRLNVEVDAAPTVDLNRV, SEQ ID NO:3073   LRSQLGDRLNVEVDAAPTVDLNRV, SEQ ID NO:3074
LRCPLGDRLNVEVDAAPTVDLNRV, SEQ ID NO:3075   LRSPLGDRLNVEVDAAPTVDLNRV, SEQ ID NO:3076
LRCQLGDRLNVEVDTAPTVDLNRV, SEQ ID NO:3077   LRSQLGDRLNVEVDTAPTVDLNRV, SEQ ID NO:3078
LRCPLGDRLNVEVDTAPTVDLNRV, SEQ ID NO:3079   LRSPLGDRLNVEVDTAPTVDLNRV, SEQ ID NO:3080
RCQLGDRLNVEVDAAPTVDLNQVL, SEQ ID NO:3081   RSQLGDRLNVEVDAAPTVDLNQVL, SEQ ID NO:3082
RCPLGDRLNVEVDAAPTVDLNQVL, SEQ ID NO:3083   RSPLGDRLNVEVDAAPTVDLNQVL, SEQ ID NO:3084
RCQLGDRLNVEVDTAPTVDLNQVL, SEQ ID NO:3085   RSQLGDRLNVEVDTAPTVDLNQVL, SEQ ID NO:3086
RCPLGDRLNVEVDTAPTVDLNQVL, SEQ ID NO:3087   RSPLGDRLNVEVDTAPTVDLNQVL, SEQ ID NO:3088
RCQLGDRLNVEVDAAPTVDLNRVL, SEQ ID NO:3089   RSQLGDRLNVEVDAAPTVDLNRVL, SEQ ID NO:3090
RCPLGDRLNVEVDAAPTVDLNRVL, SEQ ID NO:3091   RSPLGDRLNVEVDAAPTVDLNRVL, SEQ ID NO:3092
RCQLGDRLNVEVDTAPTVDLNRVL, SEQ ID NO:3093   RSQLGDRLNVEVDTAPTVDLNRVL, SEQ ID NO:3094
RCPLGDRLNVEVDTAPTVDLNRVL, SEQ ID NO:3095   RSPLGDRLNVEVDTAPTVDLNRVL, SEQ ID NO:3096
CQLGDRLNVEVDAAPTVDLNQVLN, SEQ ID NO:3097   SQLGDRLNVEVDAAPTVDLNQVLN, SEQ ID NO:3098
CPLGDRLNVEVDAAPTVDLNQVLN, SEQ ID NO:3099   SPLGDRLNVEVDAAPTVDLNQVLN, SEQ ID NO:4000
CQLGDRLNVEVDTAPTVDLNQVLN, SEQ ID NO:4001   SQLGDRLNVEVDTAPTVDLNQVLN, SEQ ID NO:4002
CPLGDRLNVEVDTAPTVDLNQVLN, SEQ ID NO:4003   SPLGDRLNVEVDTAPTVDLNQVLN, SEQ ID NO:4004
CQLGDRLNVEVDAAPTVDLNRVLN, SEQ ID NO:4005   SQLGDRLNVEVDAAPTVDLNRVLN, SEQ ID NO:4006
CPLGDRLNVEVDAAPTVDLNRVLN, SEQ ID NO:4007   SPLGDRLNVEVDAAPTVDLNRVLN, SEQ ID NO:4008
CQLGDRLNVEVDTAPTVDLNRVLN, SEQ ID NO:4009   SQLGDRLNVEVDTAPTVDLNRVLN, SEQ ID NO:4010
CPLGDRLNVEVDTAPTVDLNRVLN, SEQ ID NO:4011   SPLGDRLNVEVDTAPTVDLNRVLN, SEQ ID NO:4012
QLGDRLNVEVDAAPTVDLNQVLNE, SEQ ID NO:4013   PLGDRLNVEVDAAPTVDLNQVLNE, SEQ ID NO:4014
```

-continued

```
QLGDRLNVEVDTAPTVDLNQVLNE, SEQ ID NO:4015    PLGDRLNVEVDTAPTVDLNQVLNE, SEQ ID NO:4016
QLGDRLNVEVDAAPTVDLNRVLNE, SEQ ID NO:4017    PLGDRLNVEVDAAPTVDLNRVLNE, SEQ ID NO:4018
QLGDRLNVEVDTAPTVDLNRVLNE, SEQ ID NO:4019    PLGDRLNVEVDTAPTVDLNRVLNE, SEQ ID NO:4020
LGDRLNVEVDAAPTVDLNQVLNET, SEQ ID NO:4021;   LGDRLNVEVDAAPTVDLNRVLNET, SEQ ID
                                                                     NO:4022;
LGDRLNVEVDTAPTVDLNQVLNET, SEQ ID NO:4023;   LGDRLNVEVDTAPTVDLNRVLNET, SEQ ID
                                                                     NO:4024;
GDRLNVEVDAAPTVDLNQVLNETR, SEQ ID NO:4025;   GDRLNVEVDAAPTVDLNRVLNETR, SEQ ID
                                                                     NO:4026;
GDRLNVEVDTAPTVDLNQVLNETR, SEQ ID NO:4027;   GDRLNVEVDTAPTVDLNRVLNETR, SEQ ID
                                                                     NO:4028;
DRLNVEVDAAPTVDLNQVLNETRS, SEQ ID NO:4029    DRLNVEVDTAPTVDLNQVLNETRS, SEQ ID NO:4030
DRLNVEVDAAPTVDLNRVLNETRS, SEQ ID NO:4031    DRLNVEVDTAPTVDLNRVLNETRS, SEQ ID NO:4032
DRLNVEVDAAPTVDLNQVLNETRN, SEQ ID NO:4033    DRLNVEVDTAPTVDLNQVLNETRN, SEQ ID NO:4034
DRLNVEVDAAPTVDLNRVLNETRN, SEQ ID NO:4035    DRLNVEVDTAPTVDLNRVLNETRN, SEQ ID NO:4036
RLNVEVDAAPTVDLNQVLNETRSQ, SEQ ID NO:4037
RLNVEVDTAPTVDLNQVLNETRSQ, SEQ ID NO:4038
RLNVEVDAAPTVDLNRVLNETRSQ, SEQ ID NO:4039
RLNVEVDTAPTVDLNRVLNETRSQ, SEQ ID NO:4040
RLNVEVDAAPTVDLNQVLNETRNQ, SEQ ID NO:4041
RLNVEVDTAPTVDLNQVLNETRNQ, SEQ ID NO:4042
RLNVEVDAAPTVDLNRVLNETRNQ, SEQ ID NO:4043
RLNVEVDTAPTVDLNRVLNETRNQ, SEQ ID NO:4044
LNVEVDAAPTVDLNQVLNETRSQY, SEQ ID NO:4045
LNVEVDTAPTVDLNQVLNETRSQY, SEQ ID NO:4046
LNVEVDAAPTVDLNRVLNETRSQY, SEQ ID NO:4047
LNVEVDTAPTVDLNRVLNETRSQY, SEQ ID NO:4048
LNVEVDAAPTVDLNQVLNETRNQY, SEQ ID NO:4049
LNVEVDTAPTVDLNQVLNETRNQY, SEQ ID NO:4050
LNVEVDAAPTVDLNRVLNETRNQY, SEQ ID NO:4051
LNVEVDTAPTVDLNRVLNETRNQY, SEQ ID NO:4052
NVEVDAAPTVDLNQVLNETRSQYE, SEQ ID NO:4053
NVEVDTAPTVDLNQVLNETRSQYE, SEQ ID NO:4054
NVEVDAAPTVDLNRVLNETRSQYE, SEQ ID NO:4055
NVEVDTAPTVDLNRVLNETRSQYE, SEQ ID NO:4056
NVEVDAAPTVDLNQVLNETRNQYE, SEQ ID NO:4057
NVEVDTAPTVDLNQVLNETRNQYE, SEQ ID NO:4058
NVEVDAAPTVDLNRVLNETRNQYE, SEQ ID NO:4059
NVEVDTAPTVDLNRVLNETRNQYE, SEQ ID NO:4060
VEVDAAPTVDLNQVLNETRSQYEA, SEQ ID NO:4061
VEVDTAPTVDLNQVLNETRSQYEA, SEQ ID NO:4062
VEVDAAPTVDLNRVLNETRSQYEA, SEQ ID NO:4063
VEVDTAPTVDLNRVLNETRSQYEA, SEQ ID NO:4064
VEVDAAPTVDLNQVLNETRNQYEA, SEQ ID NO:4065
VEVDTAPTVDLNQVLNETRNQYEA, SEQ ID NO:4066
VEVDAAPTVDLNRVLNETRNQYEA, SEQ ID NO:4067
VEVDTAPTVDLNRVLNETRNQYEA, SEQ ID NO:4068
EVDAAPTVDLNQVLNETRSQYEAL, SEQ ID NO:4069
EVDTAPTVDLNQVLNETRSQYEAL, SEQ ID NO:4070
EVDAAPTVDLNRVLNETRSQYEAL, SEQ ID NO:4071
EVDTAPTVDLNRVLNETRSQYEAL, SEQ ID NO:4072
EVDAAPTVDLNQVLNETRNQYEAL, SEQ ID NO:4073
EVDTAPTVDLNQVLNETRNQYEAL, SEQ ID NO:4074
EVDAAPTVDLNRVLNETRNQYEAL, SEQ ID NO:4075
EVDTAPTVDLNRVLNETRNQYEAL, SEQ ID NO:4076
EVNTLRCQLGDRLNVEVDAAPTVDL, SEQ ID NO:4077
EVNTLRSQLGDRLNVEVDAAPTVDL, SEQ ID NO:4078
EVNTLRCPLGDRLNVEVDAAPTVDL, SEQ ID NO:4079
EVNTLRSPLGDRLNVEVDAAPTVDL, SEQ ID NO:4080
EVNTLRCQLGDRLNVEVDTAPTVDL, SEQ ID NO:4081
EVNTLRSQLGDRLNVEVDTAPTVDL, SEQ ID NO:4082
EVNTLRCPLGDRLNVEVDTAPTVDL, SEQ ID NO:4083
EVNTLRSPLGDRLNVEVDTAPTVDL, SEQ ID NO:4084
VNTLRCQLGDRLNVEVDAAPTVDLN, SEQ ID NO:4085
VNTLRSQLGDRLNVEVDAAPTVDLN, SEQ ID NO:4086
VNTLRCPLGDRLNVEVDAAPTVDLN, SEQ ID NO:4087
VNTLRSPLGDRLNVEVDANPTVDLN, SEQ ID NO:4088
VNTLRCQLGDRLNVEVDTAPTVDLN, SEQ ID NO:4089
VNTLRSQLGDRLNVEVDTAPTVDLN, SEQ ID NO:4090
VNTLRCPLGDRLNVEVDTAPTVDLN, SEQ ID NO:4091
VNTLRSPLGDRLNVEVDTAPTVDLN, SEQ ID NO:4091
NTLRCQLGDRLNVEVDAAPTVDLNQ, SEQ ID NO:4093
NTLRSQLGDRLNVEVDAAPTVDLNQ, SEQ ID NO:4094
NTLRCPLGDRLNVEVDAAPTVDLNQ, SEQ ID NO:4095
NTLRSPLGDRLNVEVDAAPTVDLNQ, SEQ ID NO:4096
NTLRCQLGDRLNVEVDTAPTVDLNQ, SEQ ID NO:4097
NTLRSQLGDRLNVEVDTAPTVDLNQ, SEQ ID NO:4098
NTLRCPLGDRLNVEVDTAPTVDLNQ, SEQ ID NO:4099
NTLRSPLGDRLNVEVDTAPTVDLNQ, SEQ ID NO:4100
NTLRCQLGDRLNVEVDAAPTVDLNR, SEQ ID NO:4101
```

-continued

```
NTLRSQLGDRLNVEVDAAPTVDLNR,   SEQ ID NO:4102
NTLRCPLGDRLNVEVDAAPTVDLNR,   SEQ ID NO:4103
NTLRSPLGDRLNVEVDAAPTVDLNR,   SEQ ID NO:4104
NTLRCQLGDRLNVEVDTAPTVDLNR,   SEQ ID NO:4105
NTLRSQLGDRLNVEVDTAPTVDLNR,   SEQ ID NO:4106
NTLRCPLGDRLNVEVDTAPTVDLNR,   SEQ ID NO:4107
NTLRSPLGDRLNVEVDTAPTVDLNR,   SEQ ID NO:4108
TLRCQLGDRLNVEVDAAPTVDLNQV,   SEQ ID NO:4109
TLRSQLGDRLNVEVDAAPTVDLNQV,   SEQ ID NO:4110
TLRCPLGDRLNVEVDAAPTVDLNQV,   SEQ ID NO:4111
TLRSPLGDRLNVEVDAAPTVDLNQV,   SEQ ID NO:4112
TLRCQLGDRLNVEVDTAPTVDLNQV,   SEQ ID NO:4113
TLRSQLGDRLNVEVDTAPTVDLNQV,   SEQ ID NO:4114
TLRCPLGDRLNVEVDTAPTVDLNQV,   SEQ ID NO:4115
TLRSPLGDRLNVEVDTAPTVDLNQV,   SEQ ID NO:4116
TLRCQLGDRLNVEVDAAPTVDLNRV,   SEQ ID NO:4117
TLRSQLGDRLNVEVDAAPTVDLNRV,   SEQ ID NO:4118
TLRCPLGDRLNVEVDAAPTVDLNRV,   SEQ ID NO:4119
TLRSPLGDRLNVEVDAAPTVDLNRV,   SEQ ID NO:4120
TLRCQLGDRLNVEVDTAPTVDLNRV,   SEQ ID NO:4121
TLRSQLGDRLNVEVDTAPTVDLNRV,   SEQ ID NO:4122
TLRCPLGDRLNVEVDTAPTVDLNRV,   SEQ ID NO:4123
TLRSPLGDRLNVEVDTAPTVDLNRV,   SEQ ID NO:4124
LRCQLGDRLNVEVDAAPTVDLNQVL,   SEQ ID NO:4125
LRSQLGDRLNVEVDAAPTVDLNQVL,   SEQ ID NO:4126
LRCPLGDRLNVEVDAAPTVDLNQVL,   SEQ ID NO:4127
LRSPLGDRLNVEVDAAPTVDLNQVL,   SEQ ID NO:4128
LRCQLGDRLNVEVDTAPTVDLNQVL,   SEQ ID NO:4129
LRSQLGDRLNVEVDTAPTVDLNQVL,   SEQ ID NO:4130
LRCPLGDRLNVEVDTAPTVDLNQVL,   SEQ ID NO:4131
LRSPLGDRLNVEVDTAPTVDLNQVL,   SEQ ID NO:4132
LRCQLGDRLNVEVDAAPTVDLNRVL,   SEQ ID NO:4133
LRSQLGDRLNVEVDAAPTVDLNRVL,   SEQ ID NO:4134
LRCPLGDRLNVEVDAAPTVDLNRVL,   SEQ ID NO:4135
LRSPLGDRLNVEVDAAPTVDLNRVL,   SEQ ID NO:4136
LRCQLGDRLNVEVDTAPTVDLNRVL,   SEQ ID NO:4137
LRSQLGDRLNVEVDTAPTVDLNRVL,   SEQ ID NO:4138
LRCPLGDRLNVEVDTAPTVDLNRVL,   SEQ ID NO:4139
LRSPLGDRLNVEVDTAPTVDLNRV,    SEQ ID NO:4140
RCQLGDRLNVEVDAAPTVDLNQVLN,   SEQ ID NO:4141
RSQLGDRLNVEVDAAPTVDLNQVLN,   SEQ ID NO:4142
RCPLGDRLNVEVDAAPTVDLNQVLN,   SEQ ID NO:4143
RSPLGDRLNVEVDAAPTVDLNQVLN,   SEQ ID NO:4144
RCQLGDRLNVEVDTAPTVDLNQVLN,   SEQ ID NO:4145
RSQLGDRLNVEVDTAPTVDLNQVLN,   SEQ ID NO:4146
RCPLGDRLNVEVDTAPTVDLNQVLN,   SEQ ID NO:4147
RSPLGDRLNVEVDTAPTVDLNQVLN,   SEQ ID NO:4148
RCQLGDRLNVEVDAAPTVDLNRVLN,   SEQ ID NO:4149
RSQLGDRLNVEVDAAPTVDLNRVLN,   SEQ ID NO:4150
RCPLGDRLNVEVDAAPTVDLNRVLN,   SEQ ID NO:4151
RSPLGDRLNVEVDAAPTVDLNRVLN,   SEQ ID NO:4152
RCQLGDRLNVEVDTAPTVDLNRVLN,   SEQ ID NO:4153
RSQLGDRLNVEVDTAPTVDLNRVLN,   SEQ ID NO:4154
RCPLGDRLNVEVDTAPTVDLNRVLN,   SEQ ID NO:4155
RSPLGDRLNVEVDTAPTVDLNRVLN,   SEQ ID NO:4156
CQLGDRLNVEVDAAPTVDLNQVLNE,   SEQ ID NO:4157
SQLGDRLNVEVDAAPTVDLNQVLNE,   SEQ ID NO:4158
CPLGDRLNVEVDAAPTVDLNQVLNE,   SEQ ID NO:4159
SPLGDRLNVEVDAAPTVDLNQVLNE,   SEQ ID NO:4160
CQLGDRLNVEVDTAPTVDLNQVLNE,   SEQ ID NO:4161
SQLGDRLNVEVDTAPTVDLNQVLNE,   SEQ ID NO:4162
CPLGDRLNVEVDTAPTVDLNQVLNE,   SEQ ID NO:4163
SPLGDRLNVEVDTAPTVDLNQVLNE,   SEQ ID NO:4164
CQLGDRLNVEVDAAPTVDLNRVLNE,   SEQ ID NO:4165
SQLGDRLNVEVDAAPTVDLNRVLNE,   SEQ ID NO:4166
CPLGDRLNVEVDAAPTVDLNRVLNE,   SEQ ID NO:4167
SPLGDRLNVEVDAAPTVDLNRVLNE,   SEQ ID NO:4168
CQLGDRLNVEVDTAPTVDLNRVLNE,   SEQ ID NO:4169
SQLGDRLNVEVDTAPTVDLNRVLNE,   SEQ ID NO:4170
CPLGDRLNVEVDTAPTVDLNRVLNE,   SEQ ID NO:4171
SPLGDRLNVEVDTAPTVDLNRVLNE,   SEQ ID NO:4172
QLGDRLNVEVDAAPTVDLNQVLNET,   SEQ ID NO:4173
PLGDRLNVEVDAAPTVDLNQVLNET,   SEQ ID NO:4174
QLGDRLNVEVDTAPTVDLNQVLNET,   SEQ ID NO:4175
PLGDRLNVEVDTAPTVDLNQVLNET,   SEQ ID NO:4176
QLGDRLNVEVDAAPTVDLNRVLNET,   SEQ ID NO:4177
PLGDRLNVEVDAAPTVDLNRVLNET,   SEQ ID NO:4178
QLGDRLNVEVDTAPTVDLNRVLNET,   SEQ ID NO:4179
PLGDRLNVEVDTAPTVDLNRVLNET,   SEQ ID NO:4180
LGDRLNVEVDAAPTVDLNQVLNETR,   SEQ ID NO:4181;
```

-continued

```
LGDRLNVEVDAAPTVDLNRVLNETR,     SEQ ID NO:4182;
LGDRLNVEVDTAPTVDLNQVLNETR,     SEQ ID NO:4183;
LGDRLNVEVDTAPTVDLNRVLNETR,     SEQ ID NO:4184;
GDRLNVEVDAAPTVDLNQVLNETRS,     SEQ ID NO:4185
GDRLNVEVDTAPTVDLNQVLNETRS,     SEQ ID NO:4186
GDRLNVEVDAAPTVDLNRVLNETRS,     SEQ ID NO:4187
GDRLNVEVDTAPTVDLNRVLNETRS,     SEQ ID NO:4188
GDRLNVEVDAAPTVDLNQVLNETRN,     SEQ ID NO:4189
GDRLNVEVDTAPTVDLNQVLNETRN,     SEQ ID NO:4190
GDRLNVEVDAAPTVDLNRVLNETRN,     SEQ ID NO:4191
GDRLNVEVDTAPTVDLNRVLNETRN,     SEQ ID NO:4192
DRLNVEVDAAPTVDLNQVLNETRSQ,     SEQ ID NO:4193
DRLNVEVDTAPTVDLNQVLNETRSQ,     SEQ ID NO:4194
DRLNVEVDAAPTVDLNRVLNETRSQ,     SEQ ID NO:4195
DRLNVEVDTAPTVDLNRVLNETRSQ,     SEQ ID NO:4196
DRLNVEVDAAPTVDLNQVLNETRNQ,     SEQ ID NO:4197
DRLNVEVDTAPTVDLNQVLNETRNQ,     SEQ ID NO:4198
DRLNVEVDAAPTVDLNRVLNETRNQ,     SEQ ID NO:4199
DRLNVEVDTAPTVDLNRVLNETRNQ,     SEQ ID NO:4200
RLNVEVDAAPTVDLNQVLNETRSQY,     SEQ ID NO:4201
RLNVEVDTAPTVDLNQVLNETRSQY,     SEQ ID NO:4202
RLNVEVDAAPTVDLNRVLNETRSQY,     SEQ ID NO:4203
RLNVEVDTAPTVDLNRVLNETRSQY,     SEQ ID NO:4204
RLNVEVDAAPTVDLNQVLNETRNQY,     SEQ ID NO:4205
RLNVEVDTAPTVDLNQVLNETRNQY,     SEQ ID NO:4206
RLNVEVDAAPTVDLNRVLNETRNQY,     SEQ ID NO:4207
RLNVEVDTAPTVDLNRVLNETRNQY,     SEQ ID NO:4208
LNVEVDAAPTVDLNQVLNETRSQYE,     SEQ ID NO:4209
LNVEVDTAPTVDLNQVLNETRSQYE,     SEQ ID NO:4210
LNVEVDAAPTVDLNRVLNETRSQYE,     SEQ ID NO:4211
LNVEVDTAPTVDLNRVLNETRSQYE,     SEQ ID NO:4212
LNVEVDAAPTVDLNQVLNETRNQYE,     SEQ ID NO:4213
LNVEVDTAPTVDLNQVLNETRNQYE,     SEQ ID NO:4214
LNVEVDAAPTVDLNRVLNETRNQYE,     SEQ ID NO:4215
LNVEVDTAPTVDLNRVLNETRNQYE,     SEQ ID NO:4216
NVEVDAAPTVDLNQVLNETRSQYEA,     SEQ ID NO:4217
NVEVDTAPTVDLNQVLNETRSQYEA,     SEQ ID NO:4218
NVEVDAAPTVDLNRVLNETRSQYEA,     SEQ ID NO:4219
NVEVDTAPTVDLNRVLNETRSQYEA,     SEQ ID NO:4220
NVEVDAAPTVDLNQVLNETRNQYEA,     SEQ ID NO:4221
NVEVDTAPTVDLNQVLNETRNQYEA,     SEQ ID NO:4222
NVEVDAAPTVDLNRVLNETRNQYEA,     SEQ ID NO:4223
NVEVDTAPTVDLNRVLNETRNQYEA,     SEQ ID NO:4224
VEVDAAPTVDLNQVLNETRSQYEAL,     SEQ ID NO:4225
VEVDTAPTVDLNQVLNETRSQYEAL,     SEQ ID NO:4226
VEVDAAPTVDLNRVLNETRSQYEAL,     SEQ ID NO:4227
VEVDTAPTVDLNRVLNETRSQYEAL,     SEQ ID NO:4228
VEVDAAPTVDLNQVLNETRNQYEAL,     SEQ ID NO:4229
VEVDTAPTVDLNQVLNETRNQYEAL,     SEQ ID NO:4230
VEVDAAPTVDLNRVLNETRNQYEAL,     SEQ ID NO:4231
VEVDTAPTVDLNRVLNETRNQYEAL,     SEQ ID NO:4232
EVNTLRCQLGDRLNVEVDAAPTVDLN,    SEQ ID NO:4233
EVNTLRSQLGDRLNVEVDAAPTVDLN,    SEQ ID NO:4234
EVNTLRCPLGDRLNVEVDAAPTVDLN,    SEQ ID NO:4235
EVNTLRSPLGDRLNVEVDAAPTVDLN,    SEQ ID NO:4236
EVNTLRCQLGDRLNVEVDTAPTVDLN,    SEQ ID NO:4237
EVNTLRSQLGDRLNVEVDTAPTVDLN,    SEQ ID NO:4238
EVNTLRCPLGDRLNVEVDTAPTVDLN,    SEQ ID NO:4239
EVNTLRSPLGDRLNVEVDTAPTVDLN,    SEQ ID NO:4240
VNTLRCQLGDRLNVEVDAAPTVDLNQ,    SEQ ID NO:4241
VNTLRSQLGDRLNVEVDAAPTVDLNQ,    SEQ ID NO:4242
VNTLRCPLGDRLNVEVDAAPTVDLNQ,    SEQ ID NO:4243
VNTLRSPLGDRLNVEVDAAPTVDLNQ,    SEQ ID NO:4244
VNTLRCQLGDRLNVEVDTAPTVDLNQ,    SEQ ID NO:4245
VNTLRSQLGDRLNVEVDTAPTVDLNQ,    SEQ ID NO:4246
VNTLRCPLGDRLNVEVDTAPTVDLNQ,    SEQ ID NO:4247
VNTLRSPLGDRLNVEVDTAPTVDLNQ,    SEQ ID NO:4248
VNTLRCQLGDRLNVEVDAAPTVDLNR,    SEQ ID NO:4249
VNTLRSQLGDRLNVEVDAAPTVDLNR,    SEQ ID NO:4250
VNTLRCPLGDRLNVEVDAAPTVDLNR,    SEQ ID NO:4251
VNTLRSPLGDRLNVEVDAAPTVDLNR,    SEQ ID NO:4252
VNTLRCQLGDRLNVEVDTAPTVDLNR,    SEQ ID NO:4253
VNTLRSQLGDRLNVEVDTAPTVDLNR,    SEQ ID NO:4254
VNTLRCPLGDRLNVEVDTAPTVDLNR,    SEQ ID NO:4255
VNTLRSPLGDRLNVEVDTAPTVDLNR,    SEQ ID NO:4256
NTLRCQLGDRLNVEVDAAPTVDLNQV,    SEQ ID NO:4257
NTLRSQLGDRLNVEVDAAPTVDLNQV,    SEQ ID NO:4258
NTLRCPLGDRLNVEVDAAPTVDLNQV,    SEQ ID NO:4259
NTLRSPLGDRLNVEVDAAPTVDLNQV,    SEQ ID NO:4260
NTLRCQLGDRLNVEVDTAPTVDLNQV,    SEQ ID NO:4261
```

```
NTLRSQLGDRLNVEVDTAPTVDLNQV,   SEQ ID NO:4262
NTLRCPLGDRLNVEVDTAPTVDLNQV,   SEQ ID NO:4263
NTLRSPLGDRLNVEVDTAPTVDLNQV,   SEQ ID NO:4264
NTLRCQLGDRLNVEVDAAPTVDLNRV,   SEQ ID NO:4265
NTLRSQLGDRLNVEVDAAPTVDLNRV,   SEQ ID NO:4266
NTLRCPLGDRLNVEVDAAPTVDLNRV,   SEQ ID NO:4267
NTLRSPLGDRLNVEVDAAPTVDLNRV,   SEQ ID NO:4268
NTLRCQLGDRLNVEVDTAPTVDLNRV,   SEQ ID NO:4269
NTLRSQLGDRLNVEVDTAPTVDLNRV,   SEQ ID NO:4270
NTLRCPLGDRLNVEVDTAPTVDLNRV,   SEQ ID NO:4271
NTLRSPLGDRLNVEVDTAPTVDLNRV,   SEQ ID NO:4272
TLRCQLGDRLNVEVDAAPTVDLNQVL,   SEQ ID NO:4273
TLRSQLGDRLNVEVDAAPTVDLNQVL,   SEQ ID NO:4274
TLRCPLGDRLNVEVDAAPTVDLNQVL,   SEQ ID NO:4275
TLRSPLGDRLNVEVDAAPTVDLNQVL,   SEQ ID NO:4276
TLRCQLGDRLNVEVDTAPTVDLNQVL,   SEQ ID NO:4277
TLRSQLGDRLNVEVDTAPTVDLNQVL,   SEQ ID NO:4278
TLRCPLGDRLNVEVDTAPTVDLNQVL,   SEQ ID NO:4279
TLRSPLGDRLNVEVDTAPTVDLNQVL,   SEQ ID NO:4280
TLRCQLGDRLNVEVDAAPTVDLNRVL,   SEQ ID NO:4281
TLRSQLGDRLNVEVDAAPTVDLNRVL,   SEQ ID NO:4282
TLRCPLGDRLNVEVDAAPTVDLNRVL,   SEQ ID NO:4283
TLRSPLGDRLNVEVDAAPTVDLNRVL,   SEQ ID NO:4284
TLRCQLGDRLNVEVDTAPTVDLNRVL,   SEQ ID NO:4285
TLRSQLGDRLNVEVDTAPTVDLNRVL,   SEQ ID NO:4286
TLRCPLGDRLNVEVDTAPTVDLNRVL,   SEQ ID NO:4287
TLRSPLGDRLNVEVDTAPTVDLNRVL,   SEQ ID NO:4288
LRCQLGDRLNVEVDAAPTVDLNQVLN,   SEQ ID NO:4289
LRSQLGDRLNVEVDAAPTVDLNQVLN,   SEQ ID NO:4290
LRCPLGDRLNVEVDAAPTVDLNQVLN,   SEQ ID NO:4291
LRSPLGDRLNVEVDAAPTVDLNQVLN,   SEQ ID NO:4292
LRCQLGDRLNVEVDTAPTVDLNQVLN,   SEQ ID NO:4293
LRSQLGDRLNVEVDTAPTVDLNQVLN,   SEQ ID NO:4294
LRCPLGDRLNVEVDTAPTVDLNQVLN,   SEQ ID NO:4295
LRSPLGDRLNVEVDTAPTVDLNQVLN,   SEQ ID NO:4296
LRCQLGDRLNVEVDAAPTVDLNRVLN,   SEQ ID NO:4297
LRSQLGDRLNVEVDAAPTVDLNRVLN,   SEQ ID NO:4298
LRCPLGDRLNVEVDAAPTVDLNRVLN,   SEQ ID NO:4299
LRSPLGDRLNVEVDAAPTVDLNRVLN,   SEQ ID NO:4300
LRCQLGDRLNVEVDTAPTVDLNRVLN,   SEQ ID NO:4301
LRSQLGDRLNVEVDTAPTVDLNRVLN,   SEQ ID NO:4302
LRCPLGDRLNVEVDTAPTVDLNRVLN,   SEQ ID NO:4303
LRSPLGDRLNVEVDTAPTVDLNRVLN,   SEQ ID NO:4304
RCQLGDRLNVEVDAAPTVDLNQVLNE,   SEQ ID NO:4305
RSQLGDRLNVEVDAAPTVDLNQVLNE,   SEQ ID NO:4306
RCPLGDRLNVEVDAAPTVDLNQVLNE,   SEQ ID NO:4307
RSPLGDRLNVEVDAAPTVDLNQVLNE,   SEQ ID NO:4308
RCQLGDRLNVEVDTAPTVDLNQVLNE,   SEQ ID NO:4309
RSQLGDRLNVEVDTAPTVDLNQVLNE,   SEQ ID NO:4310
RCPLGDRLNVEVDTAPTVDLNQVLNE,   SEQ ID NO:4311
RSPLGDRLNVEVDTAPTVDLNQVLNE,   SEQ ID NO:4312
RCQLGDRLNVEVDAAPTVDLNRVLNE,   SEQ ID NO:4313
RSQLGDRLNVEVDAAPTVDLNRVLNE,   SEQ ID NO:4314
RCPLGDRLNVEVDAAPTVDLNRVLNE,   SEQ ID NO:4315
RSPLGDRLNVEVDAAPTVDLNRVLNE,   SEQ ID NO:4316
RCQLGDRLNVEVDTAPTVDLNRVLNE,   SEQ ID NO:4317
RSQLGDRLNVEVDTAPTVDLNRVLNE,   SEQ ID NO:4318
RCPLGDRLNVEVDTAPTVDLNRVLNE,   SEQ ID NO:4319
RSPLGDRLNVEVDTAPTVDLNRVLNE,   SEQ ID NO:4320
CQLGDRLNVEVDAAPTVDLNQVLNET,   SEQ ID NO:4321
SQLGDRLNVEVDAAPTVDLNQVLNET,   SEQ ID NO:4322
CPLGDRLNVEVDAAPTVDLNQVLNET,   SEQ ID NO:4323
SPLGDRLNVEVDAAPTVDLNQVLNET,   SEQ ID NO:4324
CQLGDRLNVEVDTAPTVDLNQVLNET,   SEQ ID NO:4325
SQLGDRLNVEVDTAPTVDLNQVLNET,   SEQ ID NO:4326
CPLGDRLNVEVDTAPTVDLNQVLNET,   SEQ ID NO:4327
SPLGDRLNVEVDTAPTVDLNQVLNET,   SEQ ID NO:4328
CQLGDRLNVEVDAAPTVDLNRVLNET,   SEQ ID NO:4329
SQLGDRLNVEVDAAPTVDLNRVLNET,   SEQ ID NO:4330
CPLGDRLNVEVDAAPTVDLNRVLNET,   SEQ ID NO:4331
SPLGDRLNVEVDAAPTVDLNRVLNET,   SEQ ID NO:4332
CQLGDRLNVEVDTAPTVDLNRVLNET,   SEQ ID NO:4333
SQLGDRLNVEVDTAPTVDLNRVLNET,   SEQ ID NO:4334
CPLGDRLNVEVDTAPTVDLNRVLNET,   SEQ ID NO:4335
SPLGDRLNVEVDTAPTVDLNRVLNET,   SEQ ID NO:4336
QLGDRLNVEVDAAPTVDLNQVLNETR,   SEQ ID NO:4337
PLGDRLNVEVDAAPTVDLNQVLNETR,   SEQ ID NO:4338
QLGDRLNVEVDTAPTVDLNQVLNETR,   SEQ ID NO:4339
PLGDRLNVEVDTAPTVDLNQVLNETR,   SEQ ID NO:4340
QLGDRLNVEVDAAPTVDLNRVLNETR,   SEQ ID NO:4341
```

-continued

```
PLGDRLNVEVDAAPTVDLNRVLNETR,    SEQ ID NO:4342
QLGDRLNVEVDTAPTVDLNRVLNETR,    SEQ ID NO:4343
PLGDRLNVEVDTAPTVDLNRVLNETR,    SEQ ID NO:4344
LGDRLNVEVDAAPTVDLNQVLNETRS,    SEQ ID NO:4345
LGDRLNVEVDTAPTVDLNQVLNETRS,    SEQ ID NO:4346
LGDRLNVEVDAAPTVDLNRVLNETRS,    SEQ ID NO:4347
LGDRLNVEVDTAPTVDLNRVLNETRS,    SEQ ID NO:4348
LGDRLNVEVDAAPTVDLNQVLNETRN,    SEQ ID NO:4349
LGDRLNVEVDTAPTVDLNQVLNETRN,    SEQ ID NO:4350
LGDRLNVEVDAAPTVDLNRVLNETRN,    SEQ ID NO:4351
LGDRLNVEVDTAPTVDLNRVLNETRN,    SEQ ID NO:4352
GDRLNVEVDAAPTVDLNQVLNETRSQ,    SEQ ID NO:4353
GDRLNVEVDTAPTVDLNQVLNETRSQ,    SEQ ID NO:4354
GDRLNVEVDAAPTVDLNRVLNETRSQ,    SEQ ID NO:4355
GDRLNVEVDTAPTVDLNRVLNETRSQ,    SEQ ID NO:4356
GDRLNVEVDAAPTVDLNQVLNETRNQ,    SEQ ID NO:4357
GDRLNVEVDTAPTVDLNQVLNETRNQ,    SEQ ID NO:4358
GDRLNVEVDAAPTVDLNRVLNETRNQ,    SEQ ID NO:4359
GDRLNVEVDTAPTVDLNRVLNETRNQ,    SEQ ID NO:4360
DRLNVEVDAAPTVDLNQVLNETRSQY,    SEQ ID NO:4361
DRLNVEVDTAPTVDLNQVLNETRSQY,    SEQ ID NO:4362
DRLNVEVDANPTVDLNRVLNETRSQY,    SEQ ID NO:4363
DRLNVEVDTAPTVDLNRVLNETRSQY,    SEQ ID NO:4364
DRLNVEVDAAPTVDLNQVLNETRNQY,    SEQ ID NO:4365
DRLNVEVDTAPTVDLNQVLNETRNQY,    SEQ ID NO:4366
DRLNVEVDAAPTVDLNRVLNETRNQY,    SEQ ID NO:4367
DRLNVEVDTAPTVDLNRVLNETRNQY,    SEQ ID NO:4368
RLNVEVDAAPTVDLNQVLNETRSQYE,    SEQ ID NO:4369
RLNVEVDTAPTVDLNQVLNETRSQYE,    SEQ ID NO:4370
RLNVEVDAAPTVDLNRVLNETRSQYE,    SEQ ID NO:4371
RLNVEVDTAPTVDLNRVLNETRSQYE,    SEQ ID NO:4372
RLNVEVDAAPTVDLNQVLNETRNQYE,    SEQ ID NO:4373
RLNVEVDTAPTVDLNQVLNETRNQYE,    SEQ ID NO:4374
RLNVEVDAAPTVDLNRVLNETRNQYE,    SEQ ID NO:4375
RLNVEVDTAPTVDLNRVLNETRNQYE,    SEQ ID NO:4376
LNVEVDAAPTVDLNQVLNETRSQYEA,    SEQ ID NO:4377
LNVEVDTAPTVDLNQVLNETRSQYEA,    SEQ ID NO:4378
LNVEVDAAPTVDLNRVLNETRSQYEA,    SEQ ID NO:4379
LNVEVDTAPTVDLNRVLNETRSQYEA,    SEQ ID NO:4380
LNVEVDAAPTVDLNQVLNETRNQYEA,    SEQ ID NO:4381
LNVEVDTAPTVDLNQVLNETRNQYEA,    SEQ ID NO:4382
LNVEVDAAPTVDLNRVLNETRNQYEA,    SEQ ID NO:4383
LNVEVDTAPTVDLNRVLNETRNQYEA,    SEQ ID NO:4384
NVEVDAAPTVDLNQVLNETRSQYEAL,    SEQ ID NO:4385
NVEVDTAPTVDLNQVLNETRSQYEAL,    SEQ ID NO:4386
NVEVDAAPTVDLNRVLNETRSQYEAL,    SEQ ID NO:4387
NVEVDTAPTVDLNRVLNETRSQYEAL,    SEQ ID NO:4388
NVEVDAAPTVDLNQVLNETRNQYEAL,    SEQ ID NO:4389
NVEVDTAPTVDLNQVLNETRNQYEAL,    SEQ ID NO:4390
NVEVDAAPTVDLNRVLNETRNQYEAL,    SEQ ID NO:4391
NVEVDTAPTVDLNRVLNETRNQYEAL,    SEQ ID NO:4392
EVNTLRCQLGDRLNVEVDAAPTVDLNQ,   SEQ ID NO:4393
EVNTLRSQLGDRLNVEVDAAPTVDLNQ,   SEQ ID NO:4394
EVNTLRCPLGDRLNVEVDAAPTVDLNQ,   SEQ ID NO:4395
EVNTLRSPLGDRLNVEVDAAPTVDLNQ,   SEQ ID NO:4396
EVNTLRCQLGDRLNVEVDTAPTVDLNQ,   SEQ ID NO:4397
EVNTLRSQLGDRLNVEVDTAPTVDLNQ,   SEQ ID NO:4398
EVNTLRCPLGDRLNVEVDTAPTVDLNQ,   SEQ ID NO:4399
EVNTLRSPLGDRLNVEVDTAPTVDLNQ,   SEQ ID NO:4400
EVNTLRCQLGDRLNVEVDAAPTVDLNR,   SEQ ID NO:4401
EVNTLRSQLGDRLNVEVDAAPTVDLNR,   SEQ ID NO:4402
EVNTLRCPLGDRLNVEVDAAPTVDLNR,   SEQ ID NO:4403
EVNTLRSPLGDRLNVEVDAAPTVDLNR,   SEQ ID NO:4404
EVNTLRCQLGDRLNVEVDTAPTVDLNR,   SEQ ID NO:4405
EVNTLRSQLGDRLNVEVDTAPTVDLNR,   SEQ ID NO:4406
EVNTLRCPLGDRLNVEVDTAPTVDLNR,   SEQ ID NO:4407
EVNTLRSPLGDRLNVEVDTAPTVDLNR,   SEQ ID NO:4408
VNTLRCQLGDRLNVEVDAAPTVDLNQV,   SEQ ID NO:4409
VNTLRSQLGDRLNVEVDAAPTVDLNQV,   SEQ ID NO:4410
VNTLRCPLGDRLNVEVDAAPTVDLNQV,   SEQ ID NO:4411
VNTLRSPLGDRLNVEVDAAPTVDLNQV,   SEQ ID NO:4412
VNTLRCQLGDRLNVEVDTAPTVDLNQV,   SEQ ID NO:4413
VNTLRSQLGDRLNVEVDTAPTVDLNQV,   SEQ ID NO:4414
VNTLRCPLGDRLNVEVDTAPTVDLNQV,   SEQ ID NO:4415
VNTLRSPLGDRLNVEVDTAPTVDLNQV,   SEQ ID NO:4416
VNTLRCQLGDRLNVEVDAAPTVDLNRV,   SEQ ID NO:4417
VNTLRSQLGDRLNVEVDAAPTVDLNRV,   SEQ ID NO:4418
VNTLRCPLGDRLNVEVDAAPTVDLNRV,   SEQ ID NO:4419
VNTLRSPLGDRLNVEVDAAPTVDLNRV,   SEQ ID NO:4420
VNTLRCQLGDRLNVEVDTAPTVDLNRV,   SEQ ID NO:4421
```

```
VNTLRSQLGDRLNVEVDTAPTVDLNRV,   SEQ ID NO:4422
VNTLRCPLGDRLNVEVDTAPTVDLNRV,   SEQ ID NO:4423
VNTLRSPLGDRLNVEVDTAPTVDLNRV,   SEQ ID NO:4424
NTLRCQLGDRLNVEVDAAPTVDLNQVL,   SEQ ID NO:4425
NTLRSQLGDRLNVEVDAAPTVDLNQVL,   SEQ ID NO:4426
NTLRCPLGDRLNVEVDAAPTVDLNQVL,   SEQ ID NO:4427
NTLRSPLGDRLNVEVDAAPTVDLNQVL,   SEQ ID NO:4428
NTLRCQLGDRLNVEVDTAPTVDLNQVL,   SEQ ID NO:4429
NTLRSQLGDRLNVEVDTAPTVDLNQVL,   SEQ ID NO:4430
NTLRCPLGDRLNVEVDTAPTVDLNQVL,   SEQ ID NO:4431
NTLRSPLGDRLNVEVDTAPTVDLNQVL,   SEQ ID NO:4432
NTLRCQLGDRLNVEVDAAPTVDLNRVL,   SEQ ID NO:4433
NTLRSQLGDRLNVEVDAAPTVDLNRVL,   SEQ ID NO:4434
NTLRCPLGDRLNVEVDAAPTVDLNRVL,   SEQ ID NO:4435
NTLRSPLGDRLNVEVDAAPTVDLNRVL,   SEQ ID NO:4436
NTLRCQLGDRLNVEVDTAPTVDLNRVL,   SEQ ID NO:4437
NTLRSQLGDRLNVEVDTAPTVDLNRVL,   SEQ ID NO:4438
NTLRCPLGDRLNVEVDTAPTVDLNRVL,   SEQ ID NO:4439
NTLRSPLGDRLNVEVDTAPTVDLNRVL,   SEQ ID NO:4440
TLRCQLGDRLNVEVDAAPTVDLNQVLN,   SEQ ID NO:4441
TLRSQLGDRLNVEVDAAPTVDLNQVLN,   SEQ ID NO:4442
TLRCPLGDRLNVEVDAAPTVDLNQVLN,   SEQ ID NO:4443
TLRSPLGDRLNVEVDAAPTVDLNQVLN,   SEQ ID NO:4444
TLRCQLGDRLNVEVDTAPTVDLNQVLN,   SEQ ID NO:4445
TLRSQLGDRLNVEVDTAPTVDLNQVLN,   SEQ ID NO:4446
TLRCPLGDRLNVEVDTAPTVDLNQVLN,   SEQ ID NO:4447
TLRSPLGDRLNVEVDTAPTVDLNQVLN,   SEQ ID NO:4448
TLRCQLGDRLNVEVDAAPTVDLNRVLN,   SEQ ID NO:4449
TLRSQLGDRLNVEVDAAPTVDLNRVLN,   SEQ ID NO:4450
TLRCPLGDRLNVEVDAAPTVDLNRVLN,   SEQ ID NO:4451
TLRSPLGDRLNVEVDAAPTVDLNRVLN,   SEQ ID NO:4452
TLRCQLGDRLNVEVDTAPTVDLNRVLN,   SEQ ID NO:4453
TLRSQLGDRLNVEVDTAPTVDLNRVLN,   SEQ ID NO:4454
TLRCPLGDRLNVEVDTAPTVDLNRVLN,   SEQ ID NO:4455
TLRSPLGDRLNVEVDTAPTVDLNRVLN,   SEQ ID NO:4456
LRCQLGDRLNVEVDAAPTVDLNQVLNE,   SEQ ID NO:4457
LRSQLGDRLNVEVDAAPTVDLNQVLNE,   SEQ ID NO:4458
LRCPLGDRLNVEVDAAPTVDLNQVLNE,   SEQ ID NO:4459
LRSPLGDRLNVEVDAAPTVDLNQVLNE,   SEQ ID NO:4460
LRCQLGDRLNVEVDTAPTVDLNQVLNE,   SEQ ID NO:4461
LRSQLGDRLNVEVDTAPTVDLNQVLNE,   SEQ ID NO:4462
LRCPLGDRLNVEVDTAPTVDLNQVLNE,   SEQ ID NO:4463
LRSPLGDRLNVEVDTAPTVDLNQVLNE,   SEQ ID NO:4464
LRCQLGDRLNVEVDAAPTVDLNRVLNE,   SEQ ID NO:4465
LRSQLGDRLNVEVDAAPTVDLNRVLNE,   SEQ ID NO:4466
LRCPLGDRLNVEVDAAPTVDLNRVLNE,   SEQ ID NO:4467
LRSPLGDRLNVEVDAAPTVDLNRVLNE,   SEQ ID NO:4468
LRCQLGDRLNVEVDTAPTVDLNRVLNE,   SEQ ID NO:4469
LRSQLGDRLNVEVDTAPTVDLNRVLNE,   SEQ ID NO:4470
LRCPLGDRLNVEVDTAPTVDLNRVLNE,   SEQ ID NO:4471
LRSPLGDRLNVEVDTAPTVDLNRVLNE,   SEQ ID NO:4472
RCQLGDRLNVEVDAAPTVDLNQVLNET,   SEQ ID NO:4473
RSQLGDRLNVEVDAAPTVDLNQVLNET,   SEQ ID NO:4474
RCPLGDRLNVEVDAAPTVDLNQVLNET,   SEQ ID NO:4475
RSPLGDRLNVEVDAAPTVDLNQVLNET,   SEQ ID NO:4476
RCQLGDRLNVEVDTAPTVDLNQVLNET,   SEQ ID NO:4477
RSQLGDRLNVEVDTAPTVDLNQVLNET,   SEQ ID NO:4478
RCPLGDRLNVEVDTAPTVDLNQVLNET,   SEQ ID NO:4479
RSPLGDRLNVEVDTAPTVDLNQVLNET,   SEQ ID NO:4480
RCQLGDRLNVEVDAAPTVDLNRVLNET,   SEQ ID NO:4481
RSQLGDRLNVEVDAAPTVDLNRVLNET,   SEQ ID NO:4482
RCPLGDRLNVEVDAAPTVDLNRVLNET,   SEQ ID NO:4483
RSPLGDRLNVEVDAAPTVDLNRVLNET,   SEQ ID NO:4484
RCQLGDRLNVEVDTAPTVDLNRVLNET,   SEQ ID NO:4485
RSQLGDRLNVEVDTAPTVDLNRVLNET,   SEQ ID NO:4486
RCPLGDRLNVEVDTAPTVDLNRVLNET,   SEQ ID NO:4487
RSPLGDRLNVEVDTAPTVDLNRVLNET,   SEQ ID NO:4488
CQLGDRLNVEVDAAPTVDLNQVLNETR,   SEQ ID NO:4489
SQLGDRLNVEVDAAPTVDLNQVLNETR,   SEQ ID NO:4490
CPLGDRLNVEVDAAPTVDLNQVLNETR,   SEQ ID NO:4491
SPLGDRLNVEVDAAPTVDLNQVLNETR,   SEQ ID NO:4492
CQLGDRLNVEVDTAPTVDLNQVLNETR,   SEQ ID NO:4493
SQLGDRLNVEVDTAPTVDLNQVLNETR,   SEQ ID NO:4494
CPLGDRLNVEVDTAPTVDLNQVLNETR,   SEQ ID NO:4495
SPLGDRLNVEVDTAPTVDLNQVLNETR,   SEQ ID NO:4496
CQLGDRLNVEVDAAPTVDLNRVLNETR,   SEQ ID NO:4497
SQLGDRLNVEVDAAPTVDLNRVLNETR,   SEQ ID NO:4498
CPLGDRLNVEVDAAPTVDLNRVLNETR,   SEQ ID NO:4499
SPLGDRLNVEVDAAPTVDLNRVLNETR,   SEQ ID NO:4500
CQLGDRLNVEVDTAPTVDLNRVLNETR,   SEQ ID NO:4501
```

-continued

```
SQLGDRLNVEVDTAPTVDLNRVLNETR,    SEQ ID NO:4502
CPLGDRLNVEVDTAPTVDLNRVLNETR,    SEQ ID NO:4503
SPLGDRLNVEVDTAPTVDLNRVLNETR,    SEQ ID NO:4504
QLGDRLNVEVDAAPTVDLNQVLNETRS,    SEQ ID NO:4505
PLGDRLNVEVDAAPTVDLNQVLNETRS,    SEQ ID NO:4506
QLGDRLNVEVDTAPTVDLNQVLNETRS,    SEQ ID NO:4507
PLGDRLNVEVDTAPTVDLNQVLNETRS,    SEQ ID NO:4508
QLGDRLNVEVDAAPTVDLNRVLNETRS,    SEQ ID NO:4509
PLGDRLNVEVDAAPTVDLNRVLNETRS,    SEQ ID NO:4510
QLGDRLNVEVDTAPTVDLNRVLNETRS,    SEQ ID NO:4511
PLGDRLNVEVDTAPTVDLNRVLNETRS,    SEQ ID NO:4512
QLGDRLNVEVDAAPTVDLNQVLNETRN,    SEQ ID NO:4513
PLGDRLNVEVDAAPTVDLNQVLNETRN,    SEQ ID NO:4514
QLGDRLNVEVDTAPTVDLNQVLNETRN,    SEQ ID NO:4515
PLGDRLNVEVDTAPTVDLNQVLNETRN,    SEQ ID NO:4516
QLGDRLNVEVDAAPTVDLNRVLNETRN,    SEQ ID NO:4517
PLGDRLNVEVDAAPTVDLNRVLNETRN,    SEQ ID NO:4518
QLGDRLNVEVDTAPTVDLNRVLNETRN,    SEQ ID NO:4519
PLGDRLNVEVDTAPTVDLNRVLNETRN,    SEQ ID NO:4520
LGDRLNVEVDAAPTVDLNQVLNETRSQ,    SEQ ID NO:4521
LGDRLNVEVDTAPTVDLNQVLNETRSQ,    SEQ ID NO:4522
LGDRLNVEVDAAPTVDLNRVLNETRSQ,    SEQ ID NO:4523
LGDRLNVEVDTAPTVDLNRVLNETRSQ,    SEQ ID NO :4524
LGDRLNVEVDAAPTVDLNQVLNETRNQ,    SEQ ID NO:4525
LGDRLNVEVDTAPTVDLNQVLNETRNQ,    SEQ ID NO:4526
LGDRLNVEVDAAPTVDLNRVLNETRNQ,    SEQ ID NO:4527
LGDRLNVEVDTAPTVDLNRVLNETRNQ,    SEQ ID NO:4528
GDRLNVEVDAAPTVDLNQVLNETRSQY,    SEQ ID NO:4529
GDRLNVEVDTAPTVDLNQVLNETRSQY,    SEQ ID NO:4530
GDRLNVEVDAAPTVDLNRVLNETRSQY,    SEQ ID NO:4531
GDRLNVEVDTAPTVDLNRVLNETRSQY,    SEQ ID NO:4532
GDRLNVEVDAAPTVDLNQVLNETRNQY,    SEQ ID NO:4533
GDRLNVEVDTAPTVDLNQVLNETRNQY,    SEQ ID NO:4534
GDRLNVEVDAAPTVDLNRVLNETRNQY,    SEQ ID NO:4535
GDRLNVEVDTAPTVDLNRVLNETRNQY,    SEQ ID NO:4536
DRLNVEVDAAPTVDLNQVLNETRSQYE,    SEQ ID NO:4537
DRLNVEVDTAPTVDLNQVLNETRSQYE,    SEQ ID NO:4538
DRLNVEVDAAPTVDLNRVLNETRSQYE,    SEQ ID NO:4539
DRLNVEVDTAPTVDLNRVLNETRSQYE,    SEQ ID NO:4540
DRLNVEVDAAPTVDLNQVLNETRNQYE,    SEQ ID NO:4541
DRLNVEVDTAPTVDLNQVLNETRNQYE,    SEQ ID NO:4542
DRLNVEVDAAPTVDLNRVLNETRNQYE,    SEQ ID NO:4543
DRLNVEVDTAPTVDLNRVLNETRNQYE,    SEQ ID NO:4544
RLNVEVDAAPTVDLNQVLNETRSQYEA,    SEQ ID NO:4545
RLNVEVDTAPTVDLNQVLNETRSQYEA,    SEQ ID NO:4546
RLNVEVDAAPTVDLNRVLNETRSQYEA,    SEQ ID NO:4547
RLNVEVDTAPTVDLNRVLNETRSQYEA,    SEQ ID NO:4548
RLNVEVDAAPTVDLNQVLNETRNQYEA,    SEQ ID NO:4549
RLNVEVDTAPTVDLNQVLNETRNQYEA,    SEQ ID NO:4550
RLNVEVDAAPTVDLNRVLNETRNQYEA,    SEQ ID NO:4551
RLNVEVDTAPTVDLNRVLNETRNQYEA,    SEQ ID NO:4552
LNVEVDAAPTVDLNQVLNETRSQYEAL,    SEQ ID NO:4553
LNVEVDTAPTVDLNQVLNETRSQYEAL,    SEQ ID NO:4554
LNVEVDAAPTVDLNRVLNETRSQYEAL,    SEQ ID NO:4555
LNVEVDTAPTVDLNRVLNETRSQYEAL,    SEQ ID NO:4556
LNVEVDAAPTVDLNQVLNETRNQYEAL,    SEQ ID NO:4557
LNVEVDTAPTVDLNQVLNETRNQYEAL,    SEQ ID NO:4558
LNVEVDAAPTVDLNRVLNETRNQYEAL,    SEQ ID NO:4559
LNVEVDTAPTVDLNRVLNETRNQYEAL,    SEQ ID NO:4560
EVNTLRCQLGDRLNVEVDAAPTVDLNQV,   SEQ ID NO:4561
EVNTLRSQLGDRLNVEVDAAPTVDLNQV,   SEQ ID NO:4562
EVNTLRCPLGDRLNVEVDAAPTVDLNQV,   SEQ ID NO:4563
EVNTLRSPLGDRLNVEVDAAPTVDLNQV,   SEQ ID NO:4564
EVNTLRCQLGDRLNVEVDTAPTVDLNQV,   SEQ ID NO:4565
EVNTLRSQLGDRLNVEVDTAPTVDLNQV,   SEQ ID NO:4566
EVNTLRCPLGDRLNVEVDTAPTVDLNQV,   SEQ ID NO:4567
EVNTLRSPLGDRLNVEVDTAPTVDLNQV,   SEQ ID NO:4568
EVNTLRCQLGDRLNVEVDAAPTVDLNRV,   SEQ ID NO:4569
EVNTLRSQLGDRLNVEVDAAPTVDLNRV,   SEQ ID NO:4570
EVNTLRCPLGDRLNVEVDAAPTVDLNRV,   SEQ ID NO:4571
EVNTLRSPLGDRLNVEVDAAPTVDLNRV,   SEQ ID NO:4572
EVNTLRCQLGDRLNVEVDTAPTVDLNRV,   SEQ ID NO:4573
EVNTLRSQLGDRLNVEVDTAPTVDLNRV,   SEQ ID NO:4574
EVNTLRCPLGDRLNVEVDTAPTVDLNRV,   SEQ ID NO:4575
EVNTLRSPLGDRLNVEVDTAPTVDLNRV,   SEQ ID NO:4576
VNTLRCQLGDRLNVEVDAAPTVDLNQVL,   SEQ ID NO:4577
VNTLRSQLGDRLNVEVDAAPTVDLNQVL,   SEQ ID NO:4578
VNTLRCPLGDRLNVEVDAAPTVDLNQVL,   SEQ ID NO:4579
VNTLRSPLGDRLNVEVDAAPTVDLNQVL,   SEQ ID NO:4580
VNTLRCQLGDRLNVEVDTAPTVDLNQVL,   SEQ ID NO:4581
```

-continued

| Sequence | SEQ ID NO: |
|---|---|
| VNTLRSQLGDRLNVEVDTAPTVDLNQVL, | SEQ ID NO:4582 |
| VNTLRCPLGDRLNVEVDTAPTVDLNQVL, | SEQ ID NO:4583 |
| VNTLRSPLGDRLNVEVDTAPTVDLNQVL, | SEQ ID NO:4584 |
| VNTLRCQLGDRLNVEVDAAPTVDLNRVL, | SEQ ID NO:4585 |
| VNTLRSQLGDRLNVEVDAAPTVDLNRVL, | SEQ ID NO:4586 |
| VNTLRCPLGDRLNVEVDAAPTVDLNRVL, | SEQ ID NO:4587 |
| VNTLRSPLGDRLNVEVDAAPTVDLNRVL, | SEQ ID NO:4588 |
| VNTLRCQLGDRLNVEVDTAPTVDLNRVL, | SEQ ID NO:4589 |
| VNTLRSQLGDRLNVEVDTAPTVDLNRVL, | SEQ ID NO:4590 |
| VNTLRCPLGDRLNVEVDTAPTVDLNRVL, | SEQ ID NO:4591 |
| VNTLRSPLGDRLNVEVDTAPTVDLNRVL, | SEQ ID NO:4592 |
| NTLRCQLGDRLNVEVDAAPTVDLNQVLN, | SEQ ID NO:4593 |
| NTLRSQLGDRLNVEVDAAPTVDLNQVLN, | SEQ ID NO:4594 |
| NTLRCPLGDRLNVEVDAAPTVDLNQVLN, | SEQ ID NO:4595 |
| NTLRSPLGDRLNVEVDAAPTVDLNQVLN, | SEQ ID NO:4596 |
| NTLRCQLGDRLNVEVDTAPTVDLNQVLN, | SEQ ID NO:4597 |
| NTLRSQLGDRLNVEVDTAPTVDLNQVLN, | SEQ ID NO:4598 |
| NTLRCPLGDRLNVEVDTAPTVDLNQVLN, | SEQ ID NO:4599 |
| NTLRSPLGDRLNVEVDTAPTVDLNQVLN, | SEQ ID NO:4600 |
| NTLRCQLGDRLNVEVDAAPTVDLNRVLN, | SEQ ID NO:4601 |
| NTLRSQLGDRLNVEVDAAPTVDLNRVLN, | SEQ ID NO:4602 |
| NTLRCPLGDRLNVEVDAAPTVDLNRVLN, | SEQ ID NO:4603 |
| NTLRSPLGDRLNVEVDAAPTVDLNRVLN, | SEQ ID NO:4604 |
| NTLRCQLGDRLNVEVDTAPTVDLNRVLN, | SEQ ID NO:4605 |
| NTLRSQLGDRLNVEVDTAPTVDLNRVLN, | SEQ ID NO:4606 |
| NTLRCPLGDRLNVEVDTAPTVDLNRVLN, | SEQ ID NO:4607 |
| NTLRSPLGDRLNVEVDTAPTVDLNRVLN, | SEQ ID NO:4608 |
| TLRCQLGDRLNVEVDAAPTVDLNQVLNE, | SEQ ID NO:4609 |
| TLRSQLGDRLNVEVDAAPTVDLNQVLNE, | SEQ ID NO:4610 |
| TLRCPLGDRLNVEVDAAPTVDLNQVLNE, | SEQ ID NO:4611 |
| TLRSPLGDRLNVEVDAAPTVDLNQVLNE, | SEQ ID NO:4612 |
| TLRCQLGDRLNVEVDTAPTVDLNQVLNE, | SEQ ID NO:4613 |
| TLRSQLGDRLNVEVDTAPTVDLNQVLNE, | SEQ ID NO:4614 |
| TLRCPLGDRLNVEVDTAPTVDLNQVLNE, | SEQ ID NO:4615 |
| TLRSPLGDRLNVEVDTAPTVDLNQVLNE, | SEQ ID NO:4616 |
| TLRCQLGDRLNVEVDAAPTVDLNRVLNE, | SEQ ID NO:4617 |
| TLRSQLGDRLNVEVDAAPTVDLNRVLNE, | SEQ ID NO:4618 |
| TLRCPLGDRLNVEVDAAPTVDLNRVLNE, | SEQ ID NO:4619 |
| TLRSPLGDRLNVEVDAAPTVDLNRVLNE, | SEQ ID NO:4620 |
| TLRCQLGDRLNVEVDTAPTVDLNRVLNE, | SEQ ID NO:4621 |
| TLRSQLGDRLNVEVDTAPTVDLNRVLNE, | SEQ ID NO:4622 |
| TLRCPLGDRLNVEVDTAPTVDLNRVLNE, | SEQ ID NO:4623 |
| TLRSPLGDRLNVEVDTAPTVDLNRVLNE, | SEQ ID NO:4624 |
| LRCQLGDRLNVEVDAAPTVDLNQVLNET, | SEQ ID NO:4625 |
| LRSQLGDRLNVEVDAAPTVDLNQVLNET, | SEQ ID NO:4626 |
| LRCPLGDRLNVEVDAAPTVDLNQVLNET, | SEQ ID NO:4627 |
| LRSPLGDRLNVEVDAAPTVDLNQVLNET, | SEQ ID NO:4628 |
| LRCQLGDRLNVEVDTAPTVDLNQVLNET, | SEQ ID NO:4629 |
| LRSQLGDRLNVEVDTAPTVDLNQVLNET, | SEQ ID NO:4630 |
| LRCPLGDRLNVEVDTAPTVDLNQVLNET, | SEQ ID NO:4631 |
| LRSPLGDRLNVEVDTAPTVDLNQVLNET, | SEQ ID NO:4632 |
| LRCQLGDRLNVEVDAAPTVDLNRVLNET, | SEQ ID NO:4633 |
| LRSQLGDRLNVEVDAAPTVDLNRVLNET, | SEQ ID NO:4634 |
| LRCPLGDRLNVEVDAAPTVDLNRVLNET, | SEQ ID NO:4635 |
| LRSPLGDRLNVEVDAAPTVDLNRVLNET, | SEQ ID NO:4636 |
| LRCQLGDRLNVEVDTAPTVDLNRVLNET, | SEQ ID NO:4637 |
| LRSQLGDRLNVEVDTAPTVDLNRVLNET, | SEQ ID NO:4638 |
| LRCPLGDRLNVEVDTAPTVDLNRVLNET, | SEQ ID NO:4639 |
| LRSPLGDRLNVEVDTAPTVDLNRVLNET, | SEQ ID NO:4640 |
| RCQLGDRLNVEVDAAPTVDLNQVLNETR, | SEQ ID NO:4641 |
| RSQLGDRLNVEVDAAPTVDLNQVLNETR, | SEQ ID NO:4642 |
| RCPLGDRLNVEVDAAPTVDLNQVLNETR, | SEQ ID NO:4643 |
| RSPLGDRLNVEVDAAPTVDLNQVLNETR, | SEQ ID NO:4644 |
| RCQLGDRLNVEVDTAPTVDLNQVLNETR, | SEQ ID NO:4645 |
| RSQLGDRLNVEVDTAPTVDLNQVLNETR, | SEQ ID NO:4646 |
| RCPLGDRLNVEVDTAPTVDLNQVLNETR, | SEQ ID NO:4647 |
| RSPLGDRLNVEVDTAPTVDLNQVLNETR, | SEQ ID NO:4648 |
| RCQLGDRLNVEVDAAPTVDLNRVLNETR, | SEQ ID NO:4649 |
| RSQLGDRLNVEVDAAPTVDLNRVLNETR, | SEQ ID NO:4650 |
| RCPLGDRLNVEVDAAPTVDLNRVLNETR, | SEQ ID NO:4651 |
| RSPLGDRLNVEVDAAPTVDLNRVLNETR, | SEQ ID NO:4652 |
| RCQLGDRLNVEVDTAPTVDLNRVLNETR, | SEQ ID NO:4653 |
| RSQLGDRLNVEVDTAPTVDLNRVLNETR, | SEQ ID NO:4654 |
| RCPLGDRLNVEVDTAPTVDLNRVLNETR, | SEQ ID NO:4655 |
| RSPLGDRLNVEVDTAPTVDLNRVLNETR, | SEQ ID NO:4656 |
| CQLGDRLNVEVDAAPTVDLNQVLNETRS, | SEQ ID NO:4657 |
| SQLGDRLNVEVDAAPTVDLNQVLNETRS, | SEQ ID NO:4658 |
| CPLGDRLNVEVDAAPTVDLNQVLNETRS, | SEQ ID NO:4659 |
| SPLGDRLNVEVDAAPTVDLNQVLNETRS, | SEQ ID NO:4660 |
| CQLGDRLNVEVDTAPTVDLNQVLNETRS, | SEQ ID NO:4661 |

-continued

```
SQLGDRLNVEVDTAPTVDLNQVLNETRS,   SEQ ID NO:4662
CPLGDRLNVEVDTAPTVDLNQVLNETRS,   SEQ ID NO:4663
SPLGDRLNVEVDTAPTVDLNQVLNETRS,   SEQ ID NO:4664
CQLGDRLNVEVDAAPTVDLNRVLNETRS,   SEQ ID NO:4665
SQLGDRLNVEVDAAPTVDLNRVLNETRS,   SEQ ID NO:4666
CPLGDRLNVEVDAAPTVDLNRVLNETRS,   SEQ ID NO:4667
SPLGDRLNVEVDAAPTVDLNRVLNETRS,   SEQ ID NO:4668
CQLGDRLNVEVDTAPTVDLNRVLNETRS,   SEQ ID NO:4669
SQLGDRLNVEVDTAPTVDLNRVLNETRS,   SEQ ID NO:4670
CPLGDRLNVEVDTAPTVDLNRVLNETRS,   SEQ ID NO:4671
SPLGDRLNVEVDTAPTVDLNRVLNETRS,   SEQ ID NO:4672
CQLGDRLNVEVDAAPTVDLNQVLNETRN,   SEQ ID NO:4673
SQLGDRLNVEVDAAPTVDLNQVLNETRN,   SEQ ID NO:4674
CPLGDRLNVEVDAAPTVDLNQVLNETRN,   SEQ ID NO:4675
SPLGDRLNVEVDAAPTVDLNQVLNETRN,   SEQ ID NO:4676
CQLGDRLNVEVDTAPTVDLNQVLNETRN,   SEQ ID NO:4677
SQLGDRLNVEVDTAPTVDLNQVLNETRN,   SEQ ID NO:4678
CPLGDRLNVEVDTAPTVDLNQVLNETRN,   SEQ ID NO:4679
SPLGDRLNVEVDTAPTVDLNQVLNETRN,   SEQ ID NO:4680
CQLGDRLNVEVDAAPTVDLNRVLNETRN,   SEQ ID NO:4681
SQLGDRLNVEVDAAPTVDLNRVLNETRN,   SEQ ID NO:4682
CPLGDRLNVEVDAAPTVDLNRVLNETRN,   SEQ ID NO:4683
SPLGDRLNVEVDAAPTVDLNRVLNETRN,   SEQ ID NO:4684
CQLGDRLNVEVDTAPTVDLNRVLNETRN,   SEQ ID NO:4685
SQLGDRLNVEVDTAPTVDLNRVLNETRN,   SEQ ID NO:4686
CPLGDRLNVEVDTAPTVDLNRVLNETRN,   SEQ ID NO:4687
SPLGDRLNVEVDTAPTVDLNRVLNETRN,   SEQ ID NO:4688
QLGDRLNVEVDAAPTVDLNQVLNETRSQ,   SEQ ID NO:4689
PLGDRLNVEVDAAPTVDLNQVLNETRSQ,   SEQ ID NO:4690
QLGDRLNVEVDTAPTVDLNQVLNETRSQ,   SEQ ID NO:4691
PLGDRLNVEVDTAPTVDLNQVLNETRSQ,   SEQ ID NO:4692
QLGDRLNVEVDAAPTVDLNRVLNETRSQ,   SEQ ID NO:4693
PLGDRLNVEVDAAPTVDLNRVLNETRSQ,   SEQ ID NO:4694
QLGDRLNVEVDTAPTVDLNRVLNETRSQ,   SEQ ID NO:4695
PLGDRLNVEVDTAPTVDLNRVLNETRSQ,   SEQ ID NO:4696
QLGDRLNVEVDAAPTVDLNQVLNETRNQ,   SEQ ID NO:4697
PLGDRLNVEVDAAPTVDLNQVLNETRNQ,   SEQ ID NO:4698
QLGDRLNVEVDTAPTVDLNQVLNETRNQ,   SEQ ID NO:4699
PLGDRLNVEVDTAPTVDLNQVLNETRNQ,   SEQ ID NO:4700
QLGDRLNVEVDAAPTVDLNRVLNETRNQ,   SEQ ID NO:4701
PLGDRLNVEVDAAPTVDLNRVLNETRNQ,   SEQ ID NO:4702
QLGDRLNVEVDTAPTVDLNRVLNETRNQ,   SEQ ID NO:4703
PLGDRLNVEVDTAPTVDLNRVLNETRNQ,   SEQ ID NO:4704
LGDRLNVEVDAAPTVDLNQVLNETRSQY,   SEQ ID NO:4705
LGDRLNVEVDTAPTVDLNQVLNETRSQY,   SEQ ID NO:4706
LGDRLNVEVDAAPTVDLNRVLNETRSQY,   SEQ ID NO:4707
LGDRLNVEVDTAPTVDLNRVLNETRSQY,   SEQ ID NO:4708
LGDRLNVEVDAAPTVDLNQVLNETRNQY,   SEQ ID NO:4709
LGDRLNVEVDTAPTVDLNQVLNETRNQY,   SEQ ID NO:4710
LGDRLNVEVDAAPTVDLNRVLNETRNQY,   SEQ ID NO:4711
LGDRLNVEVDTAPTVDLNRVLNETRNQY,   SEQ ID NO:4712
GDRLNVEVDAAPTVDLNQVLNETRSQYE,   SEQ ID NO:4713
GDRLNVEVDTAPTVDLNQVLNETRSQYE,   SEQ ID NO:4714
GDRLNVEVDAAPTVDLNRVLNETRSQYE,   SEQ ID NO:4715
GDRLNVEVDTAPTVDLNRVLNETRSQYE,   SEQ ID NO:4716
GDRLNVEVDAAPTVDLNQVLNETRNQYE,   SEQ ID NO:4717
GDRLNVEVDTAPTVDLNQVLNETRNQYE,   SEQ ID NO:4718
GDRLNVEVDAAPTVDLNRVLNETRNQYE,   SEQ ID NO:4719
GDRLNVEVDTAPTVDLNRVLNETRNQYE,   SEQ ID NO:4720
DRLNVEVDAAPTVDLNQVLNETRSQYEA,   SEQ ID NO:4721
DRLNVEVDTAPTVDLNQVLNETRSQYEA,   SEQ ID NO:4722
DRLNVEVDAAPTVDLNRVLNETRSQYEA,   SEQ ID NO:4723
DRLNVEVDTAPTVDLNRVLNETRSQYEA,   SEQ ID NO:4724
DRLNVEVDAAPTVDLNQVLNETRNQYEA,   SEQ ID NO:4725
DRLNVEVDTAPTVDLNQVLNETRNQYEA,   SEQ ID NO:4726
DRLNVEVDAAPTVDLNRVLNETRNQYEA,   SEQ ID NO:4727
DRLNVEVDTAPTVDLNRVLNETRNQYEA,   SEQ ID NO:4728
RLNVEVDAAPTVDLNQVLNETRSQYEAL,   SEQ ID NO:4729
RLNVEVDTAPTVDLNQVLNETRSQYEAL,   SEQ ID NO:4730
RLNVEVDAAPTVDLNRVLNETRSQYEAL,   SEQ ID NO:4731
RLNVEVDTAPTVDLNRVLNETRSQYEAL,   SEQ ID NO:4732
RLNVEVDAAPTVDLNQVLNETRNQYEAL,   SEQ ID NO:4733
RLNVEVDTAPTVDLNQVLNETRNQYEAL,   SEQ ID NO:4734
RLNVEVDAAPTVDLNRVLNETRNQYEAL,   SEQ ID NO:4735
RLNVEVDTAPTVDLNRVLNETRNQYEAL,   SEQ ID NO:4736
EVNTLRCQLGDRLNVEVDAAPTVDLNQVL,  SEQ ID NO:4737
EVNTLRSQLGDRLNVEVDAAPTVDLNQVL,  SEQ ID NO:4738
EVINTLRCPLGDRLNVEVDAAPTVDLNQVL, SEQ ID NO:4739
EVNTLRSPLGDRLNVEVDAAPTVDLNQVL,  SEQ ID NO:4740
EVNTLRCQLGDRLNVEVDTAPTVDLNQVL,  SEQ ID NO:4741
```

-continued

```
EVNTLRSQLGDRLNVEVDTAPTVDLNQVL,   SEQ ID NO:4742
EVNTLRCPLGDRLNVEVDTAPTVDLNQVL,   SEQ ID NO:4743
EVNTLRSPLGDRLNVEVDTAPTVDLNQVL,   SEQ ID NO:4744
EVNTLRCQLGDRLNVEVDAAPTVDLNRVL,   SEQ ID NO:4745
EVNTLRSQLGDRLNVEVDAAPTVDLNRVL,   SEQ ID NO:4746
EVNTLRCPLGDRLNVEVDAAPTVDLNRVL,   SEQ ID NO:4747
EVNTLRSPLGDRLNVEVDAAPTVDLNRVL,   SEQ ID NO:4748
EVNTLRCQLGDRLNVEVDTAPTVDLNRVL,   SEQ ID NO:4749
EVNTLRSQLGDRLNVEVDTAPTVDLNRVL,   SEQ ID NO:4750
EVNTLRCPLGDRLNVEVDTAPTVDLNRVL,   SEQ ID NO:4751
EVNTLRSPLGDRLNVEVDTAPTVDLNRVL,   SEQ ID NO:4752
VNTLRCQLGDRLNVEVDAAPTVDLNQVLN,   SEQ ID NO:4753
VNTLRSQLGDRLNVEVDAAPTVDLNQVLN,   SEQ ID NO:4754
VNTLRCPLGDRLNVEVDAAPTVDLNQVLN,   SEQ ID NO:4755
VNTLRSPLGDRLNVEVDAAPTVDLNQVLN,   SEQ ID NO:4756
VNTLRCQLGDRLNVEVDTAPTVDLNQVLN,   SEQ ID NO:4757
VNTLRSQLGDRLNVEVDTAPTVDLNQVLN,   SEQ ID NO:4758
VNTLRCPLGDRLNVEVDTAPTVDLNQVLN,   SEQ ID NO:4759
VNTLRSPLGDRLNVEVDTAPTVDLNQVLN,   SEQ ID NO:4760
VNTLRCQLGDRLNVEVDAAPTVDLNRVLN,   SEQ ID NO:4761
VNTLRSQLGDRLNVEVDAAPTVDLNRVLN,   SEQ ID NO:4762
VNTLRCPLGDRLNVEVDAAPTVDLNRVLN,   SEQ ID NO:4763
VNTLRSPLGDRLNVEVDAAPTVDLNRVLN,   SEQ ID NO:4764
VNTLRCQLGDRLNVEVDTAPTVDLNRVLN,   SEQ ID NO:4765
VNTLRSQLGDRLNVEVDTAPTVDLNRVLN,   SEQ ID NO:4766
VNTLRCPLGDRLNVEVDTAPTVDLNRVLN,   SEQ ID NO:4767
VNTLRSPLGDRLNVEVDTAPTVDLNRVLN,   SEQ ID NO:4768
NTLRCQLGDRLNVEVDAAPTVDLNQVLNE,   SEQ ID NO:4769
NTLRSQLGDRLNVEVDAAPTVDLNQVLNE,   SEQ ID NO:4770
NTLRCPLGDRLNVEVDAAPTVDLNQVLNE,   SEQ ID NO:4771
NTLRSPLGDRLNVEVDAAPTVDLNQVLNE,   SEQ ID NO:4772
NTLRCQLGDRLNVEVDTAPTVDLNQVLNE,   SEQ ID NO:4773
NTLRSQLGDRLNVEVDTAPTVDLNQVLNE,   SEQ ID NO:4774
NTLRCPLGDRLNVEVDTAPTVDLNQVLNE,   SEQ ID NO:4775
NTLRSPLGDRLNVEVDTAPTVDLNQVLNE,   SEQ ID NO:4776
NTLRCQLGDRLNVEVDAAPTVDLNRVLNE,   SEQ ID NO:4777
NTLRSQLGDRLNVEVDAAPTVDLNRVLNE,   SEQ ID NO:4778
NTLRCPLGDRLNVEVDAAPTVDLNRVLNE,   SEQ ID NO:4779
NTLRSPLGDRLNVEVDAAPTVDLNRVLNE,   SEQ ID NO:4780
NTLRCQLGDRLNVEVDTAPTVDLNRVLNE,   SEQ ID NO:4781
NTLRSQLGDRLNVEVDTAPTVDLNRVLNE,   SEQ ID NO:4782
NTLRCPLGDRLNVEVDTAPTVDLNRVLNE,   SEQ ID NO:4783
NTLRSPLGDRLNVEVDTAPTVDLNRVLNE,   SEQ ID NO:4784
TLRCQLGDRLNVEVDAAPTVDLNQVLNET,   SEQ ID NO:4785
TLRSQLGDRLNVEVDAAPTVDLNQVLNET,   SEQ ID NO:4786
TLRCPLGDRLNVEVDAAPTVDLNQVLNET,   SEQ ID NO:4787
TLRSPLGDRLNVEVDAAPTVDLNQVLNET,   SEQ ID NO:4788
TLRCQLGDRLNVEVDTAPTVDLNQVLNET,   SEQ ID NO:4789
TLRSQLGDRLNVEVDTAPTVDLNQVLNET,   SEQ ID NO:4790
TLRCPLGDRLNVEVDTAPTVDLNQVLNET,   SEQ ID NO:4791
TLRSPLGDRLNVEVDTAPTVDLNQVLNET,   SEQ ID NO:4792
TLRCQLGDRLNVEVDAAPTVDLNRVLNET,   SEQ ID NO:4793
TLRSQLGDRLNVEVDAAPTVDLNRVLNET,   SEQ ID NO:4794
TLRCPLGDRLNVEVDAAPTVDLNRVLNET,   SEQ ID NO:4795
TLRSPLGDRLNVEVDAAPTVDLNRVLNET,   SEQ ID NO:4796
TLRCQLGDRLNVEVDTAPTVDLNRVLNET,   SEQ ID NO:4797
TLRSQLGDRLNVEVDTAPTVDLNRVLNET,   SEQ ID NO:4798
TLRCPLGDRLNVEVDTAPTVDLNRVLNET,   SEQ ID NO:4799
TLRSPLGDRLNVEVDTAPTVDLNRVLNET,   SEQ ID NO:4800
LRCQLGDRLNVEVDAAPTVDLNQVLNETR,   SEQ ID NO:4801
LRSQLGDRLNVEVDAAPTVDLNQVLNETR,   SEQ ID NO:4802
LRCPLGDRLNVEVDAAPTVDLNQVLNETR,   SEQ ID NO:4803
LRSPLGDRLNVEVDAAPTVDLNQVLNETR,   SEQ ID NO:4804
LRCQLGDRLNVEVDTAPTVDLNQVLNETR,   SEQ ID NO:4805
LRSQLGDRLNVEVDTAPTVDLNQVLNETR,   SEQ ID NO:4806
LRCPLGDRLNVEVDTAPTVDLNQVLNETR,   SEQ ID NO:4807
LRSPLGDRLNVEVDTAPTVDLNQVLNETR,   SEQ ID NO:4808
LRCQLGDRLNVEVDAAPTVDLNRVLNETR,   SEQ ID NO:4809
LRSQLGDRLNVEVDAAPTVDLNRVLNETR,   SEQ ID NO:4810
LRCPLGDRLNVEVDAAPTVDLNRVLNETR,   SEQ ID NO:4811
LRSPLGDRLNVEVDAAPTVDLNRVLNETR,   SEQ ID NO:4812
LRCQLGDRLNVEVDTAPTVDLNRVLNETR,   SEQ ID NO:4813
LRSQLGDRLNVEVDTAPTVDLNRVLNETR,   SEQ ID NO:4814
LRCPLGDRLNVEVDTAPTVDLNRVLNETR,   SEQ ID NO:4815
LRSPLGDRLNVEVDTAPTVDLNRVLNETR,   SEQ ID NO:4816
RCQLGDRLNVEVDAAPTVDLNQVLNETRS,   SEQ ID NO:4817
RSQLGDRLNVEVDAAPTVDLNQVLNETRS,   SEQ ID NO:4818
RCPLGDRLNVEVDAAPTVDLNQVLNETRS,   SEQ ID NO:4819
RSPLGDRLNVEVDAAPTVDLNQVLNETRS,   SEQ ID NO:4820
RCQLGDRLNVEVDTAPTVDLNQVLNETRS,   SEQ ID NO:4821
```

-continued

```
RSQLGDRLNVEVDTAPTVDLNQVLNETRS, SEQ ID NO:4822
RCPLGDRLNVEVDTAPTVDLNQVLNETRS, SEQ ID NO:4823
RSPLGDRLNVEVDTAPTVDLNQVLNETRS, SEQ ID NO:4824
RCQLGDRLNVEVDAAPTVDLNRVLNETRS, SEQ ID NO:4825
RSQLGDRLNVEVDAAPTVDLNRVLNETRS, SEQ ID NO:4826
RCPLGDRLNVEVDAAPTVDLNRVLNETRS, SEQ ID NO:4827
RSPLGDRLNVEVDAAPTVDLNRVLNETRS, SEQ ID NO:4828
RCQLGDRLNVEVDTAPTVDLNRVLNETRS, SEQ ID NO:4829
RSQLGDRLNVEVDTAPTVDLNRVLNETRS, SEQ ID NO:4830
RCPLGDRLNVEVDTAPTVDLNRVLNETRS, SEQ ID NO:4831
RSPLGDRLNVEVDTAPTVDLNRVLNETRS, SEQ ID NO:4832
RCQLGDRLNVEVDAAPTVDLNQVLNETRN, SEQ ID NO:4833
RSQLGDRLNVEVDAAPTVDLNQVLNETRN, SEQ ID NO:4834
RCPLGDRLNVEVDAAPTVDLNQVLNETRN, SEQ ID NO:4835
RSPLGDRLNVEVDAAPTVDLNQVLNETRN, SEQ ID NO:4836
RCQLGDRLNVEVDTAPTVDLNQVLNETRN, SEQ ID NO:4837
RSQLGDRLNVEVDTAPTVDLNQVLNETRN, SEQ ID NO:4838
RCPLGDRLNVEVDTAPTVDLNQVLNETRN, SEQ ID NO:4839
RSPLGDRLNVEVDTAPTVDLNQVLNETRN, SEQ ID NO:4840
RCQLGDRLNVEVDAAPTVDLNRVLNETRN, SEQ ID NO:4841
RSQLGDRLNVEVDAAPTVDLNRVLNETRN  SEQ ID NO:4842
RCPLGDRLNVEVDAAPTVDLNRVLNETRN, SEQ ID NO:4843
RSPLGDRLNVEVDAAPTVDLNRVLNETRN, SEQ ID NO:4844
RCQLGDRLNVEVDTAPTVDLNRVLNETRN, SEQ ID NO:4845
RSQLGDRLNVEVDTAPTVDLNRVLNETRN, SEQ ID NO:4846
RCPLGDRLNVEVDTAPTVDLNRVLNETRN, SEQ ID NO:4847
RSPLGDRLNVEVDTAPTVDLNRVLNETRN, SEQ ID NO:4848
CQLGDRLNVEVDAAPTVDLNQVLNETRSQ, SEQ ID NO:4849
SQLGDRLNVEVDAAPTVDLNQVLNETRSQ, SEQ ID NO:4850
CPLGDRLNVEVDAAPTVDLNQVLNETRSQ, SEQ ID NO:4851
SPLGDRLNVEVDAAPTVDLNQVLNETRSQ, SEQ ID NO:4852
CQLGDRLNVEVDTAPTVDLNQVLNETRSQ, SEQ ID NO:4853
SQLGDRLNVEVDTAPTVDLNQVLNETRSQ, SEQ ID NO:4854
CPLGDRLNVEVDTAPTVDLNQVLNETRSQ, SEQ ID NO:4855
SPLGDRLNVEVDTAPTVDLNQVLNETRSQ, SEQ ID NO:4856
CQLGDRLNVEVDAAPTVDLNRVLNETRSQ, SEQ ID NO:4857
SQLGDRLNVEVDAAPTVDLNRVLNETRSQ, SEQ ID NO:4858
CPLGDRLNVEVDAAPTVDLNRVLNETRSQ, SEQ ID NO:4859
SPLGDRLNVEVDAAPTVDLNRVLNETRSQ, SEQ ID NO:4860
CQLGDRLNVEVDTAPTVDLNRVLNETRSQ, SEQ ID NO:4861
SQLGDRLNVEVDTAPTVDLNRVLNETRSQ, SEQ ID NO:4862
CPLGDRLNVEVDTAPTVDLNRVLNETRSQ, SEQ ID NO:4863
SPLGDRLNVEVDTAPTVDLNRVLNETRSQ, SEQ ID NO:4864
CQLGDRLNVEVDAAPTVDLNQVLNETRNQ, SEQ ID NO:4865
SQLGDRLNVEVDAAPTVDLNQVLNETRNQ, SEQ ID NO:4866
CPLGDRLNVEVDAAPTVDLNQVLNETRNQ, SEQ ID NO:4867
SPLGDRLNVEVDAAPTVDLNQVLNETRNQ, SEQ ID NO:4868
CQLGDRLNVEVDTAPTVDLNQVLNETRNQ, SEQ ID NO:4869
SQLGDRLNVEVDTAPTVDLNQVLNETRNQ, SEQ ID NO:4870
CPLGDRLNVEVDTAPTVDLNQVLNETRNQ, SEQ ID NO:4871
SPLGDRLNVEVDTAPTVDLNQVLNETRNQ, SEQ ID NO:4872
CQLGDRLNVEVDAAPTVDLNRVLNETRNQ, SEQ ID NO:4873
SQLGDRLNVEVDAAPTVDLNRVLNETRNQ, SEQ ID NO:4874
CPLGDRLNVEVDAAPTVDLNRVLNETRNQ, SEQ ID NO:4875
SPLGDRLNVEVDAAPTVDLNRVLNETRNQ, SEQ ID NO:4876
CQLGDRLNVEVDTAPTVDLNRVLNETRNQ, SEQ ID NO:4877
SQLGDRLNVEVDTAPTVDLNRVLNETRNQ, SEQ ID NO:4878
CPLGDRLNVEVDTAPTVDLNRVLNETRNQ, SEQ ID NO:4879
SPLGDRLNVEVDTAPTVDLNRVLNETRNQ, SEQ ID NO:4880
QLGDRLNVEVDAAPTVDLNQVLNETRSQY, SEQ ID NO:4881
PLGDRLNVEVDAAPTVDLNQVLNETRSQY, SEQ ID NO:4882
QLGDRLNVEVDTAPTVDLNQVLNETRSQY, SEQ ID NO:4883
PLGDRLNVEVDTAPTVDLNQVLNETRSQY, SEQ ID NO:4884
QLGDRLNVEVDAAPTVDLNRVLNETRSQY, SEQ ID NO:4885
PLGDRLNVEVDAAPTVDLNRVLNETRSQY, SEQ ID NO:4886
QLGDRLNVEVDTAPTVDLNRVLNETRSQY, SEQ ID NO:4887
PLGDRLNVEVDTAPTVDLNRVLNETRSQY, SEQ ID NO:4888
QLGDRLNVEVDAAPTVDLNQVLNETRNQY, SEQ ID NO:4889
PLGDRLNVEVDAAPTVDLNQVLNETRNQY, SEQ ID NO:4890
QLGDRLNVEVDTAPTVDLNQVLNETRNQY, SEQ ID NO:4891
PLGDRLNVEVDTAPTVDLNQVLNETRNQY, SEQ ID NO:4892
QLGDRLNVEVDAAPTVDLNRVLNETRNQY, SEQ ID NO:4893
PLGDRLNVEVDAAPTVDLNRVLNETRNQY, SEQ ID NO:4894
QLGDRLNVEVDTAPTVDLNRVLNETRNQY, SEQ ID NO:4895
PLGDRLNVEVDTAPTVDLNRVLNETRNQY, SEQ ID NO:4896
LGDRLNVEVDAAPTVDLNQVLNETRSQYE, SEQ ID NO:4897
LGDRLNVEVDTAPTVDLNQVLNETRSQYE, SEQ ID NO:4898
LGDRLNVEVDAAPTVDLNRVLNETRSQYE, SEQ ID NO:4899
LGDRLNVEVDTAPTVDLNRVLNETRSQYE, SEQ ID NO:4900
LGDRLNVEVDAAPTVDLNQVLNETRNQYE, SEQ ID NO:4901
```

```
                                                    -continued
LGDRLNVEVDTAPTVDLNQVLNETRNQYE, SEQ ID NO:4902
LGDRLNVEVDAAPTVDLNRVLNETRNQYE, SEQ ID NO:4903
LGDRLNVEVDTAPTVDLNRVLNETRNQYE, SEQ ID NO:4904
GDRLNVEVDAAPTVDLNQVLNETRSQYEA, SEQ ID NO:4905
GDRLNVEVDTAPTVDLNQVLNETRSQYEA, SEQ ID NO:4906
GDRLNVEVDAAPTVDLNRVLNETRSQYEA, SEQ ID NO:4907
GDRLNVEVDTAPTVDLNRVLNETRSQYEA, SEQ ID NO:4908
GDRLNVEVDAAPTVDLNQVLNETRNQYEA, SEQ ID NO:4909
GDRLNVEVDTAPTVDLNQVLNETRNQYEA, SEQ ID NO:4910
GDRLNVEVDAAPTVDLNRVLNETRNQYEA, SEQ ID NO:4911
GDRLNVEVDTAPTVDLNRVLNETRNQYEA, SEQ ID NO:4912
DRLNVEVDAAPTVDLNQVLNETRSQYEAL, SEQ ID NO:4913
DRLNVEVDTAPTVDLNQVLNETRSQYEAL, SEQ ID NO:4914
DRLNVEVDAAPTVDLNRVLNETRSQYEAL, SEQ ID NO:4915
DRLNVEVDTAPTVDLNRVLNETRSQYEAL, SEQ ID NO:4916
DRLNVEVDAAPTVDLNQVLNETRNQYEAL, SEQ ID NO:4917
DRLNVEVDTAPTVDLNQVLNETRNQYEAL, SEQ ID NO:4918
DRLNVEVDAAPTVDLNRVLNETRNQYEAL, SEQ ID NO:4919
DRLNVEVDTAPTVDLNRVLNETRNQYEAL, SEQ ID NO:4920
EVNTLRCQLGDRLNVEVDAAPTVDLNQVLN, SEQ ID NO:4921
EVNTLRSQLGDRLNVEVDAAPTVDLNQVLN, SEQ ID NO:4922
EVNTLRCPLGDRLNVEVDAAPTVDLNQVLN, SEQ ID NO:4923
EVNTLRSPLGDRLNVEVDAAPTVDLNQVLN, SEQ ID NO:4924
EVNTLRCQLGDRLNVEVDTAPTVDLNQVLN, SEQ ID NO:4925
EVNTLRSQLGDRLNVEVDTAPTVDLNQVLN, SEQ ID NO:4926
EVNTLRCPLGDRLNVEVDTAPTVDLNQVLN, SEQ ID NO:4927
EVNTLRSPLGDRLNVEVDTAPTVDLNQVLN, SEQ ID NO:4928
EVNTLRCQLGDRLNVEVDAAPTVDLNRVLN, SEQ ID NO:4929
EVNTLRSQLGDRLNVEVDAAPTVDLNRVLN, SEQ ID NO:4930
EVNTLRCPLGDRLNVEVDAAPTVDLNRVLN, SEQ ID NO:4931
EVNTLRSPLGDRLNVEVDAAPTVDLNRVLN, SEQ ID NO:4932
EVNTLRCQLGDRLNVEVDTAPTVDLNRVLN, SEQ ID NO:4933
EVNTLRSQLGDRLNVEVDTAPTVDLNRVLN, SEQ ID NO:4934
EVNTLRCPLGDRLNVEVDTAPTVDLNRVLN, SEQ ID NO:4935
EVNTLRSPLGDRLNVEVDTAPTVDLNRVLN, SEQ ID NO:4936
VNTLRCQLGDRLNVEVDAAPTVDLNQVLNE, SEQ ID NO:4937
VNTLRSQLGDRLNVEVDAAPTVDLNQVLNE, SEQ 1D NO:4938
VNTLRCPLGDRLNVEVDAAPTVDLNQVLNE, SEQ ID NO:4939
VNTLRSPLGDRLNVEVDAAPTVDLNQVLNE, SEQ ID NO:4940
VNTLRCQLGDRLNVEVDTAPTVDLNQVLNE, SEQ ID NO:4941
VNTLRSQLGDRLNVEVDTAPTVDLNQVLNE, SEQ ID NO:4942
VNTLRCPLGDRLNVEVDTAPTVDLNQVLNE, SEQ ID NO:4943
VNTLRSPLGDRLNVEVDTAPTVDLNQVLNE, SEQ ID NO:4944
VNTLRCQLGDRLNVEVDAAPTVDLNRVLNE, SEQ ID NO:4945
VNTLRSQLGDRLNVEVDAAPTVDLNRVLNE, SEQ ID NO:4946
VNTLRCPLGDRLNVEVDAAPTVDLNRVLNE, SEQ ID NO:4947
VNTLRSPLGDRLNVEVDAAPTVDLNRVLNE, SEQ ID NO:4948
VNTLRCQLGDRLNVEVDTAPTVDLNRVLNE, SEQ ID NO:4949
VNTLRSQLGDRLNVEVDTAPTVDLNRVLNE, SEQ ID NO:4950
VNTLRCPLGDRLNVEVDTAPTVDLNRVLNE, SEQ ID NO:4951
VNTLRSPLGDRLNVEVDTAPTVDLNRVLNE, SEQ ID NO:4952
NTLRCQLGDRLNVEVDAAPTVDLNQVLNET, SEQ ID NO:4953
NTLRSQLGDRLNVEVDAAPTVDLNQVLNET, SEQ ID NO:4954
NTLRCPLGDRLNVEVDAAPTVDLNQVLNET, SEQ ID NO:4955
NTLRSPLGDRLNVEVDAAPTVDLNQVLNET, SEQ ID NO:4956
NTLRCQLGDRLNVEVDTAPTVDLNQVLNET, SEQ ID NO:4957
NTLRSQLGDRLNVEVDTAPTVDLNQVLNET, SEQ ID NO:4958
NTLRCPLGDRLNVEVDTAPTVDLNQVLNET, SEQ ID NO:4959
NTLRSPLGDRLNVEVDTAPTVDLNQVLNET, SEQ ID NO:4960
NTLRCQLGDRLNVEVDAAPTVDLNRVLNET, SEQ ID NO:4961
NTLRSQLGDRLNVEVDAAPTVDLNRVLNET, SEQ ID NO:4962
NTLRCPLGDRLNVEVDAAPTVDLNRVLNET, SEQ ID NO:4963
NTLRSPLGDRLNVEVDAAPTVDLNRVLNET, SEQ ID NO:4964
NTLRCQLGDRLNVEVDTAPTVDLNRVLNET, SEQ ID NO:4965
NTLRSQLGDRLNVEVDTAPTVDLNRVLNET, SEQ ID NO:4966
NTLRCPLGDRLNVEVDTAPTVDLNRVLNET, SEQ ID NO:4967
NTLRSPLGDRLNVEVDTAPTVDLNRVLNET, SEQ ID NO:4968
TLRCQLGDRLNVEVDAAPTVDLNQVLNETR, SEQ ID NO:4969
TLRSQLGDRLNVEVDAAPTVDLNQVLNETR, SEQ ID NO:4970
TLRCPLGDRLNVEVDAAPTVDLNQVLNETR, SEQ ID NO:4971
TLRSPLGDRLNVEVDAAPTVDLNQVLNETR, SEQ ID NO:4972
TLRCQLGDRLNVEVDTAPTVDLNQVLNETR, SEQ ID NO:4973
TLRSQLGDRLNVEVDTAPTVDLNQVLNETR, SEQ ID NO:4974
TLRCPLGDRLNVEVDTAPTVDLNQVLNETR, SEQ ID NO:4975
TLRSPLGDRLNVEVDTAPTVDLNQVLNETR, SEQ ID NO:4976
TLRCQLGDRLNVEVDAAPTVDLNRVLNETR, SEQ ID NO:4977
TLRSQLGDRLNVEVDAAPTVDLNRVLNETR, SEQ ID NO:4978
TLRCPLGDRLNVEVDAAPTVDLNRVLNETR, SEQ ID NO:4979
TLRSPLGDRLNVEVDAAPTVDLNRVLNETR, SEQ ID NO:4980
TLRCQLGDRLNVEVDTAPTVDLNRVLNETR, SEQ ID NO:4981
```

```
TLRSQLGDRLNVEVDTAPTVDLNRVLNETR,   SEQ ID NO:4982
TLRCPLGDRLNVEVDTAPTVDLNRVLNETR,   SEQ ID NO:4983
TLRSPLGDRLNVEVDTAPTVDLNRVLNETR,   SEQ ID NO:4984
LRCQLGDRLNVEVDAAPTVDLNQVLNETRS,   SEQ ID NO:4985
LRSQLGDRLNVEVDAAPTVDLNQVLNETRS,   SEQ ID NO:4986
LRCPLGDRLNVEVDAAPTVDLNQVLNETRS,   SEQ ID NO:4987
LRSPLGDRLNVEVDAAPTVDLNQVLNETRS,   SEQ ID NO:4988
LRCQLGDRLNVEVDTAPTVDLNQVLNETRS,   SEQ ID NO:4989
LRSQLGDRLNVEVDTAPTVDLNQVLNETRS,   SEQ ID NO:4900
LRCPLGDRLNVEVDTAPTVDLNQVLNETRS,   SEQ ID NO:4901
LRSPLGDRLNVEVDTAPTVDLNQVLNETRS,   SEQ ID NO:4902
LRCQLGDRLNVEVDAAPTVDLNRVLNETRS,   SEQ ID NO:4903
LRSQLGDRLNVEVDAAPTVDLNRVLNETRS,   SEQ ID NO:4904
LRCPLGDRLNYEVDAAPTVDLNRVLNETRS,   SEQ ID NO:4905
LRSPLGDRLNVEVDAAPTVDLNRVLNETRS,   SEQ ID NO:4906
LRCQLGDRLNVEVDTAPTVDLNRVLNETRS,   SEQ ID NO:4907
LRSQLGDRLNVEVDTAPTVDLNRVLNETRS,   SEQ ID NO:4908
LRCPLGDRLNVEVDTAPTVDLNRVLNETRS,   SEQ ID NO:4909
LRSPLGDRLNVEVDTAPTVDLNRVLNETRS,   SEQ ID NO:4910
LRCQLGDRLNVEVDAAPTVDLNQVLNETRN,   SEQ ID NO:4911
LRSQLGDRLNVEVDAAPTVDLNQVLNETRN,   SEQ ID NO:4912
LRCPLGDRLNVEVDAAPTVDLNQVLNETRN,   SEQ ID NO:4913
LRSPLGDRLNVEVDAAPTVDLNQVLNETRN,   SEQ ID NO:4914
LRCQLGDRLNVEVDTAPTVDLNQVLNETRN,   SEQ ID NO:4915
LRSQLGDRLNVEVDTAPTVDLNQVLNETRN,   SEQ ID NO:4916
LRCPLGDRLNVEVDTAPTVDLNQVLNETRN,   SEQ ID NO:4917
LRSPLGDRLNVEVDTAPTVDLNQVLNETRN,   SEQ ID NO:4918
LRCQLGDRLNVEVDAAPTVDLNRVLNETRN,   SEQ ID NO:4919
LRSQLGDRLNVEVDAAPTVDLNRVLNETRN,   SEQ ID NO:4920
LRCPLGDRLNVEVDAAPTVDLNRVLNETRN,   SEQ ID NO:4921
LRSPLGDRLNVEVDAAPTVDLNRVLNETRN,   SEQ ID NO:4922
LRCQLGDRLNVEVDTAPTVDLNRVLNETRN,   SEQ ID NO:4923
LRSQLGDRLNVEVDTAPTVDLNRVLNETRN,   SEQ ID NO:4924
LRCPLGDRLNVEVDTAPTVDLNRVLNETRN,   SEQ ID NO:4925
LRSPLGDRLNVEVDTAPTVDLNRVLNETRN,   SEQ ID NO:4926
RCQLGDRLNVEVDAAPTVDLNQVLNETRSQ,   SEQ ID NO:4927
RSQLGDRLNVEVDAAPTVDLNQVLNETRSQ,   SEQ ID NO:4928
RCPLGDRLNVEVDAAPTVDLNQVLNETRSQ,   SEQ ID NO:4929
RSPLGDRLNVEVDAAPTVDLNQVLNETRSQ,   SEQ ID NO:4930
RCQLGDRLNVEVDTAPTVDLNQVLNETRSQ,   SEQ ID NO:4931
RSQLGDRLNVEVDTAPTVDLNQVLNETRSQ,   SEQ ID NO:4932
RCPLGDRLNVEVDTAPTVDLNQVLNETRSQ,   SEQ ID NO:4933
RSPLGDRLNVEVDTAPTVDLNQVLNETRSQ,   SEQ ID NO:4934
RCQLGDRLNVEVDAAPTVDLNRVLNETRSQ,   SEQ ID NO:4935
RSQLGDRLNVEVDAAPTVDLNRVLNETRSQ,   SEQ ID NO:4936
RCPLGDRLNVEVDAAPTVDLNRVLNETRSQ,   SEQ ID NO:4937
RSPLGDRLNVEVDAAPTVDLNRVLNETRSQ,   SEQ ID NO:4938
RCQLGDRLNVEVDTAPTVDLNRVLNETRSQ,   SEQ ID NO:4939
RSQLGDRLNVEVDTAPTVDLNRVLNETRSQ,   SEQ ID NO:4940
RCPLGDRLNVEVDTAPTVDLNRVLNETRSQ,   SEQ ID NO:4941
RSPLGDRLNVEVDTAPTVDLNRVLNETRSQ,   SEQ ID NO:4942
RCQLGDRLNVEVDAAPTVDLNQVLNETRNQ,   SEQ ID NO:4943
RSQLGDRLNVEVDAAPTVDLNQVLNETRNQ,   SEQ ID NO:4944
RCPLGDRLNVEVDAAPTVDLNQVLNETRNQ,   SEQ ID NO:4945
RSPLGDRLNVEVDAAPTVDLNQVLNETRNQ,   SEQ ID NO:4946
RCQLGDRLNVEVDTAPTVDLNQVLNETRNQ,   SEQ ID NO:4947
RSQLGDRLNVEVDTAPTVDLNQVLNETRNQ,   SEQ ID NO:4948
RCPLGDRLNVEVDTAPTVDLNQVLNETRNQ,   SEQ ID NO:4949
RSPLGDRLNVEVDTAPTVDLNQVLNETRNQ,   SEQ ID NO:4950
RCQLGDRLNVEVDAAPTVDLNRVLNETRNQ,   SEQ ID NO:4951
RSQLGDRLNVEVDAAPTVDLNRVLNETRNQ,   SEQ ID NO:4952
RCPLGDRLNVEVDAAPTVDLNRVLNETRNQ,   SEQ ID NO:4953
RSPLGDRLNVEVDAAPTVDLNRVLNETRNQ,   SEQ ID NO:4954
RCQLGDRLNVEVDTAPTVDLNRVLNETRNQ,   SEQ ID NO:4955
RSQLGDRLNVEVDTAPTVDLNRVLNETRNQ,   SEQ ID NO:4956
RCPLGDRLNVEVDTAPTVDLNRVLNETRNQ,   SEQ ID NO:4957
RSPLGDRLNVEVDTAPTVDLNRVLNETRNQ,   SEQ ID NO:4958
CQLGDRLNVEVDAAPTVDLNQVLNETRSQY,   SEQ ID NO:4959
SQLGDRLNVEVDAAPTVDLNQVLNETRSQY,   SEQ ID NO:4960
CPLGDRLNVEVDAAPTVDLNQVLNETRSQY,   SEQ ID NO:4961
SPLGDRLNVEVDAAPTVDLNQVLNETRSQY,   SEQ ID NO:4962
CQLGDRLNVEVDTAPTVDLNQVLNETRSQY,   SEQ ID NO:4963
SQLGDRLNVEVDTAPTVDLNQVLNETRSQY,   SEQ ID NO:4964
CPLGDRLNVEVDTAPTVDLNQVLNETRSQY,   SEQ ID NO:4965
SPLGDRLNVEVDTAPTVDLNQVLNETRSQY,   SEQ ID NO:4966
CQLGDRLNVEVDAAPTVDLNRVLNETRSQY,   SEQ ID NO:4967
SQLGDRLNVEVDAAPTVDLNRVLNETRSQY,   SEQ ID NO:4968
CPLGDRLNVEVDAAPTVDLNRVLNETRSQY,   SEQ ID NO:4969
SPLGDRLNVEVDAAPTVDLNRVLNETRSQY,   SEQ ID NO:4970
CQLGDRLNVEVDTAPTVDLNRVLNETRSQY,   SEQ ID NO:4971
```

-continued

```
SQLGDRLNVEVDTAPTVDLNRVLNETRSQY,    SEQ ID NO:4972
CPLGDRLNVEVDTAPTVDLNRVLNETRSQY,    SEQ ID NO:4973
SPLGDRLNVEVDTAPTVDLNRVLNETRSQY,    SEQ ID NO:4974
CQLGDRLNVEVDAAPTVDLNQVLNETRNQY,    SEQ ID NO:4975
SQLGDRLNVEVDAAPTVDLNQVLNETRNQY,    SEQ ID NO:4976
CPLGDRLNVEVDAAPTVDLNQVLNETRNQY,    SEQ ID NO:4977
SPLGDRLNVEVDAAPTVDLNQVLNETRNQY,    SEQ ID NO:4978
CQLGDRLNVEVDTAPTVDLNQVLNETRNQY,    SEQ ID NO:4979
SQLGDRLNVEVDTAPTVDLNQVLNETRNQY,    SEQ ID NO:4980
CPLGDRLNVEVDTAPTVDLNQVLNETRNQY,    SEQ ID NO:4981
SPLGDRLNVEVDTAPTVDLNQVLNETRNQY,    SEQ ID NO:4982
CQLGDRLNVEVDAAPTVDLNRVLNETRNQY,    SEQ ID NO:4983
SQLGDRLNVEVDAAPTVDLNRVLNETRNQY,    SEQ ID NO:4984
CPLGDRLNVEVDAAPTVDLNRVLNETRNQY,    SEQ ID NO:4985
SPLGDRLNVEVDAAPTVDLNRVLNETRNQY,    SEQ ID NO:4986
CQLGDRLNVEVDTAPTVDLNRVLNETRNQY,    SEQ ID NO:4987
SQLGDRLNVEVDTAPTVDLNRVLNETRNQY,    SEQ ID NO:4988
CPLGDRLNVEVDTAPTVDLNRVLNETRNQY,    SEQ ID NO:4989
SPLGDRLNVEVDTAPTVDLNRVLNETRNQY,    SEQ ID NO:4990
QLGDRLNVEVDAAPTVDLNQVLNETRSQYE,    SEQ ID NO:4991
PLGDRLNVEVDAAPTVDLNQVLNETRSQYE,    SEQ ID NO:4992
QLGDRLNVEVDTAPTVDLNQVLNETRSQYE,    SEQ ID NO:4993
PLGDRLNVEVDTAPTVDLNQVLNETRSQYE,    SEQ ID NO:4994
QLGDRLNVEVDAAPTVDLNRVLNETRSQYE,    SEQ ID NO:4995
PLGDRLNVEVDAAPTVDLNRVLNETRSQYE,    SEQ ID NO:4996
QLGDRLNVEVDTAPTVDLNRVLNETRSQYE,    SEQ ID NO:4997
PLGDRLNVEVDTAPTVDLNRVLNETRSQYE,    SEQ ID NO:4998
QLGDRLNVEVDAAPTVDLNQVLNETRNQYE,    SEQ ID NO:4999
PLGDRLNVEVDAAPTVDLNQVLNETRNQYE,    SEQ ID NO:5000
QLGDRLNVEVDTAPTVDLNQVLNETRNQYE,    SEQ ID NO:5001
PLGDRLNVEVDTAPTVDLNQVLNETRNQYE,    SEQ ID NO:5002
QLGDRLNVEVDAAPTVDLNRVLNETRNQYE,    SEQ ID NO:5003
PLGDRLNVEVDAAPTVDLNRVLNETRNQYE,    SEQ ID NO:5004
QLGDRLNVEVDTAPTVDLNRVLNETRNQYE,    SEQ ID NO:5005
PLGDRLNVEVDTAPTVDLNRVLNETRNQYE,    SEQ ID NO:5006
LGDRLNVEVDAAPTVDLNQVLNETRSQYEA,    SEQ ID NO:5007
LGDRLNVEVDTAPTVDLNQVLNETRSQYEA,    SEQ ID NO:5008
LGDRLNVEVDAAPTVDLNRVLNETRSQYEA,    SEQ ID NO:5009
LGDRLNVEVDTAPTVDLNRVLNETRSQYEA,    SEQ ID NO:5010
LGDRLNVEVDAAPTVDLNQVLNETRNQYEA,    SEQ ID NO:5011
LGDRLNVEVDTAPTVDLNQVLNETRNQYEA,    SEQ ID NO:5012
LGDRLNVEVDAAPTVDLNRVLNETRNQYEA,    SEQ ID NO:5013
LGDRLNVEVDTAPTVDLNRVLNETRNQYEA,    SEQ ID NO:5014
GDRLNVEVDAAPTVDLNQVLNETRSQYEAL,    SEQ ID NO:5015
GDRLNVEVDTAPTVDLNQVLNETRSQYEAL,    SEQ ID NO:5016
GDRLNVEVDAAPTVDLNRVLNETRSQYEAL,    SEQ ID NO:5017
GDRLNVEVDTAPTVDLNRVLNETRSQYEAL,    SEQ ID NO:5018
GDRLNVEVDAAPTVDLNQVLNETRNQYEAL,    SEQ ID NO:5019
GDRLNVEVDTAPTVDLNQVLNETRNQYEAL,    SEQ ID NO:5020
GDRLNVEVDAAPTVDLNRVLNETRNQYEAL,    SEQ ID NO:5021
GDRLNVEVDTAPTVDLNRVLNETRNQYEAL,    SEQ ID NO:5022
EVNTLRCQLGDRLNVEVDAAPTVDLNQVLNE,   SEQ ID NO:5023
EVNTLRSQLGDRLNVEVDAAPTVDLNQVLNE,   SEQ ID NO:5024
EVNTLRCPLGDRLNVEVDAAPTVDLNQVLNE,   SEQ ID NO:5025
EVNTLRSPLGDRLNVEVDAAPTVDLNQVLNE,   SEQ ID NO:5026
EVNTLRCQLGDRLNVEVDTAPTVDLNQVLNE,   SEQ ID NO:5027
EVNTLRSQLGDRLNVEVDTAPTVDLNQVLNE,   SEQ ID NO:5028
EVNTLRCPLGDRLNVEVDTAPTVDLNQVLNE,   SEQ ID NO:5029
EVNTLRSPLGDRLNVEVDTAPTVDLNQVLNE,   SEQ ID NO:5030
EVNTLRCQLGDRLNVEVDAAPTVDLNRVLNE,   SEQ ID NO:5031
EVNTLRSQLGDRLNVEVDAAPTVDLNRVLNE,   SEQ ID NO:5032
EVNTLRCPLGDRLNVEVDAAPTVDLNRVLNE,   SEQ ID NO:5033
EVNTLRSPLGDRLNVEVDAAPTVDLNRVLNE,   SEQ ID NO:5034
EVNTLRCQLGDRLNVEVDTAPTVDLNRVLNE,   SEQ ID NO:5035
EVNTLRSQLGDRLNVEVDTAPTVDLNRVLNE,   SEQ ID NO:5036
EVNTLRCPLGDRLNVEVDTAPTVDLNRVLNE,   SEQ ID NO:5037
EVNTLRSPLGDRLNVEVDTAPTVDLNRVLNE,   SEQ ID NO:5038
VNTLRCQLGDRLNVEVDAAPTVDLNQVLNET,   SEQ ID NO:5039
VNTLRSQLGDRLNVEVDAAPTVDLNQVLNET,   SEQ ID NO:5040
VNTLRCPLGDRLNVEVDAAPTVDLNQVLNET,   SEQ ID NO:5041
NTLRSPLGDRLNVEVDAAPTVDLNQVLNET,    SEQ ID NO:5042
VNTLRCQLGDRLNVEVDTAPTVDLNQVLNET,   SEQ ID NO:5043
VNTLRSQLGDRLNVEVDTAPTVDLNQVLNET,   SEQ ID NO:5044
VNTLRCPLGDRLNVEVDTAPTVDLNQVLNET,   SEQ ID NO:5045
VNTLRSPLGDRLNVEVDTAPTVDLNQVLNET,   SEQ ID NO:5046
VNTLRCQLGDRLNVEVDAAPTVDLNRVLNET,   SEQ ID NO:5047
VNTLRSQLGDRLNVEVDAAPTVDLNRVLNET,   SEQ ID NO:5048
VNTLRCPLGDRLNVEVDAAPTVDLNRVLNET,   SEQ ID NO:5049
VNTLRSPLGDRLNVEVDAAPTVDLNRVLNET,   SEQ ID NO:5050
VNTLRCQLGDRLNVEVDTAPTVDLNRVLNET,   SEQ ID NO:5051
```

-continued

```
VNTLRSQLGDRLNVEVDTAPTVDLNRVLNET,   SEQ ID NO:5052
VNTLRCPLGDRLNVEVDTAPTVDLNRVLNET,   SEQ ID NO:5053
VNTLRSPLGDRLNVEVDTAPTVDLNRVLNET,   SEQ ID NO:5054
NTLRCQLGDRLNVEVDAAPTVDLNQVLNETR,   SEQ ID NO:5055
NTLRSQLGDRLNVEVDAAPTVDLNQVLNETR,   SEQ ID NO:5056
NTLRCPLGDRLNVEVDAAPTVDLNQVLNETR,   SEQ ID NO:5057
NTLRSPLGDRLNVEVDAAPTVDLNQVLNETR,   SEQ ID NO:5058
NTLRCQLGDRLNVEVDTAPTVDLNQVLNETR,   SEQ ID NO:5059
NTLRSQLGDRLNVEVDTAPTVDLNQVLNETR,   SEQ ID NO:5060
NTLRCPLGDRLNVEVDTAPTVDLNQVLNETR,   SEQ ID NO:5061
NTLRSPLGDRLNVEVDTAPTVDLNQVLNETR,   SEQ ID NO:5062
NTLRCQLGDRLNVEVDAAPTVDLNRVLNETR,   SEQ ID NO:5063
NTLRSQLGDRLNVEVDAAPTVDLNRVLNETR,   SEQ ID NO:5064.
NTLRCPLGDRLNVEVDAAPTVDLNRVLNETR,   SEQ ID NO:5065
NTLRSPLGDRLNVEVDAAPTVDLNRVLNETR,   SEQ ID NO:5066
NTLRCQLGDRLNVEVDTAPTVDLNRVLNETR,   SEQ ID NO:5067
NTLRSQLGDRLNVEVDTAPTVDLNRVLNETR,   SEQ ID NO:5068
NTLRCPLGDRLNVEVDTAPTVDLNRVLNETR,   SEQ ID NO:5069
NTLRSPLGDRLNVEVDTAPTVDLNRVLNETR,   SEQ ID NO:5070
TLRCQLGDRLNVEVDAAPTVDLNQVLNETRS,   SEQ ID NO:5071
TLRSQLGDRLNVEVDAAPTVDLNQVLNETRS,   SEQ ID NO:5072
TLRCPLGDRLNVEVDAAPTVDLNQVLNETRS,   SEQ ID NO:5073
TLRSPLGDRLNVEVDAAPTVDLNQVLNETRS,   SEQ ID NO:5074
TLRCQLGDRLNVEVDTAPTVDLNQVLNETRS,   SEQ ID NO:5075
TLRSQLGDRLNVEVDTAPTVDLNQVLNETRS,   SEQ ID NO:5076
TLRCPLGDRLNVEVDTAPTVDLNQVLNETRS,   SEQ ID NO:5077
TLRSPLGDRLNVEVDTAPTVDLNQVLNETRS,   SEQ ID NO:5078
TLRCQLGDRLNVEVDAAPTVDLNRVLNETRS,   SEQ ID NO:5079
TLRSQLGDRLNVEVDAAPTVDLNRVLNETRS,   SEQ ID NO:5080
TLRCPLGDRLNVEVDAAPTVDLNRVLNETRS,   SEQ ID NO:5081
TLRSPLGDRLNVEVDAAPTVDLNRVLNETRS,   SEQ ID NO:5082
TLRCQLGDRLNVEVDTAPTVDLNRVLNETRS,   SEQ ID NO:5083
TLRSQLGDRLNVEVDTAPTVDLNRVLNETRS,   SEQ ID NO:5084
TLRCPLGDRLNVEVDTAPTVDLNRVLNETRS,   SEQ ID NO:5085
TLRSPLGDRLNVEVDTAPTVDLNRVLNETRS,   SEQ ID NO:5086
TLRCQLGDRLNVEVDAAPTVDLNQVLNETRN,   SEQ ID NO:5087
TLRSQLGDRLNVEVDAAPTVDLNQVLNETRN,   SEQ ID NO:5088
TLRCPLGDRLNVEVDAAPTVDLNQVLNETRN,   SEQ ID NO:5089
TLRSPLGDRLNVEVDAAPTVDLNQVLNETRN,   SEQ ID NO:5090
TLRCQLGDRLNVEVDTAPTVDLNQVLNETRN,   SEQ ID NO:5091
TLRSQLGDRLNVEVDTAPTVDLNQVLNETRN,   SEQ ID NO:5092
TLRCPLGDRLNVEVDTAPTVDLNQVLNETRN,   SEQ ID NO:5093
TLRSPLGDRLNVEVDTAPTVDLNQVLNETRN,   SEQ ID NO:5094
TLRCQLGDRLNVEVDAAPTVDLNRVLNETRN,   SEQ ID NO:5095
TLRSQLGDRLNVEVDAAPTVDLNRVLNETRN,   SEQ ID NO:5096
TLRCPLGDRLNVEVDAAPTVDLNRVLNETRN,   SEQ ID NO:5097
TLRSPLGDRLNVEVDAAPTVDLNRVLNETRN,   SEQ ID NO:5098
TLRCQLGDRLNVEVDTAPTVDLNRVLNETRN,   SEQ ID NO:5099
TLRSQLGDRLNVEVDTAPTVDLNRVLNETRN,   SEQ ID NO:5100
TLRCPLGDRLNVEVDTAPTVDLNRVLNETRN,   SEQ ID NO:5101
TLRSPLGDRLNVEVDTAPTVDLNRVLNETRN,   SEQ ID NO:5102
LRCQLGDRLNVEVDAAPTVDLNQVLNETRSQ,   SEQ ID NO:5103
LRSQLGDRLNVEVDAAPTVDLNQVLNETRSQ,   SEQ ID NO:5104
LRCPLGDRLNVEVDAAPTVDLNQVLNETRSQ,   SEQ ID NO:5105
LRSPLGDRLNVEVDAAPTVDLNQVLNETRSQ,   SEQ ID NO:5106
LRCQLGDRLNVEVDTAPTVDLNQVLNETRSQ,   SEQ ID NO:5107
LRSQLGDRLNVEVDTAPTVDLNQVLNETRSQ,   SEQ ID NO:5108
LRCPLGDRLNVEVDTAPTVDLNQVLNETRSQ,   SEQ ID NO:5109
LRSPLGDRLNVEVDTAPTVDLNQVLNETRSQ,   SEQ ID NO:5110
LRCQLGDRLNVEVDAAPTVDLNRVLNETRSQ,   SEQ ID NO:5111
LRSQLGDRLNVEVDAAPTVDLNRVLNETRSQ,   SEQ ID NO:5112
LRCPLGDRLNVEVDAAPTVDLNRVLNETRSQ,   SEQ ID NO:5113
LRSPLGDRLNVEVDAAPTVDLNRVLNETRSQ,   SEQ ID NO:5114
LRCQLGDRLNVEVDTAPTVDLNRVLNETRSQ,   SEQ ID NO:5115
LRSQLGDRLNVEVDTAPTVDLNRVLNETRSQ,   SEQ ID NO:5116
LRCPLGDRLNVEVDTAPTVDLNRVLNETRSQ,   SEQ ID NO:5117
LRSPLGDRLNVEVDTAPTVDLNRVLNETRSQ,   SEQ ID NO:5118
LRCQLGDRLNVEVDAAPTVDLNQVLNETRNQ,   SEQ ID NO:5119
LRSQLGDRLNVEVDAAPTVDLNQVLNETRNQ,   SEQ ID NO:5120
LRCPLGDRLNVEVDAAPTVDLNQVLNETRNQ,   SEQ ID NO:5121
LRSPLGDRLNVEVDAAPTVDLNQVLNETRNQ,   SEQ ID NO:5122
LRCQLGDRLNVEVDTAPTVDLNQVLNETRNQ,   SEQ ID NO:5123
LRSQLGDRLNVEVDTAPTVDLNQVLNETRNQ,   SEQ ID NO:5124
LRCPLGDRLNVEVDTAPTVDLNQVLNETRNQ,   SEQ ID NO:5125
LRSPLGDRLNVEVDTAPTVDLNQVLNETRNQ,   SEQ ID NO:5126
LRCQLGDRLNVEVDAAPTVDLNRVLNETRNQ,   SEQ ID NO:5127
LRSQLGDRLNVEVDAAPTVDLNRVLNETRNQ,   SEQ ID NO:5128
LRCPLGDRLNVEVDAAPTVDLNRVLNETRNQ,   SEQ ID NO:5129
LRSPLGDRLNVEVDAAPTVDLNRVLNETRNQ,   SEQ ID NO:5130
LRCQLGDRLNVEVDTAPTVDLNRVLNETRNQ,   SEQ ID NO:5131
```

```
                                        -continued
LRSQLGDRLNVEVDTAPTVDLNRVLNETRNQ,        SEQ ID NO:5132
LRCPLGDRLNVEVDTAPTVDLNRVLNETRNQ,        SEQ ID NO:5133
LRSPLGDRLNVEVDTAPTVDLNRVLNETRNQ,        SEQ ID NO:5134
RCQLGDRLNYEVDAAPTVDLNQVLNETRSQY,        SEQ ID NO:5135
RSQLGDRLNVEVDAAPTVDLNQVLNETRSQY,        SEQ ID NO:5136
RCPLGDRLNVEVDAAPTVDLNQVLNETRSQY,        SEQ ID NO:5137
RSPLGDRLNVEVDAAPTVDLNQVLNETRSQY,        SEQ ID NO:5138
RCQLGDRLNVEVDTAPTVDLNQVLNETRSQY,        SEQ ID NO:5139
RSQLGDRLNVEVDTAPTVDLNQVLNETRSQY,        SEQ ID NO:5140
RCPLGDRLNVEVDTAPTVDLNQVLNETRSQY,        SEQ ID NO:5141
RSPLGDRLNVEVDTAPTVDLNQVLNETRSQY,        SEQ ID NO:5142
RCQLGDRLNVEVDAAPTVDLNRVLNETRSQY,        SEQ ID NO:5143
RSQLGDRLNVEVDAAPTVDLNRVLNETRSQY,        SEQ ID NO:5144
RCPLGDRLNVEVDAAPTVDLNRVLNETRSQY,        SEQ ID NO:5145
RSPLGDRLNVEVDAAPTVDLNRVLNETRSQY,        SEQ ID NO:5146
RCQLGDRLNVEVDTAPTVDLNRVLNETRSQY,        SEQ ID NO:5147
RSQLGDRLNVEVDTAPTVDLNRVLNETRSQY,        SEQ ID NO:5148
RCPLGDRLNVEVDTAPTVDLNRVLNETRSQY,        SEQ ID NO:5149
RSPLGDRLNVEVDTAPTVDLNRVLNETRSQY,        SEQ ID NO:5150
RCQLGDRLNVEVDAAPTVDLNQVLNETRNQY,        SEQ ID NO:5151
RSQLGDRLNVEVDAAPTVDLNQVLNETRNQY,        SEQ ID NO:5152
RCPLGDRLNVEVDAAPTVDLNQVLNETRNQY,        SEQ ID NO:5153
RSPLGDRLNVEVDAAPTVDLNQVLNETRNQY,        SEQ ID NO:5154
RCQLGDRLNVEVDTAPTVDLNQVLNETRNQY,        SEQ ID NO:5155
RSQLGDRLNVEVDTAPTVDLNQVLNETRNQY,        SEQ ID NO:5156
RCPLGDRLNVEVDTAPTVDLNQVLNETRNQY,        SEQ ID NO:5157
RSPLGDRLNVEVDTAPTVDLNQVLNETRNQY,        SEQ ID NO:5158
RCQLGDRLNVEVDAAPTVDLNRVLNETRNQY,        SEQ ID NO:5159
RSQLGDRLNVEVDAAPTVDLNRVLNETRNQY,        SEQ ID NO:5160
RCPLGDRLNVEVDAAPTVDLNRVLNETRNQY,        SEQ ID NO:5161
RSPLGDRLNVEVDAAPTVDLNRVLNETRNQY,        SEQ ID NO:5162
RCQLGDRLNVEVDTAPTVDLNRVLNETRNQY,        SEQ ID NO:5163
RSQLGDRLNVEVDTAPTVDLNRVLNETRNQY,        SEQ ID NO:5164
RCPLGDRLNVEVDTAPTVDLNRVLNETRNQY,        SEQ ID NO:5165
RSPLGDRLNVEVDTAPTVDLNRVLNETRNQY,        SEQ ID NO:5166
CQLGDRLNVEVDAAPTVDLNQVLNETRSQYE,        SEQ ID NO:5167
SQLGDRLNVEVDAAPTVDLNQVLNETRSQYE,        SEQ ID NO:5168
CPLGDRLNVEVDAAPTVDLNQVLNETRSQYE,        SEQ ID NO:5169
SPLGDRLNVEVDAAPTVDLNQVLNETRSQYE,        SEQ ID NO:5160
CQLGDRLNVEVDTAPTVDLNQVLNETRSQYE,        SEQ ID NO:5161
SQLGDRLNVEVDTAPTVDLNQVLNETRSQYE,        SEQ ID NO:5162
CPLGDRLNVEVDTAPTVDLNQVLNETRSQYE,        SEQ ID NO:5163
SPLGDRLNVEVDTAPTVDLNQVLNETRSQYE,        SEQ ID NO:5164
CQLGDRLNVEVDAAPTVDLNRVLNETRSQYE,        SEQ ID NO:5165
SQLGDRLNVEVDAAPTVDLNRVLNETRSQYE,        SEQ ID NO:5166
CPLGDRLNVEVDAAPTVDLNRVLNETRSQYE,        SEQ ID NO:5167
SPLGDRLNVEVDAAPTVDLNRVLNETRSQYE,        SEQ ID NO:5168
CQLGDRLNVEVDTAPTVDLNRVLNETRSQYE,        SEQ ID NO:5169
SQLGDRLNVEVDTAPTVDLNRVLNETRSQYE,        SEQ ID NO:5170
CPLGDRLNVEVDTAPTVDLNRVLNETRSQYE,        SEQ ID NO:5171
SPLGDRLNVEVDTAPTVDLNRVLNETRSQYE,        SEQ ID NO:5172
CQLGDRLNVEVDAAPTVDLNQVLNETRNQYE,        SEQ ID NO:5173
SQLGDRLNVEVDAAPTVDLNQVLNETRNQYE,        SEQ ID NO:5174
CPLGDRLNVEVDAAPTVDLNQVLNETRNQYE,        SEQ ID NO:5175
SPLGDRLNVEVDAAPTVDLNQVLNETRNQYE,        SEQ ID NO:5176
CQLGDRLNVEVDTAPTVDLNQVLNETRNQYE,        SEQ ID NO:5177
SQLGDRLNVEVDTAPTVDLNQVLNETRNQYE,        SEQ ID NO:5178
CPLGDRLNVEVDTAPTVDLNQVLNETRNQYE,        SEQ ID NO:5179
SPLGDRLNVEVDTAPTVDLNQVLNETRNQYE,        SEQ ID NO:5180
CQLGDRLNVEVDAAPTVDLNRVLNETRNQYE,        SEQ ID NO:5181
SQLGDRLNVEVDAAPTVDLNRVLNETRNQYE,        SEQ ID NO:5182
CPLGDRLNVEVDAAPTVDLNRVLNETRNQYE,        SEQ ID NO:5183
SPLGDRLNVEVDAAPTVDLNRVLNETRNQYE,        SEQ ID NO:5184
CQLGDRLNVEVDTAPTVDLNRVLNETRNQYE,        SEQ ID NO:5185
SQLGDRLNVEVDTAPTVDLNRVLNETRNQYE,        SEQ ID NO:5186
CPLGDRLNVEVDTAPTVDLNRVLNETRNQYE,        SEQ ID NO:5187
SPLGDRLNVEVDTAPTVDLNRVLNETRNQYE,        SEQ ID NO:5188
QLGDRLNVEVDAAPTVDLNQVLNETRSQYEA,        SEQ ID NO:5189
PLGDRLNVEVDAAPTVDLNQVLNETRSQYEA,        SEQ ID NO:5190
QLGDRLNVEVDTAPTVDLNQVLNETRSQYEA,        SEQ ID NO:5191
PLGDRLNVEVDTAPTVDLNQVLNETRSQYEA,        SEQ ID NO:5192
QLGDRLNVEVDAAPTVDLNRVLNETRSQYEA,        SEQ ID NO:5193
PLGDRLNVEVDAAPTVDLNRVLNETRSQYEA,        SEQ ID NO:5194
QLGDRLNVEVDTAPTVDLNRVLNETRSQYEA,        SEQ ID NO:5195
PLGDRLNVEVDTAPTVDLNRVLNETRSQYEA,        SEQ ID NO:5196
QLGDRLNVEVDAAPTVDLNQVLNETRNQYEA,        SEQ ID NO:5197
PLGDRLNVEVDAAPTVDLNQVLNETRNQYEA,        SEQ ID NO:5198
QLGDRLNVEVDTAPTVDLNQVLNETRNQYEA,        SEQ ID NO:5199
PLGDRLNVEVDTAPTVDLNQVLNETRNQYEA,        SEQ ID NO:5200
QLGDRLNVEVDAAPTVDLNRVLNETRNQYEA,        SEQ ID NO:5201
```

-continued

```
PLGDRLNVEVDAAPTVDLNRVLNETRNQYEA,   SEQ ID NO:5202
QLGDRLNVEVDTAPTVDLNRVLNETRNQYEA,   SEQ ID NO:5203
PLGDRLNVEVDTAPTVDLNRVLNETRNQYEA,   SEQ ID NO:5204
LGDRLNVEVDAAPTVDLNQVLNETRSQYEAL,   SEQ ID NO:5205
LGDRLNVEVDTAPTVDLNQVLNETRSQYEAL,   SEQ ID NO:5206
LGDRLNVEVDAAPTVDLNRVLNETRSQYEAL,   SEQ ID NO:5207
LGDRLNVEVDTAPTVDLNRVLNETRSQYEAL,   SEQ ID NO:5208
LGDRLNVEVDAAPTVDLNQVLNETRNQYEAL,   SEQ ID NO:5209
LGDRLNVEVDTAPTVDLNQVLNETRNQYEAL,   SEQ ID NO:5210
ELGDRLNVEVDAAPTVDLNRVLNETRNQYEAL,  SEQ ID NO:5211
LGDRLNVEVDTAPTVDLNRVLNETRNQYEAL,   SEQ ID NO:5212
EVNTLRCQLGDRLNVEVDAAPTVDLNQVLNET,  SEQ ID NO:5213
EVNTLRSQLGDRLNVEVDAAPTVDLNQVLNET,  SEQ ID NO:5214
EVNTLRCPLGDRLNVEVDAAPTVDLNQVLNET,  SEQ ID NO:5215
EVNTLRSPLGDRLNVEVDAAPTVDLNQVLNET,  SEQ ID NO:5216
EVNTLRCQLGDRLNVEVDTAPTVDLNQVLNET,  SEQ ID NO:5217
EVNTLRSQLGDRLNVEVDTAPTVDLNQVLNET,  SEQ ID NO:5218
EVNTLRCPLGDRLNVEVDTAPTVDLNQVLNET,  SEQ ID NO:5219
EVNTLRSPLGDRLNVEVDTAPTVDLNQVLNET,  SEQ ID NO:5220
EVNTLRCQLGDRLNVEVDAAPTVDLNRVLNET,  SEQ ID NO:5221
EVNTLRSQLGDRLNVEVDAAPTVDLNRVLNET,  SEQ ID NO:5222
EVNTLRCPLGDRLNVEVDAAPTVDLNRVLNET,  SEQ ID NO:5223
EVNTLRSPLGDRLNVEVDAAPTVDLNRVLNET,  SEQ ID NO:5224
EVNTLRCQLGDRLNVEVDTAPTVDLNRVLNET,  SEQ ID NO:5225
EVNTLRSQLGDRLNVEVDTAPTVDLNRVLNET,  SEQ ID NO:5226
EVNTLRCPLGDRLNVEVDTAPTVDLNRVLNET,  SEQ ID NO:5227
EVNTLRSPLGDRLNVEVDTAPTVDLNRVLNET,  SEQ ID NO:5228
VNTLRCQLGDRLNVEVDAAPTVDLNQVLNETR,  SEQ ID NO:5229
VNTLRSQLGDRLNVEVDAAPTVDLNQVLNETR,  SEQ ID NO:5230
VNTLRCPLGDRLNVEVDAAPTVDLNQVLNETR,  SEQ ID NO:5231
VNTLRSPLGDRLNVEVDAAPTVDLNQVLNETR,  SEQ ID NO:5232
VNTLRCQLGDRLNVEVDTAPTVDLNQVLNETR,  SEQ ID NO:5233
VNTLRSQLGDRLNVEVDTAPTVDLNQVLNETR,  SEQ ID NO:5234
VNTLRCPLGDRLNVEVDTAPTVDLNQVLNETR,  SEQ ID NO:5235
VNTLRSPLGDRLNVEVDTAPTVDLNQVLNETR,  SEQ ID NO:5236
VNTLRCQLGDRLNVEVDAAPTVDLNRVLNETR,  SEQ ID NO:5237
VNTLRSQLGDRLNVEVDAAPTVDLNRVLNETR,  SEQ ID NO:5238
VNTLRCPLGDRLNVEVDAAPTVDLNRVLNETR,  SEQ ID NO:5239
VNTLRSPLGDRLNVEVDAAPTVDLNRVLNETR,  SEQ ID NO:5240
VNTLRCQLGDRLNVEVDTAPTVDLNRVLNETR,  SEQ ID NO:5241
VNTLRSQLGDRLNVEVDTAPTVDLNRVLNETR,  SEQ ID NO:5242
VNTLRCPLGDRLNVEVDTAPTVDLNRVLNETR,  SEQ ID NO:5243
VNTLRSPLGDRLNVEVDTAPTVDLNRVLNETR,  SEQ ID NO:5244
NTLRCQLGDRLNVEVDAAPTVDLNQVLNETRS,  SEQ ID NO:5245
NTLRSQLGDRLNVEVDAAPTVDLNQVLNETRS,  SEQ ID NO:5246
NTLRCPLGDRLNVEVDAAPTVDLNQVLNETRS,  SEQ ID NO:5247
NTLRSPLGDRLNVEVDAAPTVDLNQVLNETRS,  SEQ ID NO:5248
NTLRCQLGDRLNVEVDTAPTVDLNQVLNETRS,  SEQ ID NO:5249
NTLRSQLGDRLNVEVDTAPTVDLNQVLNETRS,  SEQ ID NO:5250
NTLRCPLGDRLNVEVDTAPTVDLNQVLNETRS,  SEQ ID NO:5251
NTLRSPLGDRLNVEVDTAPTVDLNQVLNETRS,  SEQ ID NO:5252
NTLRCQLGDRLNVEVDAAPTVDLNRVLNETRS,  SEQ ID NO:5253
NTLRSQLGDRLNVEVDAAPTVDLNRVLNETRS,  SEQ ID NO:5254
NTLRCPLGDRLNVEVDAAPTVDLNRVLNETRS,  SEQ ID NO:5255
NTLRSPLGDRLNVEVDAAPTVDLNRVLNETRS,  SEQ ID NO:5256
NTLRCQLGDRLNVEVDTAPTVDLNRVLNETRS,  SEQ ID NO:5257
NTLRSQLGDRLNVEVDTAPTVDLNRVLNETRS,  SEQ ID NO:5258
NTLRCPLGDRLNVEVDTAPTVDLNRVLNETRS,  SEQ ID NO:5259
NTLRSPLGDRLNVEVDTAPTVDLNRVLNETRS,  SEQ ID NO:5260
NTLRCQLGDRLNVEVDAAPTVDLNQVLNETRN,  SEQ ID NO:5261
NTLRSQLGDRLNVEVDAAPTVDLNQVLNETRN,  SEQ ID NO:5262
NTLRCPLGDRLNVEVDAAPTVDLNQVLNETRN,  SEQ ID NO:5263
NTLRSPLGDRLNVEVDAAPTVDLNQVLNETRN,  SEQ ID NO:5264
NTLRCQLGDRLNVEVDTAPTVDLNQVLNETRN,  SEQ ID NO:5265
NTLRSQLGDRLNVEVDTAPTVDLNQVLNETRN,  SEQ ID NO:5266
NTLRCPLGDRLNVEVDTAPTVDLNQVLNETRN,  SEQ ID NO:5267
NTLRSPLGDRLNVEVDTAPTVDLNQVLNETRN,  SEQ ID NO:5268
NTLRCQLGDRLNVEVDAAPTVDLNRVLNETRN,  SEQ ID NO:5269
NTLRSQLGDRLNVEVDAAPTVDLNRVLNETRN,  SEQ ID NO:5270
NTLRCPLGDRLNVEVDAAPTVDLNRVLNETRN,  SEQ ID NO:5271
NTLRSPLGDRLNVEVDAAPTVDLNRVLNETRN,  SEQ ID NO:5272
NTLRCQLGDRLNVEVDTAPTVDLNRVLNETRN,  SEQ ID NO:5273
NTLRSQLGDRLNVEVDTAPTVDLNRVLNETRN,  SEQ ID NO:5274
NTLRCPLGDRLNVEVDTAPTVDLNRVLNETRN,  SEQ ID NO:5275
NTLRSPLGDRLNVEVDTAPTVDLNRVLNETRN,  SEQ ID NO:5276
TLRCQLGDRLNVEVDAAPTVDLNQVLNETRSQ,  SEQ ID NO:5277
TLRSQLGDRLNVEVDAAPTVDLNQVLNETRSQ,  SEQ ID NO:5278
TLRCPLGDRLNVEVDAAPTVDLNQVLNETRSQ,  SEQ ID NO:5279
TLRSPLGDRLNVEVDAAPTVDLNQVLNETRSQ,  SEQ ID NO:5280
TLRCQLGDRLNVEVDTAPTVDLNQVLNETRSQ,  SEQ ID NO:5281
```

```
                                        -continued
TLRSQLGDRLNVEVDTAPTVDLNQVLNETRSQ,  SEQ ID NO:5282
TLRCPLGDRLNVEVDTAPTVDLNQVLNETRSQ,  SEQ ID NO:5283
TLRSPLGDRLNVEVDTAPTVDLNQVLNETRSQ,  SEQ ID NO:5284
TLRCQLGDRLNVEVDAAPTVDLNRVLNETRSQ,  SEQ ID NO:5285
TLRSQLGDRLNVEVDAAPTVDLNRVLNETRSQ,  SEQ ID NO:5286
TLRCPLGDRLNVEVDAAPTVDLNRVLNETRSQ,  SEQ ID NO:5287
TLRSPLGDRLNVEVDAAPTVDLNRVLNETRSQ,  SEQ ID NO:5288
TLRCQLGDRLNVEVDTAPTVDLNRVLNETRSQ,  SEQ ID NO:5289
TLRSQLGDRLNVEVDTAPTVDLNRVLNETRSQ,  SEQ ID NO:5290
TLRCPLGDRLNVEVDTAPTVDLNRVLNETRSQ,  SEQ ID NO:5291
TLRSPLGDRLNVEVDTAPTVDLNRVLNETRSQ,  SEQ ID NO:5292
TLRCQLGDRLNVEVDAAPTVDLNQVLNETRNQ,  SEQ ID NO:5293
TLRSQLGDRLNVEVDAAPTVDLNQVLNETRNQ,  SEQ ID NO:5294
TLRCPLGDRLNVEVDAAPTVDLNQVLNETRNQ,  SEQ ID NO:5295
TLRSPLGDRLNVEVDAAPTVDLNQVLNETRNQ,  SEQ ID NO:5296
TLRCQLGDRLNVEVDTAPTVDLNQVLNETRNQ,  SEQ ID NO:5297
TLRSQLGDRLNVEVDTAPTVDLNQVLNETRNQ,  SEQ ID NO:5298
TLRCPLGDRLNVEVDTAPTVDLNQVLNETRNQ,  SEQ ID NO:5299
TLRSPLGDRLNVEVDTAPTVDLNQVLNETRNQ,  SEQ ID NO:5300
TLRCQLGDRLNVEVDAAPTVDLNRVLNETRNQ,  SEQ ID NO:5301
TLRSQLGDRLNVEVDAAPTVDLNRVLNETRNQ,  SEQ ID NO:5302
TLRCPLGDRLNVEVDAAPTVDLNRVLNETRNQ,  SEQ ID NO:5303
TLRSPLGDRLNVEVDAAPTVDLNRVLNETRNQ,  SEQ ID NO:5304
TLRCQLGDRLNVEVDTAPTVDLNRVLNETRNQ,  SEQ ID NO:5305
TLRSQLGDRLNVEVDTAPTVDLNRVLNETRNQ,  SEQ ID NO:5306
TLRCPLGDRLNVEVDTAPTVDLNRVLNETRNQ,  SEQ ID NO:5307
TLRSPLGDRLNVEVDTAPTVDLNRVLNETRNQ,  SEQ ID NO:5308
LRCQLGDRLNVEVDAAPTVDLNQVLNETRSQY,  SEQ ID NO:5309
LRSQLGDRLNVEVDAAPTVDLNQVLNETRSQY,  SEQ ID NO:5310
LRCPLGDRLNVEVDAAPTVDLNQVLNETRSQY,  SEQ ID NO:5311
LRSPLGDRLNVEVDAAPTVDLNQVLNETRSQY,  SEQ ID NO:5312
LRCQLGDRLNVEVDTAPTVDLNQVLNETRSQY,  SEQ ID NO:5313
LRSQLGDRLNVEVDTAPTVDLNQVLNETRSQY,  SEQ ID NO:5314
LRCPLGDRLNVEVDTAPTVDLNQVLNETRSQY,  SEQ ID NO:5315
LRSPLGDRLNVEVDTAPTVDLNQVLNETRSQY,  SEQ ID NO:5316
LRCQLGDRLNVEVDAAPTVDLNRVLNETRSQY,  SEQ ID NO:5317
LRSQLGDRLNVEVDAAPTVDLNRVLNETRSQY,  SEQ ID NO:5318
LRCPLGDRLNVEVDAAPTVDLNRVLNETRSQY,  SEQ ID NO:5319
LRSPLGDRLNVEVDAAPTVDLNRVLNETRSQY,  SEQ ID NO:5320
LRCQLGDRLNVEVDTAPTVDLNRVLNETRSQY,  SEQ ID NO:5321
LRSQLGDRLNVEVDTAPTVDLNRVLNETRSQY,  SEQ ID NO:5322
LRCPLGDRLNVEVDTAPTVDLNRVLNETRSQY,  SEQ ID NO:5323
LRSPLGDRLNVEVDTAPTVDLNRVLNETRSQY,  SEQ ID NO:5324
LRCQLGDRLNVEVDAAPTVDLNQVLNETRNQY,  SEQ ID NO:5325
LRSQLGDRLNVEVDAAPTVDLNQVLNETRNQY,  SEQ ID NO:5326
LRCPLGDRLNVEVDAAPTVDLNQVLNETRNQY,  SEQ ID NO:5327
LRSPLGDRLNVEVDAAPTVDLNQVLNETRNQY,  SEQ ID NO:5328
LRCQLGDRLNVEVDTAPTVDLNQVLNETRNQY,  SEQ ID NO:5329
LRSQLGDRLNVEVDTAPTVDLNQVLNETRNQY,  SEQ ID NO:5330
LRCPLGDRLNVEVDTAPTVDLNQVLNETRNQY,  SEQ ID NO:5331
LRSPLGDRLNVEVDTAPTVDLNQVLNETRNQY,  SEQ ID NO:5332
LRCQLGDRLNVEVDAAPTVDLNRVLNETRNQY,  SEQ ID NO:5333
LRSQLGDRLNVEVDAAPTVDLNRVLNETRNQY,  SEQ ID NO:5334
LRCPLGDRLNVEVDAAPTVDLNRVLNETRNQY,  SEQ ID NO:5335
LRSPLGDRLNVEVDAAPTVDLNRVLNETRNQY,  SEQ ID NO:5336
LRCQLGDRLNVEVDTAPTVDLNRVLNETRNQY,  SEQ ID NO:5337
LRSQLGDRLNVEVDTAPTVDLNRVLNETRNQY,  SEQ ID NO:5338
LRCPLGDRLNVEVDTAPTVDLNRVLNETRNQY,  SEQ ID NO:5339
LRSPLGDRLNVEVDTAPTVDLNRVLNETRNQY,  SEQ ID NO:5340
RCQLGDRLNVEVDAAPTVDLNQVLNETRSQYE,  SEQ ID NO:5341
RSQLGDRLNVEVDAAPTVDLNQVLNETRSQYE,  SEQ ID NO:5342
RCPLGDRLNVEVDAAPTVDLNQVLNETRSQYE,  SEQ ID NO:5343
RSPLGDRLNVEVDAAPTVDLNQVLNETRSQYE,  SEQ ID NO:5344
RCQLGDRLNVEVDTAPTVDLNQVLNETRSQYE,  SEQ ID NO:5345
RSQLGDRLNVEVDTAPTVDLNQVLNETRSQYE,  SEQ ID NO:5346
RCPLGDRLNVEVDTAPTVDLNQVLNETRSQYE,  SEQ ID NO:5347
RSPLGDRLNVEVDTAPTVDLNQVLNETRSQYE,  SEQ ID NO:5348
RCQLGDRLNVEVDAAPTVDLNRVLNETRSQYE,  SEQ ID NO:5349
RSQLGDRLNVEVDAAPTVDLNRVLNETRSQYE,  SEQ ID NO:5350
RCPLGDRLNVEVDAAPTVDLNRVLNETRSQYE,  SEQ ID NO:5351
RSPLGDRLNVEVDAAPTVDLNRVLNETRSQYE,  SEQ ID NO:5352
RCQLGDRLNVEVDTAPTVDLNRVLNETRSQYE,  SEQ ID NO:5353
RSQLGDRLNVEVDTAPTVDLNRVLNETRSQYE,  SEQ ID NO:5354
RCPLGDRLNVEVDTAPTVDLNRVLNETRSQYE,  SEQ ID NO:5355
RSPLGDRLNVEVDTAPTVDLNRVLNETRSQYE,  SEQ ID NO:5356
RCQLGDRLNVEVDAAPTVDLNQVLNETRNQYE,  SEQ ID NO:5357
RSQLGDRLNVEVDAAPTVDLNQVLNETRNQYE,  SEQ ID NO:5358
RCPLGDRLNVEVDAAPTVDLNQVLNETRNQYE,  SEQ ID NO:5359
RSPLGDRLNVEVDAAPTVDLNQVLNETRNQYE,  SEQ ID NO:5360
RCQLGDRLNVEVDTAPTVDLNQVLNETRNQYE,  SEQ ID NO:5361
```

-continued

```
RSQLGDRLNVEVDTAPTVDLNQVLNETRNQYE,   SEQ ID NO:5362
RCPLGDRLNVEVDTAPTVDLNQVLNETRNQYE,   SEQ ID NO:5363
RSPLGDRLNVEVDTAPTVDLNQVLNETRNQYE,   SEQ ID NO:5364
RCQLGDRLNVEVDAAPTVDLNRVLNETRNQYE,   SEQ ID NO:5365
RSQLGDRLNVEVDAAPTVDLNRVLNETRNQYE,   SEQ ID NO:5366
RCPLGDRLNVEVDAAPTVDLNRVLNETRNQYE,   SEQ ID NO:5367
RSPLGDRLNVEVDAAPTVDLNRVLNETRNQYE,   SEQ ID NO:5368
RCQLGDRLNVEVDTAPTVDLNRVLNETRNQYE,   SEQ ID NO:5369
RSQLGDRLNVEVDTAPTVDLNRVLNETRNQYE,   SEQ ID NO:5370
RCPLGDRLNVEVDTAPTVDLNRVLNETRNQYE,   SEQ ID NO:5371
RSPLGDRLNVEVDTAPTVDLNRVLNETRNQYE,   SEQ ID NO:5372
CQLGDRLNVEVDAAPTVDLNQVLNETRSQYEA,   SEQ ID NO:5373
SQLGDRLNVEVDAAPTVDLNQVLNETRSQYEA,   SEQ ID NO:5374
CPLGDRLNVEVDAAPTVDLNQVLNETRSQYEA,   SEQ ID NO:5375
SPLGDRLNVEVDAAPTVDLNQVLNETRSQYEA,   SEQ ID NO:5376
CQLGDRLNVEVDTAPTVDLNQVLNETRSQYEA,   SEQ ID NO:5377
SQLGDRLNVEVDTAPTVDLNQVLNETRSQYEA,   SEQ ID NO:5378
CPLGDRLNVEVDTAPTVDLNQVLNETRSQYEA,   SEQ ID NO:5379
SPLGDRLNVEVDTAPTVDLNQVLNETRSQYEA,   SEQ ID NO:5380
CQLGDRLNVEVDAAPTVDLNRVLNETRSQYEA,   SEQ ID NO:5381
SQLGDRLNVEVDAAPTVDLNRVLNETRSQYEA,   SEQ ID NO:5382
CPLGDRLNVEVDAAPTVDLNRVLNETRSQYEA,   SEQ ID NO:5383
SPLGDRLNVEVDAAPTVDLNRVLNETRSQYEA,   SEQ ID NO:5384
CQLGDRLNVEVDTAPTVDLNRVLNETRSQYEA,   SEQ ID NO:5385
SQLGDRLNVEVDTAPTVDLNRVLNETRSQYEA,   SEQ ID NO:5386
CPLGDRLNVEVDTAPTVDLNRVLNETRSQYEA,   SEQ ID NO:5387
SPLGDRLNVEVDTAPTVDLNRVLNETRSQYEA,   SEQ ID NO:5388
CQLGDRLNVEVDAAPTVDLNQVLNETRNQYEA,   SEQ ID NO:5389
SQLGDRLNVEVDAAPTVDLNQVLNETRNQYEA,   SEQ ID NO:5390
CPLGDRLNVEVDAAPTVDLNQVLNETRNQYEA,   SEQ ID NO:5391
SPLGDRLNVEVDAAPTVDLNQVLNETRNQYEA,   SEQ ID NO:5392
CQLGDRLNVEVDTAPTVDLNQVLNETRNQYEA,   SEQ ID NO:5393
SQLGDRLNVEVDTAPTVDLNQVLNETRNQYEA,   SEQ ID NO:5394
CPLGDRLNVEVDTAPTVDLNQVLNETRNQYEA,   SEQ ID NO:5395
SPLGDRLNVEVDTAPTVDLNQVLNETRNQYEA,   SEQ ID NO:5396
CQLGDRLNVEVDAAPTVDLNRVLNETRNQYEA,   SEQ ID NO:5397
SQLGDRLNVEVDAAPTVDLNRVLNETRNQYEA,   SEQ ID NO:5398
CPLGDRLNVEVDAAPTVDLNRVLNETRNQYEA,   SEQ ID NO:5399
SPLGDRLNVEVDAAPTVDLNRVLNETRNQYEA,   SEQ ID NO:5400
CQLGDRLNVEVDTAPTVDLNRVLNETRNQYEA,   SEQ ID NO:5401
SQLGDRLNVEVDTAPTVDLNRVLNETRNQYEA,   SEQ ID NO:5402
CPLGDRLNVEVDTAPTVDLNRVLNETRNQYEA,   SEQ ID NO:5403
SPLGDRLNVEVDTAPTVDLNRVLNETRNQYEA,   SEQ ID NO:5404
QLGDRLNVEVDAAPTVDLNQVLNETRSQYEAL,   SEQ ID NO:5405
PLGDRLNVEVDAAPTVDLNQVLNETRSQYEAL,   SEQ ID NO:5406
QLGDRLNVEVDTAPTVDLNQVLNETRSQYEAL,   SEQ ID NO:5407
PLGDRLNVEVDTAPTVDLNQVLNETRSQYEAL,   SEQ ID NO:5408
QLGDRLNVEVDAAPTVDLNRVLNETRSQYEAL,   SEQ ID NO:5409
PLGDRLNVEVDAAPTVDLNRVLNETRSQYEAL,   SEQ ID NO:5410
QLGDRLNVEVDTAPTVDLNRVLNETRSQYEAL,   SEQ ID NO:5411
PLGDRLNVEVDTAPTVDLNRVLNETRSQYEAL,   SEQ ID NO:5412
QLGDRLNVEVDAAPTVDLNQVLNETRNQYEAL,   SEQ ID NO:5413
PLGDRLNVEVDAAPTVDLNQVLNETRNQYEAL,   SEQ ID NO:5414
QLGDRLNVEVDTAPTVDLNQVLNETRNQYEAL,   SEQ ID NO:5415
PLGDRLNVEVDTAPTVDLNQVLNETRNQYEAL,   SEQ ID NO:5416
QLGDRLNVEVDAAPTVDLNRVLNETRNQYEAL,   SEQ ID NO:5417
PLGDRLNVEVDAAPTVDLNRVLNETRNQYEAL,   SEQ ID NO:5418
QLGDRLNVEVDTAPTVDLNRVLNETRNQYEAL,   SEQ ID NO:5419
PLGDRLNVEVDTAPTVDLNRVLNETRNQYEAL,   SEQ ID NO:5420
EVNTLRCQLGDRLNVEVDAAPTVDLNQVLNETR,  SEQ ID NO:5421
EVNTLRSQLGDRLNVEVDAAPTVDLNQVLNETR,  SEQ ID NO:5422
EVNTLRCPLGDRLNVEVDAAPTVDLNQVLNETR,  SEQ ID NO:5423
EVNTLRSPLGDRLNVEVDAAPTVDLNQVLNETR,  SEQ ID NO:5424
EVNTLRCQLGDRLNVEVDTAPTVDLNQVLNETR,  SEQ ID NO:5425
EVNTLRSQLGDRLNVEVDTAPTVDLNQVLNETR,  SEQ ID NO:5426
EVNTLRCPLGDRLNVEVDTAPTVDLNQVLNETR,  SEQ ID NO:5427
EVNTLRSPLGDRLNVEVDTAPTVDLNQVLNETR,  SEQ ID NO:5428
EVNTLRCQLGDRLNVEVDAAPTVDLNRVLNETR,  SEQ ID NO:5429
EVNTLRSQLGDRLNVEVDAAPTVDLNRVLNETR,  SEQ ID NO:5430
EVNTLRCPLGDRLNVEVDAAPTVDLNRVLNETR,  SEQ ID NO:5431
EVNTLRSPLGDRLNVEVDAAPTVDLNRVLNETR,  SEQ ID NO:5432
EVNTLRCQLGDRLNVEVDTAPTVDLNRVLNETR,  SEQ ID NO:5433
EVNTLRSQLGDRLNVEVDTAPTVDLNRVLNETR,  SEQ ID NO:5434
EVNTLRCPLGDRLNVEVDTAPTVDLNRVLNETR,  SEQ ID NO:5435
EVNTLRSPLGDRLNVEVDTAPTVDLNRVLNETR,  SEQ ID NO:5436
VNTLRCQLGDRLNVEVDAAPTVDLNQVLNETRS,  SEQ ID NO:5437
VNTLRSQLGDRLNVEVDAAPTVDLNQVLNETRS,  SEQ ID NO:5438
VNTLRCPLGDRLNVEVDAAPTVDLNQVLNETRS,  SEQ ID NO:5439
VNTLRSPLGDRLNVEVDAAPTVDLNQVLNETRS,  SEQ ID NO:5440
VNTLRCQLGDRLNVEVDTAPTVDLNQVLNETRS,  SEQ ID NO:5441
```

-continued

```
VNTLRSQLGDRLNVEVDTAPTVDLNQVLNETRS,  SEQ ID NO:5442
VNTLRCPLGDRLNVEVDTAPTVDLNQVLNETRS,  SEQ ID NO:5443
VNTLRSPLGDRLNVEVDTAPTVDLNQVLNETRS,  SEQ ID NO:5444
VNTLRCQLGDRLNVEVDAAPTVDLNRVLNETRS,  SEQ ID NO:5445
VNTLRSQLGDRLNVEVDAAPTVDLNRVLNETRS,  SEQ ID NO:5446
VNTLRCPLGDRLNVEVDAAPTVDLNRVLNETRS,  SEQ ID NO:5447
VNTLRSPLGDRLNVEVDAAPTVDLNRVLNETRS,  SEQ ID NO:5448
VNTLRCQLGDRLNVEVDTAPTVDLNRVLNETRS,  SEQ ID NO:5449
VNTLRSQLGDRLNVEVDTAPTVDLNRVLNETRS,  SEQ ID NO:5450
VNTLRCPLGDRLNVEVDTAPTVDLNRVLNETRS,  SEQ ID NO:5451
VNTLRSPLGDRLNVEVDTAPTVDLNRVLNETRS,  SEQ ID NO:5452
VNTLRCQLGDRLNVEVDAAPTVDLNQVLNETRN,  SEQ ID NO:5453
VNTLRSQLGDRLNVEVDAAPTVDLNQVLNETRN,  SEQ ID NO:5454
VNTLRCPLGDRLNVEVDAAPTVDLNQVLNETRN,  SEQ ID NO:5455
VNTLRSPLGDRLNVEVDAAPTVDLNQVLNETRN,  SEQ ID NO:5456
VNTLRCQLGDRLNVEVDTAPTVDLNQVLNETRN,  SEQ ID NO:5457
VNTLRSQLGDRLNVEVDTAPTVDLNQVLNETRN,  SEQ ID NO:5458
VNTLRCPLGDRLNYEVDTAPTVDLNQVLNETRN,  SEQ ID NO:5459
VNTLRSPLGDRLNVEVDTAPTVDLNQVLNETRN,  SEQ ID NO:5460
VNTLRCQLGDRLNVEVDAAPTVDLNRVLNETRN,  SEQ ID NO:5461
VNTLRSQLGDRLNVEVDAAPTVDLNRVLNETRN,  SEQ ID NO:5462
VNTLRCPLGDRLNVEVDAAPTVDLNRVLNETRN,  SEQ ID NO:5463
VNTLRSPLGDRLNVEVDAAPTVDLNRVLNETRN,  SEQ ID NO:5464
VNTLRCQLGDRLNVEVDTAPTVDLNRVLNETRN,  SEQ ID NO:5465
VNTLRSQLGDRLNVEVDTAPTVDLNRVLNETRN,  SEQ ID NO:5466
VNTLRCPLGDRLNVEVDTAPTVDLNRVLNETRN,  SEQ ID NO:5467
VNTLRSPLGDRLNVEVDTAPTVDLNRVLNETRN,  SEQ ID NO:5468
NTLRCQLGDRLNVEVDAAPTVDLNQVLNETRSQ,  SEQ ID NO:5469
NTLRSQLGDRLNVEVDAAPTVDLNQVLNETRSQ,  SEQ ID NO:5470
NTLRCPLGDRLNVEVDAAPTVDLNQVLNETRSQ,  SEQ ID NO:5471
NTLRSPLGDRLNVEVDAAPTVDLNQVLNETRSQ,  SEQ ID NO:5472
NTLRCQLGDRLNVEVDTAPTVDLNQVLNETRSQ,  SEQ ID NO:5473
NTLRSQLGDRLNVEVDTAPTVDLNQVLNETRSQ,  SEQ ID NO:5474
NTLRCPLGDRLNVEVDTAPTVDLNQVLNETRSQ,  SEQ ID NO:5475
NTLRSPLGDRLNVEVDTAPTVDLNQVLNETRSQ,  SEQ ID NO:5476
NTLRCQLGDRLNVEVDAAPTVDLNRVLNETRSQ,  SEQ ID NO:5477
NTLRSQLGDRLNVEVDAAPTVDLNRVLNETRSQ,  SEQ ID NO:5478
NTLRCPLGDRLNVEVDAAPTVDLNRVLNETRSQ,  SEQ ID NO:5479
NTLRSPLGDRLNVEVDAAPTVDLNRVLNETRSQ,  SEQ ID NO:5480
NTLRCQLGDRLNVEVDTAPTVDLNRVLNETRSQ,  SEQ ID NO:5481
NTLRSQLGDRLNVEVDTAPTVDLNRVLNETRSQ,  SEQ ID NO:5482
NTLRCPLGDRLNVEVDTAPTVDLNRVLNETRSQ,  SEQ ID NO:5483
NTLRSPLGDRLNVEVDTAPTVDLNRVLNETRSQ,  SEQ ID NO:5484
NTLRCQLGDRLNVEVDAAPTVDLNQVLNETRNQ,  SEQ ID NO:5485
NTLRSQLGDRLNVEVDAAPTVDLNQVLNETRNQ,  SEQ ID NO:5486
NTLRCPLGDRLNVEVDAAPTVDLNQVLNETRNQ,  SEQ ID NO:5487
NTLRSPLGDRLNVEVDAAPTVDLNQVLNETRNQ,  SEQ ID NO:5488
NTLRCQLGDRLNVEVDTAPTVDLNQVLNETRNQ,  SEQ ID NO:5489
NTLRSQLGDRLNVEVDTAPTVDLNQVLNETRNQ,  SEQ ID NO:5490
NTLRCPLGDRLNVEVDTAPTVDLNQVLNETRNQ,  SEQ ID NO:5491
NTLRSPLGDRLNVEVDTAPTVDLNQVLNETRNQ,  SEQ ID NO:5492
NTLRCQLGDRLNVEVDAAPTVDLNRVLNETRNQ,  SEQ ID NO:5493
NTLRSQLGDRLNVEVDAAPTVDLNRVLNETRNQ,  SEQ ID NO:5494
NTLRCPLGDRLNVEVDAAPTVDLNRVLNETRNQ,  SEQ ID NO:5495
NTLRSPLGDRLNVEVDAAPTVDLNRVLNETRNQ,  SEQ ID NO:5496
NTLRCQLGDRLNVEVDTAPTVDLNRVLNETRNQ,  SEQ ID NO:5497
NTLRSQLGDRLNVEVDTAPTVDLNRVLNETRNQ,  SEQ ID NO:5498
NTLRCPLGDRLNVEVDTAPTVDLNRVLNETRNQ,  SEQ ID NO:5499
NTLRSPLGDRLNVEVDTAPTVDLNRVLNETRNQ,  SEQ ID NO:5500
TLRCQLGDRLNVEVDAAPTVDLNQVLNETRSQY,  SEQ ID NO:5501
TLRSQLGDRLNVEVDAAPTVDLNQVLNETRSQY,  SEQ ID NO:5502
TLRCPLGDRLNVEVDAAPTVDLNQVLNETRSQY,  SEQ ID NO:5503
TLRSPLGDRLNVEVDAAPTVDLNQVLNETRSQY,  SEQ ID NO:5504
TLRCQLGDRLNVEVDTAPTVDLNQVLNETRSQY,  SEQ ID NO:5505
TLRSQLGDRLNVEVDTAPTVDLNQVLNETRSQY,  SEQ ID NO:5506
TLRCPLGDRLNVEVDTAPTVDLNQVLNETRSQY,  SEQ ID NO:5507
TLRSPLGDRLNVEVDTAPTVDLNQVLNETRSQY,  SEQ ID NO:5508
TLRCQLGDRLNVEVDAAPTVDLNRVLNETRSQY,  SEQ ID NO:5509
TLRSQLGDRLNVEVDAAPTVDLNRVLNETRSQY,  SEQ ID NO:5510
TLRCPLGDRLNVEVDAAPTVDLNRVLNETRSQY,  SEQ ID NO:5511
TLRSPLGDRLNVEVDAAPTVDLNRVLNETRSQY,  SEQ ID NO:5512
TLRCQLGDRLNVEVDTAPTVDLNRVLNETRSQY,  SEQ ID NO:5513
TLRSQLGDRLNVEVDTAPTVDLNRVLNETRSQY,  SEQ ID NO:5514
TLRCPLGDRLNVEVDTAPTVDLNRVLNETRSQY,  SEQ ID NO:5515
TLRSPLGDRLNVEVDTAPTVDLNRVLNETRSQY,  SEQ ID NO:5516
TLRCQLGDRLNVEVDAAPTVDLNQVLNETRNQY,  SEQ ID NO:5517
TLRSQLGDRLNVEVDAAPTVDLNQVLNETRNQY,  SEQ ID NO:5518
TLRCPLGDRLNVEVDAAPTVDLNQVLNETRNQY,  SEQ ID NO:5519
TLRSPLGDRLNVEVDAAPTVDLNQVLNETRNQY,  SEQ ID NO:5520
TLRCQLGDRLNVEVDTAPTVDLNQVLNETRNQY,  SEQ ID NO:5521
```

-continued

```
TLRSQLGDRLNVEVDTAPTVDLNQVLNETRNQY,  SEQ ID NO:5522
TLRCPLGDRLNVEVDTAPTVDLNQVLNETRNQY,  SEQ ID NO:5523
TLRSPLGDRLNVEVDTAPTVDLNQVLNETRNQY,  SEQ ID NO:5524
TLRCQLGDRLNVEVDAAPTVDLNRVLNETRNQY,  SEQ ID NO:5525
TLRSQLGDRLNVEVDAAPTVDLNRVLNETRNQY,  SEQ ID NO:5526
TLRCPLGDRLNVEVDAAPTVDLNRVLNETRNQY,  SEQ ID NO:5527
TLRSPLGDRLNVEVDAAPTVDLNRVLNETRNQY,  SEQ ID NO:5528
TLRCQLGDRLNVEVDTAPTVDLNRVLNETRNQY,  SEQ ID NO:5529
TLRSQLGDRLNVEVDTAPTVDLNRVLNETRNQY,  SEQ ID NO:5530
TLRCPLGDRLNVEVDTAPTVDLNRVLNETRNQY,  SEQ ID NO:5531
TLRSPLGDRLNVEVDTAPTVDLNRVLNETRNQY,  SEQ ID NO:5532
LRCQLGDRLNVEVDAAPTVDLNQVLNETRSQYE,  SEQ ID NO:5533
LRSQLGDRLNVEVDAAPTVDLNQVLNETRSQYE,  SEQ ID NO:5534
LRCPLGDRLNVEVDAAPTVDLNQVLNETRSQYE,  SEQ ID NO:5535
LRSPLGDRLNVEVDAAPTVDLNQVLNETRSQYE,  SEQ ID NO:5536
LRCQLGDRLNVEVDTAPTVDLNQVLNETRSQYE,  SEQ ID NO:5537
LRSQLGDRLNVEVDTAPTVDLNQVLNETRSQYE,  SEQ ID NO:5538
LRCPLGDRLNVEVDTAPTVDLNQVLNETRSQYE,  SEQ ID NO:5539
LRSPLGDRLNVEVDTAPTVDLNQVLNETRSQYE,  SEQ ID NO:5540
LRCQLGDRLNVEVDAAPTVDLNRVLNETRSQYE,  SEQ ID NO:5541
LRSQLGDRLNVEVDAAPTVDLNRVLNETRSQYE,  SEQ ID NO:5542
LRCPLGDRLNVEVDAAPTVDLNRVLNETRSQYE,  SEQ ID NO:5543
LRSPLGDRLNVEVDAAPTVDLNRVLNETRSQYE,  SEQ ID NO:5544
LRCQLGDRLNVEVDTAPTVDLNRVLNETRSQYE,  SEQ ID NO:5545
LRSQLGDRLNVEVDTAPTVDLNRVLNETRSQYE,  SEQ ID NO:5546
LRCPLGDRLNVEVDTAPTVDLNRVLNETRSQYE,  SEQ ID NO:5547
LRSPLGDRLNVEVDTAPTVDLNRVLNETRSQYE,  SEQ ID NO:5548
LRCQLGDRLNVEVDAAPTVDLNQVLNETRNQYE,  SEQ ID NO:5549
LRSQLGDRLNVEVDAAPTVDLNQVLNETRNQYE,  SEQ ID NO:5550
LRCPLGDRLNVEVDAAPTVDLNQVLNETRNQYE,  SEQ ID NO:5551
LRSPLGDRLNVEVDAAPTVDLNQVLNETRNQYE,  SEQ ID NO:5552
LRCQLGDRLNVEVDTAPTVDLNQVLNETRNQYE,  SEQ ID NO:5553
LRSQLGDRLNVEVDTAPTVDLNQVLNETRNQYE,  SEQ ID NO:5554
LRCPLGDRLNVEVDTAPTVDLNQVLNETRNQYE,  SEQ ID NO:5555
LRSPLGDRLNVEVDTAPTVDLNQVLNETRNQYE,  SEQ ID NO:5556
LRCQLGDRLNVEVDAAPTVDLNRVLNETRNQYE,  SEQ ID NO:5557
LRSQLGDRLNVEVDAAPTVDLNRVLNETRNQYE,  SEQ ID NO:5558
LRCPLGDRLNVEVDAAPTVDLNRVLNETRNQYE,  SEQ ID NO:5559
LRSPLGDRLNVEVDAAPTVDLNRVLNETRNQYE,  SEQ ID NO:5560
LRCQLGDRLNVEVDTAPTVDLNRVLNETRNQYE,  SEQ ID NO:5561
LRSQLGDRLNVEVDTAPTVDLNRVLNETRNQYE,  SEQ ID NO:5562
LRCPLGDRLNVEVDTAPTVDLNRVLNETRNQYE,  SEQ ID NO:5563
LRSPLGDRLNVEVDTAPTVDLNRVLNETRNQYE,  SEQ ID NO:5564
RCQLGDRLNVEVDAAPTVDLNQVLNETRSQYEA,  SEQ ID NO:5565
RSQLGDRLNVEVDAAPTVDLNQVLNETRSQYEA,  SEQ ID NO:5566
RCPLGDRLNVEVDAAPTVDLNQVLNETRSQYEA,  SEQ ID NO:5567
RSPLGDRLNVEVDAAPTVDLNQVLNETRSQYEA,  SEQ ID NO:5568
RCQLGDRLNVEVDTAPTVDLNQVLNETRSQYEA,  SEQ ID NO:5569
RSQLGDRLNVEVDTAPTVDLNQVLNETRSQYEA,  SEQ ID NO:5570
RCPLGDRLNVEVDTAPTVDLNQVLNETRSQYEA,  SEQ ID NO:5571
RSPLGDRLNVEVDTAPTVDLNQVLNETRSQYEA,  SEQ ID NO:5572
RCQLGDRLNVEVDAAPTVDLNRVLNETRSQYEA,  SEQ ID NO:5573
RSQLGDRLNVEVDAAPTVDLNRVLNETRSQYEA,  SEQ ID NO:5574
RCPLGDRLNVEVDAAPTVDLNRVLNETRSQYEA,  SEQ ID NO:5575
RSPLGDRLNVEVDAAPTVDLNRVLNETRSQYEA,  SEQ ID NO:5576
RCQLGDRLNVEVDTAPTVDLNRVLNETRSQYEA,  SEQ ID NO:5577
RSQLGDRLNVEVDTAPTVDLNRVLNETRSQYEA,  SEQ ID NO:5578
RCPLGDRLNVEVDTAPTVDLNRVLNETRSQYEA,  SEQ ID NO:5579
RSPLGDRLNVEVDTAPTVDLNRVLNETRSQYEA,  SEQ ID NO:5580
RCQLGDRLNVEVDAAPTVDLNQVLNETRNQYEA,  SEQ ID NO:5581
RSQLGDRLNVEVDAAPTVDLNQVLNETRNQYEA,  SEQ ID NO:5582
RCPLGDRLNVEVDAAPTVDLNQVLNETRNQYEA,  SEQ ID NO:5583
RSPLGDRLNVEVDAAPTVDLNQVLNETRNQYEA,  SEQ ID NO:5584
RCQLGDRLNVEVDTAPTVDLNQVLNETRNQYEA,  SEQ ID NO:5585
RSQLGDRLNVEVDTAPTVDLNQVLNETRNQYEA,  SEQ ID NO:5586
RCPLGDRLNVEVDTAPTVDLNQVLNETRNQYEA,  SEQ ID NO:5587
RSPLGDRLNVEVDTAPTVDLNQVLNETRNQYEA,  SEQ ID NO:5588
RCQLGDRLNVEVDAAPTVDLNRVLNETRNQYEA,  SEQ ID NO:5589
RSQLGDRLNVEVDAAPTVDLNRVLNETRNQYEA,  SEQ ID NO:5590
RCPLGDRLNVEVDAAPTVDLNRVLNETRNQYEA,  SEQ ID NO:5591
RSPLGDRLNVEVDAAPTVDLNRVLNETRNQYEA,  SEQ ID NO:5592
RCQLGDRLNVEVDTAPTVDLNRVLNETRNQYEA,  SEQ ID NO:5593
RSQLGDRLNVEVDTAPTVDLNRVLNETRNQYEA,  SEQ ID NO:5594
RCPLGDRLNVEVDTAPTVDLNRVLNETRNQYEA,  SEQ ID NO:5595
RSPLGDRLNVEVDTAPTVDLNRVLNETRNQYEA,  SEQ ID NO:5596
CQLGDRLNVEVDAAPTVDLNQVLNETRSQYEAL, SEQ ID NO:5597
SQLGDRLNVEVDAAPTVDLNQVLNETRSQYEAL, SEQ ID NO:5598
CPLGDRLNVEVDAAPTVDLNQVLNETRSQYEAL, SEQ ID NO:5599
SPLGDRLNVEVDAAPTVDLNQVLNETRSQYEAL, SEQ ID NO:5600
CQLGDRLNVEVDTAPTVDLNQVLNETRSQYEAL, SEQ ID NO:5601
```

```
SQLGDRLNVEVDTAPTVDLNQVLNETRSQYEAL,   SEQ ID NO:5602
CPLGDRLNVEVDTAPTVDLNQVLNETRSQYEAL,   SEQ ID NO:5603
SPLGDRLNVEVDTAPTVDLNQVLNETRSQYEAL,   SEQ ID NO:5604
CQLGDRLNVEVDAAPTVDLNRVLNETRSQYEAL,   SEQ ID NO:5605
SQLGDRLNVEVDAAPTVDLNRVLNETRSQYEAL,   SEQ ID NO:5606
CPLGDRLNVEVDAAPTVDLNRVLNETRSQYEAL,   SEQ ID NO:5607
SPLGDRLNVEVDAAPTVDLNRVLNETRSQYEAL,   SEQ ID NO:5608
CQLGDRLNVEVDTAPTVDLNRVLNETRSQYEAL,   SEQ ID NO:5609
SQLGDRLNVEVDTAPTVDLNRVLNETRSQYEAL,   SEQ ID NO:5610
CPLGDRLNVEVDTAPTVDLNRVLNETRSQYEAL,   SEQ ID NO:5611
SPLGDRLNVEVDTAPTVDLNRVLNETRSQYEAL,   SEQ ID NO:5612
CQLGDRLNVEVDAAPTVDLNQVLNETRNQYEAL,   SEQ ID NO:5613
SQLGDRLNVEVDAAPTVDLNQVLNETRNQYEAL,   SEQ ID NO:5614
CPLGDRLNVEVDAAPTVDLNQVLNETRNQYEAL,   SEQ ID NO:5615
SPLGDRLNVEVDAAPTVDLNQVLNETRNQYEAL,   SEQ ID NO:5616
CQLGDRLNVEVDTAPTVDLNQVLNETRNQYEAL,   SEQ ID NO:5617
SQLGDRLNVEVDTAPTVDLNQVLNETRNQYEAL,   SEQ ID NO:5618
CPLGDRLNVEVDTAPTVDLNQVLNETRNQYEAL,   SEQ ID NO:5619
SPLGDRLNVEVDTAPTVDLNQVLNETRNQYEAL,   SEQ ID NO:5620
CQLGDRLNVEVDAAPTVDLNRVLNETRNQYEAL,   SEQ ID NO:5621
SQLGDRLNVEVDAAPTVDLNRVLNETRNQYEAL,   SEQ ID NO:5622
CPLGDRLNVEVDAAPTVDLNRVLNETRNQYEAL,   SEQ ID NO:5623
SPLGDRLNVEVDAAPTVDLNRVLNETRNQYEAL,   SEQ ID NO:5624
CQLGDRLNVEVDTAPTVDLNRVLNETRNQYEAL,   SEQ ID NO:5625
SQLGDRLNVEVDTAPTVDLNRVLNETRNQYEAL,   SEQ ID NO:5626
CPLGDRLNVEVDTAPTVDLNRVLNETRNQYEAL,   SEQ ID NO:5627
SPLGDRLNVEVDTAPTVDLNRVLNETRNQYEAL,   SEQ ID NO:5628
EVNTLRCQLGDRLNVEVDAAPTVDLNQVLNETRS,  SEQ ID NO:5629
EVNTLRSQLGDRLNVEVDAAPTVDLNQVLNETRS,  SEQ ID NO:5630
EVNTLRCPLGDRLNVEVDAAPTVDLNQVLNETRS,  SEQ ID NO:5631
EVNTLRSPLGDRLNVEVDAAPTVDLNQVLNETRS,  SEQ ID NO:5632
EVNTLRCQLGDRLNVEVDTAPTVDLNQVLNETRS,  SEQ ID NO:5633
EVNTLRSQLGDRLNVEVDTAPTVDLNQVLNETRS,  SEQ ID NO:5634
EVNTLRCPLGDRLNVEVDTAPTVDLNQVLNETRS,  SEQ ID NO:5635
EVNTLRSPLGDRLNVEVDTAPTVDLNQVLNETRS,  SEQ ID NO:5636
EVNTLRCQLGDRLNVEVDAAPTVDLNRVLNETRS,  SEQ ID NO:5637
EVNTLRSQLGDRLNVEVDAAPTVDLNRVLNETRS,  SEQ ID NO:5638
EVNTLRCPLGDRLNVEVDAAPTVDLNRVLNETRS,  SEQ ID NO:5639
EVNTLRSPLGDRLNVEVDAAPTVDLNRVLNETRS,  SEQ ID NO:5640
EVNTLRCQLGDRLNVEVDTAPTVDLNRVLNETRS,  SEQ ID NO:5641
EVNTLRSQLGDRLNVEVDTAPTVDLNRVLNETRS,  SEQ ID NO:5642
EVNTLRCPLGDRLNVEVDTAPTVDLNRVLNETRS,  SEQ ID NO:5643
EVNTLRSPLGDRLNVEVDTAPTVDLNRVLNETRS,  SEQ ID NO:5644
EVNTLRCQLGDRLNVEVDAAPTVDLNQVLNETRN,  SEQ ID NO:5645
EVNTLRSQLGDRLNVEVDAAPTVDLNQVLNETRN,  SEQ ID NO:5646
EVNTLRCPLGDRLNVEVDAAPTVDLNQVLNETRN,  SEQ ID NO:5647
EVNTLRSPLGDRLNVEVDAAPTVDLNQVLNETRN,  SEQ ID NO:5648
EVNTLRCQLGDRLNVEVDTAPTVDLNQVLNETRN,  SEQ ID NO:5649
EVNTLRSQLGDRLNVEVDTAPTVDLNQVLNETRN,  SEQ ID NO:5650
EVNTLRCPLGDRLNVEVDTAPTVDLNQVLNETRN,  SEQ ID NO:5651
EVNTLRSPLGDRLNVEVDTAPTVDLNQVLNETRN,  SEQ ID NO:5652
EVNTLRCQLGDRLNVEVDAAPTVDLNRVLNETRN,  SEQ ID NO:5653
EVNTLRSQLGDRLNVEVDAAPTVDLNRVLNETRN,  SEQ ID NO:5654
EVNTLRCPLGDRLNVEVDAAPTVDLNRVLNETRN,  SEQ ID NO:5655
EVNTLRSPLGDRLNVEVDAAPTVDLNRVLNETRN,  SEQ ID NO:5656
EVNTLRCQLGDRLNVEVDTAPTVDLNRVLNETRN,  SEQ ID NO:5657
EVNTLRSQLGDRLNVEVDTAPTVDLNRVLNETRN,  SEQ ID NO:5658
EVNTLRCPLGDRLNVEVDTAPTVDLNRVLNETRN,  SEQ ID NO:5659
EVNTLRSPLGDRLNVEVDTAPTVDLNRVLNETRN,  SEQ ID NO:5660
VNTLRCQLGDRLNVEVDAAPTVDLNQVLNETRSQ,  SEQ ID NO:5661
VNTLRSQLGDRLNVEVDAAPTVDLNQVLNETRSQ,  SEQ ID NO:5662
VNTLRCPLGDRLNVEVDAAPTVDLNQVLNETRSQ,  SEQ ID NO:5663
VNTLRSPLGDRLNVEVDAAPTVDLNQVLNETRSQ,  SEQ ID NO:5664
VNTLRCQLGDRLNVEVDTAPTVDLNQVLNETRSQ,  SEQ ID NO:5665
VNTLRSQLGDRLNVEVDTAPTVDLNQVLNETRSQ,  SEQ ID NO:5666
VNTLRCPLGDRLNVEVDTAPTVDLNQVLNETRSQ,  SEQ ID NO:5667
VNTLRSPLGDRLNVEVDTAPTVDLNQVLNETRSQ,  SEQ ID NO:5668
VNTLRCQLGDRLNVEVDAAPTVDLNRVLNETRSQ,  SEQ ID NO:5669
VNTLRSQLGDRLNVEVDAAPTVDLNRVLNETRSQ,  SEQ ID NO:5670
VNTLRCPLGDRLNVEVDAAPTVDLNRVLNETRSQ,  SEQ ID NO:5671
VNTLRSPLGDRLNVEVDAAPTVDLNRVLNETRSQ,  SEQ ID NO:5672
VNTLRCQLGDRLNVEVDTAPTVDLNRVLNETRSQ,  SEQ ID NO:5673
VNTLRSQLGDRLNVEVDTAPTVDLNRVLNETRSQ,  SEQ ID NO:5674
VNTLRCPLGDRLNVEVDTAPTVDLNRVLNETRSQ,  SEQ ID NO:5675
VNTLRSPLGDRLNVEVDTAPTVDLNRVLNETRSQ,  SEQ ID NO:5676
VNTLRCQLGDRLNVEVDAAPTVDLNQVLNETRNQ,  SEQ ID NO:5678
VNTLRSQLGDRLNVEVDAAPTVDLNQVLNETRNQ,  SEQ ID NO:5679
VNTLRCPLGDRLNVEVDAAPTVDLNQVLNETRNQ,  SEQ ID NO:5680
VNTLRSPLGDRLNVEVDAAPTVDLNQVLNETRNQ,  SEQ ID NO:5681
VNTLRCQLGDRLNVEVDTAPTVDLNQVLNETRNQ,  SEQ ID NO:5682
```

```
VNTLRSQLGDRLNVEVDTAPTVDLNQVLNETRNQ,   SEQ ID NO:5683
VNTLRCPLGDRLNVEVDTAPTVDLNQVLNETRNQ,   SEQ ID NO:5684
VNTLRSPLGDRLNVEVDTAPTVDLNQVLNETRNQ,   SEQ ID NO:5685
VNTLRCQLGDRLNVEVDAAPTVDLNRVLNETRNQ,   SEQ ID NO:5686
VNTLRSQLGDRLNVEVDAAPTVDLNRVLNETRNQ,   SEQ ID NO:5687
VNTLRCPLGDRLNVEVDAAPTVDLNRVLNETRNQ,   SEQ ID NO:5688
VNTLRSPLGDRLNVEVDAAPTVDLNRVLNETRNQ,   SEQ ID NO:5689
VNTLRCQLGDRLNVEVDTAPTVDLNRVLNETRNQ,   SEQ ID NO:5690
VNTLRSQLGDRLNVEVDTAPTVDLNRVLNETRNQ,   SEQ ID NO:5691
VNTLRCPLGDRLNVEVDTAPTVDLNRVLNETRNQ,   SEQ ID NO:5692
VNTLRSPLGDRLNVEVDTAPTVDLNRVLNETRNQ,   SEQ ID NO:5693
NTLRCQLGDRLNVEVDAAPTVDLNQVLNETRSQY,   SEQ ID NO:5694
NTLRSQLGDRLNVEVDAAPTVDLNQVLNETRSQY,   SEQ ID NO:5695
NTLRCPLGDRLNVEVDAAPTVDLNQVLNETRSQY,   SEQ ID NO:5696
NTLRSPLGDRLNVEVDAAPTVDLNQVLNETRSQY,   SEQ ID NO:5697
NTLRCQLGDRLNVEVDTAPTVDLNQVLNETRSQY,   SEQ ID NO:5698
NTLRSQLGDRLNVEVDTAPTVDLNQVLNETRSQY,   SEQ ID NO:5699
NTLRCPLGDRLNVEVDTAPTVDLNQVLNETRSQY,   SEQ ID NO:5700
NTLRSPLGDRLNVEVDTAPTVDLNQVLNETRSQY,   SEQ ID NO:5701
NTLRCQLGDRLNVEVDAAPTVDLNRVLNETRSQY,   SEQ ID NO:5702
NTLRSQLGDRLNVEVDAAPTVDLNRVLNETRSQY,   SEQ ID NO:5703
NTLRCPLGDRLNVEVDAAPTVDLNRVLNETRSQY,   SEQ ID NO:5704
NTLRSPLGDRLNVEVDAAPTVDLNRVLNETRSQY,   SEQ ID NO:5705
NTLRCQLGDRLNVEVDTAPTVDLNRVLNETRSQY,   SEQ ID NO:5706
NTLRSQLGDRLNVEVDTAPTVDLNRVLNETRSQY,   SEQ ID NO:5077
NTLRCPLGDRLNVEVDTAPTVDLNRVLNETRSQY,   SEQ ID NO:5708
NTLRSPLGDRLNVEVDTAPTVDLNRVLNETRSQY,   SEQ TD NO:5709
NTLRCQLGDRLNVEVDAAPTVDLNQVLNETRNQY,   SEQ ID NO:5710
NTLRSQLGDRLNVEVDAAPTVDLNQVLNETRNQY,   SEQ ID NO:5711
NTLRCPLGDRLNVEVDAAPTVDLNQVLNETRNQY,   SEQ ID NO:5712
NTLRSPLGDRLNVEVDAAPTVDLNQVLNETRNQY,   SEQ ID NO:5713
NTLRCQLGDRLNVEVDTAPTVDLNQVLNETRNQY,   SEQ ID NO:5714
NTLRSQLGDRLNVEVDTAPTVDLNQVLNETRNQY,   SEQ ID NO:5715
NTLRCPLGDRLNVEVDTAPTVDLNQVLNETRNQY,   SEQ ID NO:5716
NTLRSPLGDRLNVEVDTAPTVDLNQVLNETRNQY,   SEQ ID NO:5717
NTLRCQLGDRLNVEVDAAPTVDLNRVLNETRNQY,   SEQ ID NO:5718
NTLRSQLGDRLNVEVDAAPTVDLNRVLNETRNQY,   SEQ ID NO:5719
NTLRCPLGDRLNVEVDAAPTVDLNRVLNETRNQY,   SEQ ID NO:5720
NTLRSPLGDRLNVEVDAAPTVDLNRVLNETRNQY,   SEQ ID NO:5721
NTLRCQLGDRLNVEVDTAPTVDLNRVLNETRNQY,   SEQ ID NO:5722
NTLRSQLGDRLNVEVDTAPTVDLNRVLNETRNQY,   SEQ ID NO:5723
NTLRCPLGDRLNVEVDTAPTVDLNRVLNETRNQY,   SEQ ID NO:5724
NTLRSPLGDRLNVEVDTAPTVDLNRVLNETRNQY,   SEQ ID NO:5725
TLRCQLGDRLNVEVDAAPTVDLNQVLNETRSQYE,   SEQ ID NO:5726
TLRSQLGDRLNVEVDAAPTVDLNQVLNETRSQYE,   SEQ ID NO:5727
TLRCPLGDRLNVEVDAAPTVDLNQVLNETRSQYE,   SEQ ID NO:5728
TLRSPLGDRLNVEVDAAPTVDLNQVLNETRSQYE,   SEQ ID NO:5729
TLRCQLGDRLNVEVDTAPTVDLNQVLNETRSQYE,   SEQ ID NO:5730
TLRSQLGDRLNVEVDTAPTVDLNQVLNETRSQYE,   SEQ ID NO:5731
TLRCPLGDRLNVEVDTAPTVDLNQVLNETRSQYE,   SEQ ID NO:5732
TLRSPLGDRLNVEVDTAPTVDLNQVLNETRSQYE,   SEQ ID NO:5733
TLRCQLGDRLNVEVDAAPTVDLNRVLNETRSQYE,   SEQ ID NO:5734
TLRSQLGDRLNVEVDAAPTVDLNRVLNETRSQYE,   SEQ ID NO:5735
TLRCPLGDRLNVEVDAAPTVDLNRVLNETRSQYE,   SEQ ID NO:5736
TLRSPLGDRLNVEVDAAPTVDLNRVLNETRSQYE,   SEQ ID NO:5737
TLRCQLGDRLNVEVDTAPTVDLNRVLNETRSQYE,   SEQ ID NO:5738
TLRSQLGDRLNVEVDTAPTVDLNRVLNETRSQYE,   SEQ ID NO:5739
TLRCPLGDRLNVEVDTAPTVDLNRVLNETRSQYE,   SEQ ID NO:5740
TLRSPLGDRLNVEVDTAPTVDLNRVLNETRSQYE,   SEQ ID NO:5741
TLRCQLGDRLNVEVDAAPTVDLNQVLNETRNQYE,   SEQ ID NO:5742
TLRSQLGDRLNVEVDAAPTVDLNQVLNETRNQYE,   SEQ ID NO:5743
TLRCPLGDRLNVEVDAAPTVDLNQVLNETRNQYE,   SEQ ID NO:5744
TLRSPLGDRLNVEVDAAPTVDLNQVLNETRNQYE,   SEQ ID NO:5745
TLRCQLGDRLNVEVDTAPTVDLNQVLNETRNQYE,   SEQ ID NO:5746
TLRSQLGDRLNVEVDTAPTVDLNQVLNETRNQYE,   SEQ ID NO:5747
TLRCPLGDRLNVEVDTAPTVDLNQVLNETRNQYE,   SEQ ID NO:5748
TLRSPLGDRLNVEVDTAPTVDLNQVLNETRNQYE,   SEQ ID NO:5749
TLRCQLGDRLNVEVDAAPTVDLNRVLNETRNQYE,   SEQ ID NO:5750
TLRSQLGDRLNVEVDAAPTVDLNRVLNETRNQYE,   SEQ ID NO:5751
TLRCPLGDRLNVEVDAAPTVDLNRVLNETRNQYE,   SEQ ID NO:5752
TLRSPLGDRLNVEVDAAPTVDLNRVLNETRNQYE,   SEQ ID NO:5753
TLRCQLGDRLNVEVDTAPTVDLNRVLNETRNQYE,   SEQ ID NO:5754
TLRSQLGDRLNVEVDTAPTVDLNRVLNETRNQYE,   SEQ ID NO:5755
TLRCPLGDRLNVEVDTAPTVDLNRVLNETRNQYE,   SEQ ID NO:5756
TLRSPLGDRLNVEVDTAPTVDLNRVLNETRNQYE,   SEQ ID NO:5757
LRCQLGDRLNVEVDAAPTVDLNQVLNETRSQYEA,   SEQ ID NO:5758
LRSQLGDRLNVEVDAAPTVDLNQVLNETRSQYEA,   SEQ ID NO:5759
LRCPLGDRLNVEVDAAPTVDLNQVLNETRSQYEA,   SEQ ID NO:5760
LRSPLGDRLNVEVDAAPTVDLNQVLNETRSQYEA,   SEQ ID NO:5761
LRCQLGDRLNVEVDTAPTVDLNQVLNETRSQYEA,   SEQ ID NO:5762
```

-continued

```
LRSQLGDRLNVEVDTAPTVDLNQVLNETRSQYEA,   SEQ ID NO:5763
LRCPLGDRLNVEVDTAPTVDLNQVLNETRSQYEA,   SEQ ID NO:5764
LRSPLGDRLNVEVDTAPTVDLNQVLNETRSQYEA,   SEQ ID NO:5765
LRCQLGDRLNVEVDAAPTVDLNRVLNETRSQYEA,   SEQ ID NO:5766
LRSQLGDRLNVEVDAAPTVDLNRVLNETRSQYEA,   SEQ ID NO:5767
LRCPLGDRLNVEVDAAPTVDLNRVLNETRSQYEA,   SEQ ID NO:5768
LRSPLGDRLNVEVDAAPTVDLNRVLNETRSQYEA,   SEQ ID NO:5769
LRCQLGDRLNVEVDTAPTVDLNRVLNETRSQYEA,   SEQ ID NO:5770
LRSQLGDRLNVEVDTAPTVDLNRVLNETRSQYEA,   SEQ ID NO:5771
LRCPLGDRLNVEVDTAPTVDLNRVLNETRSQYEA,   SEQ ID NO:5772
LRSPLGDRLNVEVDTAPTVDLNRVLNETRSQYEA,   SEQ ID NO:5773
LRCQLGDRLNVEVDAAPTVDLNQVLNETRNQYEA,   SEQ ID NO:5774
LRSQLGDRLNVEVDAAPTVDLNQVLNETRNQYEA,   SEQ ID NO:5775
LRCPLGDRLNVEVDAAPTVDLNQVLNETRNQYEA,   SEQ ID NO:5776
LRSPLGDRLNVEVDAAPTVDLNQVLNETRNQYEA,   SEQ ID NO:5777
LRCQLGDRLNVEVDTAPTVDLNQVLNETRNQYEA,   SEQ ID NO:5778
LRSQLGDRLNVEVDTAPTVDLNQVLNETRNQYEA,   SEQ ID NO:5779
LRCPLGDRLNVEVDTAPTVDLNQVLNETRNQYEA,   SEQ ID NO:5780
LRSPLGDRLNVEVDTAPTVDLNQVLNETRNQYEA,   SEQ ID NO:5781
LRCQLGDRLNVEVDAAPTVDLNRVLNETRNQYEA,   SEQ ID NO:5782
LRSQLGDRLNVEVDAAPTVDLNRVLNETRNQYEA,   SEQ ID NO:5783
LRCPLGDRLNVEVDAAPTVDLNRVLNETRNQYEA,   SEQ ID NO:5784
LRSPLGDRLNVEVDAAPTVDLNRVLNETRNQYEA,   SEQ ID NO:5785
LRCQLGDRLNVEVDTAPTVDLNRVLNETRNQYEA,   SEQ ID NO:5786
LRSQLGDRLNVEVDTAPTVDLNRVLNETRNQYEA,   SEQ ID NO:5787
LRCPLGDRLNVEVDTAPTVDLNRVLNETRNQYEA,   SEQ ID NO:5788
LRSPLGDRLNVEVDTAPTVDLNRVLNETRNQYEA,   SEQ ID NO:5789
RCQLGDRLNVEVDAAPTVDLNQVLNETRSQYEAL,   SEQ ID NO:5790
RSQLGDRLNVEVDAAPTVDLNQVLNETRSQYEAL,   SEQ ID NO:5791
RCPLGDRLNVEVDAAPTVDLNQVLNETRSQYEAL,   SEQ ID NO:5792
RSPLGDRLNVEVDAAPTVDLNQVLNETRSQYEAL,   SEQ ID NO:5793
RCQLGDRLNVEVDTAPTVDLNQVLNETRSQYEAL,   SEQ ID NO:5794
RSQLGDRLNVEVDTAPTVDLNQVLNETRSQYEAL,   SEQ ID NO:5795
RCPLGDRLNVEVDTAPTVDLNQVLNETRSQYEAL,   SEQ ID NO:5796
RSPLGDRLNVEVDTAPTVDLNQVLNETRSQYEAL,   SEQ ID NO:5797
RCQLGDRLNVEVDAAPTVDLNRVLNETRSQYEAL,   SEQ ID NO:5798
RSQLGDRLNVEVDAAPTVDLNRVLNETRSQYEAL,   SEQ ID NO:5799
RCPLGDRLNVEVDAAPTVDLNRVLNETRSQYEAL,   SEQ ID NO:5800
RSPLGDRLNVEVDAAPTVDLNRVLNETRSQYEAL,   SEQ ID NO:5801
RCQLGDRLNVEVDTAPTVDLNRVLNETRSQYEAL,   SEQ ID NO:5802
RSQLGDRLNVEVDTAPTVDLNRVLNETRSQYEAL,   SEQ ID NO:5803
RCPLGDRLNVEVDTAPTVDLNRVLNETRSQYEAL,   SEQ ID NO:5804
RSPLGDRLNVEVDTAPTVDLNRVLNETRSQYEAL,   SEQ ID NO:5805
RCQLGDRLNVEVDAAPTVDLNQVLNETRNQYEAL,   SEQ ID NO:5806
RSQLGDRLNVEVDAAPTVDLNQVLNETRNQYEAL,   SEQ ID NO:5807
RCPLGDRLNVEVDAAPTVDLNQVLNETRNQYEAL,   SEQ ID NO:5809
RSPLGDRLNVEVDAAPTVDLNQVLNETRNQYEAL,   SEQ ID NO:5810
RCQLGDRLNVEVDTAPTVDLNQVLNETRNQYEAL,   SEQ ID NO:5811
RSQLGDRLNVEVDTAPTVDLNQVLNETRNQYEAL,   SEQ ID NO:5812
RCPLGDRLNVEVDTAPTVDLNQVLNETRNQYEAL,   SEQ ID NO:5813
RSPLGDRLNVEVDTAPTVDLNQVLNETRNQYEAL,   SEQ ID NO:5814
RCQLGDRLNVEVDAAPTVDLNRVLNETRNQYEAL,   SEQ ID NO:5815
RSQLGDRLNVEVDAAPTVDLNRVLNETRNQYEAL,   SEQ ID NO:5816
RCPLGDRLNVEVDAAPTVDLNRVLNETRNQYEAL,   SEQ ID NO:5817
RSPLGDRLNVEVDAAPTVDLNRVLNETRNQYEAL,   SEQ ID NO:5818
RCQLGDRLNVEVDTAPTVDLNRVLNETRNQYEAL,   SEQ ID NO:5819
RSQLGDRLNVEVDTAPTVDLNRVLNETRNQYEAL,   SEQ ID NO:5820
RCPLGDRLNVEVDTAPTVDLNRVLNETRNQYEAL,   SEQ ID NO:5821
RSPLGDRLNVEVDTAPTVDLNRVLNETRNQYEAL,   SEQ ID NO:5822
EVNTLRCQLGDRLNVEVDAAPTVDLNQVLNETRSQ,  SEQ ID NO:5823
EVNTLRSQLGDRLNVEVDAAPTVDLNQVLNETRSQ,  SEQ ID NO:5824
EVNTLRCPLGDRLNVEVDAAPTVDLNQVLNETRSQ,  SEQ ID NO:5825
EVNTLRSPLGDRLNVEVDAAPTVDLNQVLNETRSQ,  SEQ ID NO:5826
EVNTLRCQLGDRLNVEVDTAPTVDLNQVLNETRSQ,  SEQ ID NO:5827
EVNTLRSQLGDRLNVEVDTAPTVDLNQVLNETRSQ,  SEQ ID NO:5828
EVNTLRCPLGDRLNVEVDTAPTVDLNQVLNETRSQ,  SEQ ID NO:5829
EVNTLRSPLGDRLNVEVDTAPTVDLNQVLNETRSQ,  SEQ ID NO:5830
EVNTLRCQLGDRLNVEVDAAPTVDLNRVLNETRSQ,  SEQ ID NO:5831
EVNTLRSQLGDRLNVEVDAAPTVDLNRVLNETRSQ,  SEQ ID NO:5832
EVNTLRCPLGDRLNVEVDAAPTVDLNRVLNETRSQ,  SEQ ID NO:5833
EVNTLRSPLGDRLNVEVDAAPTVDLNRVLNETRSQ,  SEQ ID NO:5834
EVNTLRCQLGDRLNVEVDTAPTVDLNRVLNETRSQ,  SEQ ID NO:5835
EVNTLRSQLGDRLNVEVDTAPTVDLNRVLNETRSQ,  SEQ ID NO:5836
EVNTLRCPLGDRLNVEVDTAPTVDLNRVLNETRSQ,  SEQ ID NO:5837
EVNTLRSPLGDRLNVEVDTAPTVDLNRVLNETRSQ,  SEQ ID NO:5838
EVNTLRCQLGDRLNVEVDAAPTVDLNQVLNETRNQ,  SEQ ID NO:5839
EVNTLRSQLGDRLNVEVDAAPTVDLNQVLNETRNQ,  SEQ ID NO:5840
EVNTLRCPLGDRLNVEVDAAPTVDLNQVLNETRNQ,  SEQ ID NO:5841
EVNTLRSPLGDRLNVEVDAAPTVDLNQVLNETRNQ,  SEQ ID NO:5842
EVNTLRCQLGDRLNVEVDTAPTVDLNQVLNETRNQ,  SEQ ID NO:5843
```

-continued

```
EVNTLRSQLGDRLNVEVDTAPTVDLNQVLNETRNQ,  SEQ ID NO:5844
EVNTLRCPLGDRLNVEVDTAPTVDLNQVLNETRNQ,  SEQ ID NO:5845
EVNTLRSPLGDRLNVEVDTAPTVDLNQVLNETRNQ,  SEQ ID NO:5846
EVNTLRCQLGDRLNVEVDAAPTVDLNRVLNETRNQ,  SEQ ID NO:5847
EVNTLRSQLGDRLNVEVDAAPTVDLNRVLNETRNQ,  SEQ ID NO:5848
EVNTLRCPLGDRLNVEVDAAPTVDLNRVLNETRNQ,  SEQ ID NO:5849
EVNTLRSPLGDRLNVEVDAAPTVDLNRVLNETRNQ,  SEQ ID NO:5850
EVNTLRCQLGDRLNVEVDTAPTVDLNRVLNETRNQ,  SEQ ID NO:5851
EVNTLRSQLGDRLNVEVDTAPTVDLNRVLNETRNQ,  SEQ ID NO:5852
EVNTLRCPLGDRLNVEVDTAPTVDLNRVLNETRNQ,  SEQ ID NO:5853
EVNTLRSPLGDRLNVEVDTAPTVDLNRVLNETRNQ,  SEQ ID NO:5854
VNTLRCQLGDRLNVEVDAAPTVDLNQVLNETRSQY,  SEQ ID NO:5855
VNTLRSQLGDRLNVEVDAAPTVDLNQVLNETRSQY,  SEQ ID NO:5856
VNTLRCPLGDRLNVEVDAAPTVDLNQVLNETRSQY,  SEQ ID NO:5857
VNTLRSPLGDRLNVEVDAAPTVDLNQVLNETRSQY,  SEQ ID NO:5858
VNTLRCQLGDRLNVEVDTAPTVDLNQVLNETRSQY,  SEQ ID NO:5859
VNTLRSQLGDRLNVEVDTAPTVDLNQVLNETRSQY,  SEQ ID NO:5860
VNTLRCPLGDRLNVEVDTAPTVDLNQVLNETRSQY,  SEQ ID NO:5861
VNTLRSPLGDRLNVEVDTAPTVDLNQVLNETRSQY,  SEQ ID NO:5862
VNTLRCQLGDRLNVEVDAAPTVDLNRVLNETRSQY,  SEQ ID NO:5863
VNTLRSQLGDRLNVEVDAAPTVDLNRVLNETRSQY,  SEQ ID NO:5864
VNTLRCPLGDRLNVEVDAAPTVDLNRVLNETRSQY,  SEQ ID NO:5865
VNTLRSPLGDRLNVEVDAAPTVDLNRVLNETRSQY,  SEQ ID NO:5866
VNTLRCQLGDRLNVEVDTAPTVDLNRVLNETRSQY,  SEQ ID NO:5867
VNTLRSQLGDRLNVEVDTAPTVDLNRVLNETRSQY,  SEQ ID NO:5868
VNTLRCPLGDRLNVEVDTAPTVDLNRVLNETRSQY,  SEQ ID NO:5869
VNTLRSPLGDRLNVEVDTAPTVDLNRVLNETRSQY,  SEQ ID NO:5870
VNTLRCQLGDRLNVEVDAAPTVDLNQVLNETRNQY,  SEQ ID NO:5871
VNTLRSQLGDRLNVEVDAAPTVDLNQVLNETRNQY,  SEQ ID NO:5872
VNTLRCPLGDRLNVEVDAAPTVDLNQVLNETRNQY,  SEQ ID NO:5873
VNTLRSPLGDRLNVEVDAAPTVDLNQVLNETRNQY,  SEQ ID NO:5874
VNTLRCQLGDRLNVEVDTAPTVDLNQVLNETRNQY,  SEQ ID NO:5875
VNTLRSQLGDRLNVEVDTAPTVDLNQVLNETRNQY,  SEQ ID NO:5876
VNTLRCPLGDRLNVEVDTAPTVDLNQVLNETRNQY,  SEQ ID NO:5877
VNTLRSPLGDRLNVEVDTAPTVDLNQVLNETRNQY,  SEQ ID NO:5878
VNTLRCQLGDRLNVEVDAAPTVDLNRVLNETRNQY,  SEQ ID NO:5879
VNTLRSQLGDRLNVEVDAAPTVDLNRVLNETRNQY,  SEQ ID NO:5880
VNTLRCPLGDRLNVEVDAAPTVDLNRVLNETRNQY,  SEQ ID NO:5881
VNTLRSPLGDRLNVEVDAAPTVDLNRVLNETRNQY,  SEQ ID NO:5882
VNTLRCQLGDRLNVEVDTAPTVDLNRVLNETRNQY,  SEQ ID NO:5883
VNTLRSQLGDRLNVEVDTAPTVDLNRVLNETRNQY,  SEQ ID NO:5884
VNTLRCPLGDRLNVEVDTAPTVDLNRVLNETRNQY,  SEQ ID NO:5885
VNTLRSPLGDRLNVEVDTAPTVDLNRVLNETRNQY,  SEQ ID NO:5886
NTLRCQLGDRLNVEVDAAPTVDLNQVLNETRSQYE,  SEQ ID NO:5887
NTLRSQLGDRLNVEVDAAPTVDLNQVLNETRSQYE,  SEQ ID NO:5888
NTLRCPLGDRLNVEVDAAPTVDLNQVLNETRSQYE,  SEQ ID NO:5889
NTLRSPLGDRLNVEVDAAPTVDLNQVLNETRSQYE,  SEQ ID NO:5890
NTLRCQLGDRLNVEVDTAPTVDLNQVLNETRSQYE,  SEQ ID NO:5891
NTLRSQLGDRLNVEVDTAPTVDLNQVLNETRSQYE,  SEQ ID NO:5892
NTLRCPLGDRLNVEVDTAPTVDLNQVLNETRSQYE,  SEQ ID NO:5893
NTLRSPLGDRLNVEVDTAPTVDLNQVLNETRSQYE,  SEQ ID NO:5894
NTLRCQLGDRLNVEVDAAPTVDLNRVLNETRSQYE,  SEQ ID NO:5895
NTLRSQLGDRLNVEVDAAPTVDLNRVLNETRSQYE,  SEQ ID NO:5896
NTLRCPLGDRLNVEVDAAPTVDLNRVLNETRSQYE,  SEQ ID NO:5897
NTLRSPLGDRLNVEVDAAPTVDLNRVLNETRSQYE,  SEQ ID NO:5898
NTLRCQLGDRLNVEVDTAPTVDLNRVLNETRSQYE,  SEQ ID NO:5899
NTLRSQLGDRLNVEVDTAPTVDLNRVLNETRSQYE,  SEQ ID NO:5900
NTLRCPLGDRLNVEVDTAPTVDLNRVLNETRSQYE,  SEQ ID NO:5901
NTLRSPLGDRLNVEVDTAPTVDLNRVLNETRSQYE,  SEQ ID NO:5902
NTLRCQLGDRLNVEVDAAPTVDLNQVLNETRNQYE,  SEQ ID NO:5903
NTLRSQLGDRLNVEVDAAPTVDLNQVLNETRNQYE,  SEQ ID NO:5904
NTLRCPLGDRLNVEVDAAPTVDLNQVLNETRNQYE,  SEQ ID NO:5905
NTLRSPLGDRLNVEVDAAPTVDLNQVLNETRNQYE,  SEQ ID NO:5906
NTLRCQLGDRLNVEVDTAPTVDLNQVLNETRNQYE,  SEQ ID NO:5907
NTLRSQLGDRLNVEVDTAPTVDLNQVLNETRNQYE,  SEQ ID NO:5908
NTLRCPLGDRLNVEVDTAPTVDLNQVLNETRNQYE,  SEQ ID NO:5909
NTLRSPLGDRLNVEVDTAPTVDLNQVLNETRNQYE,  SEQ ID NO:5910
NTLRCQLGDRLNVEVDAAPTVDLNRVLNETRNQYE,  SEQ ID NO:5911
NTLRSQLGDRLNVEVDAAPTVDLNRVLNETRNQYE,  SEQ ID NO:5912
NTLRCPLGDRLNVEVDAAPTVDLNRVLNETRNQYE,  SEQ ID NO:5913
NTLRSPLGDRLNVEVDAAPTVDLNRVLNETRNQYE,  SEQ ID NO:5914
NTLRCQLGDRLNVEVDTAPTVDLNRVLNETRNQYE,  SEQ ID NO:5915
NTLRSQLGDRLNVEVDTAPTVDLNRVLNETRNQYE,  SEQ ID NO:5916
NTLRCPLGDRLNVEVDTAPTVDLNRVLNETRNQYE,  SEQ ID NO:5917
NTLRSPLGDRLNVEVDTAPTVDLNRVLNETRNQYE,  SEQ ID NO:5918
TLRCQLGDRLNVEVDAAPTVDLNQVLNETRSQYEA,  SEQ ID NO:5919
TLRSQLGDRLNVEVDAAPTVDLNQVLNETRSQYEA,  SEQ ID NO:5920
TLRCPLGDRLNVEVDAAPTVDLNQVLNETRSQYEA,  SEQ ID NO:5921
TLRSPLGDRLNVEVDAAPTVDLNQVLNETRSQYEA,  SEQ ID NO:5922
TLRCQLGDRLNVEVDTAPTVDLNQVLNETRSQYEA,  SEQ ID NO:5923
```

-continued

```
TLRSQLGDRLNVEVDTAPTVDLNQVLNETRSQYEA, SEQ ID NO:5924
TLRCPLGDRLNVEVDTAPTVDLNQVLNETRSQYEA, SEQ ID NO:5925
TLRSPLGDRLNVEVDTAPTVDLNQVLNETRSQYEA, SEQ ID NO:5926
TLRCQLGDRLNVEVDAAPTVDLNRVLNETRSQYEA, SEQ ID NO:5927
TLRSQLGDRLNVEVDAAPTVDLNRVLNETRSQYEA, SEQ ID NO:5958
TLRCPLGDRLNVEVDAAPTVDLNRVLNETRSQYEA, SEQ ID NO:5929
TLRSPLGDRLNVEVDAAPTVDLNRVLNETRSQYEA, SEQ ID NO:5930
TLRCQLGDRLNVEVDTAPTVDLNRVLNETRSQYEA, SEQ ID NO:5931
TLRSQLGDRLNVEVDTAPTVDLNRVLNETRSQYEA, SEQ ID NO:5932
TLRCPLGDRLNVEVDTAPTVDLNRVLNETRSQYEA, SEQ ID NO:5933
TLRSPLGDRLNVEVDTAPTVDLNRVLNETRSQYEA, SEQ ID NO:5934
TLRCQLGDRLNVEVDAAPTVDLNQVLNETRNQYEA, SEQ ID NO:5935
TLRSQLGDRLNVEVDAAPTVDLNQVLNETRNQYEA, SEQ ID NO:5936
TLRCPLGDRLNVEVDAAPTVDLNQVLNETRNQYEA, SEQ ID NO:5937
TLRSPLGDRLNVEVDAAPTVDLNQVLNETRNQYEA, SEQ ID NO:5938
TLRCQLGDRLNVEVDTAPTVDLNQVLNETRNQYEA, SEQ ID NO:5938
TLRSQLGDRLNVEVDTAPTVDLNQVLNETRNQYEA, SEQ ID NO:5940
TLRCPLGDRLNVEVDTAPTVDLNQVLNETRNQYEA, SEQ ID NO:5941
TLRSPLGDRLNVEVDTAPTVDLNQVLNETRNQYEA, SEQ ID NO:5942
TLRCQLGDRLNVEVDAAPTVDLNRVLNETRNQYEA, SEQ ID NO:5943
TLRSQLGDRLNVEVDAAPTVDLNRVLNETRNQYEA, SEQ ID NO:5944
TLRCPLGDRLNVEVDAAPTVDLNRVLNETRNQYEA, SEQ ID NO:5945
TLRSPLGDRLNVEVDAAPTVDLNRVLNETRNQYEA, SEQ ID NO:5946
TLRCQLGDRLNVEVDTAPTVDLNRVLNETRNQYEA, SEQ ID NO:5947
TLRSQLGDRLNVEVDTAPTVDLNRVLNETRNQYEA, SEQ ID NO:5948
TLRCPLGDRLNVEVDTAPTVDLNRVLNETRNQYEA, SEQ ID NO:5949
TLRSPLGDRLNVEVDTAPTVDLNRVLNETRNQYEA, SEQ ID NO:5950
LRCQLGDRLNVEVDAAPTVDLNQVLNETRSQYEAL, SEQ ID NO:5951
LRSQLGDRLNVEVDAAPTVDLNQVLNETRSQYEAL, SEQ ID NO:5952
LRCPLGDRLNVEVDAAPTVDLNQVLNETRSQYEAL, SEQ ID NO:5953
LRSPLGDRLNVEVDAAPTVDLNQVLNETRSQYEAL, SEQ ID NO:5954
LRCQLGDRLNVEVDTAPTVDLNQVLNETRSQYEAL, SEQ ID NO:5955
LRSQLGDRLNVEVDTAPTVDLNQVLNETRSQYEAL, SEQ ID NO:5956
LRCPLGDRLNVEVDTAPTVDLNQVLNETRSQYEAL, SEQ ID NO:5957
LRSPLGDRLNVEVDTAPTVDLNQVLNETRSQYEAL, SEQ ID NO:5958
LRCQLGDRLNVEVDAAPTVDLNRVLNETRSQYEAL, SEQ ID NO:5959
LRSQLGDRLNVEVDAAPTVDLNRVLNETRSQYEAL, SEQ ID NO:5960
LRCPLGDRLNVEVDAAPTVDLNRVLNETRSQYEAL, SEQ ID NO:5961
LRSPLGDRLNVEVDAAPTVDLNRVLNETRSQYEAL, SEQ ID NO:5962
LRCQLGDRLNVEVDTAPTVDLNRVLNETRSQYEAL, SEQ ID NO:5963
LRSQLGDRLNVEVDTAPTVDLNRVLNETRSQYEAL, SEQ ID NO:5964
LRCPLGDRLNVEVDTAPTVDLNRVLNETRSQYEAL, SEQ ID NO:5965
LRSPLGDRLNVEVDTAPTVDLNRVLNETRSQYEAL, SEQ ID NO:5966
LRCQLGDRLNVEVDAAPTVDLNQVLNETRNQYEAL, SEQ ID NO:5967
LRSQLGDRLNVEVDAAPTVDLNQVLNETRNQYEAL, SEQ ID NO:5968
LRCPLGDRLNVEVDAAPTVDLNQVLNETRNQYEAL, SEQ ID NO:5969
LRSPLGDRLNVEVDAAPTVDLNQVLNETRNQYEAL, SEQ ID NO:5970
LRCQLGDRLNVEVDTAPTVDLNQVLNETRNQYEAL, SEQ ID NO:5971
LRSQLGDRLNVEVDTAPTVDLNQVLNETRNQYEAL, SEQ ID NO:5972
LRCPLGDRLNVEVDTAPTVDLNQVLNETRNQYEAL, SEQ ID NO:5973
LRSPLGDRLNVEVDTAPTVDLNQVLNETRNQYEAL, SEQ ID NO:5974
LRCQLGDRLNVEVDAAPTVDLNRVLNETRNQYEAL, SEQ ID NO:5975
LRSQLGDRLNVEVDAAPTVDLNRVLNETRNQYEAL, SEQ ID NO:5976
LRCPLGDRLNVEVDAAPTVDLNRVLNETRNQYEAL, SEQ ID NO:5977
LRSPLGDRLNVEVDAAPTVDLNRVLNETRNQYEAL, SEQ ID NO:5978
LRCQLGDRLNVEVDTAPTVDLNRVLNETRNQYEAL, SEQ ID NO:5979
LRSQLGDRLNVEVDTAPTVDLNRVLNETRNQYEAL, SEQ ID NO:5980
LRCPLGDRLNVEVDTAPTVDLNRVLNETRNQYEAL, SEQ ID NO:5981
LRSPLGDRLNVEVDTAPTVDLNRVLNETRNQYEAL, SEQ ID NO:5982
EVNTLRCQLGDRLNVEVDAAPTVDLNQVLNETRSQY, SEQ ID NO:5983
EVNTLRSQLGDRLNVEVDAAPTVDLNQVLNETRSQY, SEQ ID NO:5984
EVNTLRCPLGDRLNVEVDAAPTVDLNQVLNETRSQY, SEQ ID NO:5985
EVNTLRSPLGDRLNVEVDAAPTVDLNQVLNETRSQY, SEQ ID NO:5986
EVNTLRCQLGDRLNVEVDTAPTVDLNQVLNETRSQY, SEQ ID NO:5987
EVNTLRSQLGDRLNVEVDTAPTVDLNQVLNETRSQY, SEQ ID NO:5988
EVNTLRCPLGDRLNVEVDTAPTVDLNQVLNETRSQY, SEQ ID NO:5989
EVNTLRSPLGDRLNVEVDTAPTVDLNQVLNETRSQY, SEQ ID NO:5990
EVNTLRCQLGDRLNVEVDAAPTVDLNRVLNETRSQY, SEQ ID NO:5991
EVNTLRSQLGDRLNVEVDAAPTVDLNRVLNETRSQY, SEQ ID NO:5992
EVNTLRCPLGDRLNVEVDAAPTVDLNRVLNETRSQY, SEQ ID NO:5993
EVNTLRSPLGDRLNVEVDAAPTVDLNRVLNETRSQY, SEQ ID NO:5994
EVNTLRCQLGDRLNVEVDTAPTVDLNRVLNETRSQY, SEQ ID NO:5995
EVNTLRSQLGDRLNVEVDTAPTVDLNRVLNETRSQY, SEQ ID NO:5996
EVNTLRCPLGDRLNVEVDTAPTVDLNRVLNETRSQY, SEQ ID NO:5997
EVNTLRSPLGDRLNVEVDTAPTVDLNRVLNETRSQY, SEQ ID NO:5998
EVNTLRCQLGDRLNVEVDAAPTVDLNQVLNETRNQY, SEQ ID NO:5999
EVNTLRSQLGDRLNVEVDAAPTVDLNQVLNETRNQY, SEQ ID NO:6000
EVNTLRCPLGDRLNVEVDAAPTVDLNQVLNETRNQY, SEQ ID NO:6001
EVNTLRSPLGDRLNVEVDAAPTVDLNQVLNETRNQY, SEQ ID NO:6002
EVNTLRCQLGDRLNVEVDTAPTVDLNQVLNETRNQY, SEQ ID NO:6003
```

-continued

```
EVNTLRSQLGDRLNVEVDTAPTVDLNQVLNETRNQY, SEQ ID NO:6004
EVNTLRCPLGDRLNVEVDTAPTVDLNQVLNETRNQY, SEQ ID NO:6005
EVNTLRSPLGDRLNVEVDTAPTVDLNQVLNETRNQY, SEQ ID NO:6006
EVNTLRCQLGDRLNVEVDAAPTVDLNRVLNETRNQY, SEQ ID NO:6007
EVNTLRSQLGDRLNVEVDAAPTVDLNRVLNETRNQY, SEQ ID NO:6008
EVNTLRCPLGDRLNVEVDAAPTVDLNRVLNETRNQY, SEQ ID NO:6009
EVNTLRSPLGDRLNVEVDAAPTVDLNRVLNETRNQY, SEQ ID NO:6010
EVNTLRCQLGDRLNVEVDTAPTVDLNRVLNETRNQY, SEQ ID NO:6011
EVNTLRSQLGDRLNVEVDTAPTVDLNRVLNETRNQY, SEQ ID NO:6012
EVNTLRCPLGDRLNVEVDTAPTVDLNRVLNETRNQY, SEQ ID NO:6013
EVNTLRSPLGDRLNVEVDTAPTVDLNRVLNETRNQY, SEQ ID NO:6014
VNTLRCQLGDRLNVEVDAAPTVDLNQVLNETRSQYE, SEQ ID NO:6015
VNTLRSQLGDRLNVEVDAAPTVDLNQVLNETRSQYE, SEQ ID NO:6016
VNTLRCPLGDRLNVEVDAAPTVDLNQVLNETRSQYE, SEQ ID NO:6017
VNTLRSPLGDRLNVEVDAAPTVDLNQVLNETRSQYE, SEQ ID NO:6018
VNTLRCQLGDRLNVEVDTAPTVDLNQVLNETRSQYE, SEQ ID NO:6019
VNTLRSQLGDRLNVEVDTAPTVDLNQVLNETRSQYE, SEQ ID NO:6020
VNTLRCPLGDRLNVEVDTAPTVDLNQVLNETRSQYE, SEQ ID NO:6021
VNTLRSPLGDRLNVEVDTAPTVDLNQVLNETRSQYE, SEQ ID NO:6022
VNTLRCQLGDRLNVEVDAAPTVDLNRVLNETRSQYE, SEQ ID NO:6023
VNTLRSQLGDRLNVEVDAAPTVDLNRVLNETRSQYE, SEQ ID NO:6024
VNTLRCPLGDRLNVEVDAAPTVDLNRVLNETRSQYE, SEQ ID NO:6025
VNTLRSPLGDRLNVEVDAAPTVDLNRVLNETRSQYE, SEQ ID NO:6026
VNTLRCQLGDRLNVEVDTAPTVDLNRVLNETRSQYE, SEQ ID NO:6027
VNTLRSQLGDRLNVEVDTAPTVDLNRVLNETRSQYE, SEQ ID NO:6028
VNTLRCPLGDRLNVEVDTAPTVDLNRVLNETRSQYE, SEQ ID NO:6029
VNTLRSPLGDRLNVEVDTAPTVDLNRVLNETRSQYE, SEQ ID NO:6030
VNTLRCQLGDRLNVEVDAAPTVDLNQVLNETRNQYE, SEQ ID NO:6031
VNTLRSQLGDRLNVEVDAAPTVDLNQVLNETRNQYE, SEQ ID NO:6032
VNTLRCPLGDRLNVEVDAAPTVDLNQVLNETRNQYE, SEQ ID NO:6033
VNTLRSPLGDRLNVEVDAAPTVDLNQVLNETRNQYE, SEQ ID NO:6034
VNTLRCQLGDRLNVEVDTAPTVDLNQVLNETRNQYE, SEQ ID NO:6035
VNTLRSQLGDRLNVEVDTAPTVDLNQVLNETRNQYE, SEQ ID NO:6036
VNTLRCPLGDRLNVEVDTAPTVDLNQVLNETRNQYE, SEQ ID NO:6037
VNTLRSPLGDRLNVEVDTAPTVDLNQVLNETRNQYE, SEQ ID NO:6038
VNTLRCQLGDRLNVEVDAAPTVDLNRVLNETRNQYE, SEQ ID NO:6039
VNTLRSQLGDRLNVEVDAAPTVDLNRVLNETRNQYE, SEQ ID NO:6040
VNTLRCPLGDRLNVEVDAAPTVDLNRVLNETRNQYE, SEQ ID NO:6041
VNTLRSPLGDRLNVEVDAAPTVDLNRVLNETRNQYE, SEQ ID NO:6042
VNTLRCQLGDRLNVEVDTAPTVDLNRVLNETRNQYE, SEQ ID NO:6043
VNTLRSQLGDRLNVEVDTAPTVDLNRVLNETRNQYE, SEQ ID NO:6044
VNTLRCPLGDRLNVEVDTAPTVDLNRVLNETRNQYE, SEQ ID NO:6045
VNTLRSPLGDRLNVEVDTAPTVDLNRVLNETRNQYE, SEQ ID NO:6046
NTLRCQLGDRLNVEVDAAPTVDLNQVLNETRSQYEA, SEQ ID NO:6047
NTLRSQLGDRLNVEVDAAPTVDLNQVLNETRSQYEA, SEQ ID NO:6048
NTLRCPLGDRLNVEVDAAPTVDLNQVLNETRSQYEA, SEQ ID NO:6049
NTLRSPLGDRLNVEVDAAPTVDLNQVLNETRSQYEA, SEQ ID NO:6050
NTLRCQLGDRLNVEVDTAPTVDLNQVLNETRSQYEA, SEQ ID NO:6051
NTLRSQLGDRLNVEVDTAPTVDLNQVLNETRSQYEA, SEQ ID NO:6052
NTLRCPLGDRLNVEVDTAPTVDLNQVLNETRSQYEA, SEQ ID NO:6053
NTLRSPLGDRLNVEVDTAPTVDLNQVLNETRSQYEA, SEQ ID NO:6054
NTLRCQLGDRLNVEVDAAPTVDLNRVLNETRSQYEA, SEQ ID NO:6055
NTLRSQLGDRLNVEVDAAPTVDLNRVLNETRSQYEA, SEQ ID NO:6056
NTLRCPLGDRLNVEVDAAPTVDLNRVLNETRSQYEA, SEQ ID NO:6057
NTLRSPLGDRLNVEVDAAPTVDLNRVLNETRSQYEA, SEQ ID NO:6058
NTLRCQLGDRLNVEVDTAPTVDLNRVLNETRSQYEA, SEQ ID NO:6059
NTLRSQLGDRLNVEVDTAPTVDLNRVLNETRSQYEA, SEQ ID NO:6060
NTLRCPLGDRLNVEVDTAPTVDLNRVLNETRSQYEA, SEQ ID NO:6061
NTLRSPLGDRLNVEVDTAPTVDLNRVLNETRSQYEA, SEQ ID NO:6062
NTLRCQLGDRLNVEVDAAPTVDLNQVLNETRNQYEA, SEQ ID NO:6063
NTLRSQLGDRLNVEVDAAPTVDLNQVLNETRNQYEA, SEQ ID NO:6064
NTLRCPLGDRLNVEVDAAPTVDLNQVLNETRNQYEA, SEQ ID NO:6065
NTLRSPLGDRLNVEVDAAPTVDLNQVLNETRNQYEA, SEQ ID NO:6066
NTLRCQLGDRLNVEVDTAPTVDLNQVLNETRNQYEA, SEQ ID NO:6067
NTLRSQLGDRLNVEVDTAPTVDLNQVLNETRNQYEA, SEQ ID NO:6068
NTLRCPLGDRLNVEVDTAPTVDLNQVLNETRNQYEA, SEQ ID NO:6069
NTLRSPLGDRLNVEVDTAPTVDLNQVLNETRNQYEA, SEQ ID NO:6070
NTLRCQLGDRLNVEVDAAPTVDLNRVLNETRNQYEA, SEQ ID NO:6071
NTLRSQLGDRLNVEVDAAPTVDLNRVLNETRNQYEA, SEQ ID NO:6072
NTLRCPLGDRLNVEVDAAPTVDLNRVLNETRNQYEA, SEQ ID NO:6073
NTLRSPLGDRLNVEVDAAPTVDLNRVLNETRNQYEA, SEQ ID NO:6074
NTLRCQLGDRLNVEVDTAPTVDLNRVLNETRNQYEA, SEQ ID NO:6075
NTLRSQLGDRLNVEVDTAPTVDLNRVLNETRNQYEA, SEQ ID NO:6076
NTLRCPLGDRLNVEVDTAPTVDLNRVLNETRNQYEA, SEQ ID NO:6077
NTLRSPLGDRLNVEVDTAPTVDLNRVLNETRNQYEA, SEQ ID NO:6078
TLRCQLGDRLNVEVDAAPTVDLNQVLNETRSQYEAL, SEQ ID NO:6079
TLRSQLGDRLNVEVDAAPTVDLNQVLNETRSQYEAL, SEQ ID NO:6080
TLRCPLGDRLNVEVDAAPTVDLNQVLNETRSQYEAL, SEQ ID NO:6081
TLRSPLGDRLNVEVDAAPTVDLNQVLNETRSQYEAL, SEQ ID NO:6082
TLRCQLGDRLNVEVDTAPTVDLNQVLNETRSQYEAL, SEQ ID NO:6083
```

-continued

```
TLRSQLGDRLNVEVDTAPTVDLNQVLNETRSQYEAL,  SEQ ID NO:6084
TLRCPLGDRLNVEVDTAPTVDLNQVLNETRSQYEAL,  SEQ ID NO:6085
TLRSPLGDRLNVEVDTAPTVDLNQVLNETRSQYEAL,  SEQ ID NO:6086
TLRCQLGDRLNVEVDAAPTVDLNRVLNETRSQYEAL,  SEQ ID NO:6087
TLRSQLGDRLNVEVDAAPTVDLNRVLNETRSQYEAL,  SEQ ID NO:6088
TLRCPLGDRLNVEVDAAPTVDLNRVLNETRSQYEAL,  SEQ ID NO:6089
TLRSPLGDRLNVEVDAAPTVDLNRVLNETRSQYEAL,  SEQ ID NO:6090
TLRCQLGDRLNVEVDTAPTVDLNRVLNETRSQYEAL,  SEQ ID NO:6091
TLRSQLGDRLNVEVDTAPTVDLNRVLNETRSQYEAL,  SEQ ID NO:6092
TLRCPLGDRLNVEVDTAPTVDLNRVLNETRSQYEAL,  SEQ ID NO:6093
TLRSPLGDRLNVEVDTAPTVDLNRVLNETRSQYEAL,  SEQ ID NO:6094
TLRCQLGDRLNVEVDAAPTVDLNQVLNETRNQYEAL,  SEQ ID NO:6095
TLRSQLGDRLNVEVDAAPTVDLNQVLNETRNQYEAL,  SEQ ID NO:6096
TLRCPLGDRLNVEVDAAPTVDLNQVLNETRNQYEAL,  SEQ ID NO:6097
TLRSPLGDRLNVEVDAAPTVDLNQVLNETRNQYEAL,  SEQ ID NO:6098
TLRCQLGDRLNVEVDTAPTVDLNQVLNETRNQYEAL,  SEQ ID NO:6099
TLRSQLGDRLNVEVDTAPTVDLNQVLNETRNQYEAL,  SEQ ID NO:6100
TLRCPLGDRLNVEVDTAPTVDLNQVLNETRNQYEAL,  SEQ ID NO:6101
TLRSPLGDRLNVEVDTAPTVDLNQVLNETRNQYEAL,  SEQ ID NO:6102
TLRCQLGDRLNVEVDAAPTVDLNRVLNETRNQYEAL,  SEQ ID NO:6103
TLRSQLGDRLNVEVDAAPTVDLNRVLNETRNQYEAL,  SEQ ID NO:6104
TLRCPLGDRLNVEVDAAPTVDLNRVLNETRNQYEAL,  SEQ ID NO:6105
TLRSPLGDRLNVEVDAAPTVDLNRVLNETRNQYEAL,  SEQ ID NO:6106
TLRCQLGDRLNVEVDTAPTVDLNRVLNETRNQYEAL,  SEQ ID NO:6107
TLRSQLGDRLNVEVDTAPTVDLNRVLNETRNQYEAL,  SEQ ID NO:6108
TLRCPLGDRLNVEVDTAPTVDLNRVLNETRNQYEAL,  SEQ ID NO:6109
TLRSPLGDRLNVEVDTAPTVDLNRVLNETRNQYEAL,  SEQ ID NO:6110
EVNTLRCQLGDRLNVEVDAAPTVDLNQVLNETRSQYE,  SEQ ID NO:6111
EVNTLRSQLGDRLNVEVDAAPTVDLNQVLNETRSQYE,  SEQ ID NO:6112
EVNTLRCPLGDRLNVEVDAAPTVDLNQVLNETRSQYE,  SEQ ID NO:6113
EVNTLRSPLGDRLNVEVDAAPTVDLNQVLNETRSQYE,  SEQ ID NO:6114
EVNTLRCQLGDRLNVEVDTAPTVDLNQVLNETRSQYE,  SEQ ID NO:6115
EVNTLRSQLGDRLNVEVDTAPTVDLNQVLNETRSQYE,  SEQ ID NO:6116
EVNTLRCPLGDRLNVEVDTAPTVDLNQVLNETRSQYE,  SEQ ID NO:6117
EVNTLRSPLGDRLNVEVDTAPTVDLNQVLNETRSQYE,  SEQ ID NO:6118
EVNTLRCQLGDRLNVEVDAAPTVDLNRVLNETRSQYE,  SEQ ID NO:6119
EVNTLRSQLGDRLNVEVDAAPTVDLNRVLNETRSQYE,  SEQ ID NO:6120
EVNTLRCPLGDRLNVEVDAAPTVDLNRVLNETRSQYE,  SEQ ID NO:6121
EVNTLRSPLGDRLNVEVDAAPTVDLNRVLNETRSQYE,  SEQ ID NO:6122
EVNTLRCQLGDRLNVEVDTAPTVDLNRVLNETRSQYE,  SEQ ID NO:6123
EVNTLRSQLGDRLNVEVDTAPTVDLNRVLNETRSQYE,  SEQ ID NO:6124
EVNTLRCPLGDRLNVEVDTAPTVDLNRVLNETRSQYE,  SEQ ID NO:6125
EVNTLRSPLGDRLNVEVDTAPTVDLNRVLNETRSQYE,  SEQ ID NO:6126
EVNTLRCQLGDRLNVEVDAAPTVDLNQVLNETRNQYE,  SEQ ID NO:6127
EVNTLRSQLGDRLNVEVDAAPTVDLNQVLNETRNQYE,  SEQ ID NO:6128
EVNTLRCPLGDRLNVEVDAAPTVDLNQVLNETRNQYE,  SEQ ID NO:6129
EVNTLRSPLGDRLNVEVDAAPTVDLNQVLNETRNQYE,  SEQ ID NO:6130
EVNTLRCQLGDRLNVEVDTAPTVDLNQVLNETRNQYE,  SEQ ID NO:6131
EVNTLRSQLGDRLNVEVDTAPTVDLNQVLNETRNQYE,  SEQ ID NO:6132
EVNTLRCPLGDRLNVEVDTAPTVDLNQVLNETRNQYE,  SEQ ID NO:6133
EVNTLRSPLGDRLNVEVDTAPTVDLNQVLNETRNQYE,  SEQ ID NO:6134
EVNTLRCQLGDRLNVEVDAAPTVDLNRVLNETRNQYE,  SEQ ID NO:6135
EVNTLRSQLGDRLNVEVDAAPTVDLNRVLNETRNQYE,  SEQ ID NO:6136
EVNTLRCPLGDRLNVEVDAAPTVDLNRVLNETRNQYE,  SEQ ID NO:6137
EVNTLRSPLGDRLNVEVDAAPTVDLNRVLNETRNQYE,  SEQ ID NO:6138
EVNTLRCQLGDRLNVEVDTAPTVDLNRVLNETRNQYE,  SEQ ID NO:6139
EVNTLRSQLGDRLNVEVDTAPTVDLNRVLNETRNQYE,  SEQ ID NO:6140
EVNTLRCPLGDRLNVEVDTAPTVDLNRVLNETRNQYE,  SEQ ID NO:6141
EVNTLRSPLGDRLNVEVDTAPTVDLNRVLNETRNQYE,  SEQ ID NO:6142
VNTLRCQLGDRLNVEVDAAPTVDLNQVLNETRSQYEA,  SEQ ID NO:6143
VNTLRSQLGDRLNVEVDAAPTVDLNQVLNETRSQYEA,  SEQ ID NO:6144
VNTLRCPLGDRLNVEVDAAPTVDLNQVLNETRSQYEA,  SEQ ID NO:6145
VNTLRSPLGDRLNVEVDAAPTVDLNQVLNETRSQYEA,  SEQ ID NO:6146
VNTLRCQLGDRLNVEVDTAPTVDLNQVLNETRSQYEA,  SEQ ID NO:6147
VNTLRSQLGDRLNVEVDTAPTVDLNQVLNETRSQYEA,  SEQ ID NO:6148
VNTLRCPLGDRLNVEVDTAPTVDLNQVLNETRSQYEA,  SEQ ID NO:6149
VNTLRSPLGDRLNVEVDTAPTVDLNQVLNETRSQYEA,  SEQ ID NO:6150
VNTLRCQLGDRLNVEVDAAPTVDLNRVLNETRSQYEA,  SEQ ID NO:6151
VNTLRSQLGDRLNVEVDAAPTVDLNRVLNETRSQYEA,  SEQ ID NO:6152
VNTLRCPLGDRLNVEVDAAPTVDLNRVLNETRSQYEA,  SEQ ID NO:6153
VNTLRSPLGDRLNVEVDAAPTVDLNRVLNETRSQYEA,  SEQ ID NO:6154
VNTLRCQLGDRLNVEVDTAPTVDLNRVLNETRSQYEA,  SEQ ID NO:6155
VNTLRSQLGDRLNVEVDTAPTVDLNRVLNETRSQYEA,  SEQ ID NO:6156
VNTLRCPLGDRLNVEVDTAPTVDLNRVLNETRSQYEA,  SEQ ID NO:6157
VNTLRSPLGDRLNVEVDTAPTVDLNRVLNETRSQYEA,  SEQ ID NO:6158
```

-continued

```
VNTLRCQLGDRLNVEVDAAPTVDLNQVLNETRNQYEA,   SEQ ID NO:6159
VNTLRSQLGDRLNVEVDAAPTVDLNQVLNETRNQYEA,   SEQ ID NO:6160
VNTLRCPLGDRLNVEVDAAPTVDLNQVLNETRNQYEA,   SEQ ID NO:6161
VNTLRSPLGDRLNVEVDAAPTVDLNQVLNETRNQYEA,   SEQ ID NO:6162
VNTLRCQLGDRLNVEVDTAPTVDLNQVLNETRNQYEA,   SEQ ID NO:6163
VNTLRSQLGDRLNVEVDTAPTVDLNQVLNETRNQYEA,   SEQ ID NO:6164
VNTLRCPLGDRLNVEVDTAPTVDLNQVLNETRNQYEA,   SEQ ID NO:6165
VNTLRSPLGDRLNVEVDTAPTVDLNQVLNETRNQYEA,   SEQ ID NO:6166
VNTLRCQLGDRLNVEVDAAPTVDLNRVLNETRNQYEA,   SEQ ID NO:6167
VNTLRSQLGDRLNVEVDAAPTVDLNRVLNETRNQYEA,   SEQ ID NO:6168
VNTLRCPLGDRLNVEVDAAPTVDLNRVLNETRNQYEA,   SEQ ID NO:6169
VNTLRSPLGDRLNVEVDAAPTVDLNRVLNETRNQYEA,   SEQ ID NO:6170
VNTLRCQLGDRLNVEVDTAPTVDLNRVLNETRNQYEA,   SEQ ID NO:6171
VNTLRSQLGDRLNVEVDTAPTVDLNRVLNETRNQYEA,   SEQ ID NO:6172
VNTLRCPLGDRLNVEVDTAPTVDLNRVLNETRNQYEA,   SEQ ID NO:6173
VNTLRSPLGDRLNVEVDTAPTVDLNRVLNETRNQYEA,   SEQ ID NO:6174
NTLRCQLGDRLNVEVDAAPTVDLNQVLNETRSQYEAL,   SEQ ID NO:6175
NTLRSQLGDRLNVEVDAAPTVDLNQVLNETRSQYEAL,   SEQ ID NO:6176
NTLRCPLGDRLNVEVDAAPTVDLNQVLNETRSQYEAL,   SEQ ID NO:6177
NTLRSPLGDRLNVEVDAAPTVDLNQVLNETRSQYEAL,   SEQ ID NO:6178
NTLRCQLGDRLNVEVDTAPTVDLNQVLNETRSQYEAL,   SEQ ID NO:6179
NTLRSQLGDRLNVEVDTAPTVDLNQVLNETRSQYEAL,   SEQ ID NO:6180
NTLRCPLGDRLNVEVDTAPTVDLNQVLNETRSQYEAL,   SEQ ID NO:6181
NTLRSPLGDRLNVEVDTAPTVDLNQVLNETRSQYEAL,   SEQ ID NO:6182
NTLRCQLGDRLNVEVDAAPTVDLNRVLNETRSQYEAL,   SEQ ID NO:6183
NTLRSQLGDRLNVEVDAAPTVDLNRVLNETRSQYEAL,   SEQ ID NO:6184
NTLRCPLGDRLNVEVDAAPTVDLNRVLNETRSQYEAL,   SEQ ID NO:6185
NTLRSPLGDRLNVEVDAAPTVDLNRVLNETRSQYEAL,   SEQ ID NO:6186
NTLRCQLGDRLNVEVDTAPTVDLNRVLNETRSQYEAL,   SEQ ID NO:6187
NTLRSQLGDRLNVEVDTAPTVDLNRVLNETRSQYEAL,   SEQ ID NO:6188
NTLRCPLGDRLNVEVDTAPTVDLNRVLNETRSQYEAL,   SEQ ID NO:6189
NTLRSPLGDRLNVEVDTAPTVDLNRVLNETRSQYEAL,   SEQ ID NO:6190
NTLRCQLGDRLNVEVDAAPTVDLNQVLNETRNQYEAL,   SEQ ID NO:6191
NTLRSQLGDRLNVEVDAAPTVDLNQVLNETRNQYEAL,   SEQ ID NO:6192
NTLRCPLGDRLNVEVDAAPTVDLNQVLNETRNQYEAL,   SEQ ID NO:6193
NTLRSPLGDRLNVEVDAAPTVDLNQVLNETRNQYEAL,   SEQ ID NO:6194
NTLRCQLGDRLNVEVDTAPTVDLNQVLNETRNQYEAL,   SEQ ID NO:6195
NTLRSQLGDRLNVEVDTAPTVDLNQVLNETRNQYEAL,   SEQ ID NO:6196
NTLRCPLGDRLNVEVDTAPTVDLNQVLNETRNQYEAL,   SEQ ID NO:6197
NTLRSPLGDRLNVEVDTAPTVDLNQVLNETRNQYEAL,   SEQ ID NO:6198
NTLRCQLGDRLNVEVDAAPTVDLNRVLNETRNQYEAL,   SEQ ID NO:6199
NTLRSQLGDRLNVEVDAAPTVDLNRVLNETRNQYEAL,   SEQ ID NO:6200
NTLRCPLGDRLNVEVDAAPTVDLNRVLNETRNQYEAL,   SEQ ID NO:6201
NTLRSPLGDRLNVEVDAAPTVDLNRVLNETRNQYEAL,   SEQ ID NO:6202
NTLRCQLGDRLNVEVDTAPTVDLNRVLNETRNQYEAL,   SEQ ID NO:6203
NTLRSQLGDRLNVEVDTAPTVDLNRVLNETRNQYEAL,   SEQ ID NO:6204
NTLRCPLGDRLNVEVDTAPTVDLNRVLNETRNQYEAL,   SEQ ID NO:6205
NTLRSPLGDRLNVEVDTAPTVDLNRVLNETRNQYEAL,   SEQ ID NO:6206
EVNTLRCQLGDRLNVEVDAAPTVDLNQVLNETRSQYEA,  SEQ ID NO:6207
EVNTLRSQLGDRLNVEVDAAPTVDLNQVLNETRSQYEA,  SEQ ID NO:6208
EVNTLRCPLGDRLNVEVDAAPTVDLNQVLNETRSQYEA,  SEQ ID NO:6209
EVNTLRSPLGDRLNVEVDAAPTVDLNQVLNETRSQYEA,  SEQ ID NO:6210
EVNTLRCQLGDRLNVEVDTAPTVDLNQVLNETRSQYEA,  SEQ ID NO:6211
EVNTLRSQLGDRLNVEVDTAPTVDLNQVLNETRSQYEA,  SEQ ID NO:6212
EVNTLRCPLGDRLNVEVDTAPTVDLNQVLNETRSQYEA,  SEQ ID NO:6213
EVNTLRSPLGDRLNVEVDTAPTVDLNQVLNETRSQYEA,  SEQ ID NO:6214
EVNTLRCQLGDRLNVEVDAAPTVDLNRVLNETRSQYEA,  SEQ ID NO:6215
EVNTLRSQLGDRLNVEVDAAPTVDLNRVLNETRSQYEA,  SEQ ID NO:6216
EVNTLRCPLGDRLNVEVDAAPTVDLNRVLNETRSQYEA,  SEQ ID NO:6217
EVNTLRSPLGDRLNVEVDANPTVDLNRVLNETRSQYEA,  SEQ ID NO:6218
EVNTLRCQLGDRLNVEVDTAPTVDLNRVLNETRSQYEA,  SEQ ID NO:6219
EVNTLRSQLGDRLNVEVDTAPTVDLNRVLNETRSQYEA,  SEQ ID NO:6220
EVNTLRCPLGDRLNVEVDTAPTVDLNRVLNETRSQYEA,  SEQ ID NO:6221
EVNTLRSPLGDRLNVEVDTAPTVDLNRVLNETRSQYEA,  SEQ ID NO:6222
EVNTLRCQLGDRLNVEVDAAPTVDLNQVLNETRNQYEA,  SEQ ID NO:6223
EVNTLRSQLGDRLNVEVDAAPTVDLNQVLNETRNQYEA,  SEQ ID NO:6224
EVNTLRCPLGDRLNVEVDAAPTVDLNQVLNETRNQYEA,  SEQ ID NO:6225
EVNTLRSPLGDRLNVEVDAAPTVDLNQVLNETRNQYEA,  SEQ ID NO:6226
EVNTLRCQLGDRLNVEVDTAPTVDLNQVLNETRNQYEA,  SEQ ID NO:6227
EVNTLRSQLGDRLNVEVDTAPTVDLNQVLNETRNQYEA,  SEQ ID NO:6228
EVNTLRCPLGDRLNVEVDTAPTVDLNQVLNETRNQYEA,  SEQ ID NO:6229
EVNTLRSPLGDRLNVEVDTAPTVDLNQVLNETRNQYEA,  SEQ ID NO:6230
```

-continued

```
EVNTLRCQLGDRLNVEVDAAPTVDLNRVLNETRNQYEA, SEQ ID NO:6231
EVNTLRSQLGDRLNVEVDAAPTVDLNRVLNETRNQYEA, SEQ ID NO:6232
EVNTLRCPLGDRLNVEVDAAPTVDLNRVLNETRNQYEA, SEQ ID NO:6233
EVNTLRSPLGDRLNVEVDAAPTVDLNRVLNETRNQYEA, SEQ ID NO:6234
EVNTLRCQLGDRLNVEVDTAPTVDLNRVLNETRNQYEA, SEQ ID NO:6235
EVNTLRSQLGDRLNVEVDTAPTVDLNRVLNETRNQYEA, SEQ ID NO:6236
EVNTLRCPLGDRLNVEVDTAPTVDLNRVLNETRNQYEA, SEQ ID NO:6237
EVNTLRSPLGDRLNVEVDTAPTVDLNRVLNETRNQYEA, SEQ ID NO:6238
VNTLRSPLGDRLNVEVDTAPTVDLNRVLNETRSQYEAL, SEQ ID NO:6254
VNTLRCQLGDRLNVEVDAAPTVDLNQVLNETRNQYEAL, SEQ ID NO:6255
VNTLRSQLGDRLNVEVDAAPTVDLNQVLNETRNQYEAL, SEQ ID NO:6256
VNTLRCPLGDRLNVEVDAAPTVDLNQVLNETRNQYEAL, SEQ ID NO:6257
VNTLRSPLGDRLNVEVDAAPTVDLNQVLNETRNQYEAL, SEQ ID NO:6258
VNTLRCQLGDRLNVEVDTAPTVDLNQVLNETRNQYEAL, SEQ ID NO:6259
VNTLRSQLGDRLNVEVDTAPTVDLNQVLNETRNQYEAL, SEQ ID NO:6260
VNTLRCPLGDRLNVEVDTAPTVDLNQVLNETRNQYEAL, SEQ ID NO:6261
VNTLRSPLGDRLNVEVDTAPTVDLNQVLNETRNQYEAL, SEQ ID NO:6262
VNTLRCQLGDRLNVEVDAAPTVDLNRVLNETRNQYEAL, SEQ ID NO:6263
VNTLRSQLGDRLNVEVDAAPTVDLNRVLNETRNQYEAL, SEQ ID NO:6264
VNTLRCPLGDRLNVEVDAAPTVDLNRVLNETRNQYEAL, SEQ ID NO:6265
VNTLRSPLGDRLNVEVDAAPTVDLNRVLNETRNQYEAL, SEQ ID NO:6266
VNTLRCQLGDRLNVEVDTAPTVDLNRVLNETRNQYEAL, SEQ ID NO:6267
VNTLRSQLGDRLNVEVDTAPTVDLNRVLNETRNQYEAL, SEQ ID NO:6268
VNTLRCQLGDRLNVEVDAAPTVDLNQVLNETRSQYEAL, SEQ ID NO:6239
VNTLRSQLGDRLNVEVDAAPTVDLNQVLNETRSQYEAL, SEQ ID NO:6240
VNTLRCPLGDRLNVEVDAAPTVDLNQVLNETRSQYEAL, SEQ ID NO:6241
VNTLRSPLGDRLNVEVDAAPTVDLNQVLNETRSQYEAL, SEQ ID NO:6242
VNTLRCQLGDRLNVEVDTAPTVDLNQVLNETRSQYEAL, SEQ ID NO:6243
VNTLRSQLGDRLNVEVDTAPTVDLNQVLNETRSQYEAL, SEQ ID NO:6244
VNTLRCPLGDRLNVEVDTAPTVDLNQVLNETRSQYEAL, SEQ ID NO:6245
VNTLRSPLGDRLNVEVDTAPTVDLNQVLNETRSQYEAL, SEQ ID NO:6246
VNTLRCQLGDRLNVEVDAAPTVDLNRVLNETRSQYEAL, SEQ ID NO:6247
VNTLRSQLGDRLNVEVDAAPTVDLNRVLNETRSQYEAL, SEQ ID NO:6248
VNTLRCPLGDRLNVEVDAAPTVDLNRVLNETRSQYEAL, SEQ ID NO:6249
VNTLRSPLGDRLNVEVDAAPTVDLNRVLNETRSQYEAL, SEQ ID NO:6250
VNTLRCQLGDRLNVEVDTAPTVDLNRVLNETRSQYEAL, SEQ ID NO:6251
VNTLRSQLGDRLNVEVDTAPTVDLNRVLNETRSQYEAL, SEQ ID NO:6252
VNTLRCPLGDRLNVEVDTAPTVDLNRVLNETRSQYEAL, SEQ ID NO:6253
VNTLRCPLGDRLNVEVDTAPTVDLNRVLNETRNQYEAL, SEQ ID NO:6269
VNTLRSPLGDRLNVEVDTAPTVDLNRVLNETRNQYEAL, SEQ ID NO:6270
```

As is well known in the art, the use of the designation (C/S) means the amino acid at that position may be either C or S, (Q/P) means the amino acid at that position may be either Q or P, (A/T) means the amino acid at that position may be either A or T, (Q/R) means the amino acid at that position may be either Q or R and (S/N) means the amino acid at that position may be either S or N. It is also understood that the terms C-terminus or carboxy terminus are used interchangeably and are used herein as they are normally used in the art. An amino acid is composed of a carbon atom known as the a-carbon to which is attached a a-carboxylic acid, an a-amine and a side chain. In the peptide bond polymerization, the a-amino group from one amino acid binds to the a-carboxylic acid group of an adjacent amino acid in the peptide polymer. The polymer thus includes a free a-carboxylic acid on one end (the C-terminus) and a free a-amine group on the opposite end (the N-terminus or amino terminus). Any of the peptides disclosed herein may be modified to increase the stability and activity of the compositions as is well known in the art. Such modifications would include, but is not limited to bonding of acetyl or amide groups to the appropriate ends of the peptides.

It is also understood that one of skill in the art would understand that the peptides are disclosed using the one letter amino acid abbreviations as follows:

A=Ala=alanine
R=Arg=arginine
N=Asp=asparagine
D=Asp=aspartic acid
C=Cys=cysteine
E=Glu=glutamic acid
Q=Gln=glutamine
G=Gly=glycine
H=His=histidine
I=Ile=isoleucine
L=Leu=leucine
K=Lys=lysine
M=Met=methionine
F=Phe=phenylalanine
P=Pro=proline
S=Ser=serine
T=Thr=threonine
W=Trp=tryptophan
Y=Tyr=tyrosine
V=Val=valine The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Selected peptides derived from the keratin consensus sequence were chemically synthesized and used to demonstrate the bioactivity of the peptides. Normal human adult dermal fibroblasts were cultured in fibroblast growth medium (Clonetics™/BioWhittaker, San Diego, Calif., USA). Passage 5 cells were seeded into wells of 96 well plates at 5×10³ cells/well. Test peptide solutions were prepared at approximately 1.5 mg/ml in sterile water. Small volumes of 0.1N NH4OH were added dropwise to peptide the peptide solutions to completely solubilize the peptides as recommended by the manufacturer (New England Peptide, Inc., Fitchburg, Miss., USA). The volume of NH4OH added to the solution was recorded and used to adjust beginning concentration. Solutions were serially diluted in fibroblast culture medium from 100-0.001 μg/ml, then added to the cells and cultured for 5 days. At day 3, test and control media were removed from each well by vacuum and replaced with fresh test or control solutions. Samples were evaluated in 4 replicate wells. Note in each plate, wells were selected at random to be used as baseline controls to account for any variation in cell seeding between plates. After 5 days, cell proliferation was assessed spectrophotometrically using the Cell Titer96® Cell Proliferation Assay (Promega Corp., Madison, Wis., USA). Absorbance values were normalized to baseline controls and expressed as percent increased (positive values) or decreased (negative values) proliferation.

| Mitogenic Effects of 19 Peptides on Human Fibroblasts in Culture for 5 Days | | | | | | | | |
|---|---|---|---|---|---|---|---|---|
| Peptides for Cell Culture Studies | | | concentration (ug/mL) | | | | | |
| Peptide | Acidity | MW | 100 | 10 | 1 | 0.1 | 0.01 | 0.001 |
| H2N-VEVDAA-OH | acidic 2× | 602 | −9.5% | −1.3% | −4.7% | −9.0% | 2.3% | 11.0% |
| H2N-SPLGD-OH | acidic 1× | 487 | −4.3% | −1.2% | 1.5% | −4.2% | 1.7% | 11.8% |
| H2N-LGDRL-OH | acid/base | 572 | −3.8% | −3.1% | −4.8% | 0.6% | 0.0% | 10.3% |
| H2N-DLNRVL-OH | acid/base | 728 | −1.2% | −3.5% | −2.8% | −0.4% | 11.5% | 14.4% |
| H2N-DLNQ-OH | acidic 1× | 488 | −3.6% | −0.7% | −0.8% | 2.6% | 8.9% | 15.9% |
| H2N-VDTAPTV-OH | acidic 1× | 701 | −5.5% | 5.5% | 0.7% | 1.2% | 7.9% | 10.4% |
| H2N-AAPTV-OH | neutral | 457 | −5.9% | −5.9% | 2.8% | 0.3% | −0.2% | 11.0% |
| H2N-AAPTVD-OH | acidic 1× | 572 | 1.6% | −2.0% | 1.7% | −1.1% | 7.9% | 11.6% |
| H2N-DAAPTV-OH | acidic 1× | 572 | −2.7% | −6.1% | 3.5% | 7.5% | 9.5% | −3.0% |
| H2N-TAPTV-OH | neutral | 487 | 0.7% | −2.7% | 8.2% | 9.4% | −1.2% | 5.2% |
| H2N-DTAPTV-OH | acidic 1× | 602 | 7.6% | 2.2% | 2.9% | 6.7% | 2.5% | 3.2% |
| H2N-TAPTVD-OH | acidic 1× | 602 | 6.9% | 4.0% | 2.1% | −0.5% | −0.9% | 0.3% |
| H2N-APTVDLN-OH | acidic 1× | 728 | 6.7% | 8.1% | −6.0% | 2.8% | 3.9% | 1.2% |
| H2N-VDTAPT-OH | acidic 1× | 602 | 4.4% | −0.1% | 2.5% | 6.8% | 4.2% | 9.0% |
| H2N-EVDAAPT-OH | acidic 2× | 701 | 4.1% | 16.5% | 7.1% | 5.4% | 8.9% | 6.5% |
| H2N-VDAAPT-OH | acidic 1× | 572 | 13.3% | 6.2% | 4.5% | −3.6% | 2.9% | 1.6% |
| H2N-RLNVEV-OH | acid/base | 728 | 10.6% | 6.4% | 1.9% | −4.3% | −6.0% | −2.6% |
| H2N-LNVEV-OH | acidic 1× | 572 | 13.9% | 15.9% | −11.4% | −10.8% | 0.9% | −1.0% |
| H2N-TLRSP-OH | basic 1× | 572 | 18.8% | 14.7% | 6.6% | 7.7% | 1.9% | 4.7% |
| Fibroblast GF | | | | | | | | 70.3% |

It is understood that the test concentrations may be further optimized to determine the optimal concentration of each peptide formulation for either activation or inhibition of cell proliferation. However, the data contained in this example demonstrate the activity of the peptide compositions in the fibroblast assay. The test data further demonstrates like activity for peptides that contain thematic amino acid sequences LGD, DLN, APTV, SEQ ID NO:67, or LNVEV, SEQ ID NO:117.

Numerous advantages of the invention covered by this document have been set forth in the foregoing description. It will be understood, however, that this disclosure is, in many respects, only illustrative. Changes may be made in details, particularly in matters of reagents, concentrations, and step order, and still fall within the spirit and scope of the invention.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07501485B2). An electronic copy of the "Sequence Listing" will also be available from the USPTO upon request and payment of the fee set forth in 37 CFR 1.19(b)(3).

The invention claimed is:

1. An isolated bioactive peptide of from 25-39 amino acids in length wherein the amino acid sequence of the peptide consists of from 25-39 contiguous amino acids of any of SEQ ID NOS:1-32.

2. An isolated peptide, of from 25-39 amino acids in length wherein the amino acid sequence of the peptide consists of from 25-39 contiguous amino acids of any of SEQ ID NOS:1-32 wherein the N-terminal α-amine group is acetylated.

3. An isolated peptide, of from 25-39 amino acids in length wherein the amino acid sequence of the peptide consists of from 25-39 contiguous amino acids of any of SEQ ID NOS:1-32 wherein the C-terminal α-carboxy group is a carboxamide.

4. A composition comprising a mixture of peptides including the isolated peptide of claim 1, and one or more peptides with one or more of the following amino acid sequences DLNQ, SEQ ID NO:71, SPLGD, SEQ ID NO:111, LGDRL, SEQ ID NO:114, LNVEV, SEQ ID NO:118, AAPTV, SEQ ID NO:128, TAPTV, SEQ ID NO:129, NTLRSP, SEQ ID NO:162, RLNVEV, SEQ ID NO:184, VEVDAA, SEQ ID NO:188, VDAAPT, SEQ ID NO:192, VDTAPT, SEQ ID NO:193, DTAPTV, SEQ ID NO:195, AAPTVD, SEQ ID NO:196, TAPTVD, SEQ ID NO:197, DLNRVL, SEQ ID NO:205, EVDAAPT, SEQ ID NO:263, VDTAPTV, SEQ ID NO:266, DAAPTVD, SEQ ID NO:267, or APTVDLN, SEQ ID NO:271, wherein the isolated peptide is free of covalent bonds to another protein or peptide.

5. A composition in the form of a powder, lotion, hydrogel, oil, emulsion, paste, polish or cream, wherein the composition comprises the isolated bioactive peptide of claim 1 in combination with a carrier.

6. A wound dressing comprising the isolated bioactive peptide of claim 1 non-covalently associated with the dressing.

7. The wound dressing of claim 6, wherein the wound dressing is a sheet comprising a keratin derived product.

8. The wound dressing of claim 6, further defined as an adhesive bandage.

9. A tissue engineering scaffold comprising the isolated peptide of claim 1, wherein the isolated peptide is contained in or non-covalently adhered to the tissue engineering scaffold.

10. The tissue engineering scaffold of claim 9, wherein the tissue engineering scaffold comprises an insoluble material at least a part of which is obtained from a keratin product.

11. A composition in the form of a hydrogel, wherein the isolated peptide of claim 1 is contained in or associated with the hydrogel.

12. The composition of claim 11 wherein the hydrogel comprises a keratin derived hydrogel.

13. A composition for topical application to skin of a human or animal subject, said composition comprising the isolated peptide of claim 1, contained in a lotion, gel, paste, cream, or aqueous solution.

14. The composition of claim 13, for topical application to damaged epithelial tissue.

15. The composition of claim 14, wherein the damaged epithelial tissue comprises a wound, a rash, diaper rash, a burn, a sunburn, a cut, an abrasion, a puncture, a sore, a bedsore, an ulcer, or wrinkled skin.

16. The composition of claim 13, wherein the isolated peptide concentration is from about 100 μg/ml to about $1 \times 10^{-6}$ μg/ml.

17. A formulation for cosmetic application to skin comprising the isolated peptide of claim 1, wherein the isolated peptide is contained in a carrier for cosmetic application to skin.

18. The formulation of claim 17, wherein the isolated peptide is contained in a moisturizer, a deodorant, an anti-aging/skin repair preparation, a cleanser, a toner, an eye care composition, a lip care composition, a fingernail care composition, a toenail care composition, a scalp care composition, a sun care composition, a hand care composition, or a body care composition.

19. The formulation of claim 17, wherein the isolated peptide is contained in an after-care product for a skin insult.

20. The formulation of claim 19, wherein the skin insult is a chemical peel, sunburn, depilatory irritation, razor-shaving nick, an abrasion, or scalp irritation from hair treatment.

21. The formulation of claim 17, wherein the isolated peptide is contained in a water based make up.

22. The formulation of claim 17, wherein the isolated peptide is contained in a hair care product.

23. The formulation of claim 22, wherein the product is a shampoo or hair conditioner.

24. A wound dressing comprising the isolated peptide of claim 1 contained in, or non-covalently adhered to a sheet, film or fabric dressing.

25. The wound dressing of claim 24, wherein the dressing comprises a keratin derivative.

26. The wound dressing of claim 24, wherein said wound dressing is an adhesive bandage.

27. The wound dressing of claim 24, wherein the dressing comprises wool or cotton fabric.

28. The wound dressing of claim 24, wherein the dressing is a woven keratin sheet.

29. The wound dressing of claim 24, wherein the dressing is a non-woven sheet or film comprising a water insoluble keratin.

30. The composition of claim 14, wherein the epithelial tissue is skin, nasal, oral, gastro-intestinal, anal, vaginal, ear, eye, lung, or urogenital epithelial tissue.

31. A cell growth scaffold comprising a keratin derived sheet material, porous material or hydrogel, and further comprising an isolated peptide of claim 1 contained in, or non-covalently adhered thereto.

32. The cell growth scaffold of claim 31, further defined as a spinal implant, a bone growth scaffold, a scaffold for growth of epithelial tissue, a bandage, a non-woven sheet or a woven sheet.

33. The cell growth scaffold of claim 32, wherein the non-woven or woven sheets comprise wool pads, woven keratin, keratin bonded to polymer sheets, or cross-linked keratin.

34. The cell growth scaffold of claim 31, further comprising an envelope containing the isolated peptide.

35. The cell growth scaffold of claim 31, comprising the isolated peptide bonded or non-covalently adhered to the surface of a metal, silicone or polymer implant.

36. An isolated peptide of from 25-39 amino acids in length wherein the peptide consists of from 25-39 contiguous amino acids of any of SEQ ID NOS:1-32, and wherein the peptide is obtained by a process comprising treating human or animal hair with an oxidizing agent to produce a mixture of water-soluble peptides, and isolating said peptides of 25-39 amino acids therefrom.

37. A composition comprising a mixture of peptides including the isolated peptide of claim 36, and one or more peptides with one or more of the following amino acid sequences: DLNQ, SEQ ID NO:71, SPLGD, SEQ ID NO:111, LGDR, SEQ ID NO:52, LGDRL, SEQ ID NO:114, LNVEV, SEQ ID NO:118, AAPTV, SEQ ID NO:128, TAPTV, SEQ ID NO:129, NTLRSP, SEQ ID NO:162, RLNVEV, SEQ ID NO:184, VEVDAA, SEQ ID NO:188, VDAAPT, SEQ ID NO:192, VDTAPT, SEQ ID NO:193, DTAPTV, SEQ ID NO:195, APTV, SEQ ID NO:67, AAPTVD, SEQ ID NO:196, TAPTVD, SEQ ID NO:197, DLNRVL, SEQ ID NO:205, EVDAAPT, SEQ ID NO:263, VDTAPTV, SEQ ID NO:266, DAAPTVD, SEQ ID NO:267, and APTVDLN, SEQ ID NO:271.

38. A composition comprising the isolated peptide of claim 1 contained in a pharmaceutically acceptable carrier.

\* \* \* \* \*